United States Patent
Hawkins et al.

(10) Patent No.: US 9,410,214 B2
(45) Date of Patent: Aug. 9, 2016

(54) USE OF PHOSPHOKETOLASE AND PHOSPHOTRANSACETYLASE FOR PRODUCTION OF ACETYL-COENZYME A DERIVED COMPOUNDS

(71) Applicant: Amyris, Inc., Emeryville, CA (US)

(72) Inventors: Kristy Michelle Hawkins, Emeryville, CA (US); Tina Tipawan Mahatdejkul-Meadows, Emeryville, CA (US); Adam Leon Meadows, Emeryville, CA (US); Lauren Barbara Pickens, Emeryville, CA (US); Anna Tai, Emeryville, CA (US); Annie Ening Tsong, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 172 days.

(21) Appl. No.: 14/214,062

(22) Filed: Mar. 14, 2014

(65) Prior Publication Data

US 2014/0273144 A1 Sep. 18, 2014

Related U.S. Application Data

(60) Provisional application No. 61/800,356, filed on Mar. 15, 2013.

(51) Int. Cl.
| | | |
|---|---|---|
| *C12N 9/10* | (2006.01) | |
| *C12N 9/16* | (2006.01) | |
| *C12N 9/88* | (2006.01) | |
| *C12P 5/00* | (2006.01) | |
| *C12P 7/54* | (2006.01) | |

(52) U.S. Cl.
CPC ........ *C12Y 401/02009* (2013.01); *C12N 9/1029* (2013.01); *C12N 9/16* (2013.01); *C12N 9/88* (2013.01); *C12P 5/007* (2013.01); *C12P 7/54* (2013.01); *C12Y 203/01008* (2013.01); *C12Y 301/03021* (2013.01); *Y02P 20/52* (2015.11)

(58) Field of Classification Search
None
See application file for complete search history.

(56) References Cited

U.S. PATENT DOCUMENTS

| 7,253,001 B2 | 8/2007 | Wahlbom et al. |
| 8,221,982 B2 | 7/2012 | Serber et al. |
| 8,415,136 B1 | 4/2013 | Gardner et al. |
| 8,603,800 B2 | 12/2013 | Gardner et al. |
| 2012/0276587 A1 | 11/2012 | Beck et al. |
| 2013/0236942 A1 | 9/2013 | Gardner et al. |
| 2013/0330796 A1 | 12/2013 | Beck et al. |
| 2014/0154765 A1 | 6/2014 | Gardner et al. |

FOREIGN PATENT DOCUMENTS

EP 2 546 336 A1 1/2013

OTHER PUBLICATIONS

International Search Report and the Written Opinion in PCT/US2014/028421, mailed Sep. 19, 2014, 17 pages.
Byrne et al., The Yeast Gene Order Browser: Combining curated homology and syntenic context reveals gene fate in polyploid species (2005) *Genome Research* 15:1456-1461.
DeLuna et al., Need-Based Up-Regulation of Protein Levels in Response to Deletion of Their Duplicate Genes (2010) *PLoS Biology* 8:e10000347, 11 pages.
Hirayama et al., Cloning and characterization of seven cDNAs for hyperosmolarity-responsive (*HOR*) genes of *Saccharomyces cerevisiae* (1995) *Mol Gen Genet* 249:127-138.
Nevoigt et al., Osmoregulation and glycerol metabolism in the yeast *Saccharomyces cerevisiae* (1997) *FEMS Microbiol Rev* 21:231-241.
Norbeck et al., Purification and Characterization of Two Isoenzymes of $_{DL}$-Glycerol-3-phosphatase from *Saccharomyces cerevisiae* (1996) *J Biol Chem* 271: 13875-13881.
Påahlman et al. The Yeast Glycerol 3-Phosphatases Gpp1p and Gpp2p Are Required for Glycerol Biosynthesis and Differentially Involved in the Cellular Responses to Osmotic, Anaerobic, and Oxidative Stress (2001) *J Biol Chem* 276: 3555-3563.
Sonderegger et al., Metabolic Engineering of a Phosphoketolase Pathway for Pentose Catabolism in *Saccharomyces cerevisiae* (2004) *Applied and Environmental Microbiology* 70:2892-2897.

*Primary Examiner* — Suzanne M Noakes
(74) *Attorney, Agent, or Firm* — Squire Patton Boggs (US) LLP

(57) ABSTRACT

Provided herein are compositions and methods for improved production of acetyl-CoA and acetyl-CoA derived compounds in a host cell. In some embodiments, the host cell is genetically modified to comprise a heterologous nucleotide sequence encoding a phosphoketolase (PK), and a functional disruption of an endogenous enzyme that converts acetyl phosphate to acetate. In some embodiments, the host cell further comprises a heterologous nucleotide sequence encoding a phosphotransacetylase (PTA). In some embodiments, the enzyme that converts acetyl phosphate to acetate is a glycerol-1-phosphatase. In some embodiments, the glycerol-1-phosphatase is GPP1/RHR2. In some embodiments, the glycerol-1-phosphatase is GPP2/HOR2. The compositions and methods described herein provide an efficient route for the heterologous production of acetyl-CoA-derived compounds, including but not limited to, isoprenoids, polyketides, and fatty acids.

32 Claims, 11 Drawing Sheets

SEQUENCE LISTING

<160> NUMBER OF SEQ ID NOS: 37

<210> SEQ ID NO 1
<211> LENGTH: 2749
<212> TYPE: DNA
<213> ORGANISM: Leuconostoc mesenteroides
<220> FEATURE:
<221> NAME/KEY: misc_feature
<222> LOCATION: (1)..(2749)
<223> OTHER INFORMATION: Leuconostoc mesenteroides Phosphoketolase (PK)
gene sequence

<400> SEQUENCE: 1

```
gttacggaag aagtcgtggt ttacggtgtt tatgattctt gcaaaaaata aggagtactt      60
aatctcatgg cagatttcga ttcaaaagag tacttggaac ttgttgataa gtggtggcgc     120
gcaactaact atttgtcagc tgggatgatc tttttgaaga gcaacccatt gttctcagtt     180
actaatacac ctatcaaggc tgaagatgta aaagttaagc caatcggaca ctggggtact     240
atctcaggtc agacattctt gtatgcacat gctaaccgtt tgatcaacaa gtatggtttg     300
aacatgtttt acgttggtgg tcctggtcac ggtggccaag ttatggttac taacgcttac     360
ttagacggcg catatactga agattatcct gaaattactc aagatatcga aggtatgagc     420
cacttgttca gcgtttctc attccctggc ggtattggat cacacatgac agctcaaaca     480
cctggttcat tacacgaagg tggtgaattg ggctattcat tgagccacgc ttttggtgcc     540
gttttggaca atcctgacca agttgctttc gcagttgttg gtgatggtga agctgaaaca     600
ggtccttcaa tggcttcatg gcactcaatt aagttttga atgctaagaa tgatggtgcc     660
gttttgcctg tcttggattt gaacggattc aagatttcaa acccaactat cttctcacgt     720
atgagtgatg aagaaatcac aaagttcttt gaaggtttgg gttattcacc tcgcttcatc     780
gaaaacgatg atattcatga ctacgcaaca tatcaccaac ttgcagcaaa cattttggat     840
caagctattg aagatattca agctattcaa atgatgcac gtgaaaatgg taagtatcaa     900
gatggtgaaa tccctgcatg gccagtaatt attgctcgct tgccaaaggg ctggggtgga     960
ccaacgcacg atgcaagtaa caatcctatt gaaaactcat tccgtgcgca ccaagtgcca    1020
ttgcctcttg aacaacacga tcttgcaaca ttgcctgaat tcgaagactg gatgaactca    1080
tacaagcctg aagaattatt caatgctgat ggttctttga aggatgaatt gaaagctatc    1140
gctcctaagg gtgacaagcg tatgtcagct aaccctatta caaatggtgg tgctgatcgt    1200
tcagacttga agttgcctaa ctggagagaa ttcgctaacg atatcaatga tgatacacgt    1260
ggtaaggaat tcgctgatag caagcgcaat atggacatgg caacattgtc aaactacttg    1320
ggtgctgttt cacaattgaa cccaactcgt ttccgcttct tcggtcctga tgaaacaatg    1380
tcaaaccgtt tgtggggatt gttcaatgtt acaccacgtc aatggatgga agaaatcaag    1440
gaaccacaag atcaattgtt gagccctacg ggtcgcatta ttgattcaca attgtctgaa    1500
catcaagctg aaggttggct tgaaggatat actttgactg gtcgtgttgg aatcttcgca    1560
tcatacgagt cattccttgcg tgttgtcgat acaatggtta cgcaacactt caagtggttg    1620
cgtcacgctt cagaacaagc atggcgtaat gactatccat cattgaactt gattgcaact    1680
tcaactgctt ccaacaaga tcacaatgga tatactcacc aagatccagg tatgttgact    1740
cacttggctg aaaagaagtc taactttatt cgtgaatatt tgccagctga tggtaactca    1800
ttgttggctg ttcaagaacg tgctttctca gaacgtcata aggttaactt gttgattgct    1860
tctaagcaac cacgtcaaca atggtttaca gttgaagaag ctgaagtatt ggctaacgaa    1920
```

-continued

```
ggtttgaaga tcattgattg ggcttctact gcaccttcta gtgatgttga tattacattc    1980
gcatctgctg gtactgaacc aacaattgaa actttggctg ctttgtggtt gattaaccaa    2040
gcattcccag atgttaagtt ccgttatgtt aacgttgttg aattactacg tttgcaaaag    2100
aagtcagaac ctaacatgaa tgatgaacgt gaattatcag ccgaagaatt caacaagtat    2160
ttccaagctg ataccccagt tatcttcggt ttccatgctt atgaaaactt gattgaatca    2220
ttcttcttcg aacgtaagtt cacgggtgat gtatacgttc atggatatcg tgaagatggt    2280
gacatcacaa cgacatatga tatgcgtgta tattcacact tggatcgctt ccatcaagct    2340
aaggaagctg ctgaaatctt gtctgcaaat ggtaagattg atcaagctgc tgctgataca    2400
ttcatcgcta agatggatga tactttggca aagcatttcc aagttactcg taacgaaggt    2460
cgtgatatcg aagaattcac tgactggaca tggtcaccac ttaagtaatt taaaattatt    2520
ttatcaaaac caactattat ttttaatagt tggttttttt atggctaaat tgactacata    2580
ctaaacgaaa ccatgtaaaa gtgccacata gttttactta ataagttcct tttattttt     2640 gatttgcaat gcaaaattgt aagcgtaata tgaataataa aaaccccccaa ttagttagct   2700 aattgggggt tttgtaaatc accatatcag ccgctcatag tcttagacg                2749
```

<210> SEQ ID NO 2
<211> LENGTH: 813
<212> TYPE: PRT
<213> ORGANISM: Leuconostoc mesenteroides
<220> FEATURE:
<221> NAME/KEY: misc_feature
<222> LOCATION: (1)..(813)
<223> OTHER INFORMATION: Leuconostoc mesenteroides Phosphoketolase (PK) protein sequence

<400> SEQUENCE: 2

```
Met Ala Asp Phe Asp Ser Lys Glu Tyr Leu Glu Leu Val Asp Lys Trp
1               5                   10                  15

Trp Arg Ala Thr Asn Tyr Leu Ser Ala Gly Met Ile Phe Leu Lys Ser
            20                  25                  30

Asn Pro Leu Phe Ser Val Thr Asn Thr Pro Ile Lys Ala Glu Asp Val
        35                  40                  45

Lys Val Lys Pro Ile Gly His Trp Gly Thr Ile Ser Gly Gln Thr Phe
    50                  55                  60

Leu Tyr Ala His Ala Asn Arg Leu Ile Asn Lys Tyr Gly Leu Asn Met
65                  70                  75                  80

Phe Tyr Val Gly Gly Pro Gly His Gly Gly Gln Val Met Val Thr Asn
                85                  90                  95

Ala Tyr Leu Asp Gly Ala Tyr Thr Glu Asp Tyr Pro Glu Ile Thr Gln
            100                 105                 110

Asp Ile Glu Gly Met Ser His Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Ser Leu Ser His Ala Phe Gly Ala Val Leu
145                 150                 155                 160

Asp Asn Pro Asp Gln Val Ala Phe Ala Val Val Gly Asp Gly Glu Ala
                165                 170                 175

Glu Thr Gly Pro Ser Met Ala Ser Trp His Ser Ile Lys Phe Leu Asn
            180                 185                 190

Ala Lys Asn Asp Gly Ala Val Leu Pro Val Leu Asp Leu Asn Gly Phe
        195                 200                 205
```

-continued

Lys Ile Ser Asn Pro Thr Ile Phe Ser Arg Met Ser Asp Glu Glu Ile
    210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Thr Tyr His Gln Leu Ala Ala Asn Ile
                245                 250                 255

Leu Asp Gln Ala Ile Glu Asp Ile Gln Ala Ile Gln Asn Asp Ala Arg
            260                 265                 270

Glu Asn Gly Lys Tyr Gln Asp Gly Glu Ile Pro Ala Trp Pro Val Ile
        275                 280                 285

Ile Ala Arg Leu Pro Lys Gly Trp Gly Gly Pro Thr His Asp Ala Ser
    290                 295                 300

Asn Asn Pro Ile Glu Asn Ser Phe Arg Ala His Gln Val Pro Leu Pro
305                 310                 315                 320

Leu Glu Gln His Asp Leu Ala Thr Leu Pro Glu Phe Glu Asp Trp Met
                325                 330                 335

Asn Ser Tyr Lys Pro Glu Glu Leu Phe Asn Ala Asp Gly Ser Leu Lys
            340                 345                 350

Asp Glu Leu Lys Ala Ile Ala Pro Lys Gly Asp Lys Arg Met Ser Ala
        355                 360                 365

Asn Pro Ile Thr Asn Gly Gly Ala Asp Arg Ser Asp Leu Lys Leu Pro
    370                 375                 380

Asn Trp Arg Glu Phe Ala Asn Asp Ile Asn Asp Asp Thr Arg Gly Lys
385                 390                 395                 400

Glu Phe Ala Asp Ser Lys Arg Asn Met Asp Met Ala Thr Leu Ser Asn
                405                 410                 415

Tyr Leu Gly Ala Val Ser Gln Leu Asn Pro Thr Arg Phe Arg Phe Phe
            420                 425                 430

Gly Pro Asp Glu Thr Met Ser Asn Arg Leu Trp Gly Leu Phe Asn Val
        435                 440                 445

Thr Pro Arg Gln Trp Met Glu Glu Ile Lys Glu Pro Gln Asp Gln Leu
    450                 455                 460

Leu Ser Pro Thr Gly Arg Ile Ile Asp Ser Gln Leu Ser Glu His Gln
465                 470                 475                 480

Ala Glu Gly Trp Leu Glu Gly Tyr Thr Leu Thr Gly Arg Val Gly Ile
                485                 490                 495

Phe Ala Ser Tyr Glu Ser Phe Leu Arg Val Val Asp Thr Met Val Thr
            500                 505                 510

Gln His Phe Lys Trp Leu Arg His Ala Ser Glu Gln Ala Trp Arg Asn
        515                 520                 525

Asp Tyr Pro Ser Leu Asn Leu Ile Ala Thr Ser Thr Ala Phe Gln Gln
    530                 535                 540

Asp His Asn Gly Tyr Thr His Gln Asp Pro Gly Met Leu Thr His Leu
545                 550                 555                 560

Ala Glu Lys Lys Ser Asn Phe Ile Arg Glu Tyr Leu Pro Ala Asp Gly
                565                 570                 575

Asn Ser Leu Leu Ala Val Gln Glu Arg Ala Phe Ser Glu Arg His Lys
            580                 585                 590

Val Asn Leu Leu Ile Ala Ser Lys Gln Pro Arg Gln Gln Trp Phe Thr
        595                 600                 605

Val Glu Glu Ala Glu Val Leu Ala Asn Glu Gly Leu Lys Ile Ile Asp
    610                 615                 620

```
Trp Ala Ser Thr Ala Pro Ser Ser Asp Val Asp Ile Thr Phe Ala Ser
625                 630                 635                 640

Ala Gly Thr Glu Pro Thr Ile Glu Thr Leu Ala Ala Leu Trp Leu Ile
            645                 650                 655

Asn Gln Ala Phe Pro Asp Val Lys Phe Arg Tyr Val Asn Val Glu
        660                 665                 670

Leu Leu Arg Leu Gln Lys Lys Ser Glu Pro Asn Met Asn Asp Glu Arg
        675                 680                 685

Glu Leu Ser Ala Glu Glu Phe Asn Lys Tyr Phe Gln Ala Asp Thr Pro
        690                 695                 700

Val Ile Phe Gly Phe His Ala Tyr Glu Asn Leu Ile Glu Ser Phe Phe
705                 710                 715                 720

Phe Glu Arg Lys Phe Thr Gly Asp Val Tyr Val His Gly Tyr Arg Glu
            725                 730                 735

Asp Gly Asp Ile Thr Thr Thr Tyr Asp Met Arg Val Tyr Ser His Leu
            740                 745                 750

Asp Arg Phe His Gln Ala Lys Glu Ala Ala Glu Ile Leu Ser Ala Asn
        755                 760                 765

Gly Lys Ile Asp Gln Ala Ala Ala Asp Thr Phe Ile Ala Lys Met Asp
770                 775                 780

Asp Thr Leu Ala Lys His Phe Gln Val Thr Arg Asn Glu Gly Arg Asp
785                 790                 795                 800

Ile Glu Glu Phe Thr Asp Trp Thr Trp Ser Pro Leu Lys
                805                 810

<210> SEQ ID NO 3
<211> LENGTH: 1002
<212> TYPE: DNA
<213> ORGANISM: Clostridium kluyveri
<220> FEATURE:
<221> NAME/KEY: misc_feature
<222> LOCATION: (1)..(1002)
<223> OTHER INFORMATION: Clostridium kluyveri Phosphotransacetylase
      (PTA) gene sequence

<400> SEQUENCE: 3
atgaaattaa tggaaaatat ttttggttta gccaaagcag ataagaaaaa aattgttttg      60
gcagaaggag aagaagaaag gaacattaga gcttccgaag aaataataag ggatggtatt     120
gcagatataa ttttagtagg aagtgaaagt gtaataaaag agaatgcagc taaatttggg     180
gttaacttag ctggagtgga aatagtagat cctgaaactt caagtaaaac tgcaggctat     240
gccaatgctt tttatgaaat tagaaagaat aaaggagtta cactggaaaa agcagataaa     300
atagttagag atcctatata ttttgcaaca atgatggtga aacttggaga tgcagatggt     360
ttagtttcag gtgcaataca tacaacggga gatcttttga gaccaggact tcaaatagtg     420
aagacagttc aggtgcttca tgtggttttcc agtgtatttt taatgagtgt accagattgt     480
gaatatggag aagatggatt cttgttattt gctgattgtg ctgtaaatgt atgtcctact     540
gctgaagaat tatcttcaat tgcaataact acagcagaaa ctgcaaaaaa tttgtgtaaa     600
atagaaccaa gagttgccat gctttcattt tctactatgg aagtgctag tcatgaattg     660 gtagataaag ttacaaaagc aacaaaactt gctaagagaa ctagacctga tttggatata     720
gatggagaac ttcaattgga tgcttcccta gtaaaaaaag ttgcagactt aaaagctccg     780
ggcagtaaag tggcaggaaa agccaatgta cttatattcc ctgatataca agcaggaaat     840
ataggatata agttagttca aagatttgca aaagctgagg ctataggacc tatatgtcag     900
```

```
ggatttgcaa agcctataaa tgatttatca agaggctgca gcgttgatga tatagtaaag    960
gtagtggctg taactgcagt tcaagcacag gcacagggtt ag                        1002
```

<210> SEQ ID NO 4
<211> LENGTH: 333
<212> TYPE: PRT
<213> ORGANISM: Clostridium kluyveri
<220> FEATURE:
<221> NAME/KEY: misc_feature
<222> LOCATION: (1)..(333)
<223> OTHER INFORMATION: Clostridium kluyveri Phosphotransacetylase
      (PTA) protein sequence

<400> SEQUENCE: 4

```
Met Lys Leu Met Glu Asn Ile Phe Gly Leu Ala Lys Ala Asp Lys Lys
1               5                   10                  15

Lys Ile Val Leu Ala Glu Gly Glu Glu Arg Asn Ile Arg Ala Ser
            20                  25                  30

Glu Glu Ile Ile Arg Asp Gly Ile Ala Asp Ile Ile Leu Val Gly Ser
        35                  40                  45

Glu Ser Val Ile Lys Glu Asn Ala Ala Lys Phe Gly Val Asn Leu Ala
    50                  55                  60

Gly Val Glu Ile Val Asp Pro Glu Thr Ser Ser Lys Thr Ala Gly Tyr
65                  70                  75                  80

Ala Asn Ala Phe Tyr Glu Ile Arg Lys Asn Lys Gly Val Thr Leu Glu
                85                  90                  95

Lys Ala Asp Lys Ile Val Arg Asp Pro Ile Tyr Phe Ala Thr Met Met
            100                 105                 110

Val Lys Leu Gly Asp Ala Asp Gly Leu Val Ser Gly Ala Ile His Thr
        115                 120                 125

Thr Gly Asp Leu Leu Arg Pro Gly Leu Gln Ile Val Lys Thr Val Pro
    130                 135                 140

Gly Ala Ser Val Val Ser Ser Val Phe Leu Met Ser Val Pro Asp Cys
145                 150                 155                 160

Glu Tyr Gly Glu Asp Gly Phe Leu Leu Phe Ala Asp Cys Ala Val Asn
                165                 170                 175

Val Cys Pro Thr Ala Glu Glu Leu Ser Ser Ile Ala Ile Thr Thr Ala
            180                 185                 190

Glu Thr Ala Lys Asn Leu Cys Lys Ile Glu Pro Arg Val Ala Met Leu
        195                 200                 205

Ser Phe Ser Thr Met Gly Ser Ala Ser His Glu Leu Val Asp Lys Val
    210                 215                 220

Thr Lys Ala Thr Lys Leu Ala Lys Glu Ala Arg Pro Asp Leu Asp Ile
225                 230                 235                 240

Asp Gly Glu Leu Gln Leu Asp Ala Ser Leu Val Lys Lys Val Ala Asp
                245                 250                 255

Leu Lys Ala Pro Gly Ser Lys Val Ala Gly Lys Ala Asn Val Leu Ile
            260                 265                 270

Phe Pro Asp Ile Gln Ala Gly Asn Ile Gly Tyr Lys Leu Val Gln Arg
        275                 280                 285

Phe Ala Lys Ala Glu Ala Ile Gly Pro Ile Cys Gln Gly Phe Ala Lys
    290                 295                 300

Pro Ile Asn Asp Leu Ser Arg Gly Cys Ser Val Asp Asp Ile Val Lys
305                 310                 315                 320

Val Val Ala Val Thr Ala Val Gln Ala Gln Ala Gln Gly
                325                 330
```

<210> SEQ ID NO 5
<211> LENGTH: 753
<212> TYPE: DNA
<213> ORGANISM: S. cerevisiae
<220> FEATURE:
<221> NAME/KEY: misc_feature
<222> LOCATION: (1)..(753)
<223> OTHER INFORMATION: Nucleotide sequence of GPP1/RHR2 of S. cerevisiae

<400> SEQUENCE: 5

```
atgcctttga ccacaaaacc tttatctttg aaaatcaacg ccgctctatt cgatgttgac      60
ggtaccatca tcatctctca accagccatt gctgctttct ggagagattt cggtaaagac     120
aagccttact tcgatgccga acacgttatt cacatctctc acggttggag aacttacgat     180
gccattgcca agttcgctcc agactttgct gatgaagaat acgttaacaa gctagaaggt     240
gaaatcccag aaaagtacgg tgaacactcc atcgaagttc caggtgctgt caagttgtgt     300
aatgctttga cgccttgcc aaaggaaaaa tgggctgtcg ccacctctgg tacccgtgac     360
atggccaaga atggttcga cattttgaag atcaagagac cagaatactt catcaccgcc     420
aatgatgtca agcaaggtaa gcctcaccca gaaccatact taaagggtag aaacggtttg     480
ggtttcccaa ttaatgaaca agacccatcc aaatctaagg ttgttgtctt gaagacgca      540
ccagctggta ttgctgctgg taaggctgct ggctgtaaaa tcgttggtat tgctaccact     600
ttcgatttgg acttcttgaa ggaaaagggt tgtgacatca ttgtcaagaa ccacgaatct     660
atcagagtcg gtaatacaa cgctgaaacc gatgaagtcg aattgatctt tgatgactac     720
ttatacgcta aggatgactt gttgaaatgg taa                                   753
```

<210> SEQ ID NO 6
<211> LENGTH: 250
<212> TYPE: PRT
<213> ORGANISM: S. cerevisiae
<220> FEATURE:
<221> NAME/KEY: misc_feature
<222> LOCATION: (1)..(250)
<223> OTHER INFORMATION: Protein sequence of Gpp1/Rhr2 of S. cerevisiae

<400> SEQUENCE: 6

Met Pro Leu Thr Thr Lys Pro Leu Ser Leu Lys Ile Asn Ala Ala Leu
1               5                   10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile His Ile Ser His Gly Trp Arg Thr Tyr Asp Ala Ile Ala Lys
    50                  55                  60

Phe Ala Pro Asp Phe Ala Asp Glu Glu Tyr Val Asn Lys Leu Glu Gly
65                  70                  75                  80

Glu Ile Pro Glu Lys Tyr Gly Glu His Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Lys Lys Trp Phe Asp Ile
        115                 120                 125

Leu Lys Ile Lys Arg Pro Glu Tyr Phe Ile Thr Ala Asn Asp Val Lys
    130                 135                 140

| Gln | Gly | Lys | Pro | His | Pro | Glu | Pro | Tyr | Leu | Lys | Gly | Arg | Asn | Gly | Leu |
| 145 | | | | 150 | | | | | 155 | | | | | 160 | |

| Gly | Phe | Pro | Ile | Asn | Glu | Gln | Asp | Pro | Ser | Lys | Ser | Lys | Val | Val | Val |
| | | | 165 | | | | | 170 | | | | | 175 | | |

| Phe | Glu | Asp | Ala | Pro | Ala | Gly | Ile | Ala | Ala | Gly | Lys | Ala | Ala | Gly | Cys |
| | | | 180 | | | | | 185 | | | | | 190 | | |

| Lys | Ile | Val | Gly | Ile | Ala | Thr | Thr | Phe | Asp | Leu | Asp | Phe | Leu | Lys | Glu |
| | | 195 | | | | | 200 | | | | | 205 | | | |

| Lys | Gly | Cys | Asp | Ile | Ile | Val | Lys | Asn | His | Glu | Ser | Ile | Arg | Val | Gly |
| | 210 | | | | | 215 | | | | | 220 | | | | |

| Glu | Tyr | Asn | Ala | Glu | Thr | Asp | Glu | Val | Glu | Leu | Ile | Phe | Asp | Asp | Tyr |
| 225 | | | | | 230 | | | | | 235 | | | | | 240 |

| Leu | Tyr | Ala | Lys | Asp | Asp | Leu | Leu | Lys | Trp |
| | | | 245 | | | | | 250 | |

<210> SEQ ID NO 7
<211> LENGTH: 753
<212> TYPE: DNA
<213> ORGANISM: S. cerevisiae
<220> FEATURE:
<221> NAME/KEY: misc_feature
<222> LOCATION: (1)..(753)
<223> OTHER INFORMATION: Nucleotide sequence of GPP2/HOR2 of S.
      cerevisiae

<400> SEQUENCE: 7

```
atgggattga ctactaaacc tctatctttg aaagttaacg ccgctttgtt cgacgtcgac      60
ggtaccatta tcatctctca accagccatt gctgcattct ggagggattt cggtaaggac     120
aaaccttatt tcgatgctga acacgttatc caagtctcgc atggttggag aacgtttgat     180
gccattgcta agttcgctcc agactttgcc aatgaagagt atgttaacaa attagaagct     240
gaaattccgg tcaagtacgg tgaaaaatcc attgaagtcc aggtgcagt taagctgtgc      300
aacgctttga cgctctacc aaaagagaaa tgggctgtgg caacttccgg tacccgtgat     360
atggcacaaa atggttcga gcatctggga atcaggagac caaagtactt cattaccgct     420
aatgatgtca acagggtaa gcctcatcca gaaccatatc tgaagggcag gaatggctta     480
ggatatccga tcaatgagca agaccctccc aaatctaagg tagtagtatt tgaagacgct     540
ccagcaggta ttgccgccgg aaaagccgcc ggttgtaaga tcattggtat tgccactact     600
ttcgacttgg acttcctaaa ggaaaaaggc tgtgacatca ttgtcaaaaa ccacgaatcc     660
atcagagttg gcggctacaa tgccgaaaca gacgaagttg aattcatttt tgacgactac     720
ttatatgcta aggacgatct gttgaaatgg taa                                  753
```

<210> SEQ ID NO 8
<211> LENGTH: 250
<212> TYPE: PRT
<213> ORGANISM: S. cerevisiae
<220> FEATURE:
<221> NAME/KEY: misc_feature
<222> LOCATION: (1)..(250)
<223> OTHER INFORMATION: Protein sequence of Gpp2/Hor2 of S. cerevisiae

<400> SEQUENCE: 8

| Met | Gly | Leu | Thr | Thr | Lys | Pro | Leu | Ser | Leu | Lys | Val | Asn | Ala | Ala | Leu |
| 1 | | | | 5 | | | | | 10 | | | | | 15 | |

| Phe | Asp | Val | Asp | Gly | Thr | Ile | Ile | Ile | Ser | Gln | Pro | Ala | Ile | Ala | Ala |
| | | | 20 | | | | | 25 | | | | | 30 | | |

| Phe | Trp | Arg | Asp | Phe | Gly | Lys | Asp | Lys | Pro | Tyr | Phe | Asp | Ala | Glu | His |

```
                35                  40                  45
Val Ile Gln Val Ser His Gly Trp Arg Thr Phe Asp Ala Ile Ala Lys
 50                  55                  60

Phe Ala Pro Asp Phe Ala Asn Glu Glu Tyr Val Asn Lys Leu Glu Ala
 65                  70                  75                  80

Glu Ile Pro Val Lys Tyr Gly Glu Lys Ser Ile Glu Val Pro Gly Ala
                 85                  90                  95

Val Lys Leu Cys Asn Ala Leu Asn Ala Leu Pro Lys Glu Lys Trp Ala
                100                 105                 110

Val Ala Thr Ser Gly Thr Arg Asp Met Ala Gln Lys Trp Phe Glu His
                115                 120                 125

Leu Gly Ile Arg Arg Pro Lys Tyr Phe Ile Thr Ala Asn Asp Val Lys
                130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
                180                 185                 190

Lys Ile Ile Gly Ile Ala Thr Thr Phe Asp Leu Asp Phe Leu Lys Glu
                195                 200                 205

Lys Gly Cys Asp Ile Ile Val Lys Asn His Glu Ser Ile Arg Val Gly
                210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250

<210> SEQ ID NO 9
<211> LENGTH: 1380
<212> TYPE: DNA
<213> ORGANISM: Dickeya zeae
<220> FEATURE:
<221> NAME/KEY: misc_feature
<222> LOCATION: (1)..(1380)
<223> OTHER INFORMATION: Dickeya zeae eutE gene sequence

<400> SEQUENCE: 9
atggagcatt cagttatcga accgacagtg cccatgccgc tgccagccat gtttgacgcg        60
ccatctggaa tcttttctag cctggacgat gcagtccagg cggcaaccct ggcacaacaa       120
cagttgtcgt ctgtggagtt acgccagcaa gttattaaag caattagagt tgcaggcgaa       180
cgctatgcac aggttctggc ggaaatggcg gtggctgaaa caggtatggg tcgggtagtg       240
gataaataca ttaaaaatgt tcacaggct cgccatacac ccggcattga atgtctgagc        300
gcggaagttc tgacaggcga caatggcctg acactgattg aaaatgcccc ttggggagtg       360
gtggcttccg tgacgccaag cacgaaccca gccgccacag tcatcaataa tgcaatttcc       420
atgattgcgg cagggaattc agtcgttttt gcaccgcacc catccgccaa aaatgtgtcc       480
ttacgcacaa tatcgcttct taacaaagca attgtggcga caggtgggcc agaaaatctg       540
ctggtatccg tcgcaaatcc caacatcgaa acagctcaac gcctgttccg ttatccaggt       600
attggattac tcgtcgtaac aggtggtgag gcggtggtgg aagcggcgcg caaacacact       660
gataaacgtt taattgccgc aggcgccgga accccccag tagtcgttga cgaaacagcg        720
gatataccga aagccgctcg cgcaatagta aagggcgctt cgtttgacaa caatattatt       780
```

```
tgtgccgacg agaaagtatt aatcgtggtt gatcgcgtag ccgacgcctt attagccgaa      840
atgcaacgca acaatgctgt tttactgacg cctgaacaga cagaacgact tctgcccgct      900
ttgctgagcg atatagatga gcaggggaag ggacgcgtga accgcgatta tgtggggagg      960
gatgccgcta aactagcggc ggccattggt ttagaagtgt cagaacacac aagattatta     1020
cttgctgaaa cagatgctga tcatcctttt gcagtaaccg aattaatgat gcccgtattg     1080
cctgttatcc gtgtaaaaaa cgttgatgac gccattgccc tcgctgtaaa acttgagagt     1140
ggttgtcgtc acactgcagc aatgcattcg acaaacatta ggaacctgaa tcggatggca     1200
aatgctataa atacatcaat ttttgttaaa aatggtccgt gtatcgctgg gctgggcctg     1260
ggtggcgagg gctggacgtc gatgactata tctacaccca caggggaagg agttacctca     1320
gcacgcacct tcgtacgttt acgtagatgt gtattggttg acatgttcag aatcgcgtaa     1380
```

<210> SEQ ID NO 10
<211> LENGTH: 459
<212> TYPE: PRT
<213> ORGANISM: Dickeya zeae
<220> FEATURE:
<221> NAME/KEY: misc_feature
<222> LOCATION: (1)..(459)
<223> OTHER INFORMATION: Dickeya zeae eutE protein sequence

<400> SEQUENCE: 10

```
Met Glu His Ser Val Ile Glu Pro Thr Val Pro Met Pro Leu Pro Ala
1               5                   10                  15

Met Phe Asp Ala Pro Ser Gly Ile Phe Ser Ser Leu Asp Asp Ala Val
            20                  25                  30

Gln Ala Ala Thr Leu Ala Gln Gln Gln Leu Ser Ser Val Glu Leu Arg
        35                  40                  45

Gln Gln Val Ile Lys Ala Ile Arg Val Ala Gly Glu Arg Tyr Ala Gln
    50                  55                  60

Val Leu Ala Glu Met Ala Val Ala Glu Thr Gly Met Gly Arg Val Val
65                  70                  75                  80

Asp Lys Tyr Ile Lys Asn Val Ser Gln Ala Arg His Thr Pro Gly Ile
                85                  90                  95

Glu Cys Leu Ser Ala Glu Val Leu Thr Gly Asp Asn Gly Leu Thr Leu
            100                 105                 110

Ile Glu Asn Ala Pro Trp Gly Val Val Ala Ser Val Thr Pro Ser Thr
        115                 120                 125

Asn Pro Ala Ala Thr Val Ile Asn Asn Ala Ile Ser Met Ile Ala Ala
    130                 135                 140

Gly Asn Ser Val Val Phe Ala Pro His Pro Ser Ala Lys Asn Val Ser
145                 150                 155                 160

Leu Arg Thr Ile Ser Leu Leu Asn Lys Ala Ile Val Ala Thr Gly Gly
                165                 170                 175

Pro Glu Asn Leu Leu Val Ser Val Ala Asn Pro Asn Ile Glu Thr Ala
            180                 185                 190

Gln Arg Leu Phe Arg Tyr Pro Gly Ile Gly Leu Leu Val Val Thr Gly
        195                 200                 205

Gly Glu Ala Val Val Glu Ala Ala Arg Lys His Thr Asp Lys Arg Leu
    210                 215                 220

Ile Ala Ala Gly Ala Gly Asn Pro Pro Val Val Val Asp Glu Thr Ala
225                 230                 235                 240

Asp Ile Pro Lys Ala Ala Arg Ala Ile Val Lys Gly Ala Ser Phe Asp
                245                 250                 255
```

Asn Asn Ile Ile Cys Ala Asp Glu Lys Val Leu Ile Val Val Asp Arg
              260                 265                 270

Val Ala Asp Ala Leu Leu Ala Glu Met Gln Arg Asn Asn Ala Val Leu
          275                 280                 285

Leu Thr Pro Glu Gln Thr Glu Arg Leu Leu Pro Ala Leu Leu Ser Asp
290                 295                 300

Ile Asp Glu Gln Gly Lys Gly Arg Val Asn Arg Asp Tyr Val Gly Arg
305                 310                 315                 320

Asp Ala Ala Lys Leu Ala Ala Ile Gly Leu Glu Val Ser Glu His
              325                 330                 335

Thr Arg Leu Leu Leu Ala Glu Thr Asp Ala Asp His Pro Phe Ala Val
              340                 345                 350

Thr Glu Leu Met Met Pro Val Leu Pro Val Ile Arg Val Lys Asn Val
              355                 360                 365

Asp Asp Ala Ile Ala Leu Ala Val Lys Leu Glu Ser Gly Cys Arg His
              370                 375                 380

Thr Ala Ala Met His Ser Thr Asn Ile Arg Asn Leu Asn Arg Met Ala
385                 390                 395                 400

Asn Ala Ile Asn Thr Ser Ile Phe Val Lys Asn Gly Pro Cys Ile Ala
              405                 410                 415

Gly Leu Gly Leu Gly Gly Glu Gly Trp Thr Ser Met Thr Ile Ser Thr
              420                 425                 430

Pro Thr Gly Glu Gly Val Thr Ser Ala Arg Thr Phe Val Arg Leu Arg
              435                 440                 445

Arg Cys Val Leu Val Asp Met Phe Arg Ile Ala
              450                 455

<210> SEQ ID NO 11
<211> LENGTH: 1798
<212> TYPE: DNA
<213> ORGANISM: Saccharomyces cerevisiae
<220> FEATURE:
<221> NAME/KEY: misc_feature
<222> LOCATION: (1)..(1798)
<223> OTHER INFORMATION: Saccharomyces cerevisiae ALD4 nucleotide
      sequence

<400> SEQUENCE: 11
gcacccaggg acacacagca gcgaagtatt ttcagaatgt tcagtagatc tacgctctgc        60
ttaaagacgt ctgcatcctc cattgggaga cttcaattga gatatttctc acaccttcct       120
atgacagtgc ctatcaagct gcccaatggg ttggaatatg agcaaccaac ggggttgttc       180
atcaacaaca gtttgttcc ttctaaacag aacaagacct tcgaagtcat taacccttcc       240
acggaagaag aaatatgtca tatttatgaa ggtagagagg acgatgtgga agaggccgtg       300
caggccgccg accgtgcctt ctctaatggg tcttggaacg gtatcgaccc tattgacagg       360
ggtaaggctt tgtacaggtt agccgaatta attgaacagg acaaggatgt cattgcttcc       420
atcgagactt tggataacgg taaagctatc tcttcctcga gaggagatgt tgatttagtc       480
atcaactatt tgaaatcttc tgctggcttt gctgataaaa ttgatggtag aatgattgat       540
actggtagaa cccattttc ttacactaag agacagcctt gggtgtttg tgggcagatt       600 attccttgga atttcccact gttgatgtgg gcctggaaga ttgcccctgc tttggtcacc       660
ggtaacaccg tcgtgttgaa gactgccgaa tccaccccat gtccgctt gtatgtgtct       720 aaatacatcc cacaggcggg tattccacct ggtgtgatca acattgtatc cgggtttggt       780

```
aagattgtgg gtgaggccat tacaaaccat ccaaaaatca aaaaggttgc cttcacaggg    840
tccacggcta cgggtagaca catttaccag tccgcagccg caggcttgaa aaaagtgact    900
ttggagctgg gtggtaaatc accaaacatt gtcttcgcgg acgccgagtt gaaaaaagcc    960
gtgcaaaaca ttatccttgg tatctactac aattctggtg aggtctgttg tgcgggttca    1020
agggtgtatg ttgaagaatc tatttacgac aaattcattg aagagttcaa agccgcttct    1080
gaatccatca aggtgggcga cccattcgat gaatctactt tccaaggtgc acaaacctct    1140
caaatgcaac taaacaaaat cttgaaatac gttgacattg gtaagaatga aggtgctact    1200
ttgattaccg gtggtgaaag attaggtagc aagggttact tcattaagcc aactgtcttt    1260
ggtgacgtta aggaagacat gagaattgtc aaagaggaaa tctttggccc tgttgtcact    1320
gtaaccaaat tcaaatctgc cgacgaagtc attaacatgg cgaacgattc tgaatacggg    1380
ttggctgctg gtattcacac ctctaatatt aataccgcct taaaagtggc tgatagagtt    1440
aatgcgggta cggtctggat aaacacttat aacgatttcc accacgcagt tccttcggt    1500 gggttcaatg catctggttt gggcagggaa atgtctgttg atgctttaca aaactacttg    1560
caagttaaag cggtccgtgc caaattggac gagtaaggtc atcaataagc ctggtgtcca    1620
atcgatgctt acatacataa aattaaatat tctgtctctg ttatatttcc acatgtcatc    1680
atttcaaata tatgtacttt aaagaaaata aataaaaaa taaaattttt ttctcccgat    1740
aatcaatttt cttaattaat taattgcgtt acgaaacgcg atcgccgacg ccgccgat    1798
```

<210> SEQ ID NO 12
<211> LENGTH: 519
<212> TYPE: PRT
<213> ORGANISM: Saccharomyces cerevisiae
<220> FEATURE:
<221> NAME/KEY: misc_feature
<222> LOCATION: (1)..(519)
<223> OTHER INFORMATION: Saccharomyces cerevisiae ALD4 protein sequence

<400> SEQUENCE: 12

```
Met Phe Ser Arg Ser Thr Leu Cys Leu Lys Thr Ser Ala Ser Ser Ile
1               5                   10                  15

Gly Arg Leu Gln Leu Arg Tyr Phe Ser His Leu Pro Met Thr Val Pro
            20                  25                  30

Ile Lys Leu Pro Asn Gly Leu Glu Tyr Glu Gln Pro Thr Gly Leu Phe
        35                  40                  45

Ile Asn Asn Lys Phe Val Pro Ser Lys Gln Asn Lys Thr Phe Glu Val
    50                  55                  60

Ile Asn Pro Ser Thr Glu Glu Ile Cys His Ile Tyr Glu Gly Arg
65                  70                  75                  80

Glu Asp Asp Val Glu Glu Ala Val Gln Ala Ala Asp Arg Ala Phe Ser
                85                  90                  95

Asn Gly Ser Trp Asn Gly Ile Asp Pro Ile Asp Arg Gly Lys Ala Leu
            100                 105                 110

Tyr Arg Leu Ala Glu Leu Ile Glu Gln Asp Lys Asp Val Ile Ala Ser
        115                 120                 125

Ile Glu Thr Leu Asp Asn Gly Lys Ala Ile Ser Ser Ser Arg Gly Asp
    130                 135                 140

Val Asp Leu Val Ile Asn Tyr Leu Lys Ser Ser Ala Gly Phe Ala Asp
145                 150                 155                 160

Lys Ile Asp Gly Arg Met Ile Asp Thr Gly Arg Thr His Phe Ser Tyr
                165                 170                 175
```

```
Thr Lys Arg Gln Pro Leu Gly Val Cys Gly Gln Ile Ile Pro Trp Asn
            180                 185                 190

Phe Pro Leu Leu Met Trp Ala Trp Lys Ile Ala Pro Ala Leu Val Thr
        195                 200                 205

Gly Asn Thr Val Val Leu Lys Thr Ala Glu Ser Thr Pro Leu Ser Ala
210                 215                 220

Leu Tyr Val Ser Lys Tyr Ile Pro Gln Ala Gly Ile Pro Pro Gly Val
225                 230                 235                 240

Ile Asn Ile Val Ser Gly Phe Gly Lys Ile Val Gly Glu Ala Ile Thr
                245                 250                 255

Asn His Pro Lys Ile Lys Lys Val Ala Phe Thr Gly Ser Thr Ala Thr
            260                 265                 270

Gly Arg His Ile Tyr Gln Ser Ala Ala Ala Gly Leu Lys Lys Val Thr
        275                 280                 285

Leu Glu Leu Gly Gly Lys Ser Pro Asn Ile Val Phe Ala Asp Ala Glu
290                 295                 300

Leu Lys Lys Ala Val Gln Asn Ile Ile Leu Gly Ile Tyr Tyr Asn Ser
305                 310                 315                 320

Gly Glu Val Cys Cys Ala Gly Ser Arg Val Tyr Val Glu Ser Ile
                325                 330                 335

Tyr Asp Lys Phe Ile Glu Glu Phe Lys Ala Ala Ser Glu Ser Ile Lys
            340                 345                 350

Val Gly Asp Pro Phe Asp Glu Ser Thr Phe Gln Gly Ala Gln Thr Ser
        355                 360                 365

Gln Met Gln Leu Asn Lys Ile Leu Lys Tyr Val Asp Ile Gly Lys Asn
370                 375                 380

Glu Gly Ala Thr Leu Ile Thr Gly Gly Glu Arg Leu Gly Ser Lys Gly
385                 390                 395                 400

Tyr Phe Ile Lys Pro Thr Val Phe Gly Asp Val Lys Glu Asp Met Arg
            405                 410                 415

Ile Val Lys Glu Glu Ile Phe Gly Pro Val Val Thr Val Thr Lys Phe
        420                 425                 430

Lys Ser Ala Asp Glu Val Ile Asn Met Ala Asn Asp Ser Glu Tyr Gly
435                 440                 445

Leu Ala Ala Gly Ile His Thr Ser Asn Ile Asn Thr Ala Leu Lys Val
450                 455                 460

Ala Asp Arg Val Asn Ala Gly Thr Val Trp Ile Asn Thr Tyr Asn Asp
465                 470                 475                 480

Phe His His Ala Val Pro Phe Gly Gly Phe Asn Ala Ser Gly Leu Gly
            485                 490                 495

Arg Glu Met Ser Val Asp Ala Leu Gln Asn Tyr Leu Gln Val Lys Ala
        500                 505                 510

Val Arg Ala Lys Leu Asp Glu
        515

<210> SEQ ID NO 13
<211> LENGTH: 2744
<212> TYPE: DNA
<213> ORGANISM: Saccharomyces cerevisiae
<220> FEATURE:
<221> NAME/KEY: misc_feature
<222> LOCATION: (1)..(2744)
<223> OTHER INFORMATION: Saccharomyces cerevisiae cytosolic aldehyde
      dehydrogenase 6 (ALD6) nucleotide sequence

<400> SEQUENCE: 13
```

-continued

```
catatggcgt atccaagccg aaacccttg cctcatcccc acggaataag gcagccgaca      60
aaagaaaaac gaccgaaaag gaaccagaaa gaaaaaagag ggtgggcgcg ccgcggacgt     120
gtaaaaagat atgcatccag cttctatatc gctttaactt taccgttttg ggcatcggga    180
acgtatgtaa cattgatctc ctcttgggaa cggtgagtgc aacagatgcg atatagcacc    240
gaccatgtgg gcaaattcgt aataaattcg ggtgagggg gattcaagac aagcaacctt     300
gttagtcagc tcaaacagcg atttaacggt tgagtaacac atcaaaacac cgttcgaggt    360
caagcctggc gtgtttaaca agttcttgat atcatatata aatgtaataa gaagtttggt    420
aatattcaat tcgaagtgtt cagtctttta cttctcttgt tttatagaag aaaaaacatc    480
aagaaacatc tttaacatac acaaacacat actatcagaa tacaatgact aagctacact    540
ttgacactgc tgaaccagtc aagatcacac ttccaaatgg tttgacatac gagcaaccaa    600
ccggtctatt cattaacaac aagtttatga agctcaaga cggtaagacc tatcccgtcg     660
aagatccttc cactgaaaac accgtttgtg aggtctcttc tgccaccact gaagatgttg    720
aatatgctat cgaatgtgcc gaccgtgctt ccacgacac tgaatgggct acccaagacc     780
caagagaaag aggccgtcta ctaagtaagt tggctgacga attggaaagc caaattgact    840
tggtttcttc cattgaagct ttggacaatg gtaaaacttt ggccttaag gcccgtgggg     900
atgttaccat tgcaatcaac tgtctaagag atgctgctgc ctatgccgac aaagtcaacg    960
gtagaacaat caacaccggt gacggctaca tgaacttcac caccttagag ccaatcggtg   1020
tctgtggtca aattattcca tggaactttc caataatgat gttggcttgg aagatcgccc   1080
cagcattggc catgggtaac gtctgtatct gaaacccgc tgctgtcaca cctttaaatg    1140
ccctatactt tgcttcttta tgtaagaagg ttggtattcc agctggtgtc gtcaacatcg   1200
ttccaggtcc tggtagaact gttggtgctg ctttgaccaa cgacccaaga atcagaaagc   1260
tggcttttac cggttctaca gaagtcggta agagtgttgc tgtcgactct tctgaatcta   1320
acttgaagaa aatcactttg gaactaggtg gtaagtccgc ccatttggtc tttgacgatg   1380
ctaacattaa gaagactta ccaaatctag taaacggtat tttcaagaac gctggtcaaa    1440
tttgttcctc tggttctaga atttacgttc aagaaggtat ttacgacgaa ctattggctg   1500
ctttcaaggc ttacttggaa accgaaatca agttggtaa tccatttgac aaggctaact    1560
tccaaggtgc tatcactaac cgtcaacaat tcgacacaat tatgaactac atcgatatcg   1620
gtaagaaaga aggcgccaag atcttaactg gtggcgaaaa agttggtgac aagggttact   1680
tcatcagacc aaccgttttc tacgatgtta atgaagacat gagaattgtt aaggaagaaa   1740
tttttggacc agttgtcact gtcgcaaagt tcaagacttt agaagaaggt gtcgaaatgg   1800
ctaacagctc tgaattcggt ctaggttctg gtatcgaaac agaatctttg agcacaggtt   1860
tgaaggtggc caagatgttg aaggccggta ccgtctggat caacacatac aacgattttg   1920
actccagagt tccattcggt ggtgttaagc aatctggtta cggtagagaa atgggtgaag   1980
aagtctacca tgcatacact gaagtaaaag ctgtcagaat aagttgtaa tgtaccaacc    2040
tgcatttctt tccgtcatat acacaaaata ctttcatata aacttacttg gtcttacgtc   2100
ataaataaat atgtatacat ataaattaaa aaatttggtt ttatatttt acaaaaagaa    2160
tcgtttactt catttctccc ttttaagcga tacaatccat gaaaaagag aaaaagagag    2220
aacaggcttg tgccttcttt aaaacatccc acacaaaatc atattgaatt gaattttaca   2280
tcttaagcta gtgtacaaca actgctatat ccaagaaaa ctaacgtgga ccgctttag     2340
agttgagaaa aaggtttgaa aaaaatagca atacaaagac ttgtttcata tataaaatac   2400
```

-continued

```
agggagcaca ttgagctaat ataacataaa cactgcgaac caattccaat caaaaggtac    2460
acatgagagc attcccccga gtactgccat ttcgccatca gagatcatat aataacatcc    2520
ttcttcgaac agtaaggctt tttggttcat cactttcttc ttttgatttc tctaggcaaa    2580
tgcctaaggt ggaccctgac aataccgctg caatgctact acagaaaaac ttgatccaaa    2640
gaaacaacat gctctatggg tatggatcag ggacaatacg atgtactttg ctagactcaa    2700
ctggacgagc caaatcacca ttagtagaga taaaacgtga ggat                    2744
```

<210> SEQ ID NO 14
<211> LENGTH: 500
<212> TYPE: PRT
<213> ORGANISM: Saccharomyces cerevisiae
<220> FEATURE:
<221> NAME/KEY: misc_feature
<222> LOCATION: (1)..(500)
<223> OTHER INFORMATION: Saccharomyces cerevisiae cytosolic aldehyde
       dehydrogenase 6 (ALD6) protein sequence

<400> SEQUENCE: 14

```
Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285
```

```
Lys Thr Leu Pro Asn Leu Val Asn Gly Ile Phe Lys Asn Ala Gly Gln
        290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500

<210> SEQ ID NO 15
<211> LENGTH: 2728
<212> TYPE: DNA
<213> ORGANISM: Saccharomyces cerevisiae
<220> FEATURE:
<221> NAME/KEY: misc_feature
<222> LOCATION: (1)..(2728)
<223> OTHER INFORMATION: Saccharomyces cerevisiae ACS1 nucleotide
      sequence

<400> SEQUENCE: 15
acctcccgcg acctccaaaa tcgaactacc ttcacaatgt cgccctctgc cgtacaatca      60
tcaaaactag aagaacagtc aagtgaaatt gacaagttga agcaaaaat gtcccagtct     120 gcctccactg cgcagcagaa gaaggaacat gagtatgaac atttgacctc ggtcaagatc     180
gtgccacaac ggcccatctc agatagactg cagcccgcaa ttgctaccca ctattctcca     240
cacttggacg ggttgcagga ctatcagcgc ttgcacaagg agtctattga agaccctgct     300
aagttcttcg gttctaaagc tacccaattt ttaaactggt ctaagccatt cgataaggtg     360
ttcatcccag actctaaaac gggtaggccc tccttccaga acaatgcatg gttcctcaac     420
ggccaattaa acgcctgtta caactgtgtt gacagacatg ccttgaagac ccctaacaag     480
aaagccatta ttttcgaagg tgacgagcct ggccaaggct attccattac ctacaaggaa     540
ctacttgaag aagtttgtca agtggcacaa gtgctgactt actctatggg cgttcgcaag     600
ggcgatactt tgccgtgta catgcctatg gtccagaag caatcataac cttgttggcc     660
atttcccgta tcggcgccat tcactccgta gtctttgccg ggtttctctc caactccttg     720
```

```
agagatcgta tcaacgatgg ggactctaaa gttgtcatca ctacagatga atccaacaga    780
ggtggtaaag tcattgagac taaaagaatt gttgatgacg cgctaagaga gaccccaggc    840
gtgagacacg tcttggttta tagaaagacc aacaatccat ctgttgcttt ccatgccccc    900
agagatttag attgggcaac agaaaagaag aaatacaaga cctactatcc atgcacaccc    960
gttgattctg aggatccatt attcttgttg tatacgtctg gttctactgg tgcccccaag   1020
ggtgttcaac attctaccgc aggttacttg ctgggagctt tgttgaccat cgctacact    1080 tttgacactc accaagaaga cgttttcttc acagctggag acattggctg gattacaggc   1140
cacacttatg tggtttatgg tcccttacta tatggttgtg ccactttggt ctttgaaggg   1200
actcctgcgt acccaaatta ctcccgttat gggatatta ttgatgaaca caaagtcacc    1260 caatttatg ttgccccaac tgctttgcgt ttgttgaaaa gagctggtga ttcctacatc    1320
gaaaatcatt ccttaaaatc tttgcgttgc ttgggttcgg tcggtgaacc aattgctgct   1380
gaagtttggg agtggtactc tgaaaaaata ggtaaaaatg aaatccccat tgtagacacc   1440
tactggcaaa cagaatctgg ttcgcatctg gtcaccccgc tggctggtgg tgtcacacca   1500
atgaaaccgg ttctgcctc attccccttc ttcggtattg atgcagttgt tcttgaccct    1560
aacactggtg aagaacttaa taccagccac gcagagggtg tccttgccgt caaagctgca   1620
tggccatcat ttgcaagaac tatttggaaa aatcatgata ggtatctaga cacttatttg   1680
aacccttacc ctggctacta tttcactggt gatggtgctg caaaggataa ggatggttat   1740
atctggattt tgggtcgtgt agacgatgtg gtgaacgtct ctggtcaccg tctgtctacc   1800
gctgaaattg aggctgctat tatcgaagat ccaattgtgg ccgagtgtgc tgttgtcgga   1860
ttcaacgatg acttgactgg tcaagcagtt gctgcatttg tggtgttgaa aaacaaatct   1920
aattggtcca ccgcaacaga tgatgaatta caagatatca agaagcattt ggtctttact   1980
gttagaaaag acatcgggcc atttgccgca ccaaaattga tcattttagt ggatgacttg   2040
cccaagacaa gatctggcaa aattatgaga cgtatttaa gaaaaatcct agcaggagaa    2100
agtgaccaac taggcgacgt ttctacattg tcaaaccctg gcattgttag acatctaatt   2160
gattcggtca agttgtaatg atgatttctt tccttttat attgacgact ttttttttt     2220 cgtgtgtttt tgttctctta taaccgagct gcttacttat tattatttca ccttctcttt   2280
ttatttatac ttataattat ttattcttta catactgtta caagaaactc ttttctacat   2340
taattgcata agtgtcaat cagcacatcc tctatatcgc tatcaacaac aaatttgaca    2400
aacctgccta tcttcagg aacaactgcc gcatcgctac caccactact tgtgaagtcc     2460
ctggagttta atatgcactg aaatttacct agccgtttta cacaagacca taatccatcc   2520
atgctatcgc agtatatgat tttgtgttcg tttttcgtct tgcgaaaggc atcctcaatg   2580
gcttgtttca ttgatccatc agtgtggctc gtaggtacca gcaaaaccac ttcatcagcg   2640
gcgtactcct cccactttat gggcagtcct tgtatcgact tgctcattat aatacatttg   2700
ctctatcccc gcgtgcttgg ccggccgt                                      2728
```

<210> SEQ ID NO 16
<211> LENGTH: 713
<212> TYPE: PRT
<213> ORGANISM: Saccharomyces cerevisiae
<220> FEATURE:
<221> NAME/KEY: misc_feature
<222> LOCATION: (1)..(713)
<223> OTHER INFORMATION: Saccharomyces cerevisiae ACS1 protein sequence

```
<400> SEQUENCE: 16

Met Ser Pro Ser Ala Val Gln Ser Ser Lys Leu Glu Glu Gln Ser Ser
1               5                   10                  15

Glu Ile Asp Lys Leu Lys Ala Lys Met Ser Gln Ser Ala Ser Thr Ala
            20                  25                  30

Gln Gln Lys Lys Glu His Glu Tyr Glu His Leu Thr Ser Val Lys Ile
        35                  40                  45

Val Pro Gln Arg Pro Ile Ser Asp Arg Leu Gln Pro Ala Ile Ala Thr
    50                  55                  60

His Tyr Ser Pro His Leu Asp Gly Leu Gln Asp Tyr Gln Arg Leu His
65                  70                  75                  80

Lys Glu Ser Ile Glu Asp Pro Ala Lys Phe Gly Ser Lys Ala Thr
                85                  90                  95

Gln Phe Leu Asn Trp Ser Lys Pro Phe Asp Lys Val Phe Ile Pro Asp
            100                 105                 110

Ser Lys Thr Gly Arg Pro Ser Phe Gln Asn Asn Ala Trp Phe Leu Asn
        115                 120                 125

Gly Gln Leu Asn Ala Cys Tyr Asn Cys Val Asp Arg His Ala Leu Lys
    130                 135                 140

Thr Pro Asn Lys Lys Ala Ile Ile Phe Glu Gly Asp Glu Pro Gly Gln
145                 150                 155                 160

Gly Tyr Ser Ile Thr Tyr Lys Glu Leu Leu Glu Glu Val Cys Gln Val
                165                 170                 175

Ala Gln Val Leu Thr Tyr Ser Met Gly Val Arg Lys Gly Asp Thr Val
            180                 185                 190

Ala Val Tyr Met Pro Met Val Pro Glu Ala Ile Ile Thr Leu Leu Ala
        195                 200                 205

Ile Ser Arg Ile Gly Ala Ile His Ser Val Val Phe Ala Gly Phe Ser
    210                 215                 220

Ser Asn Ser Leu Arg Asp Arg Ile Asn Asp Gly Asp Ser Lys Val Val
225                 230                 235                 240

Ile Thr Thr Asp Glu Ser Asn Arg Gly Gly Lys Val Ile Glu Thr Lys
                245                 250                 255

Arg Ile Val Asp Asp Ala Leu Arg Glu Thr Pro Gly Val Arg His Val
            260                 265                 270

Leu Val Tyr Arg Lys Thr Asn Asn Pro Ser Val Ala Phe His Ala Pro
        275                 280                 285

Arg Asp Leu Asp Trp Ala Thr Glu Lys Lys Tyr Lys Thr Tyr Tyr
    290                 295                 300

Pro Cys Thr Pro Val Asp Ser Glu Asp Pro Leu Phe Leu Leu Tyr Thr
305                 310                 315                 320

Ser Gly Ser Thr Gly Ala Pro Lys Gly Val Gln His Ser Thr Ala Gly
                325                 330                 335

Tyr Leu Leu Gly Ala Leu Leu Thr Met Arg Tyr Thr Phe Asp Thr His
            340                 345                 350

Gln Glu Asp Val Phe Phe Thr Ala Gly Asp Ile Gly Trp Ile Thr Gly
        355                 360                 365

His Thr Tyr Val Val Tyr Gly Pro Leu Leu Tyr Gly Cys Ala Thr Leu
    370                 375                 380

Val Phe Glu Gly Thr Pro Ala Tyr Pro Asn Tyr Ser Arg Tyr Trp Asp
385                 390                 395                 400

Ile Ile Asp Glu His Lys Val Thr Gln Phe Tyr Val Ala Pro Thr Ala
                405                 410                 415
```

| Leu | Arg | Leu | Leu | Lys | Arg | Ala | Gly | Asp | Ser | Tyr | Ile | Glu | Asn | His | Ser |
|---|---|---|---|---|---|---|---|---|---|---|---|---|---|---|---|
| | | | 420 | | | | 425 | | | | | 430 | | | |

| Leu | Lys | Ser | Leu | Arg | Cys | Leu | Gly | Ser | Val | Gly | Glu | Pro | Ile | Ala | Ala |
|---|---|---|---|---|---|---|---|---|---|---|---|---|---|---|---|
| | | 435 | | | | | 440 | | | | | 445 | | | |

| Glu | Val | Trp | Glu | Trp | Tyr | Ser | Glu | Lys | Ile | Gly | Lys | Asn | Glu | Ile | Pro |
|---|---|---|---|---|---|---|---|---|---|---|---|---|---|---|---|
| | 450 | | | | | 455 | | | | | 460 | | | | |

| Ile | Val | Asp | Thr | Tyr | Trp | Gln | Thr | Glu | Ser | Gly | Ser | His | Leu | Val | Thr |
|---|---|---|---|---|---|---|---|---|---|---|---|---|---|---|---|
| 465 | | | | | 470 | | | | | 475 | | | | | 480 |

| Pro | Leu | Ala | Gly | Gly | Val | Thr | Pro | Met | Lys | Pro | Gly | Ser | Ala | Ser | Phe |
|---|---|---|---|---|---|---|---|---|---|---|---|---|---|---|---|
| | | | | 485 | | | | | 490 | | | | | 495 | |

| Pro | Phe | Phe | Gly | Ile | Asp | Ala | Val | Val | Leu | Asp | Pro | Asn | Thr | Gly | Glu |
|---|---|---|---|---|---|---|---|---|---|---|---|---|---|---|---|
| | | | | 500 | | | | | 505 | | | | | 510 | |

| Glu | Leu | Asn | Thr | Ser | His | Ala | Glu | Gly | Val | Leu | Ala | Val | Lys | Ala | Ala |
|---|---|---|---|---|---|---|---|---|---|---|---|---|---|---|---|
| | | | 515 | | | | | 520 | | | | | 525 | | |

| Trp | Pro | Ser | Phe | Ala | Arg | Thr | Ile | Trp | Lys | Asn | His | Asp | Arg | Tyr | Leu |
|---|---|---|---|---|---|---|---|---|---|---|---|---|---|---|---|
| | 530 | | | | | 535 | | | | | 540 | | | | |

| Asp | Thr | Tyr | Leu | Asn | Pro | Tyr | Pro | Gly | Tyr | Tyr | Phe | Thr | Gly | Asp | Gly |
|---|---|---|---|---|---|---|---|---|---|---|---|---|---|---|---|
| 545 | | | | | 550 | | | | | 555 | | | | | 560 |

| Ala | Ala | Lys | Asp | Lys | Asp | Gly | Tyr | Ile | Trp | Ile | Leu | Gly | Arg | Val | Asp |
|---|---|---|---|---|---|---|---|---|---|---|---|---|---|---|---|
| | | | | 565 | | | | | 570 | | | | | 575 | |

| Asp | Val | Val | Asn | Val | Ser | Gly | His | Arg | Leu | Ser | Thr | Ala | Glu | Ile | Glu |
|---|---|---|---|---|---|---|---|---|---|---|---|---|---|---|---|
| | | | 580 | | | | | 585 | | | | | 590 | | |

| Ala | Ala | Ile | Ile | Glu | Asp | Pro | Ile | Val | Ala | Glu | Cys | Ala | Val | Val | Gly |
|---|---|---|---|---|---|---|---|---|---|---|---|---|---|---|---|
| | | 595 | | | | | 600 | | | | | 605 | | | |

| Phe | Asn | Asp | Asp | Leu | Thr | Gly | Gln | Ala | Val | Ala | Phe | Val | Val | Leu |
|---|---|---|---|---|---|---|---|---|---|---|---|---|---|---|
| | 610 | | | | | 615 | | | | | 620 | | | |

| Lys | Asn | Lys | Ser | Asn | Trp | Ser | Thr | Ala | Thr | Asp | Asp | Glu | Leu | Gln | Asp |
|---|---|---|---|---|---|---|---|---|---|---|---|---|---|---|---|
| 625 | | | | | 630 | | | | | 635 | | | | | 640 |

| Ile | Lys | Lys | His | Leu | Val | Phe | Thr | Val | Arg | Lys | Asp | Ile | Gly | Pro | Phe |
|---|---|---|---|---|---|---|---|---|---|---|---|---|---|---|---|
| | | | | 645 | | | | | 650 | | | | | 655 | |

| Ala | Ala | Pro | Lys | Leu | Ile | Ile | Leu | Val | Asp | Asp | Leu | Pro | Lys | Thr | Arg |
|---|---|---|---|---|---|---|---|---|---|---|---|---|---|---|---|
| | | | 660 | | | | | 665 | | | | | 670 | | |

| Ser | Gly | Lys | Ile | Met | Arg | Arg | Ile | Leu | Arg | Lys | Ile | Leu | Ala | Gly | Glu |
|---|---|---|---|---|---|---|---|---|---|---|---|---|---|---|---|
| | | 675 | | | | | 680 | | | | | 685 | | | |

| Ser | Asp | Gln | Leu | Gly | Asp | Val | Ser | Thr | Leu | Ser | Asn | Pro | Gly | Ile | Val |
|---|---|---|---|---|---|---|---|---|---|---|---|---|---|---|---|
| | 690 | | | | | 695 | | | | | 700 | | | | |

| Arg | His | Leu | Ile | Asp | Ser | Val | Lys | Leu |
|---|---|---|---|---|---|---|---|---|
| 705 | | | | 710 | | | | |

```
<210> SEQ ID NO 17
<211> LENGTH: 2287
<212> TYPE: DNA
<213> ORGANISM: Saccharomyces cerevisiae
<220> FEATURE:
<221> NAME/KEY: misc_feature
<222> LOCATION: (1)..(2287)
<223> OTHER INFORMATION: Saccharomyces cerevisiae ACS2 nucleotide
      sequence

<400> SEQUENCE: 17
acctcccgcg acctccaaaa tcgaactacc ttcacaatga caatcaagga acataaagta      60
gtttatgaag ctcacaacgt aaaggctctt aaggctcctc aacatttta caacagccaa     120 cccggcaagg gttacgttac tgatatgcaa cattatcaag aaatgtatca acaatctatc     180
aatgagccag aaaaattctt tgataagatg gctaaggaat acttgcattg ggatgctcca     240
```
tacaccaaag ttcaatctgg ttcattgaac aatggtgatg ttgcatggtt tttgaacggt    300
aaattgaatg catcatacaa ttgtgttgac agacatgcct ttgctaatcc cgacaagcca    360
gctttgatct atgaagctga tgacgaatcc gacaacaaaa tcatcacatt tggtgaatta    420
ctcagaaaag tttcccaaat cgctggtgtc ttaaaaagct ggggcgttaa gaaaggtgac    480
acagtggcta tctatttgcc aatgattcca gaagcggtca ttgctatgtt ggctgtggct    540
cgtattggtg ctattcactc tgttgtcttt gctgggttct ccgctggttc gttgaaagat    600
cgtgtcgttg acgctaattc taaagtggtc atcacttgtg atgaaggtaa agaggtggt    660 aagaccatca acactaaaaa aattgttgac gaaggtttga acggagtcga tttggtttcc    720
cgtatcttgg ttttccaaag aactggtact gaaggtattc caatgaaggc cggtagagat    780
tactggtggc atgaggaggc cgctaagcag agaacttacc tacctcctgt ttcatgtgac    840
gctgaagatc ctctattttt attatacact tccggttcca ctggttctcc aaagggtgtc    900
gttcacacta caggtggtta tttattaggt gccgctttaa caactagata cgttttttgat    960 attcacccag aagatgttct cttcactgcc ggtgacgtcg gctggatcac gggtcacacc   1020
tatgctctat atggtccatt aaccttgggt accgcctcaa taattttcga tccactcct    1080 gcctaccccag attatggtag atattggaga attatccaac gtcacaaggc tacccatttc   1140
tatgtggctc caactgcttt aagattaatc aaacgtgtag gtgaagccga aattgccaaa   1200
tatgacactt cctcattacg tgtcttgggt tccgtcggtg aaccaatctc tccagactta   1260
tgggaatggt atcatgaaaa agtgggtaac aaaaactgtg tcatttgtga cactatgtgg   1320
caaacagagt ctggttctca tttaattgct cctttggcag gtgctgtccc aacaaaacct   1380
ggttctgcta ccgtgccatt ctttggtatt aacgcttgta tcattgaccc tgttacaggt   1440
gtggaattag aagtaatga tgtcgaaggt gtccttgccg ttaaatcacc atggccatca   1500
atggctagat ctgtttggaa ccaccacgac cgttacatgg atacttactt gaaaccttat   1560
cctggtcact atttcacagg tgatggtgct ggtagagatc atgatggtta ctactggatc   1620
aggggtagag ttgacgacgt tgtaaatgtt tccggtcata gattatccac atcagaaatt   1680
gaagcatcta tctcaaatca cgaaaacgtc tcggaagctg ctgttgtcgg tattccagat   1740
gaattgaccg gtcaaaccgt cgttgcatat gtttccctaa aagatggtta tctacaaaac   1800
aacgctactg aaggtgatgc agaacacatc acaccagata atttacgtag agaattgatc   1860
ttacaagtta ggggtgagat tggtccttc gcctcaccaa aaaccattat tctagttaga   1920
gatctaccaa gaacaaggtc aggaaagatt atgagaagag ttctaagaaa ggttgcttct   1980
aacgaagccg aacagctagg tgacctaact actttggcca acccagaagt tgtacctgcc   2040
atcatttctg ctgtagagaa ccaatttttc tctcaaaaaa agaaataact taaatgagaa   2100
aaatttcgta atgagataaa atttcgctcc ttttctgttt tctattttct attttcccaa   2160
cttttgctct attcagttat aaattactat ttatccatca gttaaaaaac aagatctttt   2220
actggtcagc taggaaagcg aaaatacaaa gactttatgc actatccccg cgtgcttggc   2280
cggccgt                                                            2287

<210> SEQ ID NO 18
<211> LENGTH: 683
<212> TYPE: PRT
<213> ORGANISM: Saccharomyces cerevisiae
<220> FEATURE:
<221> NAME/KEY: misc_feature
<222> LOCATION: (1)..(683)
<223> OTHER INFORMATION: Saccharomyces cerevisiae ACS2 protein sequence

<400> SEQUENCE: 18

```
Met Thr Ile Lys Glu His Lys Val Val Tyr Glu Ala His Asn Val Lys
1               5                   10                  15

Ala Leu Lys Ala Pro Gln His Phe Tyr Asn Ser Gln Pro Gly Lys Gly
            20                  25                  30

Tyr Val Thr Asp Met Gln His Tyr Gln Glu Met Tyr Gln Gln Ser Ile
        35                  40                  45

Asn Glu Pro Glu Lys Phe Phe Asp Lys Met Ala Lys Glu Tyr Leu His
    50                  55                  60

Trp Asp Ala Pro Tyr Thr Lys Val Gln Ser Gly Ser Leu Asn Asn Gly
65                  70                  75                  80

Asp Val Ala Trp Phe Leu Asn Gly Lys Leu Asn Ala Ser Tyr Asn Cys
                85                  90                  95

Val Asp Arg His Ala Phe Ala Asn Pro Asp Lys Pro Ala Leu Ile Tyr
            100                 105                 110

Glu Ala Asp Asp Glu Ser Asp Asn Lys Ile Ile Thr Phe Gly Glu Leu
        115                 120                 125

Leu Arg Lys Val Ser Gln Ile Ala Gly Val Leu Lys Ser Trp Gly Val
    130                 135                 140

Lys Lys Gly Asp Thr Val Ala Ile Tyr Leu Pro Met Ile Pro Glu Ala
145                 150                 155                 160

Val Ile Ala Met Leu Ala Val Ala Arg Ile Gly Ala Ile His Ser Val
                165                 170                 175

Val Phe Ala Gly Phe Ser Ala Gly Ser Leu Lys Asp Arg Val Val Asp
            180                 185                 190

Ala Asn Ser Lys Val Val Ile Thr Cys Asp Glu Gly Lys Arg Gly Gly
        195                 200                 205

Lys Thr Ile Asn Thr Lys Lys Ile Val Asp Glu Gly Leu Asn Gly Val
    210                 215                 220

Asp Leu Val Ser Arg Ile Leu Val Phe Gln Arg Thr Gly Thr Glu Gly
225                 230                 235                 240

Ile Pro Met Lys Ala Gly Arg Asp Tyr Trp Trp His Glu Glu Ala Ala
                245                 250                 255

Lys Gln Arg Thr Tyr Leu Pro Pro Val Ser Cys Asp Ala Glu Asp Pro
            260                 265                 270

Leu Phe Leu Leu Tyr Thr Ser Gly Ser Thr Gly Ser Pro Lys Gly Val
        275                 280                 285

Val His Thr Thr Gly Gly Tyr Leu Leu Gly Ala Ala Leu Thr Thr Arg
    290                 295                 300

Tyr Val Phe Asp Ile His Pro Glu Asp Val Leu Phe Thr Ala Gly Asp
305                 310                 315                 320

Val Gly Trp Ile Thr Gly His Thr Tyr Ala Leu Tyr Gly Pro Leu Thr
                325                 330                 335

Leu Gly Thr Ala Ser Ile Ile Phe Glu Ser Thr Pro Ala Tyr Pro Asp
            340                 345                 350

Tyr Gly Arg Tyr Trp Arg Ile Ile Gln Arg His Lys Ala Thr His Phe
        355                 360                 365

Tyr Val Ala Pro Thr Ala Leu Arg Leu Ile Lys Arg Val Gly Glu Ala
    370                 375                 380

Glu Ile Ala Lys Tyr Asp Thr Ser Ser Leu Arg Val Leu Gly Ser Val
385                 390                 395                 400

Gly Glu Pro Ile Ser Pro Asp Leu Trp Glu Trp Tyr His Glu Lys Val
```

```
                    405                 410                 415
Gly Asn Lys Asn Cys Val Ile Cys Asp Thr Met Trp Gln Thr Glu Ser
            420                 425                 430
Gly Ser His Leu Ile Ala Pro Leu Ala Gly Ala Val Pro Thr Lys Pro
        435                 440                 445
Gly Ser Ala Thr Val Pro Phe Phe Gly Ile Asn Ala Cys Ile Ile Asp
    450                 455                 460
Pro Val Thr Gly Val Glu Leu Glu Gly Asn Asp Val Glu Gly Val Leu
465                 470                 475                 480
Ala Val Lys Ser Pro Trp Pro Ser Met Ala Arg Ser Val Trp Asn His
            485                 490                 495
His Asp Arg Tyr Met Asp Thr Tyr Leu Lys Pro Tyr Pro Gly His Tyr
        500                 505                 510
Phe Thr Gly Asp Gly Ala Gly Arg Asp His Asp Gly Tyr Tyr Trp Ile
    515                 520                 525
Arg Gly Arg Val Asp Asp Val Val Asn Val Ser Gly His Arg Leu Ser
530                 535                 540
Thr Ser Glu Ile Glu Ala Ser Ile Ser Asn His Glu Asn Val Ser Glu
545                 550                 555                 560
Ala Ala Val Val Gly Ile Pro Asp Glu Leu Thr Gly Gln Thr Val Val
            565                 570                 575
Ala Tyr Val Ser Leu Lys Asp Gly Tyr Leu Gln Asn Asn Ala Thr Glu
        580                 585                 590
Gly Asp Ala Glu His Ile Thr Pro Asp Asn Leu Arg Arg Glu Leu Ile
    595                 600                 605
Leu Gln Val Arg Gly Glu Ile Gly Pro Phe Ala Ser Pro Lys Thr Ile
610                 615                 620
Ile Leu Val Arg Asp Leu Pro Arg Thr Arg Ser Gly Lys Ile Met Arg
625                 630                 635                 640
Arg Val Leu Arg Lys Val Ala Ser Asn Glu Ala Glu Gln Leu Gly Asp
            645                 650                 655
Leu Thr Thr Leu Ala Asn Pro Glu Val Val Pro Ala Ile Ile Ser Ala
        660                 665                 670
Val Glu Asn Gln Phe Phe Ser Gln Lys Lys Lys
    675                 680
```

<210> SEQ ID NO 19
<211> LENGTH: 2137
<212> TYPE: DNA
<213> ORGANISM: Streptomyces sp.
<220> FEATURE:
<221> NAME/KEY: misc_feature
<222> LOCATION: (1)..(2137)
<223> OTHER INFORMATION: Streptomyces sp. CL190 nphT7 gene sequence

<400> SEQUENCE: 19

```
cctgcaggcc gtcgagggcg cctggaagga ctacgcggag caggacggcc ggtcgctgga    60
ggagttcgcg gcgttcgtct accaccagcc gttcacgaag atggcctaca aggcgcaccg   120
ccacctgctg aacttcaacg gctacgacac cgacaaggac gccatcgagg cgcccctcgg   180
ccagacgacg gcgtacaaca acgtcatcgg caacagctac accgcgtcgg tgtacctggg   240
cctggccgcc ctgctcgacc aggcggacga cctgacgggc cgttccatcg gcttcctgag   300
ctacggctcg ggcagcgtcg ccgagttcct ctcgggcacc gtcgtcgccg gtaccgcga   360 gcgtctgcgc accgaggcga accaggaggc gatcgcccgg cgcaagagcg tcgactacgc   420
```

```
cacctaccgc gagctgcacg agtacacgct cccgtccgac ggcggcgacc acgccacccc    480
ggtgcagacc accggcccct tccggctggc cgggatcaac gaccacaagc gcatctacga    540
ggcgcgctag cgacacccct cggcaacggg gtgcgccact gttcggcgca ccccgtgccg    600
ggctttcgca cagctattca cgaccatttg aggggcgggc agccgcatga ccgacgtccg    660
attccgcatt atcggtacgg gtgcctacgt accggaacgg atcgtctcca acgatgaagt    720
cggcgcgccg gccggggtgg acgacgactg gatcacccgc aagaccggta tccggcagcg    780
tcgctgggcc gccgacgacc aggccacctc ggacctggcc acggccgcgg ggcgggcagc    840
gctgaaagcg gcgggcatca cgcccgagca gctgaccgtg atcgcggtcg ccacctccac    900
gccggaccgg ccgcagccgc ccacggcggc ctatgtccag caccacctcg gtgcgaccgg    960
cactgcggcg ttcgacgtca acgcggtctg ctccggcacc gtgttcgcgc tgtcctcggt   1020
ggcgggcacc ctcgtgtacc ggggcggtta cgcgctggtc atcggcgcgg acctgtactc   1080
gcgcatcctc aacccggccg accgcaagac ggtcgtgctg ttcggggacg gcgccggcgc   1140
aatggtcctc gggccgacct cgaccggcac gggccccatc gtccggcgcg tcgccctgca   1200
caccttcggc ggcctcaccg acctgatccg tgtgccgcg ggcggcagcc gccagccgct   1260
ggacacggat ggcctcgacg cgggactgca gtacttcgcg atggacgggc gtgaggtgcg   1320
ccgcttcgtc acggagcacc tgccgcagct gatcaagggc ttcctgcacg aggccggggt   1380
cgacgccgcc gacatcagcc acttcgtgcc gcatcaggcc aacggtgtca tgctcgacga   1440
ggtcttcggc gagctgcatc tgccgcgggc gaccatgcac cggacggtcg agacctacgg   1500
caacacggga gcggcctcca tcccgatcac catggacgcg gccgtgcgcg ccggttcctt   1560
ccggccgggc gagctggtcc tgctggccgg gttcggcggc ggcatggccg cgagcttcgc   1620
cctgatcgag tggtagtcgc ccgtaccacc acagcggtcc ggcgccacct gttccctgcg   1680
ccgggccgcc ctcggggcct ttaggcccca caccgcccca gccgacggat tcagtcgcgg   1740
cagtacctca gatgtccgct gcgacggcgt cccggagagc ccgggcgaga tcgcgggccc   1800
ccttctgctc gtccccggcc cctcccgcga gcaccacccg cggcggacgg ccgccgtcct   1860
ccgcgatacg ccggggcgagg tcgcaggcga gcacgccgga cccggagaag ccccccagca   1920
ccagcgaccg gccgactccg tgcgcggcca gggcaggctg cgcgccgtcg acgtcggtga   1980
gcagcaccag gagctcctgc ggccggcgt agaggtcggc cagccggtcg tagcaggtcg   2040
cgggcgcgcc cggcggcggg atcagacaga tcgtgcccgc ccgctcgtgc ctcgccgccc   2100
gcagcgtgac cagcggaatg tcccgcccag ctccgga                            2137
```

<210> SEQ ID NO 20
<211> LENGTH: 325
<212> TYPE: PRT
<213> ORGANISM: Streptomyces sp.
<220> FEATURE:
<221> NAME/KEY: misc_feature
<222> LOCATION: (1)..(325)
<223> OTHER INFORMATION: Streptomyces sp. CL190 acetyl-CoA:malonyl-CoA
      acyltransferase protein sequence

<400> SEQUENCE: 20

Arg Phe Arg Ile Ile Gly Thr Gly Ala Tyr Val Pro Glu Arg Ile Val
1               5                   10                  15

Ser Asn Asp Glu Val Gly Ala Pro Ala Gly Val Asp Asp Asp Trp Ile
            20                  25                  30

Thr Arg Lys Thr Gly Ile Arg Gln Arg Arg Trp Ala Ala Asp Asp Gln
        35                  40                  45

Ala Thr Ser Asp Leu Ala Thr Ala Ala Gly Arg Ala Ala Leu Lys Ala
 50                  55                  60

Ala Gly Ile Thr Pro Glu Gln Leu Thr Val Ile Ala Val Ala Thr Ser
 65                  70                  75                  80

Thr Pro Asp Arg Pro Gln Pro Pro Thr Ala Ala Tyr Val Gln His His
                 85                  90                  95

Leu Gly Ala Thr Gly Thr Ala Ala Phe Asp Val Asn Ala Val Cys Ser
                100                 105                 110

Gly Thr Val Phe Ala Leu Ser Ser Val Ala Gly Thr Leu Val Tyr Arg
            115                 120                 125

Gly Gly Tyr Ala Leu Val Ile Gly Ala Asp Leu Tyr Ser Arg Ile Leu
        130                 135                 140

Asn Pro Ala Asp Arg Lys Thr Val Val Leu Phe Gly Asp Gly Ala Gly
145                 150                 155                 160

Ala Met Val Leu Gly Pro Thr Ser Thr Gly Thr Gly Pro Ile Val Arg
                165                 170                 175

Arg Val Ala Leu His Thr Phe Gly Gly Leu Thr Asp Leu Ile Arg Val
                180                 185                 190

Pro Ala Gly Gly Ser Arg Gln Pro Leu Asp Thr Asp Gly Leu Asp Ala
            195                 200                 205

Gly Leu Gln Tyr Phe Ala Met Asp Gly Arg Glu Val Arg Arg Phe Val
    210                 215                 220

Thr Glu His Leu Pro Gln Leu Ile Lys Gly Phe Leu His Glu Ala Gly
225                 230                 235                 240

Val Asp Ala Ala Asp Ile Ser His Phe Val Pro His Gln Ala Asn Gly
                245                 250                 255

Val Met Leu Asp Glu Val Phe Gly Glu Leu His Leu Pro Arg Ala Thr
                260                 265                 270

Met His Arg Thr Val Glu Thr Tyr Gly Asn Thr Gly Ala Ala Ser Ile
            275                 280                 285

Pro Ile Thr Met Asp Ala Ala Val Arg Ala Gly Ser Phe Arg Pro Gly
        290                 295                 300

Glu Leu Val Leu Leu Ala Gly Phe Gly Gly Gly Met Ala Ala Ser Phe
305                 310                 315                 320

Ala Leu Ile Glu Trp
                325

<210> SEQ ID NO 21
<211> LENGTH: 1287
<212> TYPE: DNA
<213> ORGANISM: Pseudomonas mevalonii
<220> FEATURE:
<221> NAME/KEY: misc_feature
<222> LOCATION: (1)..(1287)
<223> OTHER INFORMATION: Pseudomonas mevalonii HMG-CoA reductase (mvaA)
      gene sequence

<400> SEQUENCE: 21
atgagcctcg attcccgcct gcccgctttc cgtaacctgt ccctgccgc gcgcctggac      60 cacatcggcc agttgctcgg cctgagccac gacgatgtca gcctgctggc caacgccggt     120
gccctgccga tggacatcgc caacggcatg atcgaaaacg tcatcggcac cttcgagctg     180
ccctatgccg tggccagcaa cttccagatc aatggccgtg atgtgctggt gccgctggtg     240
gtggaagagc cctcgatcgt cgccgctgct tcgtacatgg ccaagctggc ccgtgccaac     300
ggcggcttca ccacctccag cagcgccccg ctgatgcatg cccaggtaca gatcgtcggc     360

```
atacaggacc cgctcaatgc acgcctgagc ctgctgcgcc gcaaagacga aatcattgaa    420
ctggccaacc gcaaggacca gttgctcaac agcctcggcg gcggctgccg cgacatcgaa    480
gtgcacacct tcgccgatac cccgcgtggc ccgatgctgg tggcgcacct gatcgtcgat    540
gtacgcgatg ccatgggcgc caacaccgtc aataccatgg ccgaggccgt tgcgccgctg    600
atggaagcca tcaccggggg ccaggtacgc ctgcgcattc tgtccaacct ggccgacctg    660
cgcctggcca gggcccaggt gcggattact ccgcagcaac tggaaacggc cgaattcagt    720
ggcgaggcag tgatcgaagg catcctcgac gcctacgcct tcgctgcggt cgacccttac    780
cgcgcggcca cccacaacaa gggcatcatg aatggcatcg acccactgat cgtcgccact    840
ggcaacgact ggcgtgcagt ggaagccggc gcccatgcgt atgcctgccg cagtggtcac    900
tacggctcgc tgaccacctg gaaaaggac aacaacggcc atttggtcgg caccctggaa    960
atgccgatgc ccgtaggcct ggtcggcggc gccaccaaaa cccatccgct ggcgcaactg    1020
tcgctgcgca tcctcggcgt gaaaacagcc caggcgctcg ctgagattgc cgtggccgta    1080
ggcctggcgc aaaacctcgg ggccatgcgc gccctggcca ccgaaggcat ccagcgcggc    1140
cacatggccc tgcatgcgcg caatattgcc gtggtggcgg cgcccgagg cgatgaggtg    1200 gactgggttg cccggcagtt ggtggaatac cacgacgtgc gcgccgaccg cgccgtagca    1260
ctgctgaaac aaaagcgcgg ccaatga                                      1287
```

<210> SEQ ID NO 22
<211> LENGTH: 428
<212> TYPE: PRT
<213> ORGANISM: Pseudomonas mevalonii
<220> FEATURE:
<221> NAME/KEY: misc_feature
<222> LOCATION: (1)..(428)
<223> OTHER INFORMATION: Pseudomonas mevalonii hydroxymethylglutaryl-CoA
      reductase protein sequence

<400> SEQUENCE: 22

```
Met Ser Leu Asp Ser Arg Leu Pro Ala Phe Arg Asn Leu Ser Pro Ala
1               5                   10                  15

Ala Arg Leu Asp His Ile Gly Gln Leu Leu Gly Leu Ser His Asp Asp
            20                  25                  30

Val Ser Leu Leu Ala Asn Ala Gly Ala Leu Pro Met Asp Ile Ala Asn
        35                  40                  45

Gly Met Ile Glu Asn Val Ile Gly Thr Phe Glu Leu Pro Tyr Ala Val
    50                  55                  60

Ala Ser Asn Phe Gln Ile Asn Gly Arg Asp Val Leu Val Pro Leu Val
65                  70                  75                  80

Val Glu Glu Pro Ser Ile Val Ala Ala Ser Tyr Met Ala Lys Leu
                85                  90                  95

Ala Arg Ala Asn Gly Gly Phe Thr Thr Ser Ser Ala Pro Leu Met
                100                 105                 110

His Ala Gln Val Gln Ile Val Gly Ile Gln Asp Pro Leu Asn Ala Arg
            115                 120                 125

Leu Ser Leu Leu Arg Arg Lys Asp Glu Ile Ile Glu Leu Ala Asn Arg
        130                 135                 140

Lys Asp Gln Leu Leu Asn Ser Leu Gly Gly Gly Cys Arg Asp Ile Glu
145                 150                 155                 160

Val His Thr Phe Ala Asp Thr Pro Arg Gly Pro Met Leu Val Ala His
                165                 170                 175
```

Leu Ile Val Asp Val Arg Asp Ala Met Gly Ala Asn Thr Val Asn Thr
                180                 185                 190

Met Ala Glu Ala Val Ala Pro Leu Met Glu Ala Ile Thr Gly Gly Gln
                195                 200                 205

Val Arg Leu Arg Ile Leu Ser Asn Leu Ala Asp Leu Arg Leu Ala Arg
                210                 215                 220

Ala Gln Val Arg Ile Thr Pro Gln Gln Leu Glu Thr Ala Glu Phe Ser
225                 230                 235                 240

Gly Glu Ala Val Ile Glu Gly Ile Leu Asp Ala Tyr Ala Phe Ala Ala
                245                 250                 255

Val Asp Pro Tyr Arg Ala Ala Thr His Asn Lys Gly Ile Met Asn Gly
                260                 265                 270

Ile Asp Pro Leu Ile Val Ala Thr Gly Asn Asp Trp Arg Ala Val Glu
                275                 280                 285

Ala Gly Ala His Ala Tyr Ala Cys Arg Ser Gly His Tyr Gly Ser Leu
                290                 295                 300

Thr Thr Trp Glu Lys Asp Asn Asn Gly His Leu Val Gly Thr Leu Glu
305                 310                 315                 320

Met Pro Met Pro Val Gly Leu Val Gly Gly Ala Thr Lys Thr His Pro
                325                 330                 335

Leu Ala Gln Leu Ser Leu Arg Ile Leu Gly Val Lys Thr Ala Gln Ala
                340                 345                 350

Leu Ala Glu Ile Ala Val Ala Val Gly Leu Ala Gln Asn Leu Gly Ala
                355                 360                 365

Met Arg Ala Leu Ala Thr Glu Gly Ile Gln Arg Gly His Met Ala Leu
                370                 375                 380

His Ala Arg Asn Ile Ala Val Val Ala Gly Ala Arg Gly Asp Glu Val
385                 390                 395                 400

Asp Trp Val Ala Arg Gln Leu Val Glu Tyr His Asp Val Arg Ala Asp
                405                 410                 415

Arg Ala Val Ala Leu Leu Lys Gln Lys Arg Gly Gln
                420                 425

<210> SEQ ID NO 23
<211> LENGTH: 1302
<212> TYPE: DNA
<213> ORGANISM: Silicibacter pomeroyi
<220> FEATURE:
<221> NAME/KEY: misc_feature
<222> LOCATION: (1)..(1302)
<223> OTHER INFORMATION: Silicibacter pomeroyi hydroxymethylglutaryl-CoA
      reductase gene sequence

<400> SEQUENCE: 23
atgacaggca agacgggtca catcgatggt ttgaactcgc gcattgaaaa gatgcgagat    60
ctcgaccccg cacaacggct ggtgcgcgtt gccgaggcgg cgggcctcga gcccgaggcg   120
atcagcgcgc tggcgggtaa cggcgccctg cccctctcgc tggccaacgg gatgatcgag   180
aacgtcatcg gcaaattcga actgccgctg ggcgtggcca cgaatttcac tgtgaacggc   240
cgcgactatc tgatcccgat ggcggtcgaa gagccctcgg tggtggcggc cgcgtcctat   300
atggcgcgta tcgcgcgcga gaatggcgga ttcaccgcgc atggcaccgc gcccttgatg   360
cgcgcccaga tccaggtggt cgggttgggt gatcccgagg cgcccggca gcgtctcctc   420 gcccacaagg ccgcgttcat ggaggcgcg gacgctgtcg atccggtgct tgtcgggctg   480
ggtggcggct gccgcgatat cgaggttcac gtgttccggg atacgccggt gggcgcgatg   540

```
gtcgtcctgc acctgatcgt cgatgtgcgc gacgcgatgg gggccaatac ggtcaacacg    600
atggccgaac ggctggcccc cgaggtcgag cggattgccg gtggcaccgt gcggctgcgc    660
atcctgtcga acctcgccga cctgcgattg gtccgggcgc gggtggaact ggccccggaa    720
acactgacaa cgcagggcta tgacggcgcc gacgtggcgc ggggcatggt cgaggcctgc    780
gcgcttgcca tcgtcgaccc ctatcgcgcg gcgacccata caaggggat catgaacggc    840 atcgacccgg tcgtcgtcgc caccggcaat gactggcgcg cgatcgaggc gggtgcccat    900
gcctatgccg cccgcacggg tcattatacc tcgctgaccc gctgggaact ggcgaatgac    960
gggcggcttg tgggcacgat cgaactgccc ctggcgcttg gccttgtcgg cggcgcgacc   1020
aagacgcacc cgaccgcacg ggcggcgctg gccctgatgc aggtagagac tgcaaccgaa   1080
ctggcccagg tcaccgccgc cgtgggtctg gcgcagaaca tggccgccat ccgcgcgctg   1140
gcgaccgaag gcatccagcg cggtcacatg acccttcatg cgcgcaacat cgcgatcatg   1200
gccggcgcaa caggcgccga tatcgaccgc gtcacccggg tcattgtcga agcgggcgac   1260
gtcagcgtgg cccgtgcaaa acaggtgctg gaaaacacct ga                      1302
```

<210> SEQ ID NO 24
<211> LENGTH: 433
<212> TYPE: PRT
<213> ORGANISM: Silicibacter pomeroyi
<220> FEATURE:
<221> NAME/KEY: misc_feature
<222> LOCATION: (1)..(433)
<223> OTHER INFORMATION: Silicibacter pomeroyi hydroxymethylglutaryl-CoA
      reductase protein sequence

<400> SEQUENCE: 24

```
Met Thr Gly Lys Thr Gly His Ile Asp Gly Leu Asn Ser Arg Ile Glu
1               5                   10                  15

Lys Met Arg Asp Leu Asp Pro Ala Gln Arg Leu Val Arg Val Ala Glu
            20                  25                  30

Ala Ala Gly Leu Glu Pro Glu Ala Ile Ser Ala Leu Ala Gly Asn Gly
        35                  40                  45

Ala Leu Pro Leu Ser Leu Ala Asn Gly Met Ile Glu Asn Val Ile Gly
    50                  55                  60

Lys Phe Glu Leu Pro Leu Gly Val Ala Thr Asn Phe Thr Val Asn Gly
65                  70                  75                  80

Arg Asp Tyr Leu Ile Pro Met Ala Val Glu Glu Pro Ser Val Val Ala
                85                  90                  95

Ala Ala Ser Tyr Met Ala Arg Ile Ala Arg Glu Asn Gly Gly Phe Thr
            100                 105                 110

Ala His Gly Thr Ala Pro Leu Met Arg Ala Gln Ile Gln Val Val Gly
        115                 120                 125

Leu Gly Asp Pro Glu Gly Ala Arg Gln Arg Leu Leu Ala His Lys Ala
    130                 135                 140

Ala Phe Met Glu Ala Ala Asp Ala Val Asp Pro Val Leu Val Gly Leu
145                 150                 155                 160

Gly Gly Gly Cys Arg Asp Ile Glu Val His Val Phe Arg Asp Thr Pro
                165                 170                 175

Val Gly Ala Met Val Val Leu His Leu Ile Val Asp Val Arg Asp Ala
            180                 185                 190

Met Gly Ala Asn Thr Val Asn Thr Met Ala Glu Arg Leu Ala Pro Glu
        195                 200                 205

Val Glu Arg Ile Ala Gly Gly Thr Val Arg Leu Arg Ile Leu Ser Asn
```

```
                210               215               220
Leu Ala Asp Leu Arg Leu Val Arg Ala Arg Val Glu Leu Ala Pro Glu
225                 230                 235                 240

Thr Leu Thr Thr Gln Gly Tyr Asp Gly Ala Asp Val Ala Arg Gly Met
                245                 250                 255

Val Glu Ala Cys Ala Leu Ala Ile Val Asp Pro Tyr Arg Ala Ala Thr
                260                 265                 270

His Asn Lys Gly Ile Met Asn Gly Ile Asp Pro Val Val Val Ala Thr
            275                 280                 285

Gly Asn Asp Trp Arg Ala Ile Glu Ala Gly Ala His Ala Tyr Ala Ala
            290                 295                 300

Arg Thr Gly His Tyr Thr Ser Leu Thr Arg Trp Glu Leu Ala Asn Asp
305                 310                 315                 320

Gly Arg Leu Val Gly Thr Ile Glu Leu Pro Leu Ala Leu Gly Leu Val
                325                 330                 335

Gly Gly Ala Thr Lys Thr His Pro Thr Ala Arg Ala Ala Leu Ala Leu
                340                 345                 350

Met Gln Val Glu Thr Ala Thr Glu Leu Ala Gln Val Thr Ala Ala Val
                355                 360                 365

Gly Leu Ala Gln Asn Met Ala Ala Ile Arg Ala Leu Ala Thr Glu Gly
            370                 375                 380

Ile Gln Arg Gly His Met Thr Leu His Ala Arg Asn Ile Ala Ile Met
385                 390                 395                 400

Ala Gly Ala Thr Gly Ala Asp Ile Asp Arg Val Thr Arg Val Ile Val
                405                 410                 415

Glu Ala Gly Asp Val Ser Val Ala Arg Ala Lys Gln Val Leu Glu Asn
                420                 425                 430

Thr

<210> SEQ ID NO 25
<211> LENGTH: 1290
<212> TYPE: DNA
<213> ORGANISM: Delftia acidovorans
<220> FEATURE:
<221> NAME/KEY: misc_feature
<222> LOCATION: (1)..(1290)
<223> OTHER INFORMATION: Delftia acidovorans hydroxymethylglutaryl-CoA
      reductase nucleotide sequence

<400> SEQUENCE: 25
atggttgccg attcgcgact gcccaatttc cgcgccctca caccggccca gcgccgggat      60
ttcctggccg atgcctgcgg cctgtccgat gccgagcgcg ccctgctcgc tgccccgggt     120
gccctgcccc tggcgctggc cgacggcatg atcgagaacg tgttcggcag cttcgagctg     180
ccgctgggcg tggccggcaa cttccgcgtc aacggccgcg acgtgctggt gcccatggcg     240
gtggaggagc cctcggtggt ggccgccgcc tcgtacatgg ccaagctggc gcgcgaggac     300 ggggctttc agacctcaag cacgctgccg ctgatgcgcg cccaggtcca ggtgctgggc     360
gtgaccgatc acacggcgc gcgcctggcc gtgctgcagg cgcgtgcgca gatcatcgag     420
cgcgccaaca gccgcgacaa ggtgctgatc ggcctgggcg cggctgcaa ggacatcgag     480 gtccatgtct tccccgacac gccgcgcggc ccatgctgg tggtccacct gatcgtggac     540
gtgcgcgacg ccatgggcgc caacaccgtc aacaccatgg ccgaatcggt ggcgcccctg     600
gtcgagaaga tcacgggcgg cagcgtgcgg ctgcgcatcc tgtccaacct ggccgacctg     660
cggctggccc gcgccgcgt gcggctcacg ccgcagaccc tggccacgca ggatcgcagc     720
```

```
ggcgaggaga tcatcgaagg cgtgctggac gcctatacct tcgcggccat cgacccctac    780
cgcgcggcca cgcacaacaa gggaatcatg aacggcatcg accccgtcat cgtggccacg    840
ggcaacgact ggcgcgcggt cgaggccggc gcccatgcct atgccagccg cagcggcagc    900
tacacctcgc tgacgcgctg ggaaaaggat gccggcggcg ccctggtcgg cagcatcgag    960
ctgcccatgc cggtgggcct tgtcggcggc gccaccaaga cccatccgct ggcacgcctg   1020
gcgctgaaga tcatggacct gcagtccgcc cagcagctgg gcgagatcgc cgccgccgtg   1080
ggcctggcgc agaacctggg cgccctgcgc gccctggcca ccgaaggcat tcagcgcggc   1140
cacatggccc tgcacgcccg caacatcgcc ctggtggccg cgccacgggc gacgaggtc    1200 gatgccgtgg cgcgccagct ggccgccgag cacgacgtgc gcaccgaccg cgcgctggaa   1260
gtgctggccg cgctgcgcgc cagggcctga                                    1290
```

<210> SEQ ID NO 26  
<211> LENGTH: 429  
<212> TYPE: PRT  
<213> ORGANISM: Delftia acidovorans  
<220> FEATURE:  
<221> NAME/KEY: misc_feature  
<222> LOCATION: (1)..(429)  
<223> OTHER INFORMATION: Delftia acidovorans hydroxymethylglutaryl-CoA reductase protein sequence

<400> SEQUENCE: 26

```
Met Val Ala Asp Ser Arg Leu Pro Asn Phe Arg Ala Leu Thr Pro Ala
1               5                   10                  15

Gln Arg Arg Asp Phe Leu Ala Asp Ala Cys Gly Leu Ser Asp Ala Glu
            20                  25                  30

Arg Ala Leu Leu Ala Ala Pro Gly Ala Leu Pro Leu Ala Leu Ala Asp
        35                  40                  45

Gly Met Ile Glu Asn Val Phe Gly Ser Phe Glu Leu Pro Leu Gly Val
    50                  55                  60

Ala Gly Asn Phe Arg Val Asn Gly Arg Asp Val Leu Val Pro Met Ala
65                  70                  75                  80

Val Glu Glu Pro Ser Val Ala Ala Ala Ser Tyr Met Ala Lys Leu
                85                  90                  95

Ala Arg Glu Asp Gly Gly Phe Gln Thr Ser Ser Thr Leu Pro Leu Met
            100                 105                 110

Arg Ala Gln Val Gln Val Leu Gly Val Thr Asp Pro His Gly Ala Arg
        115                 120                 125

Leu Ala Val Leu Gln Ala Arg Ala Gln Ile Ile Glu Arg Ala Asn Ser
    130                 135                 140

Arg Asp Lys Val Leu Ile Gly Leu Gly Gly Gly Cys Lys Asp Ile Glu
145                 150                 155                 160

Val His Val Phe Pro Asp Thr Pro Arg Gly Pro Met Leu Val Val His
                165                 170                 175

Leu Ile Val Asp Val Arg Asp Ala Met Gly Ala Asn Thr Val Asn Thr
            180                 185                 190

Met Ala Glu Ser Val Ala Pro Leu Val Glu Lys Ile Thr Gly Gly Ser
        195                 200                 205

Val Arg Leu Arg Ile Leu Ser Asn Leu Ala Asp Leu Arg Leu Ala Arg
    210                 215                 220

Ala Arg Val Arg Leu Thr Pro Gln Thr Leu Ala Thr Gln Asp Arg Ser
225                 230                 235                 240
```

```
Gly Glu Glu Ile Ile Glu Gly Val Leu Asp Ala Tyr Thr Phe Ala Ala
            245                 250                 255

Ile Asp Pro Tyr Arg Ala Ala Thr His Asn Lys Gly Ile Met Asn Gly
        260                 265                 270

Ile Asp Pro Val Ile Val Ala Thr Gly Asn Asp Trp Arg Ala Val Glu
        275                 280                 285

Ala Gly Ala His Ala Tyr Ala Ser Arg Ser Gly Ser Tyr Thr Ser Leu
        290                 295                 300

Thr Arg Trp Glu Lys Asp Ala Gly Gly Ala Leu Val Gly Ser Ile Glu
305                 310                 315                 320

Leu Pro Met Pro Val Gly Leu Val Gly Gly Ala Thr Lys Thr His Pro
                325                 330                 335

Leu Ala Arg Leu Ala Leu Lys Ile Met Asp Leu Gln Ser Ala Gln Gln
                340                 345                 350

Leu Gly Glu Ile Ala Ala Ala Val Gly Leu Ala Gln Asn Leu Gly Ala
            355                 360                 365

Leu Arg Ala Leu Ala Thr Glu Gly Ile Gln Arg Gly His Met Ala Leu
        370                 375                 380

His Ala Arg Asn Ile Ala Leu Val Ala Gly Ala Thr Gly Asp Glu Val
385                 390                 395                 400

Asp Ala Val Ala Arg Gln Leu Ala Ala Glu His Asp Val Arg Thr Asp
                405                 410                 415

Arg Ala Leu Glu Val Leu Ala Ala Leu Arg Ala Arg Ala
                420                 425

<210> SEQ ID NO 27
<211> LENGTH: 3059
<212> TYPE: DNA
<213> ORGANISM: Artificial Sequence
<220> FEATURE:
<223> OTHER INFORMATION: Synthetic: i2235 integration construct

<400> SEQUENCE: 27
gacggcacgg ccacgcgttt aaaccgcctc gatatttcct gtgagaagtt taaatccact    60 aaggttttc attgttgctg cagatgtgtt tttccattca tcctgaaata tgcactgcta   120
ttccgcattc cattccccta gtcttttta gttctttccg ttcgaccttc atcgaaaaat   180
gacaaaacgc gttaggaaca caaccaatt gcaaacaagc agtgaaacaa accatcaag    240 gcccgaaaat acaagtgtgt actaatacag taagtaggtc aaatacgcaa tgaccaaaga   300
tgccgtgaat ctagatgctt acaccgtgag cttcatgcct ttctataccg agtatcaagg   360
accaaccgaa gagtttaagg attacaaatt cgaagatact atttactttc gtggcaagga   420
actgaagagg gaaagtctg cgacgccttc cagtagcgat aacacaacta gtaataccttt   480 cagtaatggc gccatcctct cgggaaacac aataactggc aagatagttt cagtgaataa   540
ttacgaaaga gagggcactg atcgcaacga attggcgcga ttgcaagaat tgatctccct   600
catcgatgtc ataaatcagt aaatataagc tcacacgcgg ccaggggag cccgttgagc   660 cattagtatc aatttgctta cctgtattcc tttactatcc tccttttttct ccttcttgat   720 aaatgtatgt agattgcgta tatagtttcg tctaccctat gaacatattc cattttgtaa   780
tttcgtgtcg tttctattat gaatttcatt tataaagttt atgtacaaat atcataaaaa   840
aagagaatct ttttaagcaa ggattttctt aacttcttcg gcgacagcat caccgacttc   900
ggtggtactg ttggaaccac ctaaatcacc agttctgata cctgcatcca aaacctttt    960 aactgcatct tcaatggcct taccttcttc aggcaagttc aatgacaatt tcaacatcat  1020
```

```
tgcagcagac aagatagtgg cgatagggtc aaccttattc tttggcaaat ctggagcaga    1080
accgtggcat ggttcgtaca aaccaaatgc ggtgttcttg tctggcaaag aggccaagga    1140
cgcagatggc aacaaaccca aggaacctgg gataacggag gcttcatcgg agatgatatc    1200
accaaacatg ttgctggtga ttataatacc atttaggtgg gttgggttct taactaggat    1260
catggcggca gaatcaatca attgatgttg aaccttcaat gtagggaatt cgttcttgat    1320
ggtttcctcc acagtttttc tccataatct tgaagaggcc aaaacattag ctttatccaa    1380
ggaccaaata ggcaatggtg gctcatgttg tagggccatg aaagcggcca ttcttgtgat    1440
tctttgcact tctggaacgg tgtattgttc actatcccaa cgacaccat caccatcgtc     1500
ttcctttctc ttaccaaagt aaatacctcc cactaattct ctgacaacaa cgaagtcagt    1560
accttttagca aattgtggct tgattggaga taagtctaaa agagagtcgg atgcaaagtt   1620
acatggtctt aagttggcgt acaattgaag ttctttacgg attttttagta aaccttgttc   1680
aggtctaaca ctaccggtac cccatttagg accacccaca gcacctaaca aaacggcatc    1740
aaccttcttg gaggcttcca gcgcctcatc tggaagtggg acacctgtag catcgatagc    1800
agcaccacca attaaatgat tttcgaaatc gaacttgaca ttggaacgaa catcagaaat    1860
agctttaaga accttaatgg cttcggctgt gatttcttga ccaacgtggt cacctggcaa    1920
aacgacgatc ttcttagggg cagacatagg ggcagacatt agaatggtat atccttgaaa    1980
tatatatata tattgctgaa atgtaaaagg taagaaaagt tagaaagtaa gacgattgct    2040
aaccacctat tggaaaaaac aataggtcct taaataatat tgtcaacttc aagtattgtg    2100
atgcaagcat ttagtcatga acgcttctct attctatatg aaaagccggt tccggcctct    2160
caccttttcct ttttctccca attttttcagt tgaaaaaggt atatgcgtca ggcgacctct   2220
gaaattaaca aaaaatttcc agtcatcgaa tttgattctg tgcgatagcg cccctgtgtg    2280
ttctcgttat gttgaggaaa aaaataatgg ttgctaagag attcgaactc ttgcatctta    2340
cgatacctga gtattcccac agttaactgc ggtcaagata tttcttgaat caggcgcctc    2400
gctcgtccaa cgccggcgga cctcttaaat gagaaaaatt tcgtaatgag ataaatttc     2460
gctccttttc tgtttttctat tttctatttt cccaactttt gctctattca gttataaatt   2520
actatttatc catcagttaa aaaacaagat cttttactgg tcagctagga aagcgaaaat    2580
acaaagactt tatgcactta gtgatatata tgtatagata tatccatttt tacgcactta    2640
tcatatatct tagttatcta aatacaatct agttattcgt acacaatcgc ccctgttatc    2700
cctatagtgg gaataaagta atgcactgtg acggggttct tcgcccggga tagggtaaaa    2760
ggatattgcc gtttcaagaa acttcgggga taatcgaata agataccgag aaagctattg    2820
ttcgttgtgc acgtaggatg tatattgaac aagcatgacc agaatctgat gcattacgag    2880
aaggttacgg gatgatatca gacctccgaa gtccatgttg caaaatgtgc cgactttccg    2940
cggcgctatt tggcacaaat ttcaggagaa acatcactgt cggtgttata gaattccatc    3000
tatattgttt tccccgtagg catacgtcga gcggtgttta aaccccagcg cctggcggg     3059
```

<210> SEQ ID NO 28
<211> LENGTH: 8106
<212> TYPE: DNA
<213> ORGANISM: Artificial Sequence
<220> FEATURE:
<223> OTHER INFORMATION: Synthetic: i74804 integration construct

<400> SEQUENCE: 28

```
gacggcacgg ccacgcgttt aaaccgcccg ctcgcctcat ccccacggga ataaggcagc    60
cgacaaaaga aaaacgaccg aaaaggaacc agaaagaaaa aagagggtgg gcgcgccgcg   120
gacgtgtaaa aagatatgca tccagcttct atatcgcttt aactttaccg ttttgggcat   180
cgggaacgta tgtaacattg atctcctctt gggaacggtg agtgcaacga atgcgatata   240
gcaccgacca tgtgggcaaa ttcgtaataa attcggggtg aggggattc aagacaagca    300
accttgttag tcagctcaaa cagcgattta acggttgagt aacacatcaa acaccgttc    360
gaggtcaagc ctggcgtgtt taacaagttc ttgatatcat atataaatgt aataagaagt   420
ttggtaatat tcaattcgaa gtgttcagtc ttttacttct cttgttttat agaagaaaaa   480
acatcaagaa acatctttaa catacacaaa cacatactat cagaatacac gctcgtccaa   540
cgccggcgga cctttcagac gcgactgcct catcagtaag acccgttgaa aagaacttac   600
ctgaaaaaaa cgaatatata ctagcgttga atgttagcgt caacaacaag aagtttaatg   660
acgcggaggc caaggcaaaa agattccttg attacgtaag ggagttagaa tcattttgaa   720
taaaaaacac gcttttcag ttcgagttta tcattatcaa tactgccatt tcaaagaata    780
cgtaaataat taatagtagt gattttccta actttattta gtcaaaaaat tagccttta    840
attctgctgt aacccgtaca tgcccaaaat aggggcggg ttacacagaa tataaacat    900
cgtaggtgtc tgggtgaaca gtttattcct ggcatccact aaatataatg gagcccgctt   960
tttaagctgg catccagaaa aaaaagaat cccagcacca aatattgtt tcttcacca    1020
accatcagtt cataggtcca ttctcttagc gcaactacag agaacagggg cacaaacagg   1080
caaaaaacgg gcacaacctc aatggagtga tgcaacctgc ctggagtaaa tgatgacaca   1140
aggcaattga cccacgcatg tatctatctc attttcttac accttctatt accttctgct   1200
ctctctgatt tggaaaaagc tgaaaaaaa ggttgaaacc agttccctga aattattccc    1260
ctacttgact aataagtata taagacggt aggtattgat tgtaattctg taaatctatt   1320
tcttaaactt cttaaattct actttatag ttagtctttt ttttagtttt aaaacaccaa   1380
gaacttagtt tcgacctccc gcgacctcca aaatcgaact accttcacaa tggaacattc   1440
tgtaatcgaa ccaactgtgc ccatgccgct accagccatg tttgacgctc catctggtat   1500
ttttagctct ttggacgacg ctgtgcaagc agccacctta gcccaacaac aactaagttc   1560
agttgagttg cgtcagcaag taatcaaagc cataagagtg gccggagaaa ggtatgcaca   1620
agttttggct gaaatggcag ttgctgaaac tggtatgggt agggtggtgg ataagtacat   1680
taagaatgtc tctcaagctc gtcatacgcc tggtatagaa tgtttatcgg ccgaggttct   1740
tacgggtgat aatggcctaa cattgattga aaatgcccct tggggagtcg tagcttcagt   1800
cacgccaagc acaaatccag cagctacggt aattaataat gcaatctcaa tgattgcagc   1860
ggggaattca gtcgtgttcg caccacatcc ttctgccaaa aacgtctcac taaggactat   1920
ttctttactc aacaaggcca ttgtcgctac cggcggccca gaaaatttac tagttagtgt   1980
ggcaaaccct aacatcgaaa ctgcacagag attattcaga tatccgggta ttggattgtt   2040
agttgtgaca ggtggtgaag ccgtcgttga agccgctagg aagcatacag ataaaaggtt   2100
aattgcagcc ggcgctggta atcctcctgt tgttgtggac gaaactgctg acatacctaa   2160
agccgcaaga gcaattgtca agggtgcttc tttcgacaac aacataattt gtgctgatga   2220
aaaagttttg attgtggtag acagagttgc agatgcacta ttggcagaaa tgcaaagaaa   2280
taacgccgtc ttacttacac ccgaacagac cgaaagacta ctaccgctc ttttgtccga   2340
tattgacgaa cagggcaaag gacgtgtgaa tagagattat gttggaagag atgcggctaa   2400
```

```
attagcagcg gctattggtc tggaagttag cgaacatact cgtctactcc tggcagagac    2460
agacgctgat catccattcg ccgtgacgga gctgatgatg ccagtgttac cagtaataag    2520
agtcaagaat gtagatgatg caatcgcatt ggcagttaag ctagagtcag gctgcagaca    2580
cacagctgcg atgcactcta ctaatataag aaacttaaat agaatggcta atgccatcaa    2640
tacctctatc tttgtaaaaa atggtccatg tattgcaggt ttgggtttag gcggtgaagg    2700
ttggacttca atgactatta gcactccgac cggtgaaggt gttacaagcg ctcgtacctt    2760
tgtcagatta agaaggtgtg tcttagtcga catgtttcgg attgcttaag cggccgcgag    2820
taataattat tgcttccata taatattttt atatacctct tatttttatg tattagttaa    2880
ttaagtattt ttatctatct gcttatcatt ttcttttcat ataggggggg ttggtgtttt    2940
cttgcccatc agattgatgt cctccaactc ggcactattt tacaaagggt ttttttgtaa    3000
gagaaggaga agacagatac taaaccatac gttactcgaa acaaaaaaaa aaaaaatgga    3060
aaaagctgct atcaacaaaa gacggcctca tcaaacctaa agaaccatg tcagcgtatg    3120 tatatacctt gtaatttacg tttccttaaa tcttctttct actaacgttt tcattattct    3180
atactctatg accaataaaa acagactgta ctttcaaaat ttacccagta ggccagcaaa    3240
taaagaaaat tataccagat tacttctgaa acacattaat cccaacaaca agtatgccat    3300
taatccgtcg ctaccccatc cccgcgtgct tggccggccg tacactgagt aatggtagtt    3360
ataagaaaga gaccgagtta gggacagtta gaggcggtgg agatattcct tatggcatgt    3420
ctggcgatga taaaactttt caaacggcag ccccgatcta aaagagctga cagggaaatg    3480
gtcagaaaaa gaaacgtgca cccgcccgtc tggacgcgcc gctcacccgc acggcagaga    3540
ccaatcagta aaaatcaacg gttaacgaca ttactatata tataatatag gaagcattta    3600
atagaacagc atcgtaatat atgtgtactt tgcagttatg acgccagatg gcagtagtgg    3660
aagatattct ttattgaaaa atagcttgtc accttacgta caatcttgat ccggagcttt    3720
tctttttttg ccgattaaga attcggtcga aaaagaaaa ggagagggcc aagagggagg    3780
gcattggtga ctattgagca cgtgagtata cgtgattaag cacacaaagg cagcttggag    3840
tatgtctgtt attaatttca caggtagttc tggtccattg gtgaaagttt gcggcttgca    3900
gagcacagag gccgcagaat gtgctctaga ttccgatgct gacttgctgg gtattatatg    3960
tgtgcccaat agaagagaa caattgaccc ggttattgca aggaaaattt caagtcttgt    4020
aaaagcatat aaaaatagtt caggcactcc gaaatacttg gttggcgtgt ttcgtaatca    4080
acctaaggag gatgttttgg ctctggtcaa tgattacggc attgatatcg tccaactgca    4140
tggagatgag tcgtggcaag aataccaaga gttcctcggt ttgccagtta ttaaaagact    4200
cgtatttcca aaagactgca acatactact cagtgcagct tcacagaaac ctcattcgtt    4260
tattcccttg tttgattcag aagcaggtgg gacaggtgaa cttttggatt ggaactcgat    4320
ttctgactgg gttggaaggc aagagagccc cgaaagctta cattttatgt tagctggtgg    4380
actgacgcca gaaaatgttg gtgatgcgct tagattaaat ggcgttattg gtgttgatgt    4440
aagcggaggt gtggagacaa atggtgtaaa agactctaac aaaatagcaa atttcgtcaa    4500
aaatgctaag aaataggtta ttactgagta gtatttattt aagtattgtt tgtgcacttg    4560
cctgcaggcc ttttgaaaag caagcataaa agatctaaac ataaaatctg taaaataaca    4620
agatgtaaag ataatgctaa atcatttggc tttttgattg attgtacagg aaaatataca    4680
tcgcaggggg ttgactttta ccatttcacc gcaatggaat caaacttgtt gaagagaatg    4740
```

```
ttcacaggcg catacgctac aatgacacgg ccggccaagc acgcgggat ggggtagcga    4800 cggattaatg gcatacttgt tgttgggatt aatgtgtttc agaagtaatc tggtataatt    4860
ttctttattt gctggcctac tgggtaaatt ttgaaagtac agtctgtttt tattggtcat    4920
agagtataga ataatgaaaa cgttagtaga agaagatttt aaggaaacgt aaattacaag    4980
gtatatacat acgctgacat ggtttcttta ggtttgatga ggccgtcttt tgttgatagc    5040
agctttttcc attttttttt ttttgtttc gagtaacgta tggtttagta tctgtcttct    5100
ccttctctta caaaaaaacc ctttgtaaaa tagtgccgag ttggaggaca tcaatctgat    5160
gggcaagaaa acaccaaccc cccctatatg aaagaaaat gataagcaga tagataaaaa    5220
tacttaatta actaatacat aaaaataaga ggtatataaa aatattatat ggaagcaata    5280
attattactc gcggccgctt aagcaatccg aaacatgtcg actaagcacac accttcttaa    5340 tctgacaaag gtacgagcgc ttgtaacacc ttcaccggtc ggagtgctaa tagtcattga    5400
agtccaacct tcaccgccta aacccaaacc tgcaatacat ggaccatttt ttacaaagat    5460
agaggtattg atggcattag ccattctatt taagtttctt atattagtag agtgcatcgc    5520
agctgtgtgt ctgcagcctg actctagctt aactgccaat gcgattgcat catctacatt    5580
cttgactctt attactggta acactggcat catcagctcc gtcacggcga atggatgatc    5640
agcgtctgtc tctgccagga gtagacgagt atgttcgcta acttccagac caatagccgc    5700
tgctaattta gccgcatctc ttccaacata atctctattc acacgtcctt tgccctgttc    5760
gtcaatatcg gacaaaagag cgggtagtag tctttcggtc tgttcgggtg taagtaagac    5820
ggcgttattt ctttgcattt ctgccaatag tgcatctgca actctgtcta ccacaatcaa    5880
aactttttca tcagcacaaa ttatgttgtt gtcgaaagaa gcacccttga caattgctct    5940
tgcggcttta ggtatgtcag cagtttcgtc cacaacaaca ggaggattac cagcgccggc    6000
tgcaattaac cttttatctg tatgcttcct agcggcttca acgacggctt caccacctgt    6060
cacaactaac aatccaatac ccggatatct gaataatctc tgtgcagttt cgatgttagg    6120
gtttgccaca ctaactagta aattttctgg gccgccggta gcgacaatgg ccttgttgag    6180
taaagaaata gtccttagtg agacgttttt ggcagaagga tgtggtgcga acacgactga    6240
attccccgct gcaatcattg agattgcatt attaattacc gtagctgctg gatttgtgct    6300
tggcgtgact gaagctacga ctccccaagg gcattttca atcaatgtta ggccattatc    6360
acccgtaaga acctcggccg ataaacattc tataccaggc gtatgacgag cttgagagac    6420
attcttaatg tacttatcca ccaccctacc cataccagtt tcagcaactg ccatttcagc    6480
caaaacttgt gcatacctttt ctccggccac tcttatggct ttgattactt gctgacgcaa    6540
ctcaactgaa cttagttgtt gttgggctaa ggtggctgct tgcacagcgt cgtccaaaga    6600
gctaaaaata ccagatggag cgtcaaacat ggctggtagc ggcatgggca cagttggttc    6660
gattacagaa tgttccattg tgaaggtagt tcgatttttgg aggtcgcggg aggtcgaaac    6720
taagttcttg gtgtttttaaa actaaaaaaa agactaacta taaagtaga atttaagaag    6780 tttaagaaat agatttacag aattacaatc aatacctacc gtctttatat acttattagt    6840
caagtagggg aataatttca gggaactggt ttcaaccttt tttttcagct ttttccaaat    6900
cagagagagc agaaggtaat agaaggtgta agaaaatgag atagatacat gcgtgggtca    6960
attgccttgt gtcatcattt actccaggca ggttgcatca ctccattgag gttgtgcccg    7020 tttttttgcct gtttgtgccc ctgttctctg tagttgcgct aagagaatgg acctatgaac    7080
tgatggttgg tgaagaaaac aatatttgg tgctgggatt cttttttttt ctggatgcca    7140
```

-continued

| | |
|---|---|
| gcttaaaaag cgggctccat tatatttagt ggatgccagg aataaactgt tcacccagac | 7200 |
| acctacgatg ttatatattc tgtgtaaccc gcccccctatt ttgggcatgt acgggttaca | 7260 |
| gcagaattaa aaggctaatt ttttgactaa ataaagttag gaaaatcact actattaatt | 7320 |
| atttacgtat tctttgaaat ggcagtattg ataatgataa actcgaactg aaaaagcgtg | 7380 |
| ttttttattc aaaatgattc taactcccctt acgtaatcaa ggaatctttt tgccttggcc | 7440 |
| tccgcgtcat taaacttctt gttgttgacg ctaacattca acgctagtat atattcgttt | 7500 |
| ttttcaggta agttctttc aacgggtctt actgatgagg cagtcgcgtc tgaaaggtcc | 7560 |
| gccggcgttg gacgagcgtg taccaacctg catttctttc cgtcatatac acaaaatact | 7620 |
| ttcatataaa cttacttggt cttacgtcat aaataaatat gtatacatat aaattaaaaa | 7680 |
| atttggtttt atattttac aaaaagaatc gtttacttca tttctccctt ttaagcgata | 7740 |
| caatccatga aaaagagaa aagagagaa caggcttgtg ccttctttaa aacatcccac | 7800 |
| acaaaatcat attgaattga attttacatc ttaagctagt gtacaacaac tgctatatcc | 7860 |
| aaagaaaact aacgtggacc gcttttagag ttgagaaaaa ggtttgaaaa aaatagcaat | 7920 |
| acaaagactt gtttcatata taaaatacag ggagcacatt gagctaatat aacataaaca | 7980 |
| ctgcgaacca attccaatca aaaggtacac atgagagcat tcccccgagt actgccattt | 8040 |
| cgccatcaga gatcatataa taacatcctt cttcgaacgg cggtttaaac gcgtggccgt | 8100 |
| gccgtc | 8106 |

<210> SEQ ID NO 29
<211> LENGTH: 2404
<212> TYPE: DNA
<213> ORGANISM: Artificial Sequence
<220> FEATURE:
<223> OTHER INFORMATION: Synthetic: i76220 integration construct

<400> SEQUENCE: 29

| | |
|---|---|
| gacggcacgg ccacgcgttt aaaccgccgc acgtgtatgt acggctgtgt aaatatgata | 60 |
| atcatctcgg acgaacggcg tagtactctc catcccctaa aaatgttcac gtgtgactgc | 120 |
| tccatttcgc cggatgtcga gatgaccccc ccccctcaaa aggcactcac ctgctgacat | 180 |
| gccgtggcaa atgattgggg tcatccttttt tttctgttat ctctaagatc caaagaaaag | 240 |
| taaaaaaaaa aggttggggt acgaattgcc gccgagcctc cgatgccatt attcaatggg | 300 |
| tattgcagtt ggggtatagt tcctcggtgg caaatagttc tcccttcatt ttgtatataa | 360 |
| actgggcggc tattctaagc atatttctcc cttaggttat ctggtagtac gttatatctt | 420 |
| gttcttatat tttctatcta taagcaaaac caaacatatc aaaactacta gaaagacatt | 480 |
| gccccactgt gttcgctcgt ccaacgccgg cggacctttc tcgacgtggg ccttttttctt | 540 |
| gccatatgga tccgctgcac ggtcctgttc cctagcatgt acgtgagcgt atttccttttt | 600 |
| aaaccacgac gctttgtctt cattcaacgt ttcccattgt ttttttctac tattgctttg | 660 |
| ctgtgggaaa aacttatcga aagatgacga cttttttctta attctcgttt taagagcttg | 720 |
| gtgagcgcta ggagtcactg ccaggtatcg tttgaacacg gcattagtca gggaagtcat | 780 |
| aacacagtcc tttcccgcaa ttttcttttt ctattactct tggcctcctc tagtacactc | 840 |
| tatattttt tatgcctcgg taatgatttt cattttttt tttccaccta gcggatgact | 900 |
| cttttttttt cttagcgatt ggcattatca cataatgaat tatacattat ataaagtaat | 960 |
| gtgatttctt cgaagaatat actaaaaaat gagcaggcaa gataaacgaa ggcaaagatg | 1020 |

```
acagagcaga aagccctagt aaagcgtatt acaaatgaaa ccaagattca gattgcgatc    1080
tctttaaagg gtggtcccct agcgatagag cactcgatct tcccagaaaa agaggcagaa    1140
gcagtagcag aacaggccac acaatcgcaa gtgattaacg tccacacagg tatagggttt    1200
ctggaccata tgatacatgc tctggccaag cattccggct ggtcgctaat cgttgagtgc    1260
attggtgact tacacataga cgaccatcac accactgaag actgcgggat tgctctcggt    1320
caagctttta aagaggccct aggggccgtg cgtggagtaa aaggttttgg atcaggatt    1380 gcgcctttgg atgaggcact ttccagagcg gtggtagatc tttcgaacag gccgtacgca    1440
gttgtcgaac ttggttttgca aagggagaaa gtaggagatc tctcttgcga gatgatcccg    1500
cattttcttg aaagctttgc agaggctagc agaattaccc tccacgttga ttgtctgcga    1560
ggcaagaatg atcatcaccg tagtgagagt gcgttcaagg ctcttgcggt tgccataaga    1620
gaagccacct cgcccaatgg taccaacgat gttccctcca ccaaaggtgt tcttatgtag    1680
tgacaccgat tatttaaagc tgcagcatac gatatatata catgtgtata tatgtatacc    1740
tatgaatgtc agtaagtatg tatacgaaca gtatgatact gaagatgaca aggtaatgca    1800
tcattctata cgtgtcattc tgaacgaggc gcgctttcct ttttttcttt tgcttttttct    1860 ttttttttct cttgaactcg aggtccgccg gcgttggacg agcgtgatga tttctttcct    1920
ttttatattg acgactttt tttttcgtg tgtttttgtt ctcttataac cgagctgctt    1980
acttattatt atttcacctt ctcttttat ttatacttat aattatttat tctttacata    2040
ctgttacaag aaactctttt ctacattaat tgcataaagt gtcaatcagc acatcctcta    2100
tatcgctatc aacaacaaat ttgacaaacc tgcctatatc ttcaggaaca actgccgcat    2160
cgctaccacc actacttgtg aagtccctgg agtttaatat gcactgaaat ttacctagcc    2220
gttttacaca agaccataat ccatccatgc tatcgcagta tatgattttg tgttcgtttt    2280
tcgtcttgcg aaaggcatcc tcaatggctt gtttcattga tccatcagtg tggctcgtag    2340
gtaccagcaa aaccacttca tcagcggcgt actcctggcg gtttaaacgc gtggccgtgc    2400
cgtc                                                                2404

<210> SEQ ID NO 30
<211> LENGTH: 8536
<212> TYPE: DNA
<213> ORGANISM: Artificial Sequence
<220> FEATURE:
<223> OTHER INFORMATION: Synthetic: i73830 integration construct

<400> SEQUENCE: 30
gacggcacgg ccacgcgttt aaaccgccac ccagccaagg tagtctaaaa gctaatttct      60
ctaaagggga gaaagttggt gattttttat ctcgcattat tatatatgca agaatagtta     120
aggtatagtt ataaagtttt atcttaattg ccacatacgt acattgacac gtagaaggac     180
tccattattt ttttcattct agcatactat tattccttgt aacgtcccag agtattccat     240
ttaattgtcc tccattttctt aacggtgacg aaggatcacc atacaacaac tactaaagat     300
tatagtacac tctcaccttg caactatttta tctgacattt gccttacttt tatctccagc    360
ttcccctcga ttttattttt caattgatt tctaaagctt tttgcttagg cataccaaac     420
catccactca tttaacacct tatttttttt ttcgaagaca gcatccaact ttatacgttc     480 actaccttt ttttttacaac aatttcatc ttcatcctat gaacgctcgt ccaacgccgg      540
cggacctttc agacgcgact gcctcatcag taagacccgt tgaaagaac ttacctgaaa      600 aaaacgaata tatactagcg ttgaatgtta gcgtcaacaa caagaagttt aatgacgcgg     660
```

```
aggccaaggc aaaaagattc cttgattacg taagggagtt agaatcattt tgaataaaaa    720
acacgctttt tcagttcgag tttatcatta tcaatactgc catttcaaag aatacgtaaa    780
taattaatag tagtgatttt cctaacttta tttagtcaaa aaattagcct tttaattctg    840
ctgtaacccg tacatgccca aaataggggg cgggttacac agaatatata acatcgtagg    900
tgtctgggtg aacagtttat tcctggcatc cactaaatat aatggagccc gcttttaag    960 ctggcatcca gaaaaaaaaa gaatcccagc accaaaatat tgttttcttc accaaccatc   1020
agttcatagg tccattctct tagcgcaact acagagaaca ggggcacaaa caggcaaaaa   1080
acgggcacaa cctcaatgga gtgatgcaac ctgcctggag taaatgatga cacaaggcaa   1140
ttgacccacg catgtatcta tctcattttc ttacaccttc tattaccttc tgctctctct   1200
gatttggaaa aagctgaaaa aaaaggttga aaccagttcc ctgaaattat tcccctactt   1260
gactaataag tatataaaga cggtaggtat tgattgtaat tctgtaaatc tatttcttaa   1320
acttcttaaa ttctactttt atagttagtc tttttttag ttttaaaaca ccaagaactt   1380
agtttcgacc tcccgcgacc tccaaaatcg aactaccttc acaatggctg atttcgattc   1440
taaagaatac ttggagttag ttgacaagtg gtggcgtgcc accaactact tgtccgctgg   1500
tatgattttc ttgaagtcca acccattatt ctctgttact aatacccaa tcaaggccga   1560 agatgtcaaa gttaaaccaa ttggtcactg gggtactatt tccggtcaaa ctttcttata   1620
cgcccacgct aaccgtttga ttaacaagta cggtctcaac atgttttacg ttggtggtcc   1680
aggtcacggt ggtcaagtca tggttactaa cgcctactta gacggtgcct acaccgaaga   1740
ttacccagaa attactcaag acatcgaagg tatgtctcat tgttcaagc gtttctcttt   1800 ccctggtggt attggttccc atatgaccgc tcaaactcca ggttccttgc acgaaggtgg   1860
tgaattgggt tactctttgt cccatgcttt cggtgctgtt ttggacaacc cagaccaagt   1920
tgcttttgct gtcgttggtg atggtgaagc tgaaactggt ccatctatgg cctcttggca   1980
ttccattaag ttcttaaatg ccaagaacga tggtgccgtt ttgccagttt tggatttaaa   2040
cggtttcaag atttccaatc caaccatttt ttctagaatg tctgatgaag aaattactaa   2100
gttcttcgaa ggtttgggtt attccctag attcattgaa aatgatgaca ttcacgacta   2160
cgccacctac caccaattgg ccgctaacat cttagatcaa gccatcgaag acattcaagc   2220
tattcaaaat gacgccagag agaatggtaa atatcaagat ggtgaaattc agcttggcc   2280 tgttattatc gctagattgc caaagggttg gggtggtcca acccacgatg cttctaataa   2340
tccaattgaa aactctttca gagctcacca agttccatta ccattggaac aacacgatt   2400 ggccaccttg ccagaattcg aagattggat gaactcttac aagccagaag aattattcaa   2460
cgctgatggt ccttgaagg atgagttgaa agctattgcc ccaaagggtg ataagagaat   2520
gtctgctaac ccaatcacca acggtggtgc tgacagatcc gacttgaaat tgccaaattg   2580
gagagaattc gctaacgaca tcaacgacga taccagaggg aaggaattcg ctgactctaa   2640
gagaaacatg gatatggcta ctttatccaa ctatttaggt gccgtttctc aattgaaccc   2700
aaccagattc agattcttcg gtccagatga accatgtcc aacagattgt ggggtttgtt   2760
taatgttacc ccacgtcaat ggatggaaga atcaaggaa ccacaagatc aattgttgtc   2820
tccaactggt cgtatcatcg attcccaatt gtctgaacac aagctgaag gttggttgga   2880 aggttacact ttgactggta gagttggtat ctttgcctct tacgaatctt tcttgagagt   2940
tgttgatacc atggtcactc aacatttcaa gtggttgcgt cacgcttccg aacaagcttg   3000
```

```
gagaaatgac tatccatcct taaatttgat cgctacctct accgctttcc aacaagatca    3060
taacggttat actcaccaag accctggtat gttaactcat ttggccgaga agaagtctaa    3120
cttcattaga gaatatttgc cagccgacgg taactctttg ttagccgttc aagagagagc    3180
tttctctgaa agacataagg ttaacttatt gatcgcttct aaacaaccaa gacaacaatg    3240
gttcactgtt gaagaagctg aagtcttagc taacgaaggt ttgaagatta tcgattgggc    3300
ttctactgct ccatcttccg atgttgatat tacttttgct tctgccggta ctgaaccaac    3360
cattgagact ttggccgcct tatggttgat taatcaagct ttccctgacg ttaagtttag    3420
atacgttaac gttgttgaat tgttaagatt gcaaaagaaa tctgaaccaa acatgaacga    3480
cgaaagagaa ttatctgccg aagaatttaa taagtacttc aagccgaca ctccagttat     3540 cttcggtttc cacgcttacg aaaacttgat tgaatctttc ttttttcgaga gaaagttcac    3600 cggtgatgtc tatgttcacg gttatagaga agatggtgat atcactacca cctacgatat    3660
gagagtctat tcccacttgg atcgtttcca tcaagccaag gaagccgccg aaatcttgtc    3720
tgctaacggt aaaatcgacc aagccgctgc cgacaccttt attgctaaga tggacgacac    3780
tttggccaaa cacttccaag ttactagaaa tgaaggtaga gatattgaag aattcactga    3840
ctggacttgg tctccattga gtaagtgaa  tttactttaa atcttgcatt taaataaatt    3900 ttcttttat  agctttatga cttagtttca atttatatac tattttaatg acattttcga    3960
ttcattgatt gaaagctttg tgttttttct tgatgcgcta ttgcattgtt cttgtctttt    4020
tcgccacatg taatatctgt agtagatacc tgatacattg tggatgctga gtgaaatttt    4080
agttaataat ggaggcgctc ttaataattt tggggatatt ggcttatccc cgcgtgcttg    4140
gccggccgta cgaaaatcgt tattgtcttg aaggtgaaat ttctactctt attaatggtg    4200
aacgttaagc tgatgctatg atggaagctg attggtctta acttgcttgt catcttgcta    4260
atggtcattg gctcgtgtta ttacttaagt tatttgtact cgttttgaac gtaatgctaa    4320
tgatcatctt atgaataat  agtgagtggt ttcagggtcc ataaagcttt tcaattcatc    4380 ttttttttt  ttgttctttt ttttgattcc ggtttctttg aaattttttt gattcggtaa    4440
tctccgagca gaaggaagaa cgaaggaagg agcacagact tagattggta tatatacgca    4500
tatgtggtgt tgaagaaaca tgaaattgcc cagtattctt aacccaactg cacagaacaa    4560
aaacctgcag gaaacgaaga taatcatgt  cgaaagctac atataaggaa cgtgctgcta    4620
ctcatcctag tcctgttgct gccaagctat ttaatatcat gcacgaaaag caaacaaact    4680
tgtgtgcttc attggatgtt cgtaccacca aggaattact ggagttagtt gaagcattag    4740
gtcccaaaat ttgtttacta aaaacacatg tggatatctt gactgatttt tccatggagg    4800
gcacagttaa gccgctaaag gcattatccg ccaagtacaa tttttactc  ttcgaagaca    4860 gaaaatttgc tgacattggt aatacagtca aattgcagta ctctgcgggt gtatacagaa    4920
tagcagaatg ggcagacatt acgaatgcac acggtgtggt gggcccaggt attgttagcg    4980
gtttgaagca ggcggcggaa gaagtaacaa aggaacctag aggccttttg atgttagcag    5040
aattgtcatg caagggctcc ctagctactg gagaatatac taagggtact gttgacattg    5100
cgaagagtga caaagatttt gttatcggct ttattgctca aagagacatg ggtgaagag     5160 atgaaggtta cgattggttg attatgacac ccggtgtggg tttagatgac aagggagacg    5220
cattgggtca acagtataga accgtggatg atgtggtctc tacaggatct gacattatta    5280
ttgttggaag aggactattt gcaagggaa  gggatgctaa ggtagagggt gaacgttaca    5340
gaaaagcagg ctgggaagca tatttgagaa gatgcggcca gcaaaactaa aaaactgtat    5400
```

```
tataagtaaa tgcatgtata ctaaactcac aaattagagc ttcaatttaa ttatatcagt    5460
tattaccacg aaaatcgtta ttgtcttgaa ggtgaaattt ctactcttat taatggtgaa    5520
cgttaagctg atgctatgat ggaagctgat tggtcttaac ttgcttgtca tcttgctaat    5580
ggtcatatgg ctcgtgttat tacttaagtt atttgtactc gttttgaacg taatgctaat    5640
gatcatctta tggaataata gtgaacggcc ggccaagcac gcggggatgg gatgagcttg    5700
gagcaggaag aatacactat actgatctaa agagtacaa tagatggata agaatattgg     5760
cagcgcaaaa aggcttcaag cttacacaac acggtttatt tcgaaataat atccttctcg    5820
aaagctttaa cgaacgcaga attttcgagt tattaaactt aaaatacgct gaacccgaac    5880
atagaaatat cgatgggaa aaaaaaactg cataaaggca ttaaaagagg agcgaatttt     5940
tttttaataa aaatcttaat aatcattaaa agataaataa tagtctatat atacgtatat    6000
aaataaaaaa tattcaaaaa ataaaataaa ctattatttt agcgtaaagg atggggaaag    6060
agaaaagaaa aaaattgatc tatcgatttc aattcaattc aatagatctt tatccttgtg    6120
cttgtgcctg aactgcggta acggcaacaa ctttgacgat gtcgtcgact gaacatcccc    6180
ttgacaaatc gttgataggt ttggcaaatc cctgacatat aggaccgatg gcttcggcct    6240
ttgcgaatct ttggaccaac ttgtatccga tgtttcctgc ctggatgtct gggaagatca    6300
agacatttgc cttaccagcg actttagatc caggggcttt caaatctgcg accttcttaa    6360
ccaatgaggc gtctaactgc aattcaccgt cgatgtctaa gtcaggccta gcctccttag    6420
ccaattttgt tgccttttgta accttgtcga ctaattcatg tgaggctgat cccatggttg    6480
agaatgacaa catggctacc cttggctcga tcttgcacaa attctttgca gtctcagcag    6540
tggtaattgc gattgaagat aactcttcag cggtaggaca aacatttaca gcgcagtcag    6600
cgaataacaa aaaccgtcc tctccatact cgcagtcagg tactgacatc aagaagactg     6660
atgagacgac agatgcacct ggtactgttt tgacaatctg caaaccaggc cttaacaagt    6720
ctcctgtagt atgtatagca ccagatacca aaccgtcagc gtcacctaac ttgaccatca    6780
ttgttgcgaa gtagattggg tccctgacga ttttgtcagc cttctccaag gtgactccct    6840
tgttttttct gatctcgtag aaagcgttgg cgtaaccggc ggtcttagaa gaagtttctg    6900
ggtcgactat ctctactccg gccaaattta ctccgaattt gcggcgtttt ccttaatga    6960 cagactctga accgaccaag attatgtcgg caataccgtc cctaataatc tcctctgaag    7020
ccctgatgtt cctctcttcc tcaccctctg ccaaaacgat tttcttcttg tcggccttgg    7080
ccaatccgaa gatattctcc atcaatttca ttgtgaaggt agttcgattt tggaggtcgc    7140
gggaggtcga aactaagttc ttggtgtttt aaaactaaaa aaaagactaa ctataaaagt    7200
agaatttaag aagtttaaga aatagattta cagaattaca atcaatacct accgtcttta    7260
tatacttatt agtcaagtag gggaataatt tcagggaact ggtttcaacc ttttttttca    7320
gcttttccca aatcagagag agcagaaggt aatagaaggt gtaagaaaat gagatagata    7380
catgcgtggg tcaattgcct tgtgtcatca tttactccag gcaggttgca tcactccatt    7440
gaggttgtgc ccgttttttg cctgtttgtg cccctgttct ctgtagttgc gctaagagaa    7500
tggacctatg aactgatggt tggtgaagaa acaatatttt ggtgctggg attctttttt     7560 tttctggatg ccagcttaaa aagcgggctc cattatattt agtggatgcc aggaataaac    7620
tgttcaccca gacacctacg atgttatata ttctgtgtaa cccgcccct atttgggca      7680 tgtacgggtt acagcagaat taaaaggcta atttttgac taaataaagt taggaaaatc     7740
```

-continued

| | |
|---|---|
| actactatta attatttacg tattctttga aatggcagta ttgataatga taaactcgaa | 7800 |
| ctgaaaaagc gtgttttta ttcaaaatga ttctaactcc cttacgtaat caaggaatct | 7860 |
| ttttgccttg gcctccgcgt cattaaactt cttgttgttg acgctaacat tcaacgctag | 7920 |
| tatatattcg ttttttttcag gtaagttctt ttcaacgggt cttactgatg aggcagtcgc | 7980 |
| gtctgaaagg tccgccggcg ttggacgagc gctccatgct ggacttactc gtcgaagatt | 8040 |
| tcctgctact ctctatataa ttagacaccc atgttataga tttcagaaaa caatgtaata | 8100 |
| atatatggta gcctcctgaa actaccaagg gaaaaatctc aacaccaaga gctcatattc | 8160 |
| gttggaatag cgataatatc tctttacctc aatcttatat gcatgttatt tgctcttata | 8220 |
| attggtctct atttagggaa aaaagtcggt ttgagagctt ctcgcgatgt gaaatctcaa | 8280 |
| tttgaactgc acgccaaagc tagcccattt cacgaacacc agaaagaaga aatccccaag | 8340 |
| gatcgcatga cagagtatgc tctctcatat cgttgagtat gaatgccaat acactgatca | 8400 |
| gctttacaag aaacgtaaaa tctggcacga tggtagactg aaatactttc agttaaacaa | 8460 |
| cagattcatg cttatacgg aaaaggataa cgttttgtta gctagtgagg cggtttaaac | 8520 |
| gcgtggccgt gccgtc | 8536 |

<210> SEQ ID NO 31
<211> LENGTH: 9734
<212> TYPE: DNA
<213> ORGANISM: Artificial Sequence
<220> FEATURE:
<223> OTHER INFORMATION: Synthetic: i74810 integration construct

<400> SEQUENCE: 31

| | |
|---|---|
| gacggcacgg ccacgcgttt aaaccgcccg ctcgcctcat ccccacggga ataaggcagc | 60 |
| cgacaaaaga aaacgaccg aaaaggaacc agaaagaaaa aagagggtgg gcgcgccgcg | 120 |
| gacgtgtaaa aagatatgca tccagcttct atatcgcttt aactttaccg ttttgggcat | 180 |
| cgggaacgta tgtaacattg atctcctctt gggaacggtg agtgcaacga atgcgatata | 240 |
| gcaccgacca tgtgggcaaa ttcgtaataa attcggggtg aggggggattc aagacaagca | 300 |
| accttgttag tcagctcaaa cagcgattta acggttgagt aacacatcaa acaccgttc | 360 |
| gaggtcaagc ctggcgtgtt taacaagttc ttgatatcat atataaatgt aataagaagt | 420 |
| ttggtaatat tcaattcgaa gtgttcagtc ttttacttct cttgttttat agaagaaaaa | 480 |
| acatcaagaa acatctttaa catacacaaa cacatactat cagaatacac gctcgtccaa | 540 |
| cgccggcgga cctttcagac gcgactgcct catcagtaag acccgttgaa aagaacttac | 600 |
| ctgaaaaaa cgaatatata ctagcgttga atgttagcgt caacaacaag aagtttaatg | 660 |
| acgcggaggc caaggcaaaa agattccttg attacgtaag ggagttagaa tcattttgaa | 720 |
| taaaaaacac gctttttcag ttcgagttta tcattatcaa tactgccatt tcaaagaata | 780 |
| cgtaaataat taatagtagt gattttccta actttattta gtcaaaaaat tagccttta | 840 |
| attctgctgt aacccgtaca tgcccaaaat aggggggcggg ttacacagaa tatataacat | 900 |
| cgtaggtgtc tgggtgaaca gtttattcct ggcatccact aaatataatg gagcccgctt | 960 |
| tttaagctgg catccagaaa aaaaagaat cccagcacca aaatattgtt tcttcacca | 1020 |
| accatcagtt cataggtcca ttctcttagc gcaactacag agaacagggg cacaaacagg | 1080 |
| caaaaaacgg gcacaacctc aatgagtga tgcaacctgc ctggagtaaa tgatgacaca | 1140 |
| aggcaattga cccacgcatg tatctatctc attttcttac accttctatt accttctgct | 1200 |
| ctctctgatt tggaaaaagc tgaaaaaaaa ggttgaaacc agttccctga aattattccc | 1260 |

```
ctacttgact aataagtata taaagacggt aggtattgat tgtaattctg taaatctatt    1320
tcttaaactt cttaaattct acttttatag ttagtctttt ttttagtttt aaaacaccaa    1380
gaacttagtt tcgacctccc gcgacctcca aaatcgaact accttcacaa tggctgattt    1440
cgattctaaa gaatacttgg agttagttga caagtggtgg cgtgccacca actacttgtc    1500
cgctggtatg attttcttga agtccaaccc attattctct gttactaata ccccaatcaa    1560
ggccgaagat gtcaaagtta aaccaattgg tcactggggt actatttccg gtcaaacttt    1620
cttatacgcc cacgctaacc gtttgattaa caagtacggt ctcaacatgt tttacgttgg    1680
tggtccaggt cacggtggtc aagtcatggt tactaacgcc tacttagacg gtgcctacac    1740
cgaagattac ccagaaatta ctcaagacat cgaaggtatg tctcatttgt tcaagcgttt    1800
ctcttttccct ggtggtattg gttcccatat gaccgctcaa actccaggtt ccttgcacga    1860
aggtggtgaa ttgggttact ctttgtccca tgctttcggt gctgttttgg acaacccaga    1920
ccaagttgct tttgctgtcg ttggtgatgg tgaagctgaa actggtccat ctatggcctc    1980
ttggcattcc attaagttct taaatgccaa gaacgatggt gccgttttgc cagttttgga    2040
tttaaacggt ttcaagattt ccaatccaac cattttttct agaatgtctg atgaagaaat    2100
tactaagttc ttcgaaggtt tgggttattc ccctagattc attgaaaatg atgacattca    2160
cgactacgcc acctaccacc aattggccgc taacatctta gatcaagcca tcgaagacat    2220
tcaagctatt caaaatgacg ccagagagaa tggtaaatat caagatggtg aaattccagc    2280
ttggcctgtt attatcgcta gattgccaaa gggttgggt ggtccaaccc acgatgcttc    2340
taataatcca attgaaaact cttttcagagc tcaccaagtt ccattaccat ggaacaaca    2400
cgatttggcc accttgccag aattcgaaga ttggatgaac tcttacaagc cagaagaatt    2460
attcaacgct gatggttcct tgaaggatga gttgaaagct attgccccaa agggtgataa    2520
gagaatgtct gctaacccaa tcaccaacgg tggtgctgac agatccgact tgaaattgcc    2580
aaaattggaga gaattcgcta acgacatcaa cgacgatacc agaggtaagg aattcgctga    2640
ctctaagaga aacatggata tggctacttt atccaactat ttaggtgccg tttctcaatt    2700
gaacccaacc agattcagat tcttcggtcc agatgaaacc atgtccaaca gattgtgggg    2760
tttgtttaat gttaccccac gtcaatggat ggaagaaatc aaggaaccac aagatcaatt    2820
gttgtctcca actggtcgta tcatcgattc ccaattgtct gaacaccaag ctgaaggttg    2880
gttggaaggt tacactttga ctggtagagt tggtatcttt gcctcttacg aatctttctt    2940
gagagttgtt gataccatgg tcactcaaca tttcaagtgg ttgcgtcacg cttccgaaca    3000
agcttggaga aatgactatc catccttaaa tttgatcgct acctctaccg ctttccaaca    3060
agatcataac ggttatactc accaagaccc tggtatgtta actcatttgg ccgagaagaa    3120
gtctaacttc attagagaat atttgccagc cgacggtaac tctttgttag ccgttcaaga    3180
gagagctttc tctgaaagac ataaggttaa cttattgatc gcttctaaac aaccaagaca    3240
acaatggttc actgttgaag aagctgaagt cttagctaac gaaggtttga agattatcga    3300
ttgggcttct actgctccat cttccgatgt tgatattact tttgcttctg ccggtactga    3360
accaaccatt gagactttgg ccgccttatg gttgattaat caagctttcc ctgacgttaa    3420
gtttagatac gttaacgttg ttgaattgtt aagattgcaa aagaaatctg aaccaaacat    3480
gaacgacgaa agagaattat ctgccgaaga atttaataag tacttccaag ccgcactcc    3540
agttatcttc ggtttccacg cttacgaaaa cttgattgaa tctttctttt tcgagagaaa    3600
```

```
gttcaccggt gatgtctatg ttcacggtta tagagaagat ggtgatatca ctaccaccta      3660
cgatatgaga gtctattccc acttggatcg tttccatcaa gccaaggaag ccgccgaaat      3720
cttgtctgct aacggtaaaa tcgaccaagc cgctgccgac acctttattg ctaagatgga      3780
cgacactttg gccaaacact tccaagttac tagaaatgaa ggtagagata ttgaagaatt      3840
cactgactgg acttggtctc cattgaagta agtgaattta ctttaaatct tgcatttaaa      3900
taaattttct ttttatagct ttatgactta gtttcaattt atatactatt ttaatgacat      3960
tttcgattca ttgattgaaa gctttgtgtt ttttcttgat gcgctattgc attgttcttg      4020 tcttttcgc cacatgtaat atctgtagta gatacctgat acattgtgga tgctgagtga      4080
aattttagtt aataatggag gcgctcttaa taattttggg gatattggct tatccccgcg      4140
tgcttggccg gccgtacact gagtaatggt agttataaga aagagaccga gttaggagca      4200
gttagaggcg gtggagatat tccttatggc atgtctggcg atgataaaac ttttcaaacg      4260
gcagccccga tctaaaagag ctgacaggga aatggtcaga aaaagaaacg tgcacccgcc      4320
cgtctggacg cgccgctcac ccgcacggca gagaccaatc agtaaaaatc aacggttaac      4380
gacattacta tatatataat ataggaagca tttaatagaa cagcatcgta atatatgtgt      4440
actttgcagt tatgacgcca gatggcagta gtggaagata ttctttattg aaaaatagct      4500 tgtcaccttta cgtacaatct tgatccggag cttttctttt tttgccgatt aagaattcgg      4560
tcgaaaaaag aaaaggagag ggccaagagg gagggcattg gtgactattg agcacgtgag      4620
tatacgtgat taagcacaca aaggcagctt ggagtatgtc tgttattaat ttcacaggta      4680
gttctggtcc attggtgaaa gtttgcggct tgcagagcac agaggccgca gaatgtgctc      4740
tagattccga tgctgacttg ctgggtatta tatgtgtgcc caatagaaag agaacaattg      4800
acccggttat tgcaaggaaa aattcaagtc ttgtaaaagc atataaaaat agttcaggca      4860
ctccgaaata cttggttggc gtgtttcgta atcaacctaa ggaggatgtt ttggctctgg      4920
tcaatgatta cggcattgat atcgtccaac tgcatggaga tgagtcgtgg caagaatacc      4980
aagagttcct cggtttgcca gttattaaaa gactcgtatt tccaaaagac tgcaacatac      5040
tactcagtgc agcttcacag aaacctcatt cgtttattcc cttgtttgat tcagaagcag      5100
gtgggacagg tgaacttttg gattggaact cgatttctga ctgggttgga aggcaagaga      5160
gccccgaaag cttacatttt atgttagctg gtggactgac gccagaaaat gttggtgatg      5220
cgcttagatt aaatggcgtt attggtgttg atgtaagcgg aggtgtggag acaaatggtg      5280
taaaagactc taacaaaata gcaaatttcg tcaaaaatgc taagaaatag gttattactg      5340
agtagtattt atttaagtat tgtttgtgca cttgcctgca ggccttttga aaagcaagca      5400
taaaagatct aaacataaaa tctgtaaaat aacaagatgt aaagataatg ctaaatcatt      5460
tggcttttta attgattgta caggaaaata tacatcgcag ggggttgact tttaccattt      5520
caccgcaatg gaatcaaact tgttgaagag aatgttcaca ggcgcatacg ctacaatgac      5580
acggccggcc aagcacgcgg ggataagcca atatccccaa aattattaag agcgcctcca      5640
ttattaacta aaatttcact cagcatccac aatgtatcag gtatctacta cagatattac      5700
atgtggcgaa aaagacaaga acaatgcaat agcgcatcaa gaaaaaacac aaagctttca      5760
atcaatgaat cgaaaatgtc attaaaatag tatataaatt gaaactaagt cataaagcta      5820 taaaagaaa atttatttaa atgcaagatt taaagtaaat tcacttactt caatggagac      5880
caagtccagt cagtgaattc ttcaatatct ctaccttcat ttctagtaac ttggaagtgt      5940
ttggccaaag tgtcgtccat cttagcaata aaggtgtcgg cagcggcttg gtcgatttta      6000
```

```
ccgttagcag acaagatttc ggcggcttcc ttggcttgat ggaaacgatc caagtgggaa    6060
tagactctca tatcgtaggt ggtagtgata tcaccatctt ctctataacc gtgaacatag    6120
acatcaccgg tgaactttct ctcgaaaaag aaagattcaa tcaagttttc gtaagcgtgg    6180
aaaccgaaga taactggagt gtcggcttgg aagtacttat taaattcttc ggcagataat    6240
tctctttcgt cgttcatgtt tggttcagat ttcttttgca atcttaacaa ttcaacaacg    6300
ttaacgtatc taaacttaac gtcagggaaa gcttgattaa tcaaccataa ggcggccaaa    6360
gtctcaatgg ttggttcagt accggcagaa gcaaaagtaa tatcaacatc ggaagatgga    6420
gcagtagaag cccaatcgat aatcttcaaa ccttcgttag ctaagacttc agcttcttca    6480
acagtgaacc attgttgtct tggttgttta gaagcgatca ataagttaac cttatgtctt    6540
tcagagaaag ctctctcttg aacgctaac aaagagttac cgtcggctgg caaatattct     6600
ctaatgaagt tagacttctt ctcggccaaa tgagttaaca taccagggtc ttggtgagta    6660
taaccgttat gatcttgttg gaaagcggta gaggtagcga tcaaatttaa ggatggatag    6720
tcatttctcc aagcttgttc ggaagcgtga cgcaaccact tgaaatgttg agtgaccatg    6780
gtatcaacaa ctctcaagaa agattcgtaa gaggcaaaga taccaactct accagtcaaa    6840
gtgtaacctt ccaaccaacc ttcagcttgg tgttcagaca attgggaatc gatgatacga    6900
ccagttggag acaacaattg atcttgtggt tccttgattt cttccatcca ttgacgtggg    6960
gtaacattaa acaaccccca caatctgttg gacatggttt catctggacc gaagaatctg    7020
aatctggttg ggttcaattg agaaacggca cctaaatagt tggataaagt agccatatcc    7080
atgtttctct tagagtcagc gaattcctta cctctggtat cgtcgttgat gtcgttagcg    7140
aattctctcc aatttggcaa tttcaagtcg gatctgtcag caccaccgtt ggtgattggg    7200
ttagcagaca ttctcttatc accctttggg gcaatagctt tcaactcatc cttcaaggaa    7260
ccatcagcgt tgaataattc ttctggcttg taagagttca tccaatcttc gaattctggc    7320
aaggtggcca atcgtgttg ttccaatggt aatggaactt ggtgagctct gaaagagttt     7380
tcaattggat tattgaaagc atcgtgggtt ggaccacccc aacccttttgg caatctagcg    7440 ataataacag gccaagctgg aatttcacca tcttgatatt taccattctc tctggcgtca    7500
ttttgaatag cttgaatgtc ttcgatggct tgatctaaga tgttagcggc caattggtgg    7560
taggtggcgt agtcgtgaat gtcatcattt tcaatgaatc taggggaata acccaaacct    7620
tcgaagaact tagtaatttc ttcatcagac attctagaaa aaatggttgg attggaaatc    7680
ttgaaaccgt ttaaatccaa aactggcaaa acggcaccat cgttcttggc atttaagaac    7740
ttaatggaat gccaagaggc catagatgga ccagtttcag cttcaccatc accaacgaca    7800
gcaaaagcaa cttggtctgg gttgtccaaa acagcaccga agcatggga caaagagtaa     7860 cccaattcac caccttcgtg caaggaacct ggagtttgag cggtcatatg gaaccaata     7920 ccaccaggga aagagaaacg cttgaacaaa tgagacatac cttcgatgtc ttgagtaatt    7980
tctgggtaat cttcggtgta ggcaccgtct aagtaggcgt tagtaaccat gacttgacca    8040
ccgtgacctg gaccaccaac gtaaaacatg ttgagaccgt acttgttaat caaacggtta    8100
gcgtgggcgt ataagaaagt ttgaccggaa atagtacccc agtgaccaat ggtttaact     8160 ttgacatctt cggccttgat tggggtatta gtaacagaga ataatgggtt ggacttcaag    8220
aaaatcatac cagcggacaa gtagttggtg gcacgccacc acttgtcaac taactccaag    8280
tattctttag aatcgaaatc agccattgtg aaggtagttc gattttggag gtcgcgggag    8340
```

```
gtcgaaacta agttcttggt gttttaaaac taaaaaaaag actaactata aaagtagaat    8400
ttaagaagtt taagaaatag atttacagaa ttacaatcaa tacctaccgt ctttatatac    8460
ttattagtca agtaggggaa taatttcagg gaactggttt caaccttttt tttcagcttt    8520
ttccaaatca gagagagcag aaggtaatag aaggtgtaag aaaatgagat agatacatgc    8580
gtgggtcaat tgccttgtgt catcatttac tccaggcagg ttgcatcact ccattgaggt    8640
tgtgcccgtt ttttgcctgt ttgtgcccct gttctctgta gttgcgctaa gagaatggac    8700
ctatgaactg atggttggtg aagaaaacaa tattttggtg ctgggattct tttttttttct   8760 ggatgccagc ttaaaaagcg ggctccatta tatttagtgg atgccaggaa taaactgttc    8820
acccagacac ctacgatgtt atatattctg tgtaacccgc cccctatttt gggcatgtac    8880
gggttacagc agaattaaaa ggctaatttt ttgactaaat aaagttagga aaatcactac    8940
tattaattat ttacgtattc tttgaaatgg cagtattgat aatgataaac tcgaactgaa    9000
aaagcgtgtt ttttattcaa aatgattcta actcccttac gtaatcaagg aatcttttg    9060 ccttggcctc cgcgtcatta aacttcttgt tgttgacgct aacattcaac gctagtatat    9120
attcgttttt ttcaggtaag ttcttttcaa cgggtcttac tgatgaggca gtcgcgtctg    9180
aaaggtccgc cggcgttgga cgagcgtgta ccaacctgca tttctttccg tcatatacac    9240
aaaatacttt catataaact tacttggtct tacgtcataa ataaatatgt atacatataa    9300
attaaaaaat ttggttttat atttttacaa aaagaatcgt ttacttcatt tctccctttt    9360
aagcgataca atccatgaaa aaagagaaaa agagagaaca ggcttgtgcc ttctttaaaa    9420
catcccacac aaaatcatat tgaattgaat tttacatctt aagctagtgt acaacaactg    9480
ctatatccaa agaaaactaa cgtggaccgc ttttagagtt gagaaaaagg tttgaaaaaa    9540
atagcaatac aaagacttgt ttcatatata aaatacaggg agcacattga gctaatataa    9600
cataaacact gcgaaccaat tccaatcaaa aggtacacat gagagcattc ccccgagtac    9660
tgccatttcg ccatcagaga tcatataata acatccttct tcgaacggcg gtttaaacgc    9720
gtggccgtgc cgtc                                                       9734
```

<210> SEQ ID NO 32
<211> LENGTH: 7980
<212> TYPE: DNA
<213> ORGANISM: Artificial Sequence
<220> FEATURE:
<223> OTHER INFORMATION: Synthetic: i76221 integration construct

<400> SEQUENCE: 32

```
gacggcacgg ccacgcgttt aaaccgccgc acgtgtatgt acggctgtgt aaatatgata     60
atcatctcgg acgaacggcg tagtactctc catcccctaa aaatgttcac gtgtgactgc    120
tccatttcgc cggatgtcga gatgacccc ccccctcaaa aggcactcac ctgctgacat     180
gccgtggcaa atgattgggg tcatcctttt tttctgttat ctctaagatc caaagaaaag    240
taaaaaaaaa aggttggggt acgaattgcc gccgagcctc cgatgccatt attcaatggg    300
tattgcagtt ggggtatagt tcctcggtgg caaatagttc tcccttcatt ttgtatataa    360
actgggcggc tattctaagc atatttctcc cttaggttat ctggtagtac gttatatctt    420
gttcttatat tttctatcta taagcaaaac caaacatatc aaaactacta gaaagacatt    480
gccccactgt gttcgctcgt ccaacgccgg cggacctttc agacgcgact gcctcatcag    540
taagacccgt tgaaaagaac ttacctgaaa aaaacgaata tatactagcg ttgaatgtta    600
gcgtcaacaa caagaagttt aatgacgcgg aggccaaggc aaaaagattc cttgattacg    660
```

```
taagggagtt agaatcattt tgaataaaaa acacgctttt tcagttcgag tttatcatta      720
tcaatactgc catttcaaag aatacgtaaa taattaatag tagtgatttt cctaacttta      780
tttagtcaaa aaattagcct tttaattctg ctgtaacccg tacatgccca aaatagggg       840 cgggttacac agaatatata acatcgtagg tgtctgggtg aacagtttat tcctggcatc      900
cactaaatat aatggagccc gcttttaag ctggcatcca gaaaaaaaaa gaatcccagc       960
accaaaatat tgttttcttc accaaccatc agttcatagg tccattctct tagcgcaact     1020
acagagaaca ggggcacaaa caggcaaaaa acgggcacaa cctcaatgga gtgatgcaac     1080
ctgcctggag taaatgatga cacaaggcaa ttgacccacg catgtatcta tctcattttc     1140
ttacaccttc tattaccttc tgctctctct gatttggaaa aagctgaaaa aaaaggttga     1200
aaccagttcc ctgaaattat tcccctactt gactaataag tatataaaga cggtaggtat     1260
tgattgtaat tctgtaaatc tatttcttaa acttcttaaa ttctacttttt atagttagtc    1320 ttttttttag tttaaaaaca ccaagaactt agtttcgacc tcccgcgacc tccaaaatcg     1380
aactaccttc acaatggaac attctgtaat cgaaccaact gtgcccatgc cgctaccagc     1440
catgtttgac gctccatctg gtattttag ctctttggac gacgctgtgc aagcagccac      1500
cttagcccaa caacaactaa gttcagttga gttgcgtcag caagtaatca aagccataag     1560
agtggccgga gaaggtatg cacaagtttt ggctgaaatg gcagttgctg aaactggtat      1620
gggtagggtg gtggataagt acattaagaa tgtctctcaa gctcgtcata cgcctggtat     1680
agaatgttta tcggccgagg ttcttacggg tgataatggc ctaacattga ttgaaaatgc     1740
cccttgggga gtcgtagctt cagtcacgcc aagcacaaat ccagcagcta cggtaattaa     1800
taatgcaatc tcaatgattg cagcggggaa ttcagtcgtg ttcgcaccac atccttctgc     1860
caaaaacgtc tcactaagga ctatttcttt actcaacaag gccattgtcg ctaccggcgg     1920
cccagaaaat ttactagtta gtgtggcaaa ccctaacatc gaaactgcac agagattatt     1980
cagatatccg ggtattggat tgttagttgt gacaggtggt gaagccgtcg ttgaagccgc     2040
taggaagcat acagataaaa ggttaattgc agccggcgct ggtaatcctc tgttgttgt      2100 ggacgaaact gctgacatac ctaaagccgc aagagcaatt gtcaagggtg cttctttcga     2160
caacaacata atttgtgctg atgaaaaagt tttgattgtg gtagacagag ttgcagatgc     2220
actattggca gaaatgcaaa gaataacgc cgtcttactt acacccgaac agaccgaaag      2280
actactaccc gctcttttgt ccgatattga cgaacagggc aaaggacgtg tgaatagaga     2340
ttatgttgga agagatgcgg ctaaattagc agcggctatt ggtctggaag ttagcgaaca     2400
tactcgtcta ctcctggcag agacagacgc tgatcatcca ttcgccgtga cggagctgat     2460
gatgccagtg ttaccagtaa taagagtcaa gaatgtagat gatgcaatcg cattggcagt     2520
taagctagag tcaggctgca gacacacagc tgcgatgcac tctactaata taagaaactt     2580
aaatagaatg gctaatgcca tcaatacctc tatctttgta aaaaatggtc catgtattgc     2640
aggtttgggt ttaggcggtg aaggttggac ttcaatgact attagcactc cgaccggtga     2700
aggtgttaca agcgctcgta cctttgtcag attaagaagg tgtgtcttag tcgacatgtt     2760
tcggattgct taagcggccg cgagtaataa ttattgcttc catataatat ttttatatac     2820
ctcttatttt tatgtattag ttaattaagt atttttatct atctgcttat catttctttt     2880 tcatatagg ggggttggtg ttttcttgcc catcagattg atgtcctcca actcggcact      2940
attttacaaa gggtttttt gtaagagaag gagaagacag atactaaacc atacgttact      3000
```

```
cgaaacaaaa aaaaaaaaaa tggaaaaagc tgctatcaac aaaagacggc ctcatcaaac    3060
ctaaagaaac catgtcagcg tatgtatata ccttgtaatt tacgtttcct taaatcttct    3120
ttctactaac gttttcatta ttctatactc tatgaccaat aaaacagac tgtactttca     3180
aaatttaccc agtaggccag caaataaaga aaattatacc agattacttc tgaaacacat    3240
taatcccaac aacaagtatg ccattaatcc gtcgctaccc catcccgcg tgcttggccg     3300
gccgtttctc gacgtgggcc ttttcttgc catatggatc cgctgcacgg tcctgttccc     3360
tagcatgtac gtgagcgtat ttccttttaa accacgacgc tttgtcttca ttcaacgttt    3420
cccattgttt ttttctacta ttgctttgct gtgggaaaaa cttatcgaaa gatgacgact    3480
ttttcttaat tctcgtttta agagcttggt gagcgctagg agtcactgcc aggtatcgtt    3540
tgaacacggc attagtcagg gaagtcataa cacagtcctt tcccgcaatt ttcttttct     3600
attactcttg gcctcctcta gtacactcta tatttttta tgcctcggta atgattttca     3660
tttttttttt tccacctagc ggatgactct ttttttttct tagcgattgg cattatcaca    3720
taatgaatta tacattatat aaagtaatgt gatttcttcg aagaatatac taaaaaatga    3780
gcaggcaaga taaacgaagg caaagatgac agagcagaaa gccctagtaa agcgtattac    3840
aaatgaaacc aagattcaga ttgcgatctc tttaaagggt ggtcccctag cgatagagca    3900
ctcgatcttc ccagaaaaag aggcagaagc agtagcagaa caggccacac aatcgcaagt    3960
gattaacgtc cacacaggta tagggtttct ggaccatatg atacatgctc tggccaagca    4020
ttccggctgg tcgctaatcg ttgagtgcat tggtgactta cacatagacg accatcacac    4080
cactgaagac tgcgggattg ctctcggtca gcttttaaa gaggccctag gggccgtgcg     4140
tggagtaaaa aggtttggat caggatttgc gcctttggat gaggcacttt ccagagcggt    4200
ggtagatctt tcgaacaggc cgtacgcagt tgtcgaactt ggtttgcaaa gggagaaagt    4260
aggagatctc tcttgcgaga tgatcccgca ttttcttgaa agctttgcag aggctagcag    4320
aattaccctc cacgttgatt gtctgcgagg caagaatgat catcaccgta gtgagagtgc    4380
gttcaaggct cttgcggttg ccataagaga agccacctcg cccaatggta ccaacgatgt    4440
tccctccacc aaaggtgttc ttatgtagtg acaccgatta tttaaagctg cagcatacga    4500
tatatataca tgtgtatata tgtataccta tgaatgtcag taagtatgta tacgaacagt    4560
atgatactga agatgacaag gtaatgcatc attctatacg tgtcattctg aacgaggcgc    4620
gctttccttt tttcttttg cttttctctt ttttttctct tgaactcgac ggccggccaa    4680
gcacgcgggg atggggtagc gacggattaa tggcatactt gttgttggga ttaatgtgtt    4740
tcagaagtaa tctggtataa ttttctttat ttgctggcct actgggtaaa ttttgaaagt    4800
acagtctgtt tttattggtc atagagtata gaataatgaa aacgttagta gaaagaagat    4860
ttaaggaaac gtaaattaca aggtatatac atacgctgac atggtttctt taggtttgat    4920
gaggccgtct tttgttgata gcagcttttt ccatttttt tttttttgtt tcgagtaacg    4980
tatggtttag tatctgtctt ctccttctct tacaaaaaaa ccctttgtaa aatagtgccg    5040
agttggagga catcaatctg atgggcaaga aaacaccaac ccccctata tgaaaagaaa     5100
atgataagca gatagataaa aatacttaat taactaatac ataaaaataa gaggtatata    5160
aaaatattat atggaagcaa taattattac tcgcggccgc ttaagcaatc cgaaacatgt    5220
cgactaagac acaccttctt aatctgacaa aggtacgagc gcttgtaaca ccttcaccgg    5280
tcggagtgct aatagtcatt gaagtccaac cttcaccgcc taaacccaaa cctgcaatac    5340
atggaccatt ttttacaaag atagaggtat tgatggcatt agccattcta tttaagtttc    5400
```

```
ttatattagt agagtgcatc gcagctgtgt gtctgcagcc tgactctagc ttaactgcca    5460
atgcgattgc atcatctaca ttcttgactc ttattactgg taacactggc atcatcagct    5520
ccgtcacggc gaatggatga tcagcgtctg tctctgccag gagtagacga gtatgttcgc    5580
taacttccag accaatagcc gctgctaatt tagccgcatc tcttccaaca taatctctat    5640
tcacacgtcc tttgccctgt tcgtcaatat cggacaaaag agcgggtagt agtctttcgg    5700
tctgttcggg tgtaagtaag acggcgttat ttctttgcat ttctgccaat agtgcatctg    5760
caactctgtc taccacaatc aaaactttt catcagcaca aattatgttg ttgtcgaaag     5820 aagcacccctt gacaattgct cttgcggctt taggtatgtc agcagtttcg tccacaacaa   5880
caggaggatt accagcgccg gctgcaatta accttttatc tgtatgcttc ctagcggctt    5940
caacgacggc ttcaccacct gtcacaacta acaatccaat acccggatat ctgaataatc    6000
tctgtgcagt ttcgatgtta gggtttgcca cactaactag taaattttct gggccgccgg    6060
tagcgacaat ggccttgttg agtaaagaaa tagtccttag tgagacgttt ttggcagaag    6120
gatgtggtgc gaacacgact gaattccccg ctgcaatcat tgagattgca ttattaatta    6180
ccgtagctgc tggatttgtg cttggcgtga ctgaagctac gactcccccaa ggggcatttt   6240 caatcaatgt taggccatta tcacccgtaa gaacctcggc cgataaacat tctataccag    6300
gcgtatgacg agcttgagag acattcttaa tgtacttatc caccacccta cccataccag    6360
tttcagcaac tgccatttca gccaaaactt gtgcatacct ttctccggcc actcttatgg    6420
ctttgattac ttgctgacgc aactcaactg aacttagttg ttgttgggct aaggtggctg    6480
cttgcacagc gtcgtccaaa gagctaaaaa taccagatgg agcgtcaaac atggctggta    6540
gcggcatggg cacagttggt tcgattacag aatgttccat tgtgaaggta gttcgatttt    6600
ggaggtcgcg ggaggtcgaa actaagttct tggtgtttta aaactaaaaa aaagactaac    6660
tataaaagta gaatttaaga agtttaagaa atagatttac agaattacaa tcaataccta    6720
ccgtctttat atacttatta gtcaagtagg ggaataattt cagggaactg gtttcaacct    6780 ttttttttcag cttttttccaa atcagagaga gcagaaggta atagaaggta taagaaaatg   6840
agatagatac atgcgtgggt caattgcctt gtgtcatcat ttactccagg caggttgcat    6900
cactccattg aggttgtgcc cgttttttgc ctgtttgtgc ccctgttctc tgtagttgcg    6960
ctaagagaat ggacctatga actgatggtt ggtgaagaaa acaatatttt ggtgctggga    7020 ttctttttt ttctggatgc cagcttaaaa agcgggctcc attatattta gtggatgcca    7080
ggaataaact gttcacccag acacctacga tgttatatat tctgtgtaac ccgccccta    7140 ttttgggcat gtacgggtta cagcagaatt aaaaggctaa ttttttgact aaataaagtt    7200
aggaaaatca ctactattaa ttatttacgt attctttgaa atggcagtat tgataatgat    7260
aaactcgaac tgaaaagcg tgtttttat tcaaaatgat tctaactccc ttacgtaatc      7320
aaggaatctt tttgccttgg cctccgcgtc attaaacttc ttgttgttga cgctaacatt    7380
caacgctagt atatattcgt ttttttcagg taagttcttt tcaacgggtc ttactgatga    7440
ggcagtcgcg tctgaaaggt ccgccggcgt tggacgagcg tgatgatttc tttccttttt    7500
atattgacga ctttttttt ttcgtgtgtt tttgttctct tataaccgag ctgcttactt     7560
attattattt caccttctct tttatttat acttataatt atttattctt tacatactgt     7620
tacaagaaac tcttttctac attaattgca taaagtgtca atcagcacat cctctatatc    7680
gctatcaaca acaaatttga caaacctgcc tatatcttca ggaacaactg ccgcatcgct    7740
```

| | |
|---|---|
| accaccacta cttgtgaagt ccctggagtt taatatgcac tgaaatttac ctagccgttt | 7800 |
| tacacaagac cataatccat ccatgctatc gcagtatatg attttgtgtt cgttttttcgt | 7860 |
| cttgcgaaag gcatcctcaa tggcttgttt cattgatcca tcagtgtggc tcgtaggtac | 7920 |
| cagcaaaacc acttcatcag cggcgtactc ctggcggttt aaacgcgtgg ccgtgccgtc | 7980 |

<210> SEQ ID NO 33
<211> LENGTH: 13266
<212> TYPE: DNA
<213> ORGANISM: Artificial Sequence
<220> FEATURE:
<223> OTHER INFORMATION: Synthetic: i84022 integration construct

<400> SEQUENCE: 33

| | |
|---|---|
| gacggcacgg ccacgcgttt aaaccgccaa gtgatgtaac taaatacacg attaccatgg | 60 |
| aaattaacgt acctttttg tgcgtgtatt gaaatattat gacatattac agaaagggtt | 120 |
| cgcaagtcct gtttctatgc ctttctctta gtaattcacg aaataaacct atggtttacg | 180 |
| aaatgatcca cgaaaatcat gttattattt acatcaacat atcgcgaaaa ttcatgtcat | 240 |
| gtccacatta acatcattgc agagcaacaa ttcattttca tagagaaatt tgctactatc | 300 |
| acccactagt actaccattg gtacctacta ctttgaattg tactaccgct gggcgttatt | 360 |
| aggtgtgaaa ccacgaaaag ttcaccataa cttcgaataa agtcgcggaa aaaagtaaac | 420 |
| agctattgct actcaaatga ggtttgcaga agcttgttga agcatgatga agcgttctaa | 480 |
| acgcactatt catcattaaa tatttaaagc tcataaaatt gtattcaatt cctattctaa | 540 |
| atggcttta tttctattac aactattagc tctaaatcca tatcctcata gcagcaatc | 600 |
| aattctatct atactttaaa cgctcgtcca acgccggcgg acctgatgtg tattactagt | 660 |
| gtcgacgaca gcattcgccc agtatttttt ttattctaca aaccttctat aatttcaaag | 720 |
| tatttacata attctgtatc agtttaatca ccataatatc gttttctttg tttagtgcaa | 780 |
| ttaattttc ctattgttac ttcgggcctt tttctgtttt atgagctatt ttttccgtca | 840 |
| tccttccgga tccagatttt cagcttcatc tccagattgt gtctacgtaa tgcacgccat | 900 |
| cattttaaga gaggacctcc cgcgacctcc aaaatcgaac taccttcaca atgaaacttc | 960 |
| ttagtagtat tgagcaggcg tgtgacatct gtagattgaa gaaattgaaa tgtagtaagg | 1020 |
| agaagcccaa atgtgcgaaa tgccttaaaa ataattggga atgcagatat agtccgaaga | 1080 |
| cgaagcgcag tccccttacc cgcgcgcacc ttacggaggt cgagagtcgc cttgagcgcc | 1140 |
| ttgagcaact tttccttctt atcttcccca gagaggattt ggatatgatc cttaagatgg | 1200 |
| acagtcttca agacattaag gcgcttctta cggggctttt cgtgcaggac aacgtcaaca | 1260 |
| aggacgcggt gacggaccgc cttgccagtg tcgaaaccga catgcccctt acgcttcgcc | 1320 |
| aacaccgcat ttccgccacg agtagtagtg aggaatcctc caataagggg cagcgccaac | 1380 |
| ttaccgtgag tatcgatagt gcggcccacc acgacaatag tacgatcccc cttgacttca | 1440 |
| tgccgcgcga cgccttgcac gggttcgact ggagtgagga agacgatatg agtgacggtc | 1500 |
| ttccgtttct taagaccgat ccgaataaca acggtttttt cggtgatggg agtttgcttt | 1560 |
| gcatcttgag aagtatcggt ttcaagcccg agaactatac caatagtaat gtcaatcgct | 1620 |
| tgcccacgat gatcaccgac cgctataccc ttgccagtcg cagtacgacg agtagacttt | 1680 |
| tgcagtccta cttgaacaac ttccatccgt attgtcccat tgtccatagt cccaccctta | 1740 |
| tgatgctta caacaatcaa atcgagattg ccagtaaaga ccagtggcag attttgttca | 1800 |
| attgtattct tgcgatcggg gcgtggtgca ttgaaggtga gagtaccgac attgacgtct | 1860 |

```
tctattacca gaacgccaag agtcacctta cctccaaagt gtttgaaagt gggagtatta    1920
tccttgtcac ggcgcttcac ttgcttagta gatacacgca atggcgccaa aagacgaaca    1980
cctcctacaa cttccattcc ttcagtattc gcatggcgat tagtcttggt cttaaccgcg    2040
atttgccgag tagttttcc gactcctcca tccttgagca gcgcagaaga atctggtgga    2100
gtgtgtatag ttgggaaatt cagcttagtc ttttgtacgg gagaagtatt caattgagtc    2160
aaaacacgat tagttttccc agtagtgtgg atgacgtcca agaacgacg acggggccga    2220 cgatttacca cggtattatc gagacggcgc gcttgcttca ggtctttacg aagatttacg    2280
agcttgataa gacggtgacc gcggagaagt ccccccatttg cgcgaagaag tgtcttatga    2340
tctgcaacga aatcgaagaa gtcagtcgcc aagcgccgaa attccttcag atggacatca    2400
gtacgacggc ccttacgaac cttcttaaag agcatccctg gcttagtttc acgcgctttg    2460
agcttaaatg gaagcaactt agtttgatta tctacgtgct tcgcgacttc tttaccaact    2520
tcacgcaaaa gaaaagtcag cttgagcaag accagaacga ccaccagtcc tacgaggtca    2580
agagatgtag tattatgctt tccgacgcgg cgcagcgcac cgtcatgagt gtgtcctcct    2640
acatggataa ccacaacgtg acgccgtact tcgcgtggaa ctgcagttac tatcttttta    2700
acgcggtgct tgtgccgatt aaaacccttt tgagtaatag taagagtaac gccgaaaaca    2760
atgaaacggc gcagcttctt cagcagatca ataccgtcct tatgcttctt aagaagcttg    2820
cgaccttcaa gattcaaacc tgcgagaagt atatccaggt gcttgaggaa gtgtgcgccc    2880
ccttccttct tagtcaatgc gcgattccgc ttccccacat ttcctacaat aactccaacg    2940
ggtccgcgat caagaacatc gtggggagtg cgaccattgc gcagtatccc accttgcccg    3000
aagagaacgt gaataacatt tccgtcaagt acgtcagtcc cggtagtgtg ggtcccagtc    3060
ccgtcccgct taagagtggg gcgtccttt ccgaccttgt gaaacttctt agtaatagac    3120
cgccgagtag aaatagtccg gtcacgattc cgcgctccac gcccagtcac agaagtgtga    3180
cccccttcct tggtcagcaa cagcaacttc agagtcttgt cccgcttacg cccagtgccc    3240
ttttcggggg tgcgaacttc aaccagtccg gtaacatcgc cgactccagt cttagttta    3300 cctttaccaa ttcctccaat gggcccaatt tgattacgac ccagacgaac agtcaggcct    3360
tgagtcagcc gatcgcgagt agtaatgtcc acgacaattt tatgaacaac gagattaccg    3420
cctccaagat cgacgacggg aacaacagta agccgcttag tcccgggtgg accgatcaga    3480
ccgcctacaa tgccttcggg attaccacgg gtatgttcaa cacgaccacg atggacgacg    3540
tgtacaatta ccttttgac gacgaggaca cgccgccgaa tccgaagaag gaatgagcca    3600
attggtgcgg caattgataa taacgaaaat gtcttttaat gatctgggta taatgaggaa    3660
ttttccgaac gtttttactt tatatatata tatacatgta acatatattc tatacgctat    3720
atcgagaaaa cgcgatggtg gggtgacttt caactcggcg tatccccgcg tgcttggccg    3780
gccgtagtta tgacaattac aacaacagaa ttctttctat atatgcacga acttgtaata    3840
tggaagaaat tatgacgtac aaactataaa gtaaatattt tacgtaacac atggtgctgt    3900
tgtgcttctt tttcaagaga ataccaatga cgtatgacta agtttatgta ttttccaaaa    3960
cctgtttagc cctggcgaca gatacgtctc cggcttcaac gatgaccctg gtgaccctgt    4020
caatgtcggc tccggtggca ccggccatga ttgcgatgtt ccttgcgtgt aaggtcatgt    4080
gtcccctttg gattccctcg gttgccaagg ccctaattgc ggccatattc tgagccaaac    4140
caacggcggc agtaacctgg gccaactcag tagcggtttc gacctgcatt aaggccaaag    4200
```

-continued

```
cggccctagc tgtagggtga gtcttggtgg ctcctcctac caaacccaag gccaaaggca    4260
attcaatggt accgaccaac ctaccgtcgt tggccaactc ccaccttgtc aaagaggtgt    4320
aatgtccggt cctggcggcg taggcgtggg ctccagcttc gatggccctc cagtcgttac    4380
ctgttgcgac gacgactggg tcaattccgt tcataattcc cttgttatgg gttgcggccc    4440
tgtaagggtc gactattgct aaggcgcagg cttcaaccat tccccttgca acgtcggcac    4500
catcgtatcc ctgggtggtc aaagtctcag gggctaactc aaccctggct cttaccaacc    4560
tcaagtcggc caagttagac aaaatcctca acctgacggt tccaccagcg atcctctcta    4620
cctctggagc taacctttca gccatggtgt taactgtgtt ggcacccatg cgtctctga    4680 catcaacaat caagtgcaat acgaccattg caccaacagg ggtgtcccta aaaacatgga    4740
cctcaatgtc tctgcaacca ccacctaaac caaccaaaac tggatctacg gcatctgctg    4800
cttccatgaa agcagcctta tgggccaaca acctttgcct agctccttct gggtctccta    4860
atccgacaac ttggatttgg gccctcatta aaggtgcagt tccgtgtgcg gtgaatccac    4920
cgttctctct agctatcctt gccatatatg aggctgcggc aacaacagat ggttcctcga    4980
ctgccatagg tattaagtag tcccttccgt tgacggtgaa gttggtggcg acacccaatg    5040
gcaactcaaa ttttccgata acattctcga tcataccgtt ggccaatgac aaaggcaaag    5100
caccgttacc ggccaatgca gaaatggctt caggttccaa tcctgcggct tcggcaaccc    5160
taactaacct ctgagcagga tccaagtccc tcatcttctc gatccttgag ttcaatccgt    5220
cgatgtgacc tgtctttcca gtcattgtaa agttagttgg ttgcgcgact tcgggtgggg    5280
taagtataga ggtatattaa caattttttg ttgatacttt tatgacattt gaataagaag    5340
taatacaaac cgaaaatgtt gaaagtatta gttaaagtgg ttatgcagct tttgcattta    5400
tatatctgtt aatagatcaa aaatcatcgc ttcgctgatt aattacccca gaaataaggc    5460
taaaaaacta atcgcattat tatcctatgg ttgttaattt gattcgttga tttgaaggtt    5520
tgtggggcca ggttactgcc aattttccct cttcataacc ataaaagcta gtattgtaga    5580
atctttattg ttcggagcag tgcggcgcga ggcacatctg cgtttcagga acgcgaccgg    5640
tgaagaccag gacgcacgga ggagagtctt ccgtcggagg gctgtcgccc gctcggcggc    5700
ttctaatccg tacttcaata tagcaatgag cagttaagcg tattactgaa agttccaaag    5760
agaaggtttt tttaggctaa gataatgggg ctctttacat ttccacaaca tataagtaag    5820
attagatatg gatatgtata tggtggtatt gccatgtaat atgattatta aacttctttg    5880
cgtccatcca aaaaaaaagt aacgcacgca cactcccgac agacaactag cttgataatg    5940
tctcagaacg tttacattgt atcgactgcc agaaccccaa ttggttcatt ccagggttct    6000
ctatcctcca agacagcagt ggaattgggt gctgttgctt taaaaggcgc cttggctaag    6060
gttccagaat tggatgcatc caaggatttt gacgaaatta ttttttggtaa cgttctttct    6120 gccaatttgg gccaagctcc ggccagacaa gttgctttgg ctgccggttt gagtaatcat    6180
atcgttgcaa gcacagttaa caaggtctgt gcatccgcta tgaaggcaat cattttgggt    6240
gctcaatcca tcaaatgtgg taatgctgat gttgtcgtag ctggtggttg tgaatctatg    6300
actaacgcac catactacat gccagcagcc cgtgcgggtg ccaaatttgg ccaaactgtt    6360
cttgttgatg gtgtcgaaag agatgggttg aacgatgcgt acgatggtct agccatgggt    6420
gtacacgcag aaaagtgtgc ccgtgattgg gatattacta gagaacaaca agacaatttt    6480
gccatcgaat cctaccaaaa atctcaaaaa tctcaaaagg aaggtaaatt cgacaatgaa    6540
attgtacctg ttaccattaa gggatttaga ggtaagcctg atactcaagt cacgaaggac    6600
```

```
gaggaacctg ctagattaca cgttgaaaaa ttgagatctg caaggactgt tttccaaaaa    6660
gaaaacggta ctgttactgc cgctaacgct tctccaatca cgatggtgc tgcagccgtc     6720 atcttggttt ccgaaaaagt tttgaaggaa aagaatttga agcctttggc tattatcaaa    6780
ggttggggtg aggccgctca tcaaccagct gattttacat gggctccatc tcttgcagtt    6840
ccaaaggctt tgaaacatgc tggcatcgaa gacatcaatt ctgttgatta ctttgaattc    6900
aatgaagcct tttcggttgt cggtttggtg aacactaaga ttttgaagct agacccatct    6960
aaggttaatg tatatggtgg tgctgttgct ctaggtcacc cattgggttg ttctggtgct    7020
agagtggttg ttacactgct atccatctta cagcaagaag gaggtaagat cggtgttgcc    7080
gccatttgta atggtggtgg tggtgcttcc tctattgtca ttgaaaagat atgattacgt    7140
tctgcgattt tctcatgatc tttttcataa aatacataaa tatataaatg ctttatgta    7200 taacaggcat aatttaaagt tttatttgcg attcatcgtt tttcaggtac tcaaacgctg    7260
aggtgtgcct tttgacttac ttttccgcct tggcaagctg gccgaacctg caggccgcga    7320
gcgccgatac gaaaatcgtt attgtcttga aggtgaaatt tctactctta ttaatggtga    7380
acgttaagct gatgctatga tggaagctga ttggtcttaa cttgcttgtc atcttgctaa    7440
tggtcattgg ctcgtgttat tacttaagtt atttgtactc gttttgaacg taatgctaat    7500
gatcatctta tggaataata gtgagtggtt tcagggtcca taaagctttt caattcatct    7560 ttttttttt tgttcttttt tttgattccg gtttctttga aatttttttg attcggtaat    7620
ctccgagcag aaggaagaac gaaggaagga gcacagactt agattggtat atatacgcat    7680
atgtggtgtt gaagaaacat gaaattgccc agtattctta acccaactgc acagaacaaa    7740
aacctgcagg aaacgaagat aaatcatgtc gaaagctaca tataaggaac gtgctgctac    7800
tcatcctagt cctgttgctg ccaagctatt taatatcatg cacgaaaagc aaacaaactt    7860
gtgtgcttca ttggatgttc gtaccaccaa ggaattactg gagttagttg aagcattagg    7920
tcccaaaatt tgtttactaa aaacacatgt ggatatcttg actgattttt ccatggaggg    7980
cacagttaag ccgctaaagg cattatccgc caagtacaat ttttactct tcgaagacag     8040 aaaatttgct gacattggta atacagtcaa attgcagtac tctgcgggtg tatacagaat    8100
agcagaatgg gcagacatta cgaatgcaca cggtgtggtg ggcccaggta ttgttagcgg    8160
tttgaagcag gcggcggaag aagtaacaaa ggaacctaga ggccttttga tgttagcaga    8220
attgtcatgc aagggctccc tagctactgg agaatatact aagggtactg ttgacattgc    8280
gaagagtgac aaagattttg ttatcggctt tattgctcaa agagacatgg gtggaagaga    8340
tgaaggttac gattggttga ttatgacacc cggtgtgggt ttagatgaca agggagacgc    8400
attgggtcaa cagtatagaa ccgtggatga tgtggtctct acaggatctg acattattat    8460
tgttggaaga ggactatttg caaagggaag ggatgctaag gtagagggtg aacgttacag    8520
aaaagcaggc tgggaagcat atttgagaag atgcggccag caaaactaaa aaactgtatt    8580
ataagtaaat gcatgtatac taaactcaca aattagagct tcaatttaat tatatcagtt    8640
attaccacga aaatcgttat tgtcttgaag gtgaaatttc tactcttatt aatggtgaac    8700
gttaagctga tgctatgatg gaagctgatt ggtcttaact tgcttgtcat cttgctaatg    8760
gtcatatggc tcgtgttatt acttaagtta tttgtactcg ttttgaacgt aatgctaatg    8820
atcatcttat ggaataatag tgaacggccg gccaagcacg cggggattga atgagaaaaa    8880
aaatcggttg ggcttaactt taaagaaaaa agttgagatt agatttattg tgttataaat    8940
```

```
atagatatac aattctttat aaaaaaaata tatatatata tcattgttat taaataaaga    9000
gttttcctag tatatagatt aaaaaactac tctattaaat gagagctaaa aaaagcaggc    9060
tgccaaaaaa ataaagcatt tatgaagggg gttcagcaag atgcaatcga tgggggaaga    9120
ttatttttta acatcgtaag atcttctaaa tttgtcatcg atgttggtca agtagtaaac    9180
accactttgc aaatgctcaa tggaaccttg aggtttgaag ttcttcttca aatgggcatt    9240
ttctctcaat tcgatggcag cttcgtaatc ctttggagtt tcggtgattc tcttggctaa    9300
tttgttagta atatctaatt ccttgataat atgttggacg tcaccaacaa ttttgcaaga    9360
atatagagat gcagctaaac cggaaccgta agaaaataaa ccaacacgct tgccttgtaa    9420
gtcgtcagat ccaacatagt ttaatagaga tgcaaaggcg cataaacag atgcggtgta     9480 catgttacct gtgtttgttg gaacaatcaa agattgggca actctctctt tgtggaatgg    9540
cttagcaaca ttaacaaaag ttttttcaat gttcttatcg gttaaagatt cgtcataatc    9600
gcgagtagct aattcggcgt caacttctgg gaacaattga ggattggctc tgaaatcgtt    9660
atatagtaat ctaccgtatg attttgtgac caatttacag gttggaacat ggaaaacgtt    9720
gtagtcgaaa tatttcaaaa cgttcaaagc atccgaacca gcgggatcgc taaccaaccc    9780
tttagaaata gccttcttgg aataactctt gtaaacttga tcaagagcct tgacgtaaca    9840
agttaatgaa aaatgaccat cgacgtaagg atattcgctg gtgaaatctg gcttgtaaaa    9900
atcgtaggcg tgttccatgt aagaagctct tacagagtca aatacaattg gagcatcagg    9960
accgatccac atagcaacag taccggcacc accggttggt cttgcggcac ccttatcgta   10020
gatggcaata tcaccgcaaa ctacaatggc gtctctacca tcccatgcgt tagattcaat   10080
ccagttcaaa gagttgaaca acgcgttggt accaccgtaa caggcattaa gcgtgtcaat   10140
accttcgacg tcagtgtttt caccaaacaa ttgcatcaag acagacttga cagacttgga   10200
cttgtcaatc agagtttcag taccgacttc taatctacca attttgttgg tgtcgatgtt   10260
gtaactcttg atcaacttag acaaaacagt tagggacatc gagtagatat cttctctgtc   10320
attgacaaaa gacatgttgg tttggcccag accaattgtg tatttacctt gagaaacgcc   10380
atcaaatttc tctagctcag attggttgac acattgagtt gggatgtaaa tttggatacc   10440
tttaataccg acattttgag gtctggtttt ttgttcagcg gtcttttgtt tttttagttc    10500
agtcatttgc aagtttgtat tgtgtaattg ttgttgcttt tgcggcctaa gtcttccttt    10560
aataccacac caacaaagtt tagttgagag tttcattgtg aaggtagttc gattttggag    10620
gtcgcgggag gttactttt ttttggatgg acgcaaagaa gttaataat catattacat      10680 ggcaataccaa ccatatacat atccatatct aatcttactt atatgttgtg gaaatgtaaa   10740
gagccccatt atcttagcct aaaaaaacct tctctttgga actttcagta atacgcttaa    10800
ctgctcattg ctatattgaa gtacggatta gaagccgccg agcgggcgac agccctccga    10860
cggaagactc tcctccgtgc gtcctggtct tcaccggtcg cgttcctgaa acgcagatgt    10920
gcctcgcgcc gcactgctcc gaacaataaa gattctacaa tactagcttt tatggttatg    10980
aagaggaaaa attggcagta acctggcccc acaaaccttc aaatcaacga atcaaattaa    11040
caaccatagg ataataatgc gattagtttt ttagccttat ttctggggta attaatcagc    11100
gaagcgatga ttttgatct attaacagat atataaatgc aaaagctgca taaccacttt     11160
aactaatact ttcaacattt tcggtttgta ttacttctta ttcaaatgtc ataaagtat     11220 caacaaaaaa ttgttaatat acctctatac ttaccccacc cgaagtcgcg caaccaacta    11280
actttacaat gactggaaag acaggtcaca tcgacggatt gaactcaagg atcgagaaga    11340
```

```
tgagggactt ggatcctgct cagaggttag ttagggttgc cgaagccgca ggattggaac    11400
ctgaagccat ttctgcattg gccggtaacg gtgctttgcc tttgtcattg gccaacggta    11460
tgatcgagaa tgttatcgga aaatttgagt tgccattggg tgtcgccacc aacttcaccg    11520
tcaacggaag ggactactta atacctatgg cagtcgagga accatctgtt gttgccgcag    11580
cctcatatat ggcaaggata gctagagaga acggtggatt caccgcacac ggaactgcac    11640
ctttaatgag ggcccaaatc caagttgtcg gattaggaga cccagaagga gctaggcaaa    11700
ggttgttggc ccataaggct gctttcatgg aagcagcaga tgccgtagat ccagttttgg    11760
ttggtttagg tggtggttgc agagacattg aggtccatgt ttttagggac acccctgttg    11820
gtgcaatggt cgtattgcac ttgattgttg atgtcagaga cgccatgggt gccaacacag    11880
ttaacaccat ggctgaaagg ttagctccag aggtagagag gatcgctggt ggaaccgtca    11940
ggttgaggat tttgtctaac ttggccgact tgaggttggt aagagccagg gttgagttag    12000
cccctgagac tttgaccacc cagggatacg atggtgccga cgttgcaagg ggaatggttg    12060
aagcctgcgc cttagcaata gtcgacccct acagggccgc aacccataac aagggaatta    12120
tgaacggaat tgacccagtc gtcgtcgcaa caggtaacga ctggagggcc atcgaagctg    12180
gagcccacgc ctacgccgcc aggaccggac attacacctc tttgacaagg tgggagttgg    12240
ccaacgacgg taggttggtc ggtaccattg aattgccttt ggccttgggt ttggtaggag    12300
gagccaccaa gactcaccct acagctaggg ccgctttggc cttaatgcag gtcgaaaccg    12360
ctactgagtt ggcccaggtt actgccgccg ttggtttggc tcagaatatg gccgcaatta    12420
gggccttggc aaccgaggga atccaaaggg gacacatgac cttacgcgca aggaacatcg    12480
caatcatggc cggtgccacc ggagccgaca ttgacagggt caccagggtc atcgttgaag    12540
ccggagacgt atctgtcgcc agggctaaac aggttttgga aaatacataa acttagtcat    12600
acgtcattgg tattctcttg aaaaagaagc acaacagcac catgtgttac gtaaaatatt    12660
tactttatag tttgtacgtc ataatttctt ccatattaca agttcgtgca tatatagaaa    12720
gaattctgtt gttgtaattg tcataactag gtccgccggc gttggacgag cgaatgtgta    12780
tattagttta aaaagttgta tgtaataaaa gtaaaattta atattttgga tgaaaaaaac    12840 cattttaga cttttctta actagaatgc tggagtagaa atacgccatc tcaagataca    12900
aaaagcgtta ccggcactga tttgtttcaa ccagtatata gattattatt gggtcttgat    12960
caactttcct cagacatatc agtaacagtt atcaagctaa atatttacgc gaaagaaaaa    13020
caaatatttt aattgtgata cttgtgaatt ttattttatt aaggatacaa agttaagaga    13080
aaacaaaatt tatatacaat ataagtaata ttcatatata tgtgatgaat gcagtcttaa    13140
cgagaagaca tggccttggt gacaactctc ttcaaaccaa cttcagcctt tctcaattca    13200
tcagcagatg ggtcttcgat ttgcaaagca gccaaagcgg cggtttaaac gcgtggccgt    13260
gccgtc                                                               13266
```

<210> SEQ ID NO 34
<211> LENGTH: 13964
<212> TYPE: DNA
<213> ORGANISM: Artificial Sequence
<220> FEATURE:
<223> OTHER INFORMATION: Synthetic: i84026 integration construct

<400> SEQUENCE: 34

```
gacggcacgg ccacgcgttt aaaccgccaa gtgatgtaac taaatacacg attaccatgg    60
```

```
aaattaacgt accttttttg tgcgtgtatt gaaatattat gacatattac agaaagggtt    120
cgcaagtcct gtttctatgc ctttctctta gtaattcacg aaataaacct atggtttacg    180
aaatgatcca cgaaaatcat gttattattt acatcaacat atcgcgaaaa ttcatgtcat    240
gtccacatta acatcattgc agagcaacaa ttcattttca tagagaaatt tgctactatc    300
acccactagt actaccattg gtacctacta ctttgaattg tactaccgct gggcgttatt    360
aggtgtgaaa ccacgaaaag ttcaccataa cttcgaataa agtcgcggaa aaaagtaaac    420
agctattgct actcaaatga ggtttgcaga agcttgttga agcatgatga agcgttctaa    480
acgcactatt catcattaaa tatttaaagc tcataaaatt gtattcaatt cctattctaa    540
atggctttta tttctattac aactattagc tctaaatcca tatcctcata agcagcaatc    600
aattctatct atactttaaa cgtcgtcca acgccggcgg acctgatgtg tattactagt    660
gtcgacgaca gcattcgccc agtattttttt ttattctaca aaccttctat aatttcaaag    720
tatttacata attctgtatc agtttaatca ccataatatc gttttctttg tttagtgcaa    780 ttaattttc ctattgttac ttcgggcctt tttctgtttt atgagctatt ttttccgtca    840
tccttccgga tccagatttt cagcttcatc tccagattgt gtctacgtaa tgcacgccat    900
cattttaaga gaggacctcc cgcgacctcc aaaatcgaac taccttcaca atgaaacttc    960
ttagtagtat tgagcaggcg tgtgacatct gtagattgaa gaaattgaaa tgtagtaagg   1020
agaagcccaa atgtgcgaaa tgccttaaaa ataattggga atgcagatat agtccgaaga   1080
cgaagcgcag tccccttacc cgcgcgcacc ttacggaggt cgagagtcgc cttgagcgcc   1140
ttgagcaact tttccttctt atcttcccca gagaggattt ggatatgatc cttaagatgg   1200
acagtcttca agacattaag gcgcttctta cggggctttt cgtgcaggac aacgtcaaca   1260
aggacgcggt gacggaccgc cttgccagtg tcgaaaccga catgccccctt acgcttcgcc   1320 aacaccgcat ttccgccacg agtagtagtg aggaatcctc caataagggg cagcgccaac   1380
ttaccgtgag tatcgatagt gcggcccacc acgacaatag tacgatcccc cttgacttca   1440
tgccgcgcga cgccttgcac gggttcgact ggagtgagga agacgatatg agtgacggtc   1500 ttccgttttct taagaccgat ccgaataaca acggttttttt cggtgatggg agtttgcttt   1560
gcatcttgag aagtatcggt ttcaagcccg agaactatac caatagtaat gtcaatcgct   1620
tgcccacgat gatcaccgac cgctataccc ttgccagtcg cagtacgacg agtagacttt   1680
tgcagtccta cttgaacaac ttccatccgt attgtcccat tgtccatagt cccaccctta   1740
tgatgcttta caacaatcaa atcgagattg ccagtaaaga ccagtggcag attttgttca   1800
attgtattct tgcgatcggg gcgtggtgca ttgaaggtga gagtaccgac attgacgtct   1860
tctattacca gaacgccaag agtcacctta cctccaaagt gtttgaaagt gggagtatta   1920
tccttgtcac ggcgcttcac ttgcttagta gatacacgca atggcgccaa aagacgaaca   1980
cctcctacaa cttccattcc ttcagtattc gcatggcgat tagtcttggt cttaaccgcg   2040
atttgccgag tagttttttcc gactcctcca tccttgagca gcgcagaaga atctggtgga   2100
gtgtgtatag ttgggaaatt cagcttagtc ttttgtacgg gagaagtatt caattgagtc   2160
aaaacacgat tagtttttccc agtagtgtgg atgacgtcca agaacgacg acggggccga   2220 cgatttacca cggtattatc gagacggcgc gcttgcttca ggtctttacg aagatttacg   2280
agcttgataa gacggtgacc gcggagaagt cccccatttg cgcgaagaag tgtcttatga   2340
tctgcaacga aatcgaagaa gtcagtcgcc aagcgccgaa attccttcag atggacatca   2400
gtacgacggc ccttacgaac cttcttaaag agcatccctg gcttagtttc acgcgctttg   2460
```

```
agcttaaatg gaagcaactt agtttgatta tctacgtgct tcgcgacttc tttaccaact    2520
tcacgcaaaa gaaaagtcag cttgagcaag accagaacga ccaccagtcc tacgaggtca    2580
agagatgtag tattatgctt tccgacgcgg cgcagcgcac cgtcatgagt gtgtcctcct    2640
acatggataa ccacaacgtg acgccgtact tcgcgtggaa ctgcagttac tatcttttta    2700
acgcggtgct tgtgccgatt aaaacccttt tgagtaatag taagagtaac gccgaaaaca    2760
atgaaacggc gcagcttctt cagcagatca ataccgtcct tatgcttctt aagaagcttg    2820
cgaccttcaa gattcaaacc tgcgagaagt atatccaggt gcttgaggaa gtgtgcgccc    2880
ccttccttct tagtcaatgc gcgattccgc ttccccacat ttcctacaat aactccaacg    2940
ggtccgcgat caagaacatc gtggggagtg cgaccattgc gcagtatccc accttgcccg    3000
aagagaacgt gaataacatt tccgtcaagt acgtcagtcc cggtagtgtg ggtcccagtc    3060
ccgtcccgct taagagtggg gcgtcctttt ccgaccttgt gaaacttctt agtaatagac    3120
cgccgagtag aaatagtccg gtcacgattc cgcgctccac gcccagtcac agaagtgtga    3180 ccccccttcct tggtcagcaa cagcaacttc agagtcttgt cccgcttacg cccagtgccc    3240
ttttcggggg tgcgaacttc aaccagtccg gtaacatcgc cgactccagt cttagtttta    3300
cctttaccaa ttcctccaat gggcccaatt tgattacgac ccagacgaac agtcaggcct    3360
tgagtcagcc gatcgcgagt agtaatgtcc acgacaattt tatgaacaac gagattaccg    3420
cctccaagat cgacgacggg aacaacagta agccgcttag tcccgggtgg accgatcaga    3480
ccgcctacaa tgccttcggg attaccacgg gtatgttcaa cacgaccacg atggacgacg    3540
tgtacaatta cctttttgac gacgaggaca cgccgccgaa tccgaagaag gaatgagcca    3600
attggtgcgg caattgataa taacgaaaat gtcttttaat gatctgggta taatgaggaa    3660
ttttccgaac gtttttactt tatatatata tatacatgta acatatattc tatacgctat    3720
atcgagaaaa cgcgatggtg gggtgacttt caactcggcg tatccccgcg tgcttggccg    3780
gccgtccgca tgactcaaga gaagcatgtg gttttttgagt tttttttcgtt gaattttcag    3840 gtaaagctca atagttatga caattacaac aacagaattc tttctatata tgcacgaact    3900
tgtaatatgg aagaaattat gacgtacaaa ctataaagta aatattttac gtaacacatg    3960
gtgctgttgt gcttcttttt caagagaata ccaatgacgt atgactaagt ttaggattta    4020
atgcaggtga cggacccatc tttcaaacga tttatatcag tggcgtccaa attgttaggt    4080
tttgttggtt cagcaggttt cctgttgtgg gtcatatgac tttgaaccaa atggccggct    4140
gctagggcag cacataagga taattcacct gccaagacgg cacaggcaac tattcttgct    4200
aattgacgtg cgttggtacc aggagcggta gcatgtgggc ctcttacacc taataagtcc    4260
aacatggcac cttgtggttc tagaacagta ccaccaccga tggtacctac ttcgatggat    4320
ggcatggata cggaaattct caaatcaccg tccacttctt tcatcaatgt tatacagttg    4380
gaactttcga cattttgtgc aggatcttgt cctaatgcca agaaaacagc tgtcactaaa    4440
ttagctgcat gtgcgttaaa tccaccaaca gacccagcca ttgcagatcc aaccaaattc    4500
ttagcaatgt tcaactcaac caatgcggaa acatcacttt ttaacacttt tctgacaaca    4560
tcaccaggaa tagtagcttc tgcgacgaca ctcttaccac gaccttcgat ccagttgatg    4620
gcagctggtt ttttgtcggt acagtagtta ccagaaacgg agacaacctc catatcttcc    4680
cagccatact cttctaccat ttgctttaat gagtattcga cacccttaga aatcatattc    4740
atacccattg cgtcaccagt agttgttcta aatctcatga agagtaaatc tcctgctaga    4800
```

```
caagtttgaa tatgttgcag acgtgcaaat cttgatgtag agttaaaagc ttttttaatt    4860
gcgttttgtc cctcttctga gtctaaccat atcttacagg caccagatct tttcaaagtt    4920
gggaaacgga ctactgggcc tcttgtcata ccatccttag ttaaaacagt tgttgcacca    4980
ccgccagcat tgattgcctt acagccacgc atggcagaag ctaccaaaca accctctgta    5040
gttgccattg gtatatgata agatgtacca tcgataacca agggcctat aacaccaacg     5100
ggcaaaggca tgtaacctat aacattttca caacaagcgc caaatacgcg gtcgtagtca    5160
taatttttat atggtaaacg atcagatgct aatacaggag cttctgccaa aattgaaaga    5220
gccttcctac gtaccgcaac cgctctcgta gtatcaccta atttttctc caaagcgtac     5280
aaaggtaact taccgtgaat aaccaaggca gcgacctctt tgttcttcaa ttgttttgta    5340
tttccactac ttaataatgc ttctaattct tctaaaggac gtattttctt atccaagctt    5400
tcaatatcgc gggaatcatc ttcctcacta gatgatgaag gtcctgatga gctcgattgc    5460
gcagatgata aacttttgac tttcgatcca gaaatgactg ttttattggt taaaactggt    5520
gtagaagcct tttgtacagg agcagtaaaa gacttcttgg tgacttcagt cttcaccaat    5580
tggtctgcag ccattgtaaa gttagttggt tgcgcgactt cgggtggggt aagtatagag    5640
gtatattaac aattttttgt tgatactttt atgacatttg aataagaagt aatacaaacc    5700
gaaaatgttg aaagtattag ttaaagtggt tatgcagctt ttgcatttat atatctgtta    5760
atagatcaaa aatcatcgct tcgctgatta attaccccag aaataaggct aaaaaactaa    5820
tcgcattatt atcctatggt tgttaatttg attcgttgat ttgaaggttt gtggggccag    5880
gttactgcca atttttcctc ttcataacca taaaagctag tattgtagaa tctttattgt    5940
tcggagcagt gcggcgcgag gcacatctgc gtttcaggaa cgcgaccggt gaagaccagg    6000
acgcacggag gagagtcttc cgtcggaggg ctgtcgcccg ctcggcggct tctaatccgt    6060
acttcaatat agcaatgagc agttaagcgt attactgaaa gttccaaaga gaaggttttt    6120
ttaggctaag ataatggggc tctttacatt tccacaacat ataagtaaga ttagatatgg    6180
atatgtatat ggtggtattg ccatgtaata tgattattaa acttctttgc gtccatccaa    6240
aaaaaaagta acgcacgcac actcccgaca gacaactagc ttgataatgt ctcagaacgt    6300
ttacattgta tcgactgcca gaaccccaat tggttcattc cagggttctc tatcctccaa    6360
gacagcagtg gaattgggtg ctgttgcttt aaaaggcgcc ttggctaagg ttccagaatt    6420
ggatgcatcc aaggattttg acgaaattat ttttggtaac gttctttctg ccaatttggg    6480
ccaagctccg gccagacaag ttgctttggc tgccggtttg agtaatcata tcgttgcaag    6540
cacagttaac aaggtctgtg catccgctat gaaggcaatc attttgggtg ctcaatccat    6600
caaatgtggt aatgctgatg ttgtcgtagc tggtggttgt gaatctatga ctaacgcacc    6660
atactacatg ccagcagccc gtgcgggtgc caaatttggc caaactgttc ttgttgatgg    6720
tgtcgaaaga gatgggttga acgatgcgta cgatggtcta gccatgggtg tacacgcaga    6780
aaagtgtgcc cgtgattggg atattactag agaacaacaa gacaattttg ccatcgaatc    6840
ctaccaaaaa tctcaaaaat ctcaaaagga aggtaaattc gacaatgaaa ttgtacctgt    6900
taccattaag ggatttagag gtaagcctga tactcaagtc acgaaggacg aggaacctgc    6960
tagattacac gttgaaaaat tgagatctgc aaggactgtt ttccaaaaag aaaacggtac    7020
tgttactgcc gctaacgctt ctccaatcaa cgatggtgct gcagccgtca tcttggtttc    7080
cgaaaaagtt ttgaaggaaa agaatttgaa gcctttggct attatcaaag gttggggtga    7140
ggccgctcat caaccagctg attttacatg ggctccatct cttgcagttc caaaggcttt    7200
```

```
gaaacatgct ggcatcgaag acatcaattc tgttgattac tttgaattca atgaagcctt   7260
ttcggttgtc ggtttggtga acactaagat tttgaagcta gacccatcta aggttaatgt   7320
atatggtggt gctgttgctc taggtcaccc attgggttgt tctggtgcta gagtggttgt   7380
tacactgcta tccatcttac agcaagaagg aggtaagatc ggtgttgccg ccatttgtaa   7440
tggtggtggt ggtgcttcct ctattgtcat tgaaaagata tgattacgtt ctgcgatttt   7500
ctcatgatct ttttcataaa atacataaat atataaatgg ctttatgtat aacaggcata   7560
atttaaagtt ttatttgcga ttcatcgttt ttcaggtact caaacgctga ggtgtgcctt   7620
ttgacttact tttccgcctt ggcaagctgg ccgaacctgc aggccgcgag cgccgatacg   7680
aaaatcgtta ttgtcttgaa ggtgaaattt ctactcttat taatggtgaa cgttaagctg   7740
atgctatgat ggaagctgat tggtcttaac ttgcttgtca tcttgctaat ggtcattggc   7800
tcgtgttatt acttaagtta tttgtactcg ttttgaacgt aatgctaatg atcatcttat   7860
ggaataatag tgagtggttt cagggtccat aaagcttttc aattcatctt ttttttttt    7920
gttcttttt ttgattccgg tttctttgaa attttttga ttcggtaatc tccgagcaga    7980
aggaagaacg aaggaaggag cacagactta gattggtata tatacgcata tgtggtgttg   8040
aagaaacatg aaattgccca gtattcttaa cccaactgca cagaacaaaa acctgcagga   8100
aacgaagata aatcatgtcg aaagctacat ataaggaacg tgctgctact catcctagtc   8160
ctgttgctgc caagctattt aatatcatgc acgaaaagca aacaaacttg tgtgcttcat   8220
tggatgttcg taccaccaag gaattactgg agttagttga agcattaggt cccaaaattt   8280
gtttactaaa aacacatgtg gatatcttga ctgattttc catggagggc acagttaagc    8340
cgctaaaggc attatccgcc aagtacaatt ttttactctt cgaagacaga aaatttgctg   8400
acattggtaa tacagtcaaa ttgcagtact ctgcgggtgt atacagaata gcagaatggg   8460
cagacattac gaatgcacac ggtgtggtgg gcccaggtat tgttagcggt ttgaagcagg   8520
cggcggaaga agtaacaaag gaacctagag gccttttgat gttagcagaa ttgtcatgca   8580
agggctccct agctactgga gaatatacta agggtactgt tgacattgcg aagagtgaca   8640
aagattttgt tatcggcttt attgctcaaa gagacatggg tggaagagat gaaggttacg   8700
attggttgat tatgacaccc ggtgtgggtt tagatgacaa gggagacgca ttgggtcaac   8760
agtatagaac cgtggatgat gtggtctcta caggatctga cattattatt gttgaagag    8820
gactatttgc aaagggaagg gatgctaagg tagagggtga acgttacaga aaagcaggct   8880
gggaagcata tttgagaaga tgcggccagc aaaactaaaa aactgtatta taagtaaatg   8940
catgtatact aaactcacaa attagagctt caatttaatt atatcagtta ttaccacgaa   9000
aatcgttatt gtcttgaagg tgaaatttct actcttatta atggtgaacg ttaagctgat   9060
gctatgatgg aagctgattg gtcttaactt gcttgtcatc ttgctaatgg tcatatggct   9120
cgtgttatta cttaagttat ttgtactcgt tttgaacgta atgctaatga tcatcttatg   9180
gaataatagt gaacggccgg ccaagcacgc ggggattgaa tgagaaaaaa aatcggttgg   9240
gcttaacttt aaagaaaaaa gttgagatta gatttattgt gttataaata tagatataca   9300
attctttata aaaaaaatat atatatatat cattgttatt aaataaagag ttttcctagt   9360
atatagatta aaaaactact ctattaaatg agagctaaaa aaagcaggct gccaaaaaaa   9420
taaagcattt atgaaggggg ttcagcaaga tgcaatcgat gggggaagat tattttttaa   9480
catcgtaaga tcttctaaat ttgtcatcga tgttggtcaa gtagtaaaca ccactttgca   9540
```

```
aatgctcaat ggaaccttga ggtttgaagt tcttcttcaa atgggcattt tctctcaatt    9600
cgatggcagc ttcgtaatcc tttggagttt cggtgattct cttggctaat ttgttagtaa    9660
tatctaattc cttgataata tgttggacgt caccaacaat tttgcaagaa tatagagatg    9720
cagctaaacc ggaaccgtaa gaaaataaac caacacgctt gccttgtaag tcgtcagatc    9780
caacatagtt taatagagat gcaaaggcgg cataaacaga tgcggtgtac atgttacctg    9840
tgtttgttgg aacaatcaaa gattgggcaa ctctctcttt gtggaatggc ttagcaacat    9900
taacaaaagt ttttcaatg ttcttatcgg ttaaagattc gtcataatcg cgagtagcta     9960
attcggcgtc aacttctggg aacaattgag gattggctct gaaatcgtta tatagtaatc   10020
taccgtatga ttttgtgacc aatttacagg ttggaacatg gaaaacgttg tagtcgaaat   10080
atttcaaaac gttcaaagca tccgaaccag cgggatcgct aaccaaccct ttagaaatag   10140
ccttcttgga ataactcttg taaacttgat caagagcctt gacgtaacaa gttaatgaaa   10200
aatgaccatc gacgtaagga tattcgctgg tgaaatctgg cttgtaaaaa tcgtaggcgt   10260
gttccatgta agaagctctt acagagtcaa atacaattgg agcatcagga ccgatccaca   10320
tagcaacagt accggcacca ccggttggtc ttgcggcacc cttatcgtag atggcaatat   10380
caccgcaaac tacaatggcg tctctaccat cccatgcgtt agattcaatc cagttcaaag   10440
agttgaacaa cgcgttggta ccaccgtaac aggcattaag cgtgtcaata ccttcgacgt   10500
cagtgttttc accaaacaat tgcatcaaga cagacttgac agacttggac ttgtcaatca   10560
gagtttcagt accgacttct aatctaccaa ttttgttggt gtcgatgttg taactcttga   10620
tcaacttaga caaaacagtt agggacatcg agtagatatc ttctctgtca ttgacaaaag   10680
acatgttggt ttggcccaga ccaattgtgt atttaccttg agaaacgcca tcaaatttct   10740
ctagctcaga ttggttgaca cattgagttg ggatgtaaat ttggatacct ttaataccga   10800
cattttgagg tctggttttt tgttcagcgg tcttttgttt ttttagttca gtcatttgca   10860
agtttgtatt gtgtaattgt tgttgctttt gcggcctaag tcttccttta ataccacacc   10920
aacaaagttt agttgagagt ttcattgtga aggtagttcg attttggagg tcgcgggagg   10980
ttactttttt tttggatgga cgcaaagaag tttaataatc atattacatg gcaataccac   11040
catatacata tccatatcta atcttactta tatgttgtgg aaatgtaaag agccccatta   11100
tcttagccta aaaaaacctt ctcttttggaa ctttcagtaa tacgcttaac tgctcattgc   11160
tatattgaag tacggattag aagccgccga gcgggcgaca gccctccgac ggaagactct   11220
cctccgtgcg tcctggtctt caccggtcgc gttcctgaaa cgcagatgtg cctcgcgccg   11280
cactgctccg aacaataaag attctacaat actagctttt atggttatga agaggaaaaa   11340
ttggcagtaa cctggcccca caaaccttca aatcaacgaa tcaaattaac aaccatagga   11400
taataatgcg attagttttt tagccttatt tctggggtaa ttaatcagcg aagcgatgat   11460
ttttgatcta ttaacagata tataaatgca aaagctgcat aacccacttta actaatactt   11520 tcaacatttt cggtttgtat tacttcttat tcaaatgtca taaaagtatc aacaaaaaat   11580
tgttaatata cctctatact taccccaccc gaagtcgcgc aaccaactaa ctttacaatg   11640
gctgcagacc aattggtgaa gactgaagtc accaagaagt cttttactgc tcctgtacaa   11700
aaggcttcta caccagtttt aaccaataaa acagtcattt ctggatcgaa agtcaaaagt   11760
ttatcatctg cgcaatcgag ctcatcagga ccttcatcat ctagtgagga agatgattcc   11820
cgcgatattg aaagcttgga taagaaaata cgtcctttag aagaattaga agcattatta   11880
agtagtggaa atacaaaaca attgaagaac aaagaggtcg ctgccttggt tattcacggt   11940
```

```
aagttacctt tgtacgcttt ggagaaaaaa ttaggtgata ctacgagagc ggttgcggta   12000
cgtaggaagg ctctttcaat tttggcagaa gctcctgtat tagcatctga tcgtttacca   12060
tataaaaatt atgactacga ccgcgtattt ggcgcttgtt gtgaaaatgt tataggttac   12120
atgcctttgc ccgttggtgt tataggcccc ttggttatcg atggtacatc ttatcatata   12180
ccaatggcaa ctacagaggg ttgtttggta gcttctgcca tgcgtggctg taaggcaatc   12240
aatgctggcg gtggtgcaac aactgtttta actaaggatg gtatgacaag aggcccagta   12300
gtccgtttcc caactttgaa aagatctggt gcctgtaaga tatggttaga ctcagaagag   12360
ggacaaaacg caattaaaaa agcttttaac tctacatcaa gatttgcacg tctgcaacat   12420
attcaaactt gtctagcagg agatttactc ttcatgagat ttagaacaac tactggtgac   12480
gcaatgggta tgaatatgat ttctaagggt gtcgaatact cattaaagca aatggtagaa   12540
gagtatggct gggaagatat ggaggttgtc tccgtttctg gtaactactg taccgacaaa   12600
aaaccagctg ccatcaactg gatcgaaggt cgtggtaaga gtgtcgtcgc agaagctact   12660
attcctggtg atgttgtcag aaaagtgtta aaaagtgatg tttccgcatt ggttgagttg   12720
aacattgcta agaatttggt tggatctgca atggctgggc ctgttggtgg atttaacgca   12780
catgcagcta atttagtgac agctgttttc ttggcattag acaagatcc tgcacaaaat   12840 gtcgaaagtt ccaactgtat aacattgatg aagaagtgg acggtgattt gagaatttcc   12900
gtatccatgc catccatcga agtaggtacc atcggtggtg gtactgttct agaaccacaa   12960
ggtgccatgt tggacttatt aggtgtaaga ggcccacatg ctaccgctcc tggtaccaac   13020
gcacgtcaat tagcaagaat agttgcctgt gccgtcttgg caggtgaatt atccttatgt   13080
gctgccctag cagccggcca tttggttcaa agtcatatga cccacaacag gaaacctgct   13140
gaaccaacaa aacctaacaa tttggacgcc actgatataa atcgtttgaa agatgggtcc   13200
gtcacctgca ttaaatccta aacttagtca tacgtcattg gtattctctt gaaaaagaag   13260
cacaacagca ccatgtgtta cgtaaaatat ttactttata gtttgtacgt cataatttct   13320
tccatattac aagttcgtgc atatatagaa agaattctgt tgttgtaatt gtcataacta   13380
ttgagcttta cctgaaaatt caacgaaaaa aactcaaaaa ccacatgctt ctcttgagtc   13440
atgcggaggt ccgccggcgt tggacgagcg aatgtgtata ttagtttaaa aagttgtatg   13500
taataaaagt aaaatttaat attttggatg aaaaaaacca ttttagact ttttcttaac   13560 tagaatgctg gagtagaaat acgccatctc aagatacaaa aagcgttacc ggcactgatt   13620
tgtttcaacc agtatataga ttattattgg gtcttgatca actttcctca gacatatcag   13680
taacagttat caagctaaat atttacgcga aagaaaaaca aatattttaa ttgtgatact   13740
tgtgaatttt atttattaa ggatacaaag ttaagagaaa acaaaattta tatacaatat   13800
aagtaatatt catatatatg tgatgaatgc agtcttaacg agaagacatg gccttggtga   13860
caactctctt caaccaact tcagcctttc tcaattcatc agcagatggg tcttcgattt   13920
gcaaagcagc caaagcggcg gtttaaacgc gtggccgtgc cgtc                    13964
```

<210> SEQ ID NO 35
<211> LENGTH: 13963
<212> TYPE: DNA
<213> ORGANISM: Artificial Sequence
<220> FEATURE:
<223> OTHER INFORMATION: Synthetic: i85207 integration construct

<400> SEQUENCE: 35

```
gacggcacgg ccacgcgttt aaaccgccag ggcaaggttg gcctctactt actccatcga     60
caattcaaga tacagaacct cctccagatg gaatccctte catagagaga aggagcaagc    120
aactgaccca atattgactg ccactggacc tgaagacatg caacaaagtg caagcatagt    180
ggggccttct tccaatgcta atccggtcac tgccactgct gctacggaaa accaacctaa    240
aggtattaac ttcttcacta taagaaaatc acacgagcgc ccggacgatg tctctgttta    300
aatggcgcaa gttttccgct tgtaatata  tatttatacc cctttcttct ctcccctgca    360
atataatagt ttaattctaa tattaataat atcctatatt ttcttcattt accggcgcac    420
tctcgcccga acgacctcaa aatgtctgct acattcataa taaccaaaag ctcataactt    480 tttttttga  acctgaatat atatacatca catgtcactg ctggtccttg ccgaccagcg    540
tatacaatct cgatagttgg tttcccgttc tttccactcc cgtccgctcg tccaacgccg    600
gcggaccttc acatgtaggg accgaattgt ttacaagttc tctgtaccac catggagaca    660
tcaaagattg aaaatctatg gaaagatatg gacggtagca acaagaatat agcacgagcc    720
gcgaagttca tttcgttact tttgatatcg ctcacaacta ttgcgaagcg cttcagtgaa    780
aaaatcataa ggaaaagttg taaatattat tggtagtatt cgtttggtaa agtagagggg    840 gtaattttc  ccctttattt tgttcataca ttcttaaatt gctttgcctc tccttttgga    900
aagctatact tcggagcact gttgagcgaa ggctcattag atatattttc tgtcattttc    960
cttaacccaa aaataaggga aagggtccaa aaagcgctcg acaactgtt  gaccgtgatc   1020 cgaaggactg gctatacagt gttcacaaaa tagccaagct gaaaataatg tgtagctatg   1080
ttcagttagt ttggctagca aagatataaa agcaggtcgg aaatatttat gggcattatt   1140
atgcagagca tcaacatgat aaaaaaacct cccgcgacct ccaaaatcga actaccttca   1200
caatgactgc cgacaacaat agtatgcccc atggtgcagt atctagttac gccaaattag   1260
tgcaaaacca acacctgaa  gacattttgg aagagtttcc tgaaattatt ccattacaac   1320
aaagacctaa taccegatct agtgagacgt caaatgacga agcggagaa  acatgttttt   1380 ctggtcatga tgaggagcaa attaagttaa tgaatgaaaa ttgtattgtt ttggattggg   1440
acgataatgc tattggtgcc ggtaccaaga agtttgtca  tttaatggaa atattgaaa    1500 agggttact  acatcgtgca ttctccgtct ttattttcaa tgaacaaggt gaattacttt   1560
tacaacaaag agccactgaa aaaataactt tccctgatct ttggactaac acatgctgct   1620
ctcatccact atgtattgat gacgaattag gtttgaaggg taagctagac gataagatta   1680
agggcgctat tactgcggcg gtgagaaaac tagatcatga attaggtatt ccagaagatg   1740
aaactaagac aagggg taag tttcactttt taaacagaat ccattacatg gcaccaagca   1800
atgaaccatg gggtgaacat gaaattgatt acatcctatt ttataagatc aacgctaaag   1860
aaaacttgac tgtcaaccca aacgtcaatg aagttagaga cttcaaatgg gtttcaccaa   1920
atgatttgaa aactatgttt gctgacccaa gttacaagtt tacgccttgg tttaagatta   1980
tttgcgagaa ttacttattc aactggtggg agcaattaga tgacctttct gaagtggaaa   2040
atgacaggca aattcataga atgctataac aacgcgtcaa taatataggc tacataaaaa   2100
tcataataac tttgttatca tagcaaaatg tgatataaaa cgtttcattt cacctgaaaa   2160
atagtaaaaa taggcgacaa aaatccttag taatatgtaa actttatttt ctttatttat   2220
ttacagaact ctgaatatac attgattgtt cacatttttt ttttctcttc tcaatttccc   2280
ttgattatat tcaaaaggtt attggcctct tgaatgtttc ccactgaatc cccgcgtgct   2340
tggccggccg tggagcgacc tcatgctata cctgagaaag caacctgacc tacaggaaag   2400
```

```
agttactcaa gaataagaat tttcgtttta aaacctaaga gtcactttaa aatttgtata    2460
cacttatttt ttttataact tatttaataa taaaaatcat aaatcataag aaattcgctc    2520
aaacgaccat tggatggaca aagaaggact tcatgtaaga tttcatgtca ccttcggcgt    2580
gagtgaaacc atcgttaaca gagtataaaa cttcacacat tctagccaag ttgatagctg    2640
gcattaacaa agggaatgga acggcggttg gtctcaaaga ttctctgtta ataaccttcc    2700
aggcgtcttc gacttttcta gagatgtatt cacaggcttc ttcttcagaa gcaccggatt    2760
ccttagaata acattcgatg gaggaggcaa catgacctct ttcttgttct tctttatgag    2820
agacaatatc atccatcaat ctaatgataa cacaagaagc ttcaacaata ggtgggtagg    2880
aagaaaccca tttaaaagtg tcctcgttaa caatgtcacc tctaccaacg taagatctag    2940
cagtgatcaa accgtaggta ccggtaacca tggaaacaga catgtactct tccaaagtag    3000
gcatgtaacc ttcttttcaac catctggctt caaccaagta gtttctgacc aattccttag    3060
ccatttcctt aacgtagtgg atttgataag ccttaccttc cttttctaaa gattcttcca    3120
tttcaacgtg caagttaacc aattcttggt agatcaactt catgtattct ggcaacatgt    3180
ccaaacaaga aatggaccac ttctcaacgg cttgagtgaa aatttccaat tcttcgtagg    3240
taccgtagtt gtcgaaggta tcatccaaaa cgaccaacca catacaagac ttcatcaaga    3300
acattctggt tctggcatgt tgtggttcat agtaaataga caaatccag aagtaacctt     3360 cgacaactct atcacgaacg aatggcaatt tgttttgcaa gtctaaatct ttccaccact    3420
tgcagatgtg agacaattct ttcttatgca tggattgcaa aacagagaaa tctaacttag    3480
ccaacttcaa caaaacctcg tcgtgagaag tttcttgttg gtaaattggc atatagtgta    3540
aagcttcgat tctggccaat cttcttctca atggttgctt caaggcttgg tggatttggg    3600
ttcttaagga agagtcacaa gatggatcct tggcaataat gtccaagtga accttagaga    3660
attccaaagc gttgtccaag atggtttcat cttcgactct catgaaagca gcttcgtaca    3720
aggccaagat accttgagcg tcgttacaca aagattcctt aaatttacct ttttcgtcca    3780
taaagtcctt gaaaacacca gaggagacat tgaaaccttg ttgacgcaac aaacgaaacc    3840
acaaggagat agattgtaaa ttttccttat cgacccattg ttcaccgtaa gtgacatgga    3900
tatgttgtaa agcttcttcg atttcttctt caaaatggta agcaatacct aaacgttgaa    3960
cagcattgat taattcgatc aacttaacat gttgcatagg ttcgttagaa cccttaatag    4020
taatcaattc cttcttaact tcctccttta actcttcgac taattgcttc ttcataacca    4080
agtcctctgg ttcatcgtaa gtcaaaaatt gatcacccca aatggaagcg ttgaagttag    4140
cggtatgtct aataacgtct ggcttggtag aatccttatc atcgacaaca attggggaag    4200
tagatggaga ggaagaaaca gaggaaatag gcaaagtgga cattgtaaag ttagttggtt    4260
gcgcgacttc gggtggggta agtatagagg tatattaaca atttttttgtt gatactttta    4320 tgacatttga ataagaagta atacaaaccg aaaatgttga aagtattagt taaagtggtt    4380
atgcagcttt tgcatttata tatctgttaa tagatcaaaa atcatcgctt cgctgattaa    4440
ttaccccaga aataaggcta aaaaactaat cgcattatta tcctatggtt gttaatttga    4500
ttcgttgatt tgaaggtttg tggggccagg ttactgccaa ttttttcctct tcataaccat    4560 aaaagctagt attgtagaat ctttattgtt cggagcagtg cggcgcgagg cacatctgcg    4620
tttcaggaac gcgaccggtg aagaccagga cgcacggagg agagtcttcc gtcggagggc    4680
tgtcgcccgc tcggcggctt ctaatccgta cttcaatata gcaatgagca gttaagcgta    4740
```

```
ttactgaaag ttccaaagag aaggttttt taggctaaga taatgggct ctttacattt    4800 ccacaacata taagtaagat tagatatgga tatgtatatg gtggtattgc catgtaatat    4860
gattattaaa cttctttgcg tccatccaaa aaaaagtaa cgcacgcaca ctcccgacag    4920
acaactagct tgataatggc ttcagaaaaa gaaattagga gagagagatt cttgaacgtt    4980
ttccctaaat tagtagagga attgaacgca tcgcttttgg cttacggtat gcctaaggaa    5040
gcatgtgact ggtatgccca ctcattgaac tacaacactc caggcggtaa gttaaataga    5100
ggtttgtccg ttgtggacac gtatgctatt ctctccaaca agaccgttga acaattgggg    5160
caagaagaat acgaaaaggt tgctattcta ggttggtgca ttgagttgtt gcaggcttac    5220
ttcttggtcg ccgatgatat gatggacaag tccattacca gaagaggcca accatgttgg    5280
tacaaggttc ctgaagttgg ggaaattgcc atcaatgacg cattcatgtt agaggctgct    5340
atctacaagc ttttgaaatc tcacttcaga aacgaaaaat actacataga tatcaccgaa    5400
ttgttccatg aagtcacctt ccaaaccgaa ttgggccaat tgatggactt aatcactgca    5460
cctgaagaca aagtcgactt gagtaagttc tccctaaaga agcactcctt catagttact    5520
ttcaagactg cttactattc tttctacttg cctgtcgcat tggctatgta cgttgccggt    5580
atcacagatg aaaaggattt gaaacaagcc agagatgtct tgattccatt gggtgaatat    5640
ttccaaattc aagatgacta cttagactgc ttcggtaccc cagaacagat cggtaagatc    5700
ggtacagata tccaagataa caaatgttct tgggtaatca acaaggcatt agaacttgct    5760
tccgcagaac aaagaaagac tttagacgaa aattacggta agaaggactc agtcgcagaa    5820
gccaaatgca aaagatttt caatgacttg aaaatcgacc agttatacca cgaatatgaa    5880
gagtctgttg ccaaggattt gaaggccaag atctcccaag tcgacgagtc tcgtggcttc    5940
aaagccgacg tcttaactgc gttttgaac aaggtttaca agagaagtaa atagaactaa    6000
cgctaatcga taaaacatta gatttcagat tagataagga ccatgtataa gaaatatata    6060
cttccactat aatatagtat aagcttacag atagtatctc tcgatctacc gttccacgtg    6120
actagtccaa gaacctgcag gccgcgagcg ccgatacgaa aatcgttatt gtcttgaagg    6180
tgaaatttct actcttatta atggtgaacg ttaagctgat gctatgatgg aagctgattg    6240
gtcttaactt gcttgtcatc ttgctaatgg tcattggctc gtgttattac ttaagttatt    6300
tgtactcgtt ttgaacgtaa tgctaatgat catcttatgg aataatagtg agtggtttca    6360
gggtccataa agcttttcaa ttcatctttt ttttttttgt tctttttttt gattccggtt    6420
tctttgaaat ttttttgatt cggtaatctc cgagcagaag gaagaacgaa ggaaggagca    6480
cagacttaga ttggtatata tacgcatatg tggtgttgaa gaaacatgaa attgcccagt    6540
attcttaacc caactgcaca gaacaaaaac ctgcaggaaa cgaagataaa tcatgtcgaa    6600
agctacatat aaggaacgtg ctgctactca tcctagtcct gttgctgcca agctatttaa    6660
tatcatgcac gaaaagcaaa caaacttgtg tgcttcattg gatgttcgta ccaccaagga    6720
attactggag ttagttgaag cattaggtcc caaaatttgt ttactaaaaa cacatgtgga    6780
tatcttgact gattttttcca tggagggcac agttaagccg ctaaaggcat tatccgccaa    6840
gtacaatttt ttactcttcg aagacagaaa atttgctgac attggtaata cagtcaaatt    6900
gcagtactct gcgggtgtat acagaatagc agaatgggca gacattacga atgcacacgg    6960
tgtggtgggc ccaggtattg ttagcggttt gaagcaggcg gcggaagaag taacaaagga    7020
acctagaggc cttttgatgt tagcagaatt gtcatgcaag ggctccctag ctactggaga    7080
atatactaag ggtactgttg acattgcgaa gagtgacaaa gattttgtta tcggctttat    7140
```

```
tgctcaaaga gacatgggtg gaagagatga aggttacgat tggttgatta tgacacccgg    7200
tgtgggttta gatgacaagg gagacgcatt gggtcaacag tatagaaccg tggatgatgt    7260
ggtctctaca ggatctgaca ttattattgt tggaagagga ctatttgcaa agggaaggga    7320
tgctaaggta gagggtgaac gttacagaaa agcaggctgg gaagcatatt tgagaagatg    7380
cggccagcaa aactaaaaaa ctgtattata agtaaatgca tgtatactaa actcacaaat    7440
tagagcttca atttaattat atcagttatt accacgaaaa tcgttattgt cttgaaggtg    7500
aaatttctac tcttattaat ggtgaacgtt aagctgatgc tatgatggaa gctgattggt    7560
cttaacttgc ttgtcatctt gctaatggtc atatggctcg tgttattact taagttattt    7620
gtactcgttt tgaacgtaat gctaatgatc atcttatgga ataatagtga atcggcgctc    7680
gcggcctgca ggtttcctca tcctagtatg tatagcttgt acccattaaa cgaattttat    7740
catgccgccg aaaggaacaa tttcaagtac tatcggaaga tgaatggtta gatgttaagc    7800
gcggtcactt caaacttcac atttataaag atgtcacatg gaccactatt atctacctta    7860
agttatttat caagataagt ttccggatct ttttctttcc taacacccca gtcagcctga    7920
gttacatcca gccattgaac cttagaaaat cttttgtcat cagcggtttg agccctaaga    7980
tcaacatctt gcttagcaat cactgcaatg gcgtcataac caccagcacc aggtattaag    8040
caagtaagaa ctccttttaa ggtctggcaa tcatccaata agctagtttg tacgggaggt    8100
tcgatatcgg caccagattc tttagttatt tttctaaagg aacgtctaat tgtggcaact    8160
gcatctctaa cttctgtgat ctcaggatac ttttgacagg tacagtcatt cctctcaaga    8220
gactcaaata tctgatcgct gtaatcgtca tgagtctcgt gtaagcgatc tagtttagat    8280
agtccatcca taaatctaga atttgcatga tcgagttctg tatatatttt caagcttttcc   8340
ggcatatgcg aatcatacca attttttacc ttctggacca gttttactgt ttctgaacca    8400
ttcttaatat cgcccatcca taaagttaat cccgaaggta aatggttact tttaatcgtt    8460
atattccagt cttcttcatt aaccaaatgc gccagtttac tgccgtaagt agcacttcca    8520
atatctggca aattagagat taatgcgggt gggaatcttc tatatctgat agatccatat    8580
gctgccgccg ctacatcaaa cccgcttcca attttacccct gagcttgaca atgagcaact    8640
tgtgataaat tatgaataac ttctctatat ttgtctacat tattttccag gtccgataca    8700
aaaaaggagg ccaaagctgt agttaaaact gtgactaaac ctgccgagga gcccagcccct   8760
gttttgggaa cttcttcaat tctgtgcgaa tgaaaactca atcttctgtt gccacgatgt    8820
tcggtaacgc tgtcctcctg agaatggtag gcatcatcag agaaaatatc aataacgaac    8880
aagtttctat tgcagtagtc gtccatgtta ggcttaaagt agctaaatac gttagcgata    8940
acttttcaa tgaaagggtt cttagatccg cctatcgaaa caggaatgaa gccagtttta    9000
ggacttatat ggtacagcca ctcccccatct ttaaattgtt tacttttcac acgcacttca    9060
aacttatcag actcttgcaa tgaaccgtaa ggatgggcta cagcatgcat tcttgccgat    9120
aatccgacta caaatgcttc atatttcgga tctaaaacta aatatccacc agctagtaac    9180
gctttccctg gggcactgaa ggctctcaac tctgacatta tcaagctagt tgtctgtcgg    9240
gagtgtgcgt gcgttttttt atcatgttga tgctctgcat aataatgccc ataaatattt    9300
ccgacctgct tttatatctt tgctagccaa actaactgaa catagctaca cattattttc    9360
agcttggcta ttttgtgaac actgtatagc cagtccttcg gatcacggtc aacagttgtc    9420
cgagcgcttt ttggacccctt tcccttattt ttgggttaag gaaaatgaca gaaaatatat    9480
```

```
ctaatgagcc ttcgctcaac agtgctccga agtatagctt tccaaaagga gaggcaaagc    9540
aatttaagaa tgtatgaaca aaataaaggg gaaaaattac cccctctact ttaccaaacg    9600
aatactacca ataatattta caacttttcc ttatgatttt ttcactgaag cgcttcgcaa    9660
tagttgtgag cgatatcaaa agtaacgaaa tgaacttcgc ggctcgtgct atattcttgt    9720
tgctaccgtc catatctttc catagatttt caatctttga tgtctccatg gtggtacaga    9780
gaacttgtaa acaattcggt ccctacatgt gaacggccgg ccaagcacgc ggggatccga    9840
agcatgtagg gaggtcatga tatgaaaaag caaagagta ggcatcaaaa agtttctcat    9900
tcaagtggta actgctgtta aaattaagat atttataaat tgaagcttgg tcgttccgac    9960
caataccgta gggaaacgta aattagctat tgtaaaaaaa ggaaagaaa agaaaagaaa    10020 aatgttacat atcgaattga tcttattcct ttggtagacc agtctttgcg tcaatcaaag    10080
attcgtttgt ttcttgtggg cctgaaccga cttgagttaa aatcactctg gcaacatcct    10140
tttgcaactc aagatccaat tcacgtgcag taaagttaga tgattcaaat tgatggttga    10200
aagcctcaag ctgctcagta gtaaatttct tgtcccatcc aggaacagag ccaaacaatt    10260
tatagataaa tgcaaagagt ttcgactcat tttcagctaa gtagtacaac acagcatttg    10320
gacctgcatc aaacgtgtat gcaacgattg tttctccgta aaactgatta atggtgtggc    10380
accaactgat gatacgcttg gaagtgtcat tcatgtagaa tattggaggg aaagagtcca    10440
aacatgtggc atggaaagag ttggaatcca tcattgtttc ctttgcaaag gtggcgaaat    10500 cttttttcaac aatggcttta cgcatgactt caaatctctt tggtacgaca tgttcaattc    10560
tttctttaaa tagttcggag gttgccacgg tcaattgcat accctgagtg gaactcacat    10620 ccttttttaat atcgctgaca actaggacac aagctttcat ctgaggccag tcagagctgt    10680
ctgcgatttg tactgccatg gaatcatgac catcttcagc ttttcccatt tcccaggcca    10740
cgtatccgcc aaacaacgat ctacaagctg aaccagaccc cttctcttgct attctagata    10800 tttctgaagt tgactgtggt aattggtata acttagcaat tgcagagacc aatgcagcaa    10860
agccagcagc ggaggaagct aaaccagctg ctgtaggaaa gttattttcg gagacaatgt    10920
ggagtttcca ttgagataat gtgggcaatg aggcgtcctt cgattccatt tccttttctta    10980 attggcgtag gtcgcgcaga caattttgag ttcttttcatt gtcgatgctg tgtggttctc    11040
catttaacca caaagtgtcg cgttcaaact caggtgcagt agccgcagag gtcaacgttc    11100
tgaggtcatc ttgcgataaa gtcactgata tggacgaatt ggtgggcaga ttcaacttcg    11160 tgtcccttt ccccccaatac ttaagggttg cgatgttgac gggtgcggta acggatgctg    11220
tgtaaacggt cattgtgaag gtagttcgat tttggaggtc gcgggaggtt acttttttt    11280 tggatgacg caaagaagtt taataatcat attacatggc aataccacca tatacatatc    11340
catatctaat cttacttata tgttgtggaa atgtaaagag ccccattatc ttagcctaaa    11400
aaaaccttct ctttggaact ttcagtaata cgcttaactg ctcattgcta tattgaagta    11460
cggattagaa gccgccgagc gggcgacagc cctccgacgg aagactctcc tccgtgcgtc    11520
ctggtcttca ccggtcgcgt tcctgaaacg cagatgtgcc tcgcgccgca ctgctccgaa    11580
caataaagat tctacaatac tagcttttat ggttatgaag aggaaaaatt ggcagtaacc    11640
tggccccaca aaccttcaaa tcaacgaatc aaattaacaa ccataggata ataatgcgat    11700 tagttttta gccttatttc tggggtaatt aatcagcgaa gcgatgattt ttgatctatt    11760
aacagatata taaatgcaaa agctgcataa ccacttttaac taatactttc aacatttcg    11820 gtttgtatta cttcttattc aaatgtcata aaagtatcaa caaaaaattg ttaatatacc    11880
```

```
tctatactta ccccacccga agtcgcgcaa ccaactaact ttacaatgtc attaccgttc    11940
ttaacttctg caccgggaaa ggttattatt tttggtgaac actctgctgt gtacaacaag    12000
cctgccgtcg ctgctagtgt gtctgcgttg agaacctacc tgctaataag cgagtcatct    12060
gcaccagata ctattgaatt ggacttcccg gacattagct ttaatcataa gtggtccatc    12120
aatgatttca atgccatcac cgaggatcaa gtaaactccc aaaaattggc caaggctcaa    12180
caagccaccg atggcttgtc tcaggaactc gttagtcttt tggatccgtt gttagctcaa    12240
ctatccgaat ccttccacta ccatgcagcg ttttgtttcc tgtatatgtt tgtttgccta    12300
tgcccccatg ccaagaatat taagtttttct ttaaagtcta ctttacccat cggtgctggg    12360
ttgggctcaa gcgcctctat ttctgtatca ctggccttag ctatggccta cttgggggg    12420 ttaataggat ctaatgactt ggaaaagctg tcagaaaacg ataagcatat agtgaatcaa    12480
tgggccttca taggtgaaaa gtgtattcac ggtaccccct caggaataga taacgctgtg    12540
gccacttatg gtaatgccct gctatttgaa aaagactcac ataatggaac aataaacaca    12600 aacaattta agttcttaga tgatttccca gccattccaa tgatcctaac ctatactaga    12660
attccaaggt ctacaaaaga tcttgttgct cgcgttcgtg tgttggtcac cgagaaattt    12720
cctgaagtta tgaagccaat tctagatgcc atgggtgaat gtgccctaca aggcttagag    12780
atcatgacta agtaagtaa atgtaaaggc accgatgacg aggctgtaga aactaataat    12840
gaactgtatg aacaactatt ggaattgata agaataaatc atggactgct tgtctcaatc    12900 ggtgttctc atcctggatt agaacttatt aaaaatctga gcgatgattt gagaattggc    12960
tccacaaaac ttaccggtgc tggtggcggc ggttgctctt tgactttgtt acgaagagac    13020
attactcaag agcaaattga cagtttcaaa aagaaattgc aagatgattt tagttacgag    13080
acatttgaaa cagacttggg tgggactggc tgctgtttgt taagcgcaaa aaatttgaat    13140
aaagatctta aaatcaaatc cctagtattc caattatttg aaaataaaac taccacaaag    13200
caacaaattg acgatctatt attgccagga aacacgaatt taccatggac ttcataagct    13260
aatttgcgat aggcattatt tattagttgt ttttaatctt aactgtgtat gaagttttat    13320
gtaataaaga tagaaagaga aacaaaaaaa aattttcgt agtatcaatt cagctttcga    13380
agacagaatg aaatttaagc agaccatagt atccttgata cattgactca ggtccgccgg    13440
cgttggacga gcgaagcatc ttgccctgtg cttggccccc agtgcagcga acgttataaa    13500
aacgaatact gagtatatat ctatgtaaaa caaccatatc atttcttgtt ctgaactttg    13560
tttacctaac tagttttaaa tttcccttttt tcgtgcatgc gggtgttctt atttattagc    13620
atactacatt tgaaatatca aatttcctta gtagaaaagt gagagaaggt gcactgacac    13680
aaaaaataaa atgctacgta taactgtcaa aactttgcag cagcgggcat ccttccatca    13740
tagcttcaaa catattagcg ttcctgatct tcatacccgt gctcaaaatg atcaaacaaa    13800
ctgttattgc caagaaataa acgcaaggct gccttcaaaa actgatccat tagatcctca    13860
tatcaagctt cctcatagaa cgcccaatta caataagcat gttttgctgt tatcaccggg    13920
tgataggttt gctcaggcgg tttaaacgcg tggccgtgcc gtc                      13963
```

<210> SEQ ID NO 36  
<211> LENGTH: 10209  
<212> TYPE: DNA  
<213> ORGANISM: Artificial Sequence  
<220> FEATURE:  
<223> OTHER INFORMATION: Synthetic: MS49253 integration construct

<400> SEQUENCE: 36

```
gacggcacgg ccacgcgttt aaaccgccac ccagccaagg tagtctaaaa gctaatttct      60
ctaaaaggga gaaagttggt gattttttat ctcgcattat tatatatgca agaatagtta     120
aggtatagtt ataaagtttt atcttaattg ccacatacgt acattgacac gtagaaggac     180
tccattattt ttttcattct agcatactat tattccttgt aacgtcccag agtattccat     240
ttaattgtcc tccatttctt aacggtgacg aaggatcacc atacaacaac tactaaagat     300
tatagtacac tctcaccttg caactattta tctgacattt gccttacttt tatctccagc     360
ttcccctcga ttttattttt caatttgatt tctaaagctt tttgcttagg cataccaaac     420
catccactca tttaacacct tattttttt ttcgaagaca gcatccaact ttatacgttc     480
actaccttt tttttacaac aatttcattc ttcatcctat gaacgctcgt ccaacgccgg     540
cggacctttc agacgcgact gcctcatcag taagacccgt tgaaaagaac ttacctgaaa     600
aaaacgaata tatactagcg ttgaatgtta gcgtcaacaa caagaagttt aatgacgcgg     660
aggccaaggc aaaaagattc cttgattacg taagggagtt agaatcattt tgaataaaaa     720
acacgctttt tcagttcgag tttatcatta tcaatactgc catttcaaag aatacgtaaa     780
taattaatag tagtgatttt cctaacttta tttagtcaaa aaattagcct tttaattctg     840
ctgtaacccg tacatgccca aaataggggg cgggttacac agaatatata acatcgtagg     900
tgtctgggtg aacagtttat tcctggcatc cactaaatat aatggagccc gcttttttaag    960
ctggcatcca gaaaaaaaaa gaatcccagc accaaaatat tgttttcttc accaaccatc    1020
agttcatagg tccattctct tagcgcaact acagagaaca ggggcacaaa caggcaaaaa    1080
acgggcacaa cctcaatgga gtgatgcaac ctgcctggag taaatgatga cacaaggcaa    1140
ttgacccacg catgtatcta tctcattttc ttacaccttc tattacccttc tgctctctct    1200
gatttggaaa aagctgaaaa aaaaggttga aaccagttcc ctgaaattat tcccctactt    1260
gactaataag tatataaaga cggtaggtat tgattgtaat tctgtaaatc tatttcttaa    1320
acttcttaaa ttctactttt atagttagtc ttttttttag ttttaaaaca ccaagaactt    1380
agtttcgacc tcccgcgacc tccaaaatcg aactaccttc acaatgacat ctccagttat    1440
cggaactcct tggaagaagt tgaacgcccc agtatctgaa gaggcaatag agggtgtcga    1500
caagtattgg agggctgcta attacttgtc aatcggacaa atctacttga ggtcaaaccc    1560
attaatgaag gaacctttca ccagggaaga tgttaagcat aggttggtcg gtcactgggg    1620
aaccacacca ggattaaact tttgattgg acacatcaac agattgattg cagatcacca    1680
acagaacacc gtcataatca tgggtccagg acatggaggt ccagctggta ccgcccagtc    1740
ttatttggat ggtacctata ccgagtattt cccaaatatt acaaaggacg aggcaggttt    1800
acagaagttt ttcagacagt tctcttaccc aggaggaatc ccttcacact acgctccaga    1860
aacaccaggt tctattcatg agggtggtga attaggatat gccttatcac atgcttacgg    1920
agcagtcatg aacaatcctt ctttgttcgt cccagccata gtaggtgatg gagaagccga    1980
gaccggtcct ttagccacag gttggcaatc taacaagtta gtaaaccctaa ggactgacgg    2040
aattgtcttg cctatttgc atttgaacgg atacaagatc gctaacccaa ccatcttgtc    2100
taggatatct gacgaggagt tgcatgagtt tttccacggt atgggatacg agccttatga    2160
gttcgtcgca ggatttgaca acgaagacca tttgtcaatc cacagaaggt tcgccgagtt    2220
gtttgagacc gtctttgacg agatctgtga cattaaggca gctgctcaga cagacgacat    2280
gaccagacct ttctatccta tgataatctt caggacacct aagggttgga cttgccctaa    2340
```

```
gtttatagac ggaaaaaaga ctgagggatc atggagatct catcaagtac ctttggcatc    2400
tgcaagagat acagaagctc acttcgaggt tttgaaaaat tggttggagt catataagcc    2460
tgaagaattg ttcgatgcaa atggagctgt taagccagag gtaactgctt ttatgcctac    2520
cggagagtta agaatcggag agaatcctaa cgctaatggt ggtagaatca gagaggaatt    2580
gaatttgcct gcattggagg attacgaggt aaaagaggtt gctgaatatg gtcatggatg    2640
gggtcagttg gaagcaacca gaagattagg tgtttacacc agggacatta taagaacaa     2700 cccagactca tttaggatct ttggaccaga tgaaaccgca tcaaataggt tacaggctgc    2760
atatgacgtt actaataagc aatgggacgc tggttactta tcagcccaag tagacgaaca    2820
tatggccgtt acaggtcaag ttacagagca attgtctgaa catcaaatgg aaggattctt    2880
ggaagcttat ttgttgaccg gaaggcatgg aatttggtca tcatatgagt cattcgtaca    2940
tgtcatcgac tcaatgttaa atcagcatgc taagtggtta aagccactg taagagagat     3000 cccatggagg aaaccaattt cttcaatgaa cttattggtt tcatctcacg tctggaggca    3060
ggatcataat ggattttctc atcaggaccc aggtgtcaca tcagttttat tgaacaagtg    3120
cttcaacaac gatcacgtta tcggaattta cttttcctgtc gattctaaca tgttgttagc    3180
tgttgccgag aagtgctaca agtctacaga catgataaac gccatcattg ccggaaagca    3240
gccagccgcc acctggttga ccttggatga ggcaagggct gaattggaga aggagcagc     3300 cgaatgggag tgggcctcaa cagccaagtc aaatgatgaa gcacagatag tattggcttc    3360
agccggtgat gttcctgctc aagaaatcat ggctgctgcc gataagttag atgctatggg    3420
tatcaagttc aaggttgtca cgtagtcga cttggtcaaa ttgcagtcta ccaaagaaaa     3480
tgacgaggcc atctctgacg ctgacttcgc agacttattt accgaagaca agccagtatt    3540
attcgcctac cattcatacg ccagagatgt taggggattg atctatgaca ggcctaacca    3600
tgacaacttc aacgtccacg gatacgaaga acagggttca accactaccc cttatgacat    3660
ggtcagagtc aacaatattg acaggtacga gttggtcgct aagcattga gaatgatcga     3720 tgcagacaaa tacgcagata aaatcgacga attggaggcc ttcagaaagg aagcattcca    3780
gtttgcagtt gataacggtt acgaccatcc tgactacacc gactgggtct attcaggagt    3840
aaataccaac aagcagggtg ctgtttcagc taccgctgca actgctggtg acaatgaata    3900
aagatctatt gaattgaatt gaatcgata gatcaatttt tttctttttct ctttccccat    3960 cctttacgct aaaataatag tttatttat ttttgaata tttttattt atatacgtat       4020 atatagacta ttatttatct tttaatgatt ttaagattt ttattaaaaa aaattcgct      4080 cctctttttaa tgcctttatg cagttttttt ttcccattcg atatttctat gttcgggttc   4140
agcgtatttt aagtttaata actcgaaaat tctgcgttcg ttaaagcttt cgagaaggat    4200
attatttcga aataaaccgt gttgtgtaag cttgaagcct ttttgcgctg ccaatattct    4260
tatccatcta ttgtactctt tagatccagt atagtgtatt cttcctgctc caagctcatc    4320
ccatccccgc gtgcttggcc ggccgtacga aaatcgttat tgtcttgaag gtgaaatttc    4380
tactcttatt aatggtgaac gttaagctga tgctatgatg gaagctgatt ggtcttaact    4440
tgcttgtcat cttgctaatg gtcattggct cgtgttatta cttaagttat ttgtactcgt    4500
tttgaacgta atgctaatga tcatcttatg gaataatagt gagtggtttc agggtccata    4560
aagcttttca attcatcttt ttttttttg ttcttttttt tgattccggt ttctttgaaa     4620 ttttttttgat tcggtaatct ccgagcagaa ggaagaacga aggaaggagc acagacttag   4680
```

-continued

```
attggtatat atacgcatat gtggtgttga agaaacatga aattgcccag tattcttaac    4740
ccaactgcac agaacaaaaa cctgcaggaa acgaagataa atcatgtcga aagctacata    4800
taaggaacgt gctgctactc atcctagtcc tgttgctgcc aagctattta atatcatgca    4860
cgaaaagcaa acaaacttgt gtgcttcatt ggatgttcgt accaccaagg aattactgga    4920
gttagttgaa gcattaggtc ccaaaatttg tttactaaaa acacatgtgg atatcttgac    4980
tgattttttcc atggagggca cagttaagcc gctaaaggca ttatccgcca agtacaattt    5040
tttactcttc gaagacagaa atttgctgac cattggtaat acagtcaaat tgcagtactc    5100
tgcgggtgta tacagaatag cagaatgggc agacattacg aatgcacacg gtgtggtggg    5160
cccaggtatt gttagcggtt tgaagcaggc ggcggaagaa gtaacaaagg aacctagagg    5220
ccttttgatg ttagcagaat tgtcatgcaa gggctcccta gctactggag aatatactaa    5280
gggtactgtt gacattgcga agagtgacaa agattttgtt atcggcttta ttgctcaaag    5340
agacatgggt ggaagagatg aaggttacga ttggttgatt atgacacccg gtgtgggttt    5400
agatgacaag ggagacgcat tgggtcaaca gtatagaacc gtggatgatg tggtctctac    5460
aggatctgac attattattg ttggaagagg actatttgca aagggaaggg atgctaaggt    5520
agagggtgaa cgttacagaa aagcaggctg ggaagcatat ttgagaagat gcggccagca    5580
aaactaaaaa actgtattat aagtaaatgc atgtatacta aactcacaaa ttagagcttc    5640
aatttaatta tatcagttat taccacgaaa atcgttattg tcttgaaggt gaaatttcta    5700
ctcttattaa tggtgaacgt taagctgatg ctatgatgga agctgattgg tcttaacttg    5760
cttgtcatct tgctaatggt catatggctc gtgttattac ttaagttatt tgtactcgtt    5820
ttgaacgtaa tgctaatgat catcttatgg aataatagtg aacggccggc caagcacgcg    5880
gggatgggat gagcttggag caggaagaat acactatact ggatctaaag agtacaatag    5940
atggataaga atattggcag cgcaaaaagg cttcaagctt acacaacacg gtttatttcg    6000
aaataatatc cttctcgaaa gctttaacga acgcagaatt ttcgagttat taaacttaaa    6060
atacgctgaa cccgaacata gaaatatcga atgggaaaaa aaaactgcat aaaggcatta    6120
aaagaggagc gaattttttt ttaataaaaa tcttaataat cattaaaaga taaataatag    6180
tctatatata cgtatataaa taaaaaatat tcaaaaaata aaataaacta ttattttagc    6240
gtaaaggatg gggaaagaga aaagaaaaaa attgatctat cgatttcaat tcaattcaat    6300
agatctttat tcattgtcac cagcagttgc agcggtagct gaaacagcac cctgcttgtt    6360
ggtatttact cctgaataga cccagtcggt gtagtcagga tggtcgtaac cgttatcaac    6420
tgcaaactgg aatgcttcct ttctgaaggc ctccaattcg tcgattttat ctgcgtattt    6480
gtctgcatcg atcattctca atgcttcagc gaccaactcg tacctgtcaa tattgttgac    6540
tctgaccatg tcataagggg tagtggttga accctgttct tcgtatccgt ggacgttgaa    6600
gttgtcatgg ttaggcctgt catagatcaa tcccctaaca tctctggcgt atgaatggta    6660
ggcgaataat actggcttgt cttcggtaaa taagtctgcg aagtcagcgt cagagatggc    6720
ctcgtcattt tctttggtag actgcaattt gaccaagtcg actacgttga caaccttgaa    6780
cttgataccc atagcatcta acttatcggc agcagccatg atttcttgag caggaacatc    6840
accggctgaa gccaatacta tctgtgcttc atcatttgac ttggctgttg aggcccactc    6900
ccattcggct gctccttttct ccaattcagc ccttgcctca tccaaggtca accaggtggc    6960
ggctggctgc tttccggcaa tgatggcgtt tatcatgtct gtagacttgt agcacttctc    7020
ggcaacagct aacaacatgt tagaatcgac aggaaagtaa attccgataa cgtgatcgtt    7080
```

```
gttgaagcac ttgttcaata aaactgatgt gacacctggg tcctgatgag aaaatccatt    7140
atgatcctgc ctccagacgt gagatgaaac caataagttc attgaagaaa ttggtttcct    7200
ccatgggatc tctcttacag tggcttctaa ccacttagca tgctgattta acattgagtc    7260
gatgacatgt acgaatgact catatgatga ccaaattcca tgccttccgg tcaacaaata    7320
agcttccaag aatccttcca tttgatgttc agacaattgc tctgtaactt gacctgtaac    7380
ggccatatgt tcgtctactt gggctgataa gtaaccagcg tcccattgct tattagtaac    7440
gtcatatgca gcctgtaacc tatttgatgc ggtttcatct ggtccaaaga tcctaaatga    7500 gtctggttg ttctttataa tgtccctggt gtaaacacct aatcttctgg ttgcttccaa    7560
ctgaccccat ccatgaccat attcagcaac ctcttttacc tcgtaatcct ccaatgcagg    7620
caaattcaat tcctctctga ttctaccacc attagcgtta ggattctctc cgattcttaa    7680
ctctccggta ggcataaaag cagttacctc tggcttaaca gctccatttg catcgaacaa    7740
ttcttcaggc ttatatgact ccaaccaatt tttcaaaacc tcgaagtgag cttctgtatc    7800
tcttgcagat gccaaaggta cttgatgaga tctccatgat ccctcagtct ttttttccgtc    7860 tataaactta gggcaagtcc aaccttagg tgtcctgaag attatcatag gatagaaagg    7920
tctggtcatg tcgtctgtct gagcagctgc cttaatgtca cagatctcgt caaagacggt    7980
ctcaaacaac tcggcgaacc ttctgtggat tgacaaatgg tcttcgttgt caaatcctgc    8040
gacgaactca taaggctcgt atcccatacc gtggaaaaac tcatgcaact cctcgtcaga    8100
tatcctagac aagatggttg ggttagcgat cttgtatccg ttcaaatgca aaataggcaa    8160
gacaattccg tcagtcctag ggtttactaa cttgttagat tgccaacctg tggctaaagg    8220
accggtctcg gcttctccat cacctactat ggctgggacg aacaaagaag gattgttcat    8280
gactgctccg taagcatgtg ataaggcata tcctaattca ccaccctcat gaatagaacc    8340
tggtgtttct ggagcgtagt gtgaagggat tcctcctggg taagagaact gtctgaaaaa    8400
cttctgtaaa cctgcctcgt cctttgtaat atttgggaaa tactcggtat aggtaccatc    8460
caaataagac tgggcggtac cagctggacc tccatgtcct ggacccatga ttatgacggt    8520
gttctgttgg tgatctgcaa tcaatctgtt gatgtgtcca atcaaaaagt ttaatcctgg    8580
tgtggttccc cagtgaccga ccaacctatg cttaacatct tccctggtga aggttccttt    8640
cattaatggg tttgacctca gtagatttg tccgattgac aagtaattag cagccctcca    8700
atacttgtcg acaccctcta ttgcctcttc agatactggg gcgttcaact tcttccaagg    8760
agttccgata actggagatg tcattgtgaa ggtagttcga ttttggaggt cgcgggaggt    8820
cgaaactaag ttcttggtgt tttaaaacta aaaaaagac taactataaa agtagaattt    8880
aagaagttta agaaatagat ttacagaatt acaatcaata cctaccgtct ttatatactt    8940
attagtcaag taggggaata atttcaggga actggtttca acctttttt tcagcttttt    9000 ccaaatcaga gagagcagaa ggtaatagaa ggtgtaagaa aatgagatag atacatgcgt    9060
gggtcaattg ccttgtgtca tcatttactc caggcaggtt gcatcactcc attgaggttg    9120
tgcccgtttt ttgcctgttt gtgccccgtt tctctgtagt tgcgctaaga gaatggacct    9180
atgaactgat ggttggtgaa gaaaacaata ttttggtgct gggattcttt ttttttctgg    9240
atgccagctt aaaaagcggg ctccattata tttagtggat gccaggaata aactgttcac    9300
ccagacacct acgatgttat atattctgtg taacccgccc cctatttggg gcatgtacgg    9360
gttacagcag aattaaaagg ctaatttttt gactaaaataa agttaggaaa atcactacta    9420
```

```
ttaattatttt  acgtattctt  tgaaatggca  gtattgataa  tgataaactc  gaactgaaaa     9480
agcgtgttttt  ttattcaaaa  tgattctaac  tcccttacgt  aatcaaggaa  tcttttttgcc    9540
ttggcctccg   cgtcattaaa  cttcttgttg  ttgacgctaa  cattcaacgc  tagtatatat     9600
tcgttttttt   caggtaagtt  cttttcaacg  ggtcttactg  atgaggcagt  cgcgtctgaa     9660
aggtccgccg   gcgttggacg  agcgctccat  gctggactta  ctcgtcgaag  atttcctgct     9720
actctctata   taattagaca  cccatgttat  agatttcaga  aaacaatgta  ataatatatg     9780
gtagcctcct   gaaactacca  agggaaaaat  ctcaacacca  agagctcata  ttcgttggaa     9840
tagcgataat   atctctttac  ctcaatctta  tatgcatgtt  atttgctctt  ataattggtc     9900
tctatttagg   gaaaaaagtc  ggtttgagag  cttctcgcga  tgtgaaatct  caatttgaac     9960
tgcacgccaa   agctagccca  tttcacgaac  accagaaaga  agaaatcccc  aaggatcgca    10020
tgacagagta   tgctctctca  tatcgttgag  tatgaatgcc  aatacactga  tcagctttac    10080
aagaaacgta   aaatctggca  cgatggtaga  ctgaaatact  ttcagttaaa  caacagattc    10140
atgctttata   cggaaaagga  taacgttttg  ttagctagtg  aggcggttta  aacgcgtggc    10200
cgtgccgtc                                                                  10209

<210> SEQ ID NO 37
<211> LENGTH: 7257
<212> TYPE: DNA
<213> ORGANISM: Artificial Sequence
<220> FEATURE:
<223> OTHER INFORMATION: Synthetic: MS49298 integration construct

<400> SEQUENCE: 37
gacggcacgg  ccacgcgttt  aaaccgccac  ccagccaagg  tagtctaaaa  gctaatttct      60
ctaaagggga  gaaagttggt  gatttttttat ctcgcattat  tatatatgca  agaatagtta     120
aggtatagtt  ataaagtttt  atcttaattg  ccacatacgt  acattgacac  gtagaaggac     180
tccattattt  ttttcattct  agcatactat  tattccttgt  aacgtcccag  agtattccat     240
ttaattgtcc  tccatttctt  aacggtgacg  aaggatcacc  atacaacaac  tactaaagat     300
tatagtacac  tctcaccttg  caactatttta tctgacattt  gccttacttt  tatctccagc     360
ttcccctcga  ttttattttt  caatttgatt  tctaaagctt  tttgcttagg  cataccaaac     420
catccactca  tttaacacct  tattttttttt ttcgaagaca  gcatccaact  ttatacgttc     480
actaccttttt ttttacaac  aatttcattc  ttcatcctat  gaacgctcgt  ccaacgccgg     540
cggaccttttc agacgcgact  gcctcatcag  taagacccgt  tgaaaagaac  ttacctgaaa     600
aaaacgaata  tatactagcg  ttgaatgtta  gcgtcaacaa  caagaagttt  aatgacgcgg     660
aggccaaggc  aaaaagattc  cttgattacg  taagggagtt  agaatcattt  tgaataaaaa     720
acacgctttt  tcagttcgag  tttatcatta  tcaatactgc  catttcaaag  aatacgtaaa     780
taattaatag  tagtgatttt  cctaaacttta tttagtcaaa  aaattagcct  tttaattctg     840
ctgtaacccg  tacatgccca  aaatagggggg cgggttacac  agaatatata  acatcgtagg     900
tgtctgggtg  aacagtttat  tcctggcatc  cactaaatat  aatggagccc  gcttttaag     960
ctggcatcca  gaaaaaaaa   gaatcccagc  accaaaatat  tgttttcttc  accaaccatc    1020
agttcatagg  tccattctct  tagcgcaact  acagagaaca  ggggcacaaa  caggcaaaaa    1080
acgggcacaa  cctcaatgga  gtgatgcaac  ctgcctggag  taaatgatga  cacaaggcaa    1140
ttgacccacg  catgtatcta  tctcattttc  ttacaccttc  tattaccttc  tgctctctct    1200
gatttggaaa  aagctgaaaa  aaaaggttga  aaccagttcc  ctgaaattat  tcccctactt    1260
```

-continued

```
gactaataag tatataaaga cggtaggtat tgattgtaat tctgtaaatc tatttcttaa    1320
acttcttaaa ttctactttt atagttagtc ttttttttag ttttaaaaca ccaagaactt    1380
agtttcgacc tcccgcgacc tccaaaatcg aactaccttc acaatgaaat tgatggagaa    1440
tatcttcgga ttggccaagg ccgacaagaa gaaaatcgtt ttggcagagg gtgaggaaga    1500
gaggaacatc agggcttcag aggagattat tagggacggt attgccgaca taatcttggt    1560
cggttcagag tctgtcatta aggaaaacgc cgcaaaattc ggagtaaatt tggccggagt    1620
agagatagtc gacccagaaa cttcttctaa gaccgccggt tacgccaacg ctttctacga    1680
gatcagaaaa aacaagggag tcaccttgga gaaggctgac aaaatcgtca gggacccaat    1740
ctacttcgca acaatgatgg tcaagttagg tgacgctgac ggtttggtat ctggtgctat    1800
acatactaca ggagacttgt taaggcctgg tttgcagatt gtcaaaacag taccaggtgc    1860
atctgtcgtc tcatcagtct tcttgatgtc agtacctgac tgcgagtatg gagaggacgg    1920
ttttttgtta ttcgctgact gcgctgtaaa tgtttgtcct accgctgaag agttatcttc    1980
aatcgcaatt accactgctg agactgcaaa gaatttgtgc aagatcgagc caagggtagc    2040
catgttgtca ttctcaacca tgggatcagc ctcacatgaa ttagtcgaca aggttacaaa    2100
ggcaacaaaa ttggctaagg aggctaggcc tgacttagac atcgacggtg aattgcagtt    2160
agacgcctca ttggttaaga aggtcgcaga tttgaaagcc cctggatcta aagtcgctgg    2220
taaggcaaat gtcttgatct tcccagacat ccaggcagga aacatcggat acaagttggt    2280
ccaaagattc gcaaaggccg aagccatcgg tcctatatgt cagggatttg ccaaaccctat   2340 caacgatttg tcaaggggat gttcagtcga cgacatcgtc aaagttgttg ccgttaccgc    2400
agttcaggca caagcacaag gataaagatc tattgaattg aattgaaatc gatagatcaa    2460 ttttttttctt ttctctttcc ccatccttta cgctaaaata atagtttatt ttatttttg    2520 aatattttt atttatatac gtatatatag actattattt atcttttaat gattattaag    2580
atttttatta aaaaaaaatt cgctcctctt ttaatgcctt tatgcagttt ttttttccca    2640
ttcgatattt ctatgttcgg gttcagcgta ttttaagttt aataactcga aaattctgcg    2700
ttcgttaaag ctttcgagaa ggatattatt tcgaaataaa ccgtgttgtg taagcttgaa    2760
gcctttttgc gctgccaata ttcttatcca tctattgtac tctttagatc cagtatagtg    2820
tattcttcct gctccaagct catcccatcc ccgcgtgctt ggccggccgt acgaaaatcg    2880
ttattgtctt gaaggtgaaa tttctactct tattaatggt gaacgttaag ctgatgctat    2940
gatggaagct gattggtctt aacttgcttg tcatcttgct aatggtcatt ggctcgtgtt    3000
attacttaag ttatttgtac tcgttttgaa cgtaatgcta atgatcatct tatggaataa    3060
tagtgagtgg tttcagggtc cataaagctt ttcaattcat ctttttttt tttgttcttt    3120 tttttgattc cggtttcttt gaattttttt tgattcggta atctccgagc agaaggaaga    3180
acgaaggaag gagcacagac ttagattggt atatatacgc atatgtggtg ttgaagaaac    3240
atgaaattgc ccagtattct taacccaact gcacagaaca aaaacctgca ggaaacgaag    3300
ataaatcatg tcgaaagcta catataagga acgtgctgct actcatccta gtcctgttgc    3360
tgccaagcta tttaatatca tgcacgaaaa gcaaacaaac ttgtgtgctt cattggatgt    3420
tcgtaccacc aaggaattac tggagttagt tgaagcatta ggtcccaaaa tttgtttact    3480
aaaaacacat gtggatatct tgactgattt ttccatggag ggcacagtta agccgctaaa    3540
ggcattatcc gccaagtaca atttttttact cttcgaagac agaaaatttg ctgacattgg    3600
```

```
taatacagtc aaattgcagt actctgcggg tgtatacaga atagcagaat gggcagacat    3660
tacgaatgca cacggtgtgg tgggcccagg tattgttagc ggtttgaagc aggcggcgga    3720
agaagtaaca aaggaaccta gaggcctttt gatgttagca gaattgtcat gcaagggctc    3780
cctagctact ggagaatata ctaagggtac tgttgacatt gcgaagagtg acaaagattt    3840
tgttatcggc tttattgctc aaagagacat gggtggaaga gatgaaggtt acgattggtt    3900
gattatgaca cccggtgtgg gtttagatga caagggagac gcattgggtc aacagtatag    3960
aaccgtggat gatgtggtct ctacaggatc tgacattatt attgttggaa gaggactatt    4020
tgcaaaggga agggatgcta aggtagaggg tgaacgttac agaaaagcag ctgggaagc     4080 atatttgaga agatgcggcc agcaaaacta aaaaactgta ttataagtaa atgcatgtat    4140
actaaactca caaattagag cttcaattta attatatcag ttattaccac gaaaatcgtt    4200
attgtcttga aggtgaaatt tctactctta ttaatggtga acgttaagct gatgctatga    4260
tggaagctga ttggtcttaa cttgcttgtc atcttgctaa tggtcatatg gctcgtgtta    4320
ttacttaagt tatttgtact cgttttgaac gtaatgctaa tgatcatctt atggaataat    4380
agtgaacggc cggccaagca cgcggggatg ggatgagctt ggagcaggaa gaatacacta    4440
tactggatct aaagagtaca atagatggat aagaatattg gcagcgcaaa aaggcttcaa    4500
gcttacacaa cacggtttat ttcgaaataa tatccttctc gaaagcttta acgaacgcag    4560
aattttcgag ttattaaact taaaatacgc tgaacccgaa catagaaata tcgaatggga    4620
aaaaaaaact gcataaaggc attaaaagag gagcgaattt ttttttaata aaaatcttaa    4680
taatcattaa aagataaata atagtctata tatacgtata taaataaaaa atattcaaaa    4740
aataaaataa actattattt tagcgtaaag gatggggaaa gagaaaagaa aaaaattgat    4800
ctatcgattt caattcaatt caatagatct ttatccttgt gcttgtgcct gaactgcggt    4860
aacggcaaca actttgacga tgtcgtcgac tgaacatccc cttgacaaat cgttgatagg    4920 tttgcaaat ccctgacata taggaccgat ggcttcggcc tttgcgaatc tttgaccaa     4980 cttgtatccg atgtttcctg cctggatgtc tgggaagatc aagacatttg ccttaccagc    5040
gactttagat ccaggggctt tcaaatctgc gaccttctta accatgagg cgtctaactg     5100 caattcaccg tcgatgtcta agtcaggcct agcctcctta gccaattttg ttgccttgt     5160 aaccttgtcg actaattcat gtgaggctga tcccatggtt gagaatgaca acatggctac    5220
ccttggctcg atcttgcaca aattctttgc agtctcagca gtggtaattg cgattgaaga    5280
taactcttca gcggtaggac aaacatttac agcgcagtca gcgaataaca aaaaaccgtc    5340
ctctccatac tcgcagtcag gtactgacat caagaagact gatgagacga cagatgcacc    5400
tggtactgtt ttgacaatct gcaaaccagg ccttaacaag tctcctgtag tatgtatagc    5460
accagatacc aaaccgtcag cgtcacctaa cttgaccatc attgttgcga agtagattgg    5520
gtccctgacg attttgtcag ccttctccaa ggtgactccc ttgttttttc tgatctcgta    5580
gaaagcgttg gcgtaaccgg cggtcttaga agaagtttct gggtcgacta tctctactcc    5640
ggccaaattt actccgaatt ttgcggcgtt ttccttaatg acagactctg aaccgaccaa    5700
gattatgtcg gcaataccgt ccctaataat ctcctctgaa gccctgatgt tcctctcttc    5760
ctcaccctct gccaaaacga ttttcttctt gtcggccttg gccaatccga agatattctc    5820
catcaatttc attgtgaagg tagttcgatt ttggaggtcg cgggaggtcg aaactaagtt    5880
cttggtgttt taaaactaaa aaaaagacta actataaaag tagaatttaa gaagtttaag    5940
aaatagattt acagaattac aatcaatacc taccgtcttt atatacttat tagtcaagta    6000
```

```
ggggaataat ttcagggaac tggtttcaac cttttttttc agcttttcc aaatcagaga      6060 gagcagaagg taatagaagg tgtaagaaaa tgagatagat acatgcgtgg gtcaattgcc    6120
ttgtgtcatc atttactcca ggcaggttgc atcactccat tgaggttgtg cccgttttt    6180 gcctgtttgt gcccctgttc tctgtagttg cgctaagaga atggacctat gaactgatgg    6240
ttggtgaaga aaacaatatt ttggtgctgg gattcttttt ttttctggat gccagcttaa    6300
aaagcgggct ccattatatt tagtggatgc caggaataaa ctgttcaccc agacacctac    6360
gatgttatat attctgtgta acccgcccc tattttgggc atgtacgggt tacagcagaa    6420
ttaaaaggct aatttttga ctaaataaag ttaggaaaat cactactatt aattatttac    6480
gtattctttg aaatggcagt attgataatg ataaactcga actgaaaaag cgtgttttt    6540 attcaaaatg attctaactc ccttacgtaa tcaaggaatc tttttgcctt ggcctccgcg    6600
tcattaaact tcttgttgtt gacgctaaca ttcaacgcta gtatatattc gttttttca    6660 ggtaagttct tttcaacggg tcttactgat gaggcagtcg cgtctgaaag gtccgccggc    6720
gttggacgag cgctccatgc tggacttact cgtcgaagat ttcctgctac tctctatata    6780
attagacacc catgttatag atttcagaaa acaatgtaat aatatatggt agcctcctga    6840
aactaccaag ggaaaaatct caacaccaag agctcatatt cgttggaata gcgataatat    6900
ctctttacct caatcttata tgcatgttat ttgctcttat aattggtctc tatttaggga    6960
aaaaagtcgg tttgagagct tctcgcgatg tgaaatctca atttgaactg cacgccaaag    7020
ctagcccatt tcacgaacac cagaaagaag aaatccccaa ggatcgcatg acagagtatg    7080
ctctctcata tcgttgagta tgaatgccaa tacactgatc agctttacaa gaaacgtaaa    7140
atctggcacg atggtagact gaaatacttt cagttaaaca acagattcat gctttatacg    7200
gaaaaggata acgttttgtt agctagtgag gcggtttaaa cgcgtggccg tgccgtc      7257
```

USE OF PHOSPHOKETOLASE AND PHOSPHOTRANSACETYLASE FOR PRODUCTION OF ACETYL-COENZYME A DERIVED COMPOUNDS

This application claims benefit of priority of U.S. Provisional Application No. 61/800,356, filed on Mar. 15, 2013, the contents of which are hereby incorporated by reference in their entirety.

1. FIELD OF THE INVENTION

The present disclosure relates to compositions and methods for producing acetyl-CoA derived compounds in engineered host cells.

2. BACKGROUND

Figure 1:
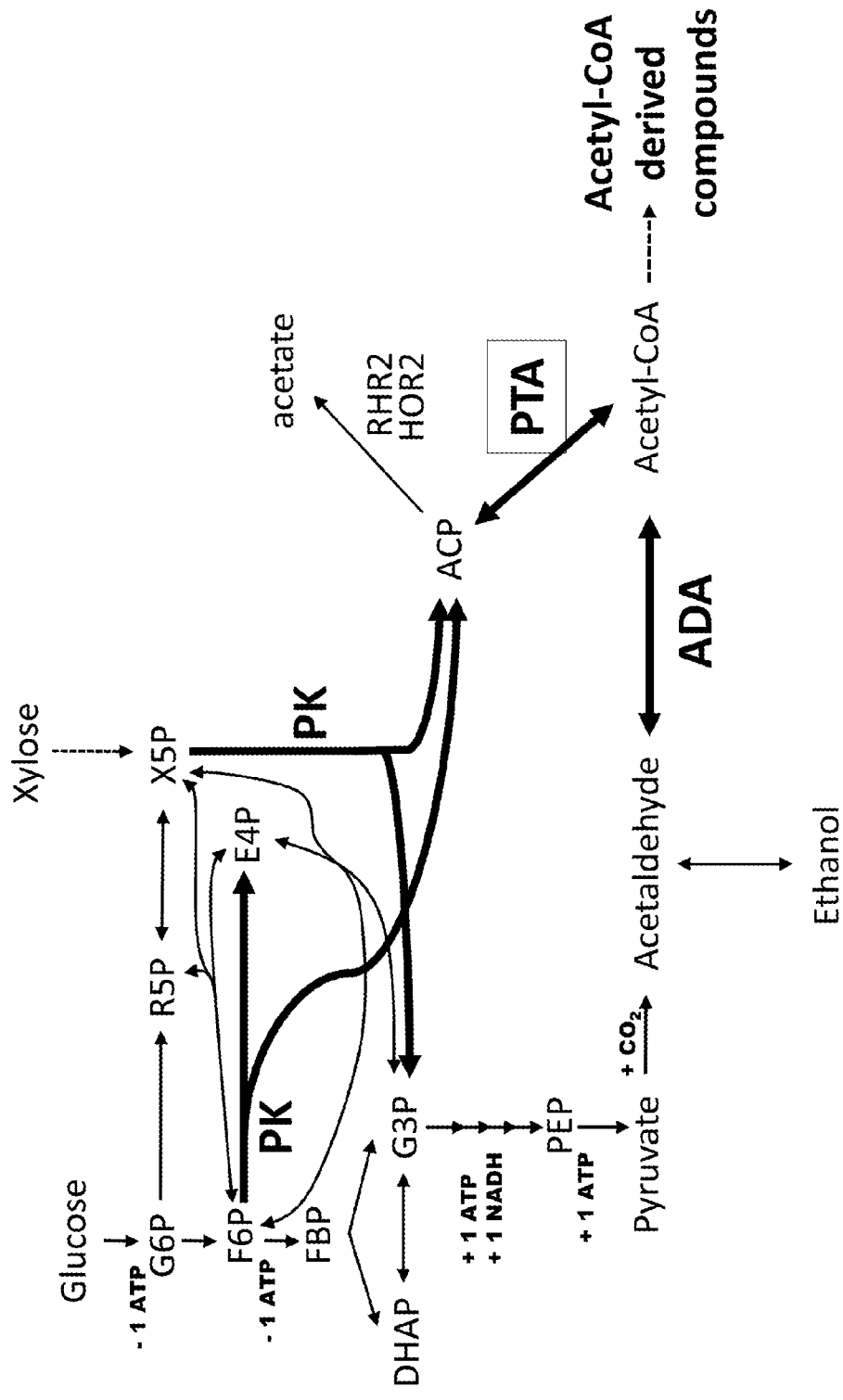

Acetyl coenzyme A (acetyl-CoA) is a key intermediate in the synthesis of essential biological compounds, including polyketides, fatty acids, isoprenoids, phenolics, alkaloids, vitamins, and amino acids. Among the metabolites derived from acetyl-CoA are primary and secondary metabolites, including compounds of industrial utility. In yeast, acetyl-CoA is biosynthesized from pyruvate metabolism (FIG. 1). However, in this biosynthetic pathway, $CO_2$ is lost via the reactions catalyzed by pyruvate carboxylase and/or pyruvate dehydrogenase. In an industrial fermentation setting, one benefit of providing an alternative to pyruvate metabolism and lower glycolysis is that less $CO_2$ is produced in the decarboxylation of pyruvate, and thus more carbon can be captured in the end product, thereby increasing the maximum theoretical yield. A second benefit is that less NADH is produced, and therefore significantly less oxygen is needed to reoxidize it. This can be accomplished by expressing phosphoketolase (PK; EC 4.1.2.9) in conjunction with phosphoacetyltransferase (PTA; EC 2.3.1.8).

PK and PTA catalyze the reactions to convert fructose-6-phosphate (F6P) or xylulose-5-phosphate (X5P) to acetyl-CoA. As shown in FIG. 1, PK draws from the pentose phosphate intermediate xyulose 5-phosphate, or from the upper glycolysis intermediate D-fructose 6-phosphate (F6P). PK splits X5P into glyceraldehyde 3-phosphate (G3P) and acetyl phosphate, or F6P into erythrose 4-phosphate (E4P) and acetyl phosphate. PTA then converts the acetyl phosphate into acetyl-CoA. G3P can re-enter lower glycolysis, and E4P can re-enter the pentose phosphate pathway or glycolysis by cycling through the non-oxidative pentose phosphate pathway network of transaldolases and transketolases.

The applicants have previously described the improved efficiency of heterologous isoprenoid production that can be gained with the introduction of PK and PTA enzymes. See U.S. application Ser. No. 13/673,819 (now U.S. Pat. No. 8,415,136), filed on Nov. 9, 2012, the contents of which are hereby incorporated by reference in their entirety. In particular, when cytosolic acetyl-CoA is synthesized from glucose using only the chemical reactions which occur in the native yeast metabolic network, the maximum possible stoichiometric yield for conversion of glucose to the isoprenoid farnesene via the mevalonate pathway is 23.6 wt %. By including the reactions catalyzed by acetaldehyde dehydrogenase, acetylating (ADA; EC 1.2.1.10) and NADH-using HMG-CoA reductase into the metabolic network for mevalonate production, the maximum theoretical stoichiometric yield is improved to 25.2 wt %. With the further introduction of PK and PTA, the reaction network, at optimality, is able to reach 29.8 wt % mass yield or greater, a significant increase in maximum theoretical yield.

Sondregger et al. have also described the benefits of PK and PTA with respect to ethanol production in a xylose-utilizing yeast strain. See Sondregger et al., *Applied and Environmental Microbiology* 70(5):2892-2897 (2004), the contents of which are hereby incorporated by reference in their entirety. The heterologous phosphoketolase pathway (PK, PTA, and ADA) was introduced in *S. cerevisiae* to address low ethanol yields that result from overexpression of NAD(P)H-dependent xylose reductase and $NAD^+$-dependent xylitol dehydrogenase from *Pichia stipitis*. The different cofactor preferences in the two oxidoreductase reactions caused an anaerobic redox balancing problem that manifested in the extensive accumulation of the reduced reaction intermediate xylitol, and thus, low ethanol yields. Redox metabolism was balanced by introducing the phosphoketolase pathway, which lead to the net reoxidation of one NADH per xylose converted to ethanol, and an improvement in ethanol yield by 25%. However, overexpression of PK also leads to an increase in acetate accumulation and a reduction in fermentation rate. Although some acetate accumulation could be reduced by combining the phosphoketolase pathway with a mutation of ALD6, which converts acetaldehyde to acetate, the flux through the recombinant phosphoketolase pathway was about 30% of the optimum flux that would be required to completely eliminate xylitol and glycerol accumulation. The authors suggested that higher activities of phosphotransacetylase and/or acetaldehyde dehydrogenase may be necessary to prevent phosphoketolase pathway-based acetate formation.

Thus, while the introduction of a heterologous PK pathway can lead to substantial improvements in the yields of acetyl-CoA derived compounds, further improvements in the implementation of this pathway appear to be required to achieve optimal carbon flux through PK and PTA. The compositions and methods provided herein address this need and provide related advantages as well.

3. SUMMARY OF THE INVENTION

Provided herein are compositions and methods for the improved utilization of phosphoketolase (PK) and phosphotransacetylase (PTA) for the production of industrially useful compounds. These compositions and methods are based on the surprising discovery that phosphoketolase pathway-based acetate accumulation results from the enzyme-catalyzed hydrolysis of acetyl phosphate, the product of PK catalysis. Hydrolysis of acetyl phosphate is an undesirable side-reaction that can negatively impact production, via depletion of carbon, of any type of product derived from acetyl-CoA, including isoprenoids, polyketides, and fatty acids. By functionally disrupting native enzymes in the host cell that catalyze acetyl phosphate hydrolysis, acetate accumulation is reduced and carbon flux through the PK/PTA pathway towards acetyl-CoA production is increased.

The compositions and methods provided herein are further based on the unexpected discovery of native enzymes in yeast that catalyze the hydrolysis of acetyl phosphate to acetate, namely GPP1/RHR2, and its closely related homolog GPP2/HOR2. Both of these enzymes have only been previously characterized as having glycerol-1-phosphatase (EC 3.1.3.21; alternately referred to as "glycerol-3-phosphatase") activity, and thus, the promiscuous acetyl-phosphatase activity of these enzymes is unexpected. In cells heterologously expressing PK and PTA, deletion of one or both of the genes encoding RHR2 and HOR2 leads to a reduction in acetate accumulation, with deletion of the gene encoding RHR2 alone leading to a substantial reduction in acetate levels. Moreover, deletion of the RHR2 gene in cells engineered to comprise PK, PTA and a mevalonate pathway resulted in a substantial increase in the production of farnesene, an acetyl-CoA derived isoprenoid.

Thus, provided herein are genetically modified host cells and methods of their use for the production of industrially useful compounds. In one aspect, provided herein is a genetically modified host cell comprising: a heterologous nucleic acid encoding a phosphoketolase (PK; EC 4.1.2.9); and a functional disruption of an endogenous enzyme that converts acetyl phosphate to acetate. In some embodiments, the genetically modified host cell further comprises a heterologous nucleic acid encoding a phosphotransacetylase (PTA; EC 2.3.1.8).

In another aspect, provided herein is a genetically modified host cell comprising: a heterologous nucleic acid encoding a phosphotransacetylase (PTA; EC 2.3.1.8); and a functional disruption of an endogenous enzyme that converts acetyl phosphate to acetate. In some embodiments, the genetically modified host cell further comprises a heterologous nucleic acid encoding a phosphoketolase (PK; EC 4.1.2.9).

In some embodiments, the enzyme that converts acetyl phosphate to acetate is a glycerol-1-phosphatase (EC 3.1.3.21). In some embodiments, the glycerol-1-phosphatase is selected from the group consisting of GPP1/RHR2, GPP2HOR2, and homologues and variants thereof. In some embodiments, the genetically modified host cell comprises a functional disruption of GPP1/RHR2. In some embodiments, the genetically modified host cell comprises a functional disruption of GPP2/HOR2. In some embodiments, the genetically modified host cell comprises a functional disruption of both GPP1/RHR2 and GPP2/HOR2.

In some embodiments, the genetically modified host cell further comprises a heterologous nucleic acid encoding an acylating acetylaldehyde dehydrogenase (ADA; EC 1.2.1.10). In some embodiments, the genetically modified host cell further comprises a functional disruption of one or more enzymes of the native pyruvate dehydrogenase (PDH)—bypass. In some embodiments, the one or more enzymes of the PDH-bypass are selected from acetyl-CoA synthetase 1 (ACS1), acetyl-CoA synthetase 2 (ACS2), and aldehyde dehydrogenase 6 (ALD6).

In some embodiments, the genetically modified host cell is capable of producing a heterologous acetyl-CoA derived compound. In some embodiments, the heterologous acetyl-CoA derived compound is selected from the group consisting of an isoprenoid, a polyketide, and a fatty acid. In particular embodiments, the genetically modified host cell is capable of producing an isoprenoid.

In some embodiments, the genetically modified host cell comprises one or more heterologous nucleic acids encoding one or more enzymes of a mevalonate (MEV) pathway for making isopentenyl pyrophosphate. In some embodiments, the one or more enzymes of the MEV pathway comprise an NADH-using HMG-CoA reductase. In some embodiments, the one or more enzymes of the MEV pathway comprise an enzyme that condenses two molecules of acetyl-CoA to form acetoacetyl-CoA. In some embodiments, the one or more enzymes of the MEV pathway comprise an enzyme that condenses acetoacetyl-CoA with acetyl-CoA to form HMG-CoA. In some embodiments, the one or more enzymes of the MEV pathway comprise an enzyme that converts HMG-CoA to mevalonate. In some embodiments, the one or more enzymes of the MEV pathway comprise an enzyme that phosphorylates mevalonate to mevalonate 5-phosphate. In some embodiments, the one or more enzymes of the MEV pathway comprise an enzyme that converts mevalonate 5-phosphate to mevalonate 5-pyrophosphate. In some embodiments, the one or more enzymes of the MEV pathway comprise an enzyme that converts mevalonate 5-pyrophosphate to isopentenyl pyrophosphate. In some embodiments, the one or more enzymes of the MEV pathway are selected from HMG-CoA synthase, mevalonate kinase, phosphomevalonate kinase and mevalonate pyrophosphate decarboxylase. In some embodiments, the host cell comprises a plurality of heterologous nucleic acids encoding all of the enzymes of the MEV pathway. In some embodiments, the one or more heterologous nucleic acids encoding one or more enzymes of the MEV pathway are under control of a single transcriptional regulator. In some embodiments, the one or more heterologous nucleic acids encoding one or more enzymes of the MEV pathway are under control of multiple heterologous transcriptional regulators. In some embodiments, the genetically modified host cell further comprises a heterologous nucleic acid encoding an enzyme that can convert isopentenyl pyrophosphate (IPP) into dimethylallyl pyrophosphate (DMAPP). In some embodiments, the genetically modified host cell further comprises a heterologous nucleic acid encoding an enzyme that can condense IPP and/or DMAPP molecules to form a polyprenyl compound. In some embodiments, the genetically modified host cell further comprises a heterologous nucleic acid encoding an enzyme that can modify IPP or a polyprenyl to form an isoprenoid compound.

In some embodiments, the enzyme that can modify IPP or a polyprenyl to form an isoprenoid compound is selected from the group consisting of carene synthase, geraniol synthase, linalool synthase, limonene synthase, myrcene synthase, ocimene synthase, α-pinene synthase, β-pinene synthase, γ-terpinene synthase, terpinolene synthase, amorphadiene synthase, α-farnesene synthase, β-farnesene synthase, farnesol synthase, nerolidol synthase, patchouliol synthase, nootkatone synthase, and abietadiene synthase.

In some embodiments, the isoprenoid is selected from the group consisting of a hemiterpene, monoterpene, diterpene, triterpene, tetraterpene, sesquiterpene, and polyterpene. In some embodiments, the isoprenoid is a sesquiterpene. In some embodiments, the isoprenoid is a $C_5$-$C_{20}$ isoprenoid. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, and valencene.

In another aspect, provided herein is a genetically modified host cell capable of producing an isoprenoid, the cell comprising: one or more heterologous nucleic acids encoding one or more enzymes of a mevalonate (MEV) pathway for making isopentenyl pyrophosphate; a heterologous nucleic acid encoding a phosphoketolase (PK); a heterologous nucleic acid encoding a phosphotransacetylase (PTA); and a functional disruption of a glycerol-1-phosphatase (EC 3.1.3.21). In some embodiments, the glycerol-1-phosphatase is GPP1/RHR2, or a homologue or variant thereof. In some embodiments, the glycerol-1-phosphatase is GPP2/HOR2, or a homologue or variant thereof.

In another aspect, provided herein is a genetically modified host cell capable of producing an isoprenoid, the cell comprising: one or more heterologous nucleic acids encoding one or more enzymes of a mevalonate (MEV) pathway for making isopentenyl pyrophosphate; a heterologous nucleic acid encoding an acetylaldehyde dehydrogenase, acetylating (ADA); a heterologous nucleic acid encoding a phosphoketolase (PK); a heterologous nucleic acid encoding a phosphotransacetylase (PTA); and a functional disruption of a glycerol-1-phosphatase (EC 3.1.3.21). In some embodiments, the glycerol-1-phosphatase is GPP1/RHR2, or a homologue or variant thereof. In some embodiments, the glycerol-1-phosphatase is GPP2/HOR2, or a homologue or variant thereof.

In another aspect, provided herein is a genetically modified host cell capable of producing an isoprenoid, the cell comprising: one or more heterologous nucleic acids encoding one or more enzymes of a mevalonate (MEV) pathway for making isopentenyl pyrophosphate; a heterologous nucleic acid encoding an acetylaldehyde dehydrogenase, acetylating (ADA); a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6); a heterologous nucleic acid encoding a phosphoketolase (PK); a heterologous nucleic acid encoding a phosphotransacetylase (PTA); and a functional disruption of a glycerol-1-phosphatase (EC 3.1.3.21). In some embodiments, the glycerol-1-phosphatase is GPP1/RHR2, or a homologue or variant thereof. In some embodiments, the glycerol-1-phosphatase is GPP2/HOR2, or a homologue or variant thereof.

In another aspect, provided herein is a genetically modified host cell capable of producing an isoprenoid, the cell comprising: one or more heterologous nucleic acids encoding one or more enzymes of a mevalonate (MEV) pathway for making isopentenyl pyrophosphate, wherein the one or more enzymes comprise a NADH-using HMG-CoA reductase; a heterologous nucleic acid encoding an acetylaldehyde dehydrogenase, acetylating (ADA); a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6); a heterologous nucleic acid encoding a phosphoketolase (PK); a heterologous nucleic acid encoding a phosphotransacetylase (PTA); and a functional disruption of a glycerol-1-phosphatase (EC 3.1.3.21). In some embodiments, the glycerol-1-phosphatase is GPP1/RHR2, or a homologue or variant thereof. In some embodiments, the glycerol-1-phosphatase is GPP2/HOR2, or a homologue or variant thereof.

In another aspect, provided herein is genetically modified host cell capable of producing an isoprenoid, the cell comprising: one or more heterologous nucleic acids encoding a plurality of enzymes of a mevalonate (MEV) pathway for making isopentenyl pyrophosphate, wherein the plurality of enzymes comprise an acetyl-CoA:malonyl-CoA acyltransferase; a heterologous nucleic acid encoding an acetylaldehyde dehydrogenase, acetylating (ADA); a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6); a heterologous nucleic acid encoding a phosphoketolase (PK); a heterologous nucleic acid encoding a phosphotransacetylase (PTA); and a functional disruption of a glycerol-1-phosphatase (EC 3.1.3.21). In some embodiments, the glycerol-1-phosphatase is GPP1/RHR2, or a homologue or variant thereof. In some embodiments, the glycerol-1-phosphatase is GPP2/HOR2, or a homologue or variant thereof.

In another aspect, provided herein is a genetically modified host cell capable of producing an polyketide, the cell comprising: one or more heterologous nucleic acids encoding one or more enzymes of polyketide biosynthetic pathway; a heterologous nucleic acid encoding a phosphoketolase (PK); a heterologous nucleic acid encoding a phosphotransacetylase (PTA); and a functional disruption of a glycerol-1-phosphatase (EC 3.1.3.21). In some embodiments, the glycerol-1-phosphatase is GPP1/RHR2, or a homologue or variant thereof. In some embodiments, the glycerol-1-phosphatase is GPP2/HOR2, or a homologue or variant thereof.

In another aspect, provided herein is a genetically modified host cell capable of producing a fatty acid, the cell comprising: one or more heterologous nucleic acids encoding one or more enzymes of fatty acid biosynthetic pathway; a heterologous nucleic acid encoding a phosphoketolase (PK); a heterologous nucleic acid encoding a phosphotransacetylase (PTA); and a functional disruption of a glycerol-1-phosphatase (EC 3.1.3.21). In some embodiments, the glycerol-1-phosphatase is GPP1/RHR2, or a homologue or variant thereof. In some embodiments, the glycerol-1-phosphatase is GPP2/HOR2, or a homologue or variant thereof.

In some embodiments, the genetically modified host cell provided herein is selected from the group consisting of a bacterial cell, a fungal cell, an algal cell, an insect cell, and a plant cell. In some embodiments, the cell is a yeast cell. In some embodiments, the yeast is *Saccharomyces cerevisiae*.

In some embodiments, the genetically modified host cell produces an increased amount of an acetyl-CoA derived compound (e.g., an isoprenoid, polyketide, or fatty acid) compared to a yeast cell not comprising a functional disruption of an endogenous enzyme that converts acetyl phosphate to acetate.

In another aspect, provided herein are methods for producing a heterologous acetyl-CoA derived compound, the method comprising: culturing a population of genetically modified host cells, capable of producing a heterologous acetyl-CoA derived compound as described herein, in a medium with a carbon source under conditions suitable for making said heterologous acetyl-CoA derived compound; and recovering said heterologous acetyl-CoA derived compound from the medium. In some embodiments, heterologous acetyl-CoA derived compound is selected from the group consisting of an isoprenoid, a polyketide, and a fatty acid.

In another aspect, provided herein is a method for increasing the production of acetyl-CoA or an acetyl-CoA derived compound in a host cell, the method comprising: expressing in the host cell a heterologous nucleic acid encoding a phosphoketolase (PK; EC 4.1.2.9); and functionally disrupting an endogenous enzyme that converts acetyl phosphate to acetate. In some embodiments, the method further comprises expressing in the host cell a heterologous nucleic acid encoding a phosphotransacetylase (PTA; EC 2.3.1.8).

In another aspect, provided herein is a method for increasing the production of acetyl-CoA in a host cell, the method comprising: expressing in the host cell a heterologous nucleic acid encoding a phosphotransacetylase (PTA; EC 2.3.1.8); and functionally disrupting an endogenous enzyme that converts acetyl phosphate to acetate. In some embodiments, the method further comprises expressing in the host cell a heterologous nucleic acid encoding a phosphoketolase (PK; EC 4.1.2.9).

In some embodiments, the enzyme that converts acetyl phosphate to acetate is a glycerol-1-phosphatase (EC 3.1.3.21). In some embodiments, the glycerol-1-phosphatase is selected from GPP1/RHR2, GPP2/HOR2, and homologues and variants thereof. In some embodiments, GPP1/RHR2, or a homologue or variant thereof, is functionally disrupted. In some embodiments, GPP2/HOR2, or a homologue or variant thereof, is functionally disrupted. In some embodiments, both GPP1/RHR2 and GPP2/HOR2, or both a homologue or variant of GPP1/RHR2 and a homologue or variant of GPP2/HOR2, are functionally disrupted. In some embodiments, the host cell is selected from the group consisting of a bacterial cell, a fungal cell, an algal cell, an insect cell, and a plant cell. In some embodiments, the host cell is a yeast cell. In some embodiments, the yeast is *Saccharomyces cerevisiae*. In some embodiments, the host cell produces an increased amount of acetyl-CoA or an acetyl-CoA derived compound compared to a yeast cell not comprising a functional disruption of an endogenous enzyme that converts acetyl phosphate to acetate.

4. BRIEF DESCRIPTION OF THE FIGURES

FIG. 1 provides a schematic representation of the pathways involved in the conversion of sugar (glucose and xylose) to acetyl-CoA, and acetyl-CoA derived compounds, in a yeast host cell. The bold arrows indicate the recombinant phosphoketolase pathway. Acetyl phosphate is an intermediate of the phosphoketolase (PK)/phosphotransacetyklase (PTA) pathway to acetyl-CoA, and is hydrolyzed to acetate by RHR2 and HOR2. Abbreviations: G6P, glucose-6-phosphate; R5P, ribulose-5-phosphate; X5P, xyulose-5-phosphate; F6P, fructose-6-phosphate; E4P, eryhtrose-4-phosphate; FBP, fructose-1,6-biphosphate; DHAP, dihydroxyacetone phosphate; G3P, glyceraldehyde-3-phosphate; PEP, phosphoenolpyruvate; ADA, acetaldehyde dehydrogenase, acetylating; ACP, acetyl phosphate.

Figure 2:
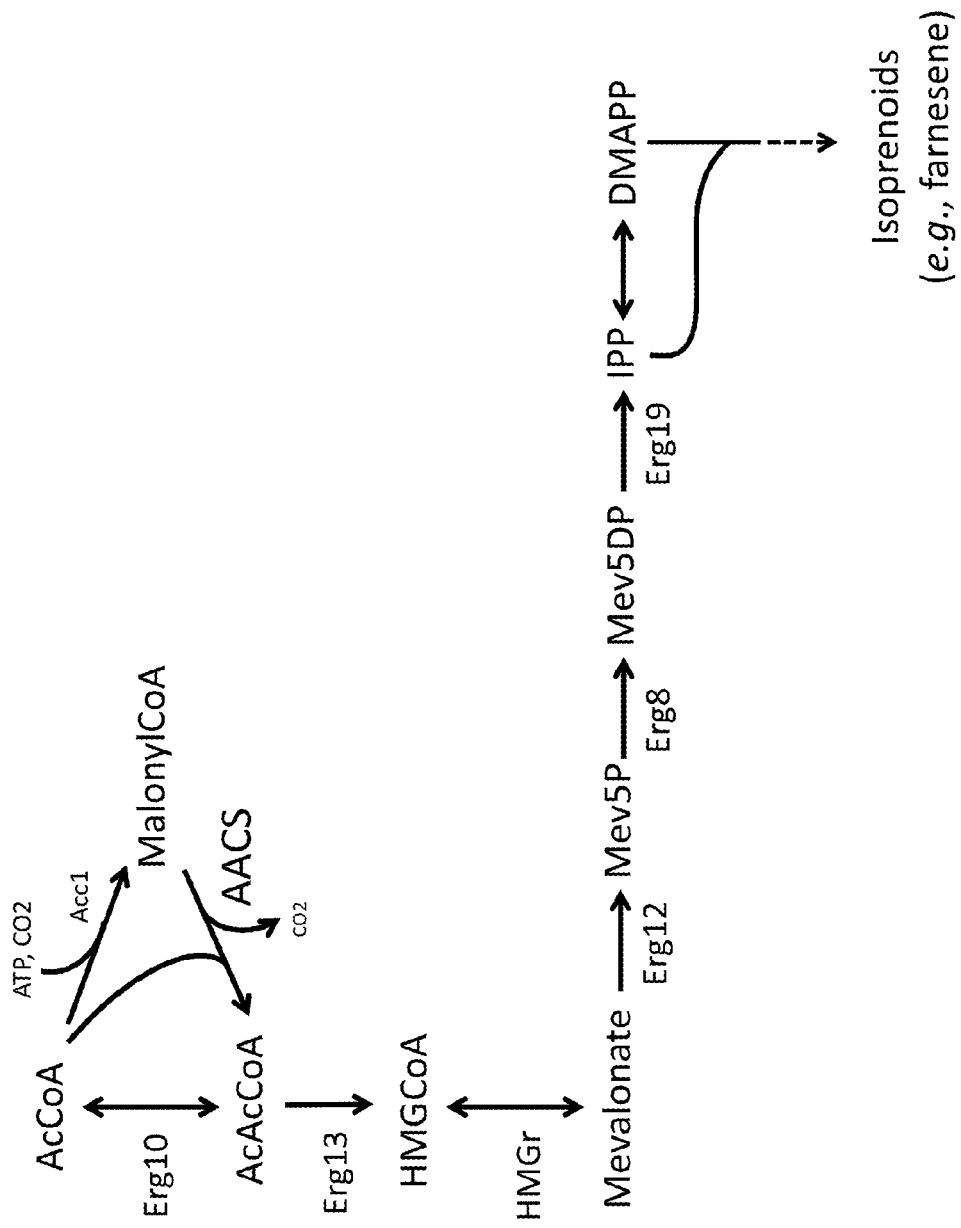

FIG. 2 provides representative enzymes of the mevalonate pathway for isoprenoid production. Abbreviations: AcCoA, acetyl-CoA; AcAcCoA, acetoacetyl-CoA; HMGCoA, 3-hydroxy-3-methylglutaryl-CoA; Mev5P, mevalonate-5-phosphate; Mev5DP, mevalonate-5-diphosphate; IPP, isopentenyl diphosphate; DMAPP, dimethylallyl pyrophosphate; Erg10, acetyl-CoA thiolase; ACCT, acetyl-CoA carboxylase; AACS, acetoacetyl-CoA synthase; Erg13, 3-hydroxy-3-methylglutaryl-CoA synthase; HMGr, 3-hydroxy-3-methylglutaryl-CoA reductase; Erg12, mevalonate kinase; Erg8, phosphomevalonate kinase; Erg19, mevalonate pyrophosphate decarboxylase.

Figures 3A, 3B:
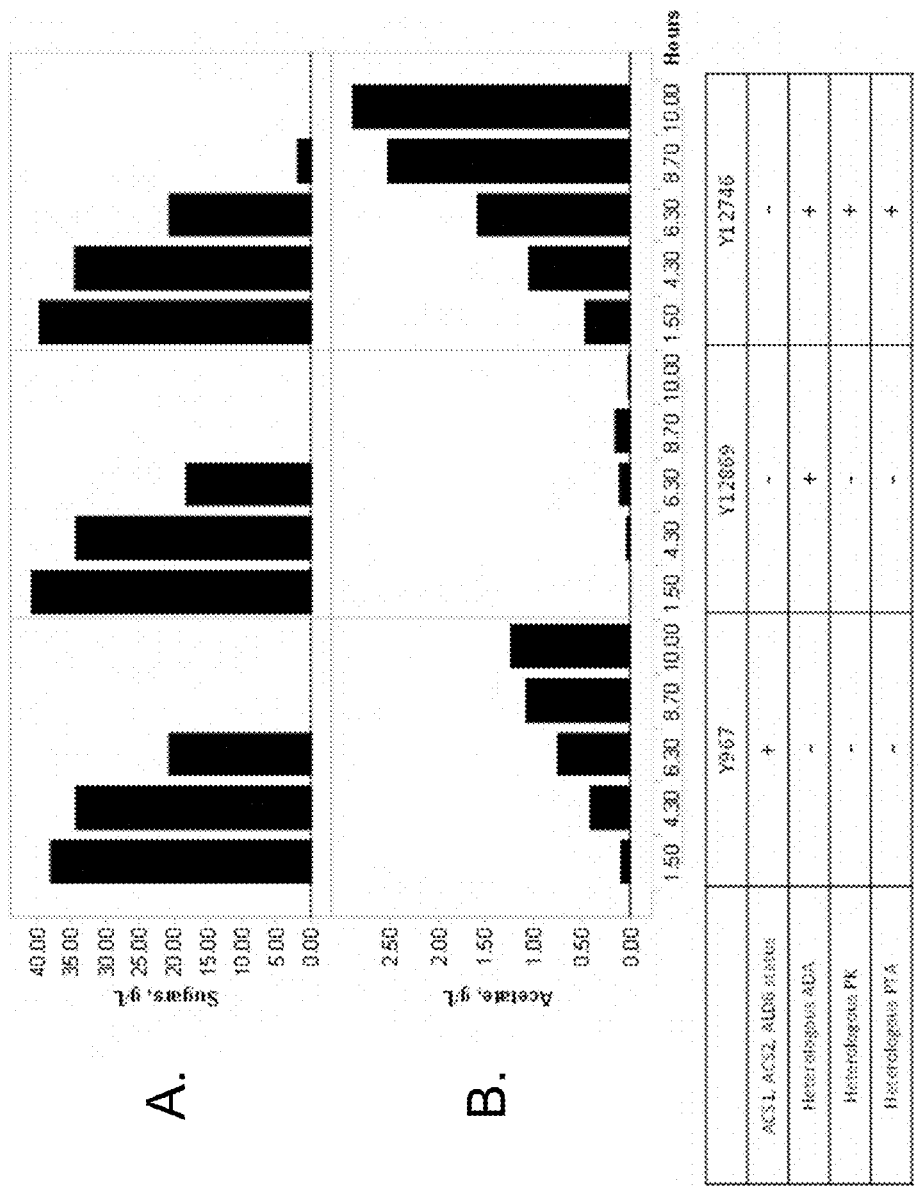

FIGS. 3A-3B provides the sugar consumption (A) and acetate production (B) of wild-type (strain Y967, left) and recombinant yeast cells (middle, right) comprising: a heterologous acetaldehyde dehydrogenase acylating (Dz.eutE) and deletion of the native PDH-bypass (acs1Δ acs2Δ ald6Δ) (strain Y12869; middle); and further comprising a heterologous phosphoketolase (Lm.PK) and phosphotransacetylase (Ck.PTA) (strain Y12746; right).

Figures 3C, 3D:
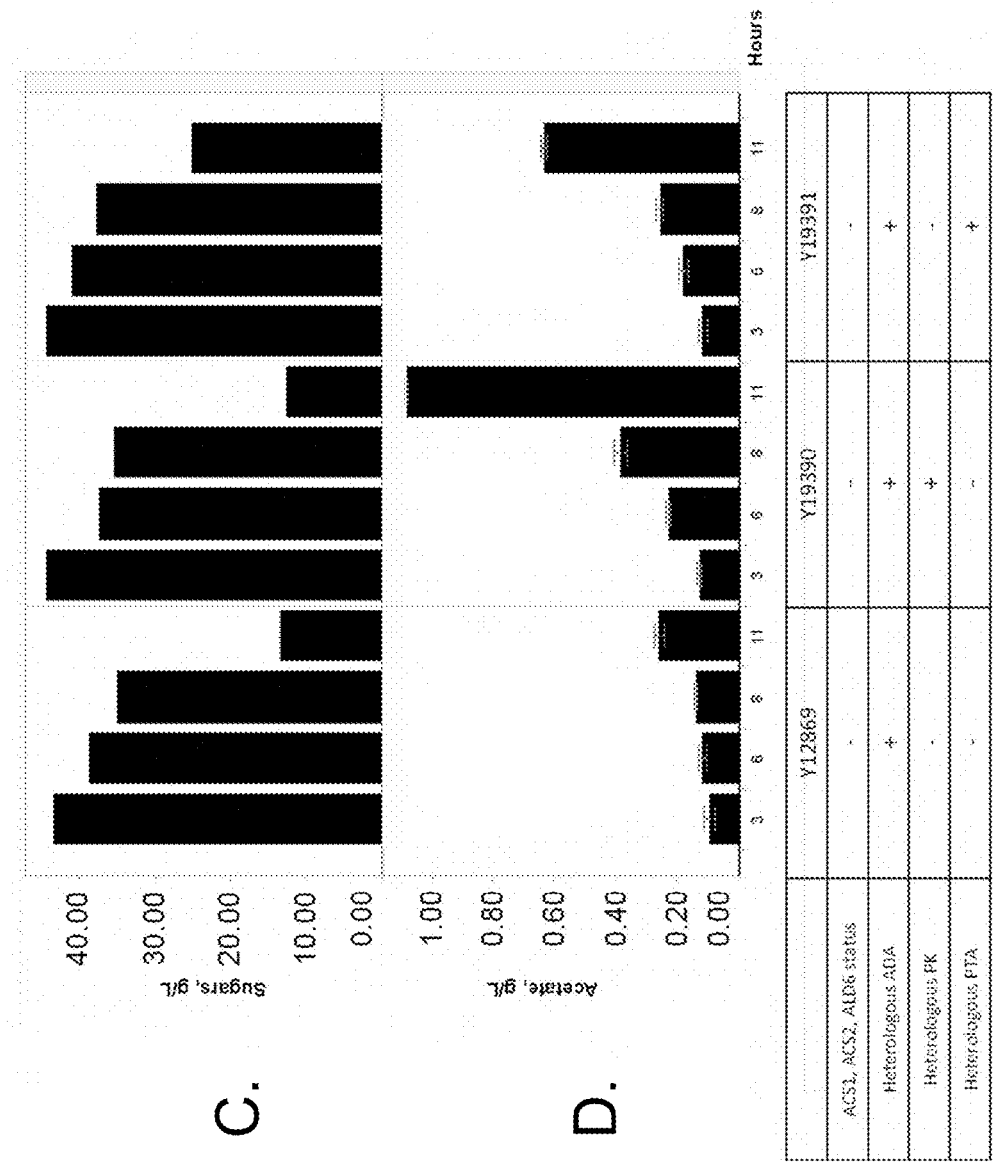

FIGS. 3C-3D provides the sugar consumption (C) and acetate production (D) of recombinant yeast cells comprising: a heterologous acetaldehyde dehydrogenase acylating (Dz.eutE) and deletion of the native PDH-bypass (acs1Δ acs2Δ ald6Δ) (strain Y12869; left); and further comprising a heterologous phosphoketolase (Lm.PK) (strain Y19390; middle) or phosphotransacetylase (Ck.PTA) (strain Y19391; right).

Figure 4:
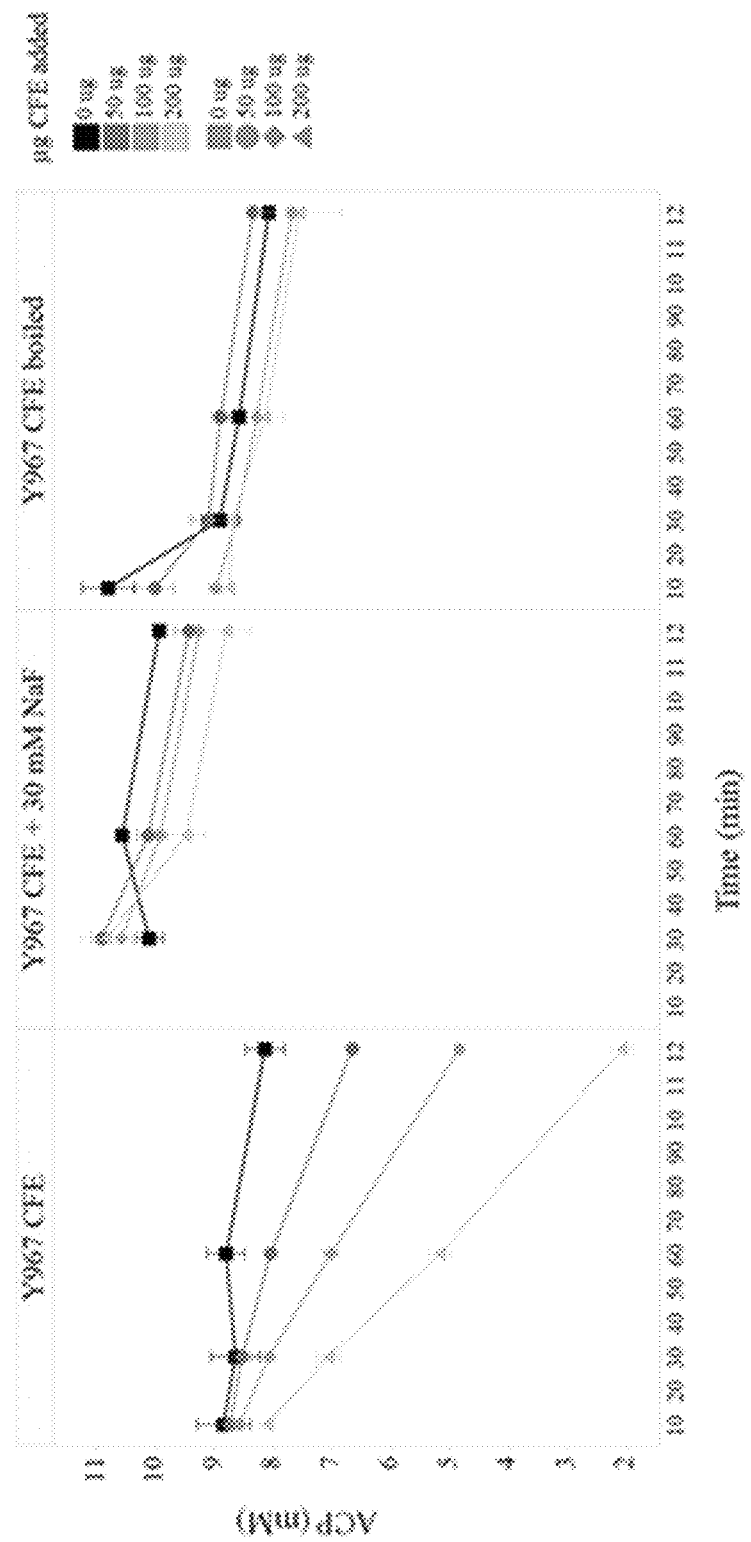

FIG. 4 provides a demonstration of acetyl phosphate hydrolysis in cell free extracts (CFE) of wild-type *S. cerevisiae* strain Y967 over a 120 minute timecourse. Shown are CFE only (left); CFE plus 30 mM sodium fluoride, a broad spectrum phosphatase inhibitor (middle); and CFE that has been heat inactivated (right).

Figure 5:
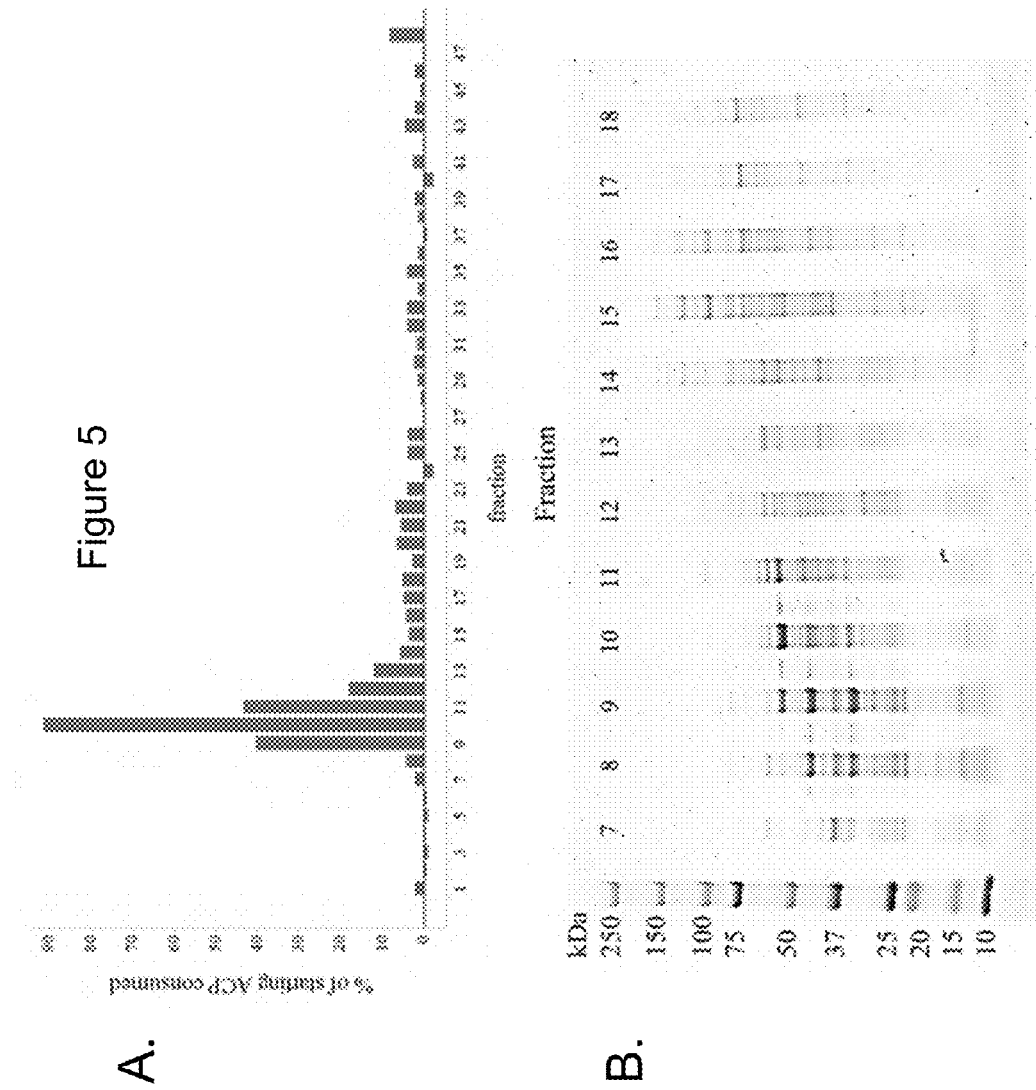

FIG. 5 provides results of anion exchange chromatography on Y967 cell free extracts. Protein was eluted with a 0-100% gradient of buffer B (20 mM Tris-Cl pH 7, 1M NaCl, 10% glycerol) over 30 column volumes at a flow rate of 0.5 mL/minute, and 1 mL fractions were collected, analyzed by protein gel electrophoresis (FIG. 5B), and assayed for acetyl phosphatase activity (FIG. 5A). ACP, acetyl phosphate.

Figure 6:
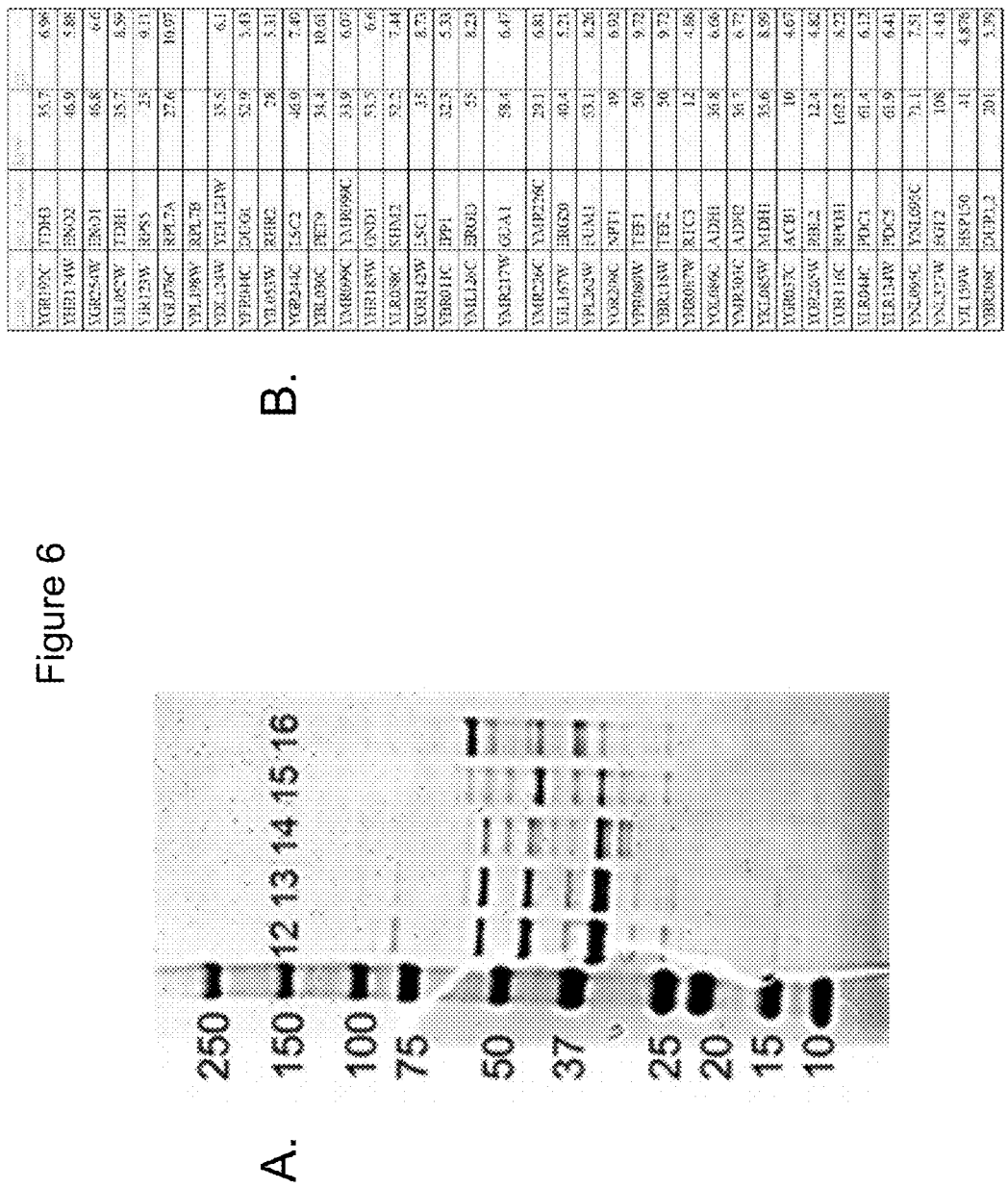

FIG. 6A provides results of anion exchange chromatography on fraction #10 of Y967. The most active fraction from this purification, #14, was analyzed by mass spectrometry to determine the identity of the proteins in the fraction (FIG. 6B). RHR2 was identified as a phosphatase in the active fraction.

Figure 7:
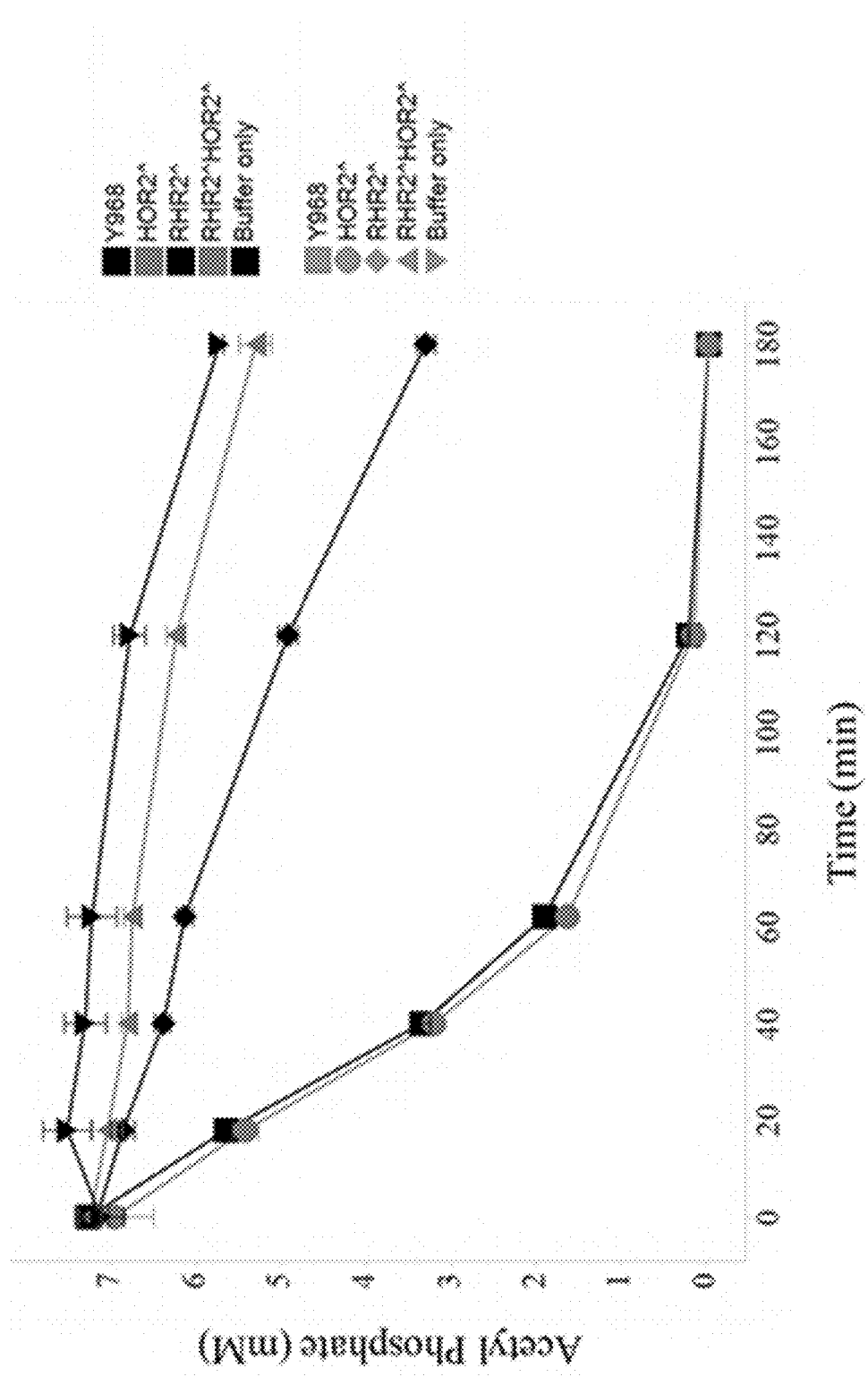

FIG. 7 provides results of acetyl phosphatase activity assays on CFEs of a wild-type yeast strain (Y968) or recombinant yeast strains comprising a deletion of RHR2, HOR2 or both RHR2 and HOR2.

Figures 8A, 8B, 8C:
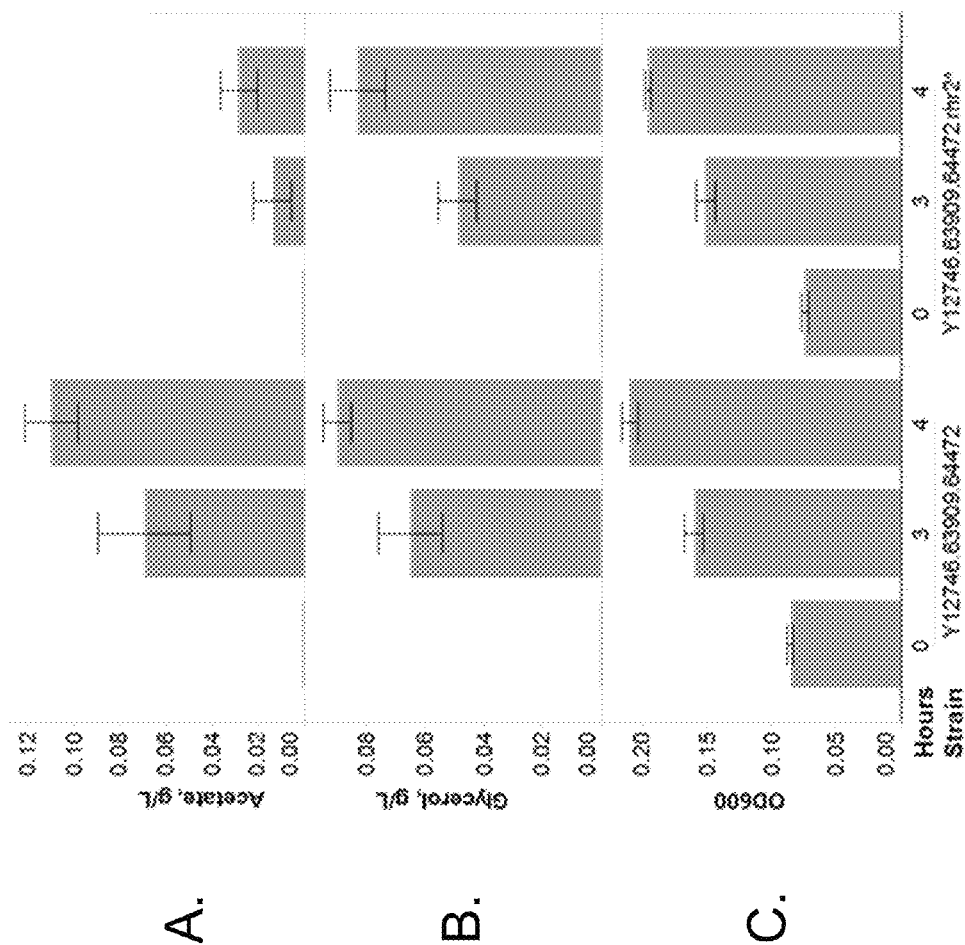

FIGS. 8A-8C provides acetate levels (A), glycerol levels (B) and optical densities (C) of recombinant yeast strain populations. Strain Y12746.ms63909.ms64472 comprises a deletion of the PDH-bypass (acs1Δ acs2Δ ald6Δ), and heterologously expresses acetaldehyde dehydrogenase aceylating (Dz.eutE), phosphoketolase (Lm.PK), phosphotransacetylase (Ck.PTA), and genes in the farnesene production pathway. Strain Y12746.ms63909.ms64472 rhr2ˆ is isogenic to strain Y12746.ms63909.ms64472 but further comprises a deletion of RHR2 (rhr2ˆ).

Figures 8D, 8E:
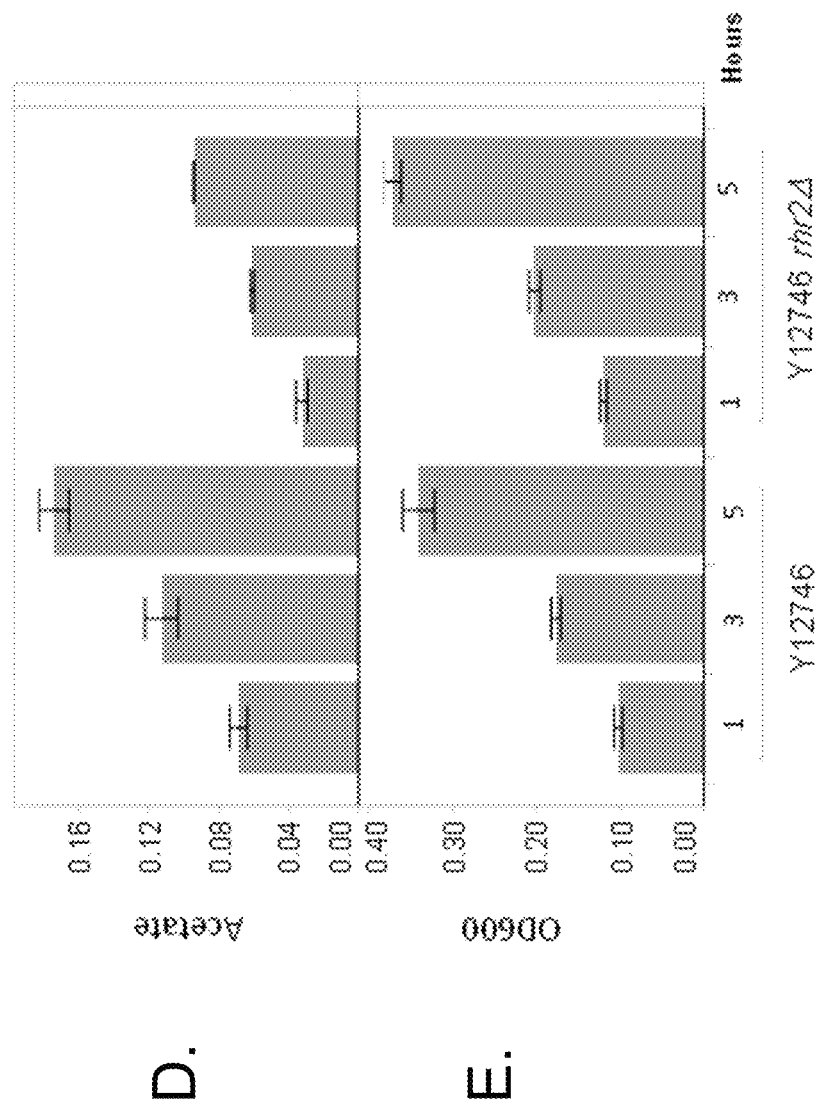

FIGS. 8D-8E provides acetate levels (D) and optical densities (E) of recombinant yeast strain populations. Strain Y12745 comprises a deletion of the PDH-bypass (acs1Δ acs2Δ ald6Δ), and heterologously expresses acetaldehyde dehydrogenase aceylating (Dz.eutE), phosphoketolase (Lm.PK), and phosphotransacetylase (Ck.PTA). Strain Y12746 rhr2ˆ is isogenic to strain Y12746 but further comprises a deletion of RHR2 (rhr2ˆ).

Figure 9:
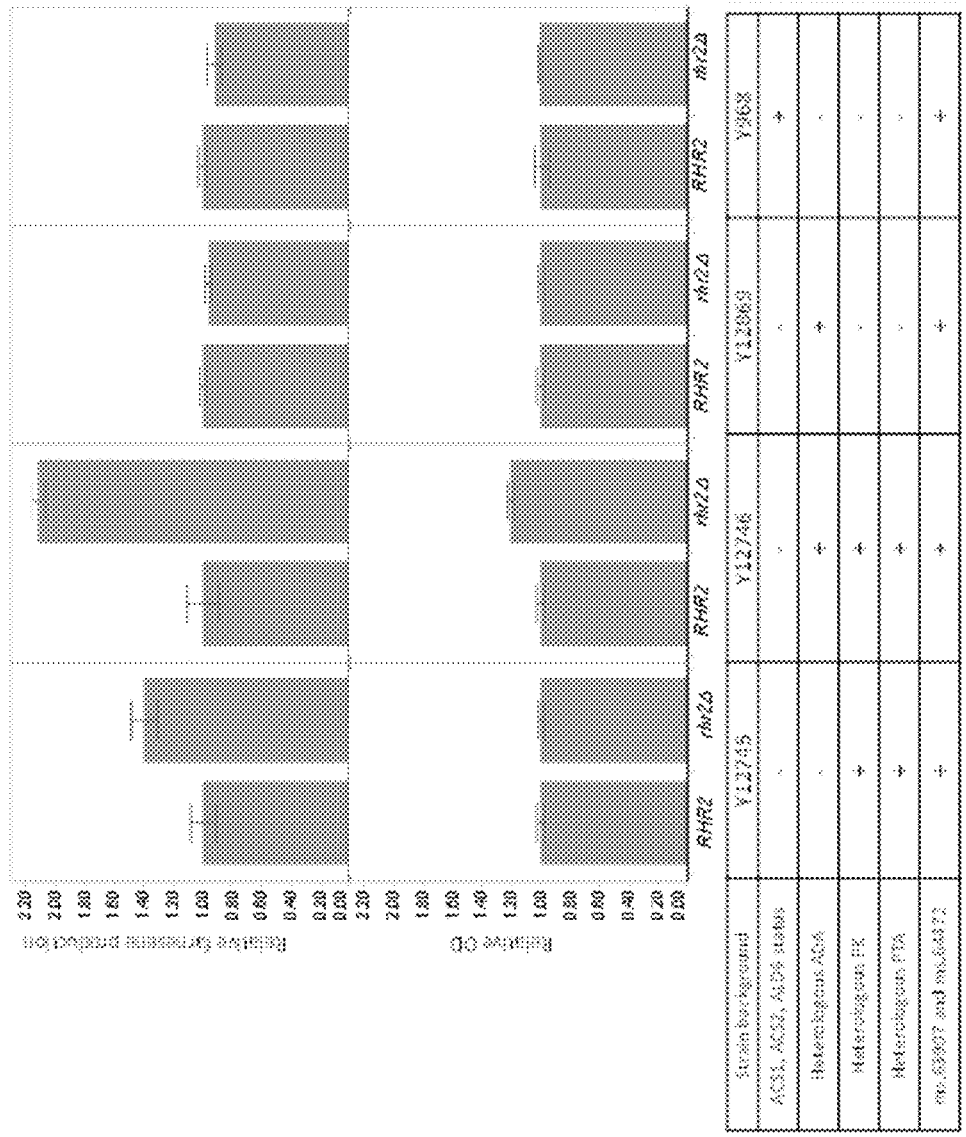

FIG. 9 provides relative farnesene levels (top) and relative optical densities (bottom) of recombinant yeast strain populations wherein the RHR2 gene is intact (RHR2+) or deleted (rhr2⁻). Y968 (right panel) is a wild-type yeast strain. Y12869.ms63907.ms64472 ("Y12869"; $2^{nd}$ from right panel) comprises a deletion of the PDH-bypass (acs1Δ acs2Δ ald6Δ), and heterologously expresses acetaldehyde dehydrogenase aceylating (Dz.eutE) and genes in the farnesene production pathway, but does not express phosphoketolase or phosphotransacetylase. Y12746.ms63907.ms64472 ("Y12746"; $2^{nd}$ from left panel) comprises a deletion of the PDH-bypass (acs1Δ acs2Δ ald6Δ), and heterologously expresses acetaldehyde dehydrogenase aceylating (Dz.eutE) and genes in the farnesene production pathway, and uses phosphoketolase and phosphotransacetylase as a pathway to produce cytosolic acetyl-CoA, which is used for synthesis of farnesene. Y12745.ms63907.ms64472 ("Y12745"; left panel) comprises a deletion of the PDH-bypass (acs1Δ acs2Δ ald6Δ), and genes in the farnesene production pathway, and uses phosphoketolase and phosphotransacetylase as a pathway to produce cytosolic acetyl-CoA, which is used for synthesis of farnesene.

5. DETAILED DESCRIPTION OF THE EMBODIMENTS

5.1 Terminology

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus. The term "heterologous enzyme" refers to an enzyme that is not normally found in a given cell in nature. The term encompasses an enzyme that is: (a) exogenous to a given cell (i.e., encoded by a nucleotide sequence that is not naturally present in the host cell or not naturally present in a given context in the host cell); and (b) naturally found in the host cell (e.g., the enzyme is encoded by a nucleotide sequence that is endogenous to the cell) but that is produced in an unnatural amount (e.g., greater or lesser than that naturally found) in the host cell.

On the other hand, the term "native" or "endogenous" as used herein with reference to molecules, and in particular enzymes and nucleic acids, indicates molecules that are expressed in the organism in which they originated or are found in nature, independently of the level of expression that can be lower, equal, or higher than the level of expression of the molecule in the native microorganism. It is understood that expression of native enzymes or polynucleotides may be modified in recombinant microorganisms.

As used herein, to "functionally disrupt" or a "functional disruption" e.g., of a target gene, for example, one or more genes of the PDH-bypass, means that the target gene is altered in such a way as to decrease in the host cell the activity of the protein encoded by the target gene. In some embodiments the functional disruption of a target gene results in a reduction by at least 5%, 10%, 15%, 20%, 25%, 30%, 35%, 40%, 45%, 50%, 55%, 60%, 65%, 70%, 75%, 80%, 85%, 90%, 95% or 100% of the expression level of the target gene compared to its expression when not functionally disrupted. Similarly, to "functionally disrupt" or a "functional disruption" e.g., of a target protein, for example, a protein having acetyl phosphatase activity, means that the target protein is altered in such a way as to decrease in the host cell the activity of the protein. In some embodiments the functional disruption of a target protein results in a reduction by at least 5%, 10%, 15%, 20%, 25%, 30%, 35%, 40%, 45%, 50%, 55%, 60%, 65%, 70%, 75%, 80%, 85%, 90%, 95% or 100% of the activity or expression level of the target protein compared to its activity or expression when not functionally disrupted. In some embodiments, the activity of the target protein encoded by the target gene is eliminated in the host cell. In other embodiments, the activity of the target protein encoded by the target gene is decreased in the host cell. Functional disruption of the target gene may be achieved by deleting all or a part of the gene so that gene expression is eliminated or reduced, or so that the activity of the gene product is eliminated or reduced. Functional disruption of the target gene may also be achieved by mutating a regulatory element of the gene, e.g., the promoter of the gene so that expression is eliminated or reduced, or by mutating the coding sequence of the gene so that the activity of the gene product is eliminated or reduced. In some embodiments, functional disruption of the target gene results in the removal of the complete open reading frame of the target gene.

As used herein, the term "parent cell" refers to a cell that has an identical genetic background as a genetically modified host cell disclosed herein except that it does not comprise one or more particular genetic modifications engineered into the modified host cell, for example, one or more modifications selected from the group consisting of: heterologous expression of an ADA, heterologous expression of an NADH-using HMG-CoA reductase, heterologous expression of an AACS, heterologous expression of a phosphoketolase, heterologous expression of a phosphotransacetylase, and heterologous expression of one or more enzymes of the mevalonate pathway.

As used herein, the term "production" generally refers to an amount of an isoprenoid produced by a genetically modified host cell provided herein. In some embodiments, production is expressed as a yield of isoprenoid by the host cell. In other embodiments, production is expressed as a productivity of the host cell in producing the isoprenoid.

As used herein, the term "productivity" refers to production of an isoprenoid by a host cell, expressed as the amount of isoprenoid produced (by weight) per amount of fermentation broth in which the host cell is cultured (by volume) over time (per hour).

As used herein, the term "yield" refers to production of an isoprenoid by a host cell, expressed as the amount of isoprenoid produced per amount of carbon source consumed by the host cell, by weight.

As used herein, the phrase "acetyl-CoA derived compound" refers to a compound which uses acetyl-CoA as a substrate in its biosynthesis. Exemplary acetyl-CoA derived compounds include, but are not limited to, isoprenoids, polyketides, fatty acids, and alcohols. In some embodiments, an acetyl-CoA derived compound is ethanol, for example, bioethanol produced from pentose substrates, as described in U.S. Pat. No. 7,253,001, the contents of which are hereby incorporated by reference in their entirety.

As used herein, the term "variant" refers to a polypeptide differing from a specifically recited "reference" polypeptide (e.g., a wild-type sequence) by amino acid insertions, deletions, mutations, and substitutions, but retains an activity that is substantially similar to the reference polypeptide. In some embodiments, the variant is created by recombinant DNA techniques, such as mutagenesis. In some embodiments, a variant polypeptide differs from its reference polypeptide by the substitution of one basic residue for another (i.e. Arg for Lys), the substitution of one hydrophobic residue for another (i.e. Leu for Ile), or the substitution of one aromatic residue for another (i.e. Phe for Tyr), etc. In some embodiments, variants include analogs wherein conservative substitutions resulting in a substantial structural analogy of the reference sequence are obtained. Examples of such conservative substitutions, without limitation, include glutamic acid for aspartic acid and vice-versa; glutamine for asparagine and vice-versa; serine for threonine and vice-versa; lysine for arginine and vice-versa; or any of isoleucine, valine or leucine for each other.

5.2 Host Cells

Host cells useful compositions and methods provided herein include archae, prokaryotic, or eukaryotic cells.

Suitable prokaryotic hosts include, but are not limited to, any of a variety of gram-positive, gram-negative, or gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus,* and *Zymomonas.* Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei,* and *Staphylococcus aureus.* In a particular embodiment, the host cell is an *Escherichia coli* cell.

Suitable archae hosts include, but are not limited to, cells belonging to the genera: *Aeropyrum, Archaeglobus, Halobacterium, Methanococcus, Methanobacterium, Pyrococcus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the host microbe is *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans*, or *Hansenula polymorphs* (now known as *Pichia angusta*). In some embodiments, the host microbe is a strain of the genus *Candida*, such as *Candida lipolytica, Candida guilliermondii, Candida krusei, Candida pseudotropicalis*, or *Candida utilis*.

In a particular embodiment, the host microbe is *Saccharomyces cerevisiae*. In some embodiments, the host is a strain of *Saccharomyces cerevisiae* selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the host microbe is a strain of *Saccharomyces cerevisiae* selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the host microbe is a microbe that is suitable for industrial fermentation. In particular embodiments, the microbe is conditioned to subsist under high solvent concentration, high temperature, expanded substrate utilization, nutrient limitation, osmotic stress due to sugar and salts, acidity, sulfite and bacterial contamination, or combinations thereof, which are recognized stress conditions of the industrial fermentation environment.

5.3 the Phosphoketolase (PK)/Phosphotransacetylase (PTA) Pathway to Acetyl-CoA

In some embodiments, the phosphoketolase pathway is activated in the genetically modified host cells provided herein by engineering the cells to express polynucleotides and/or polypeptides encoding phosphoketolase and, optionally, phosphotransacetylase. Thus, in some embodiments, the genetically modified host cells provided herein comprise a heterologous polynucleotide encoding a polypeptide having phosphoketolase activity. In other embodiments, particularly where acetyl phosphate can be supplied as a metabolic intermediate independent of phosphoketolase activity, the genetically modified host cells provided herein comprise a heterologous polynucleotide encoding a polypeptide having phosphotransacetylase activity. In other embodiments, the genetically modified host cells provided herein comprise both a heterologous polynucleotide encoding a polypeptide having phosphoketolase activity and a heterologous polynucleotide encoding a polypeptide having phosphotransacetylase activity.

5.3.1 Phosphoketolase (PK)

Phosphoketolase (EC 4.1.2.9) catalyzes the conversion of xylulose 5-phosphate into glyceraldehyde 3-phosphate and acetyl phosphate; and/or the conversion of fructose-6-phosphate into erythrose-4-phosphate and acetyl phosphate. Phosphoketolase activity has been identified in several yeast strains growing with xylose as the sole carbon source but not in yeast strains grown with glucose (Evans and Ratledge, *Arch. Microbiol.* 139: 48-52; 1984) Inhibitors of phosphoketolase include, but are not limited to, erythrose 4-phosphate and glyceraldehyde 3-phosphate.

Numerous examples of polynucleotides, genes and polypeptides encoding phosphoketolase activity are known in the art and can be used in the genetically modified host cell provided herein. In some embodiments, such a polynucleotide, gene and/or polypeptide is the xylulose 5-phosphateketolase (XpkA) of *Lactobacillus pentosus* MD363 (Posthuma et al., *Appl. Environ. Microbiol.* 68: 831-7; 2002). XpkA is the central enzyme of the phosphoketolase pathway (PKP) in lactic acid bacteria, and exhibits a specific activity of 4.455 µmol/min/mg (Posthuma et al., *Appl. Environ. Microbiol.* 68: 831-7; 2002). In other embodiments, such a polynucleotide, gene and/or polypeptide is the phosphoketolase of *Leuconostoc mesenteroides* (Lee et al., *Biotechnol Lett.* 27(12); 853-858 (2005)), which exhibits a specific activity of 9.9 µmol/min/mg and is stable at pH above 4.5 (Goldberg et al., Methods Enzymol. 9: 515-520; 1966). This phosphoketolase exhibits a Km of 4.7 mM for D-xylulose 5-phosphate and a Km of 29 mM for fructose 6-phosphate (Goldberg et al., Methods Enzymol. 9: 515-520; 1966). Representative phosphoketolase nucleotide sequences of *Leuconostoc mesenteroides* includes accession number AY804190, and SEQ ID NO: 1 as provided herein. Representative phosphoketolase protein sequences of *Leuconostoc mesenteroides* include accession numbers YP_819405, AAV66077.1, and SEQ ID NO: 2 as provided herein. In other embodiments, such a polynucleotide, gene and/or polypeptide is the D-xylulose 5-phosphate/D-fructose 6-phosphate phosphoketolase gene xfp from *B. lactis*, as described, for example, in a pentose-metabolizing *S. cerevisiae* strain by Sonderegger et al. (*Appl. Environ. Microbiol.* 70: 2892-7; 2004).

Other useful phosphoketolases include, but are not limited to, those from *Bifidobacterium dentium* ATCC 27678 (ABIX02000002.1:2350400.2352877; EDT46356.1); *Bifi-* dobacterium animalis (NC_017834.1:1127580.1130057; YP_006280131.1); and Bifidobacterium pseudolongum (AY518216.1:988.3465; AAR98788.1); Aspergillus nidulans FGSC A4 (CBF76492.1); Bifidobacterium longum (AAR98787.1); Bifidobacterium bifidum NCIMB 41171 (ZP 03646196.1); Bifidobacterium animalis subsp. lactis HN019 (ZP 02962870.1); Lactobacillus plantarum WCFS1 (NP_786060.1); Lactobacillus brevis subsp. gravesensis ATCC 27305 (ZP_03940142.1); Lactobacillus reuteri 100-23 (ZP_03073172.1); and Leuconostoc mesenteroides subsp. mesenteroides ATCC 8293 (YP_818922.1).

Other useful phosphoketolases include those described in International Publication No. WO 2011/15985, the contents of which are hereby incorporated by reference in their entirety. These phosphoketolases include: (YP_001601863.1; Gluconacetobacter diazotrophicus Pal 5), (YP_001093221.1; Shewanella loihica PV-4), (YP_926792.1; Shewanella amazonensis SB2B), (YP_735093.1; Shewanella sp. MR-4), (YP_001049439.1; Shewanella baltica OS155), (ZP_02157884.1; Shewanella benthica KT99), (YP_001472925.1; Shewanella sediminis HAW-EB3), (YP_001759669.1; Shewanella woodyi ATCC 51908), (YP_001673352.1; Shewanella halifaxensis HAW-EB4), (YP_563733.1; Shewanella denitrificans OS217), (ZP_05111697.1; Legionella drancourtii LLAP 12), (EEQ84307.1; Ajellomyces dermatitidis ER-3), (XP_002626734.1; Ajellomyces dermatitidis SLH14081), (XP_001539009.1; Ajellomyces capsulatus NAm1), (EEH04133.1; Ajellomyces capsulatus G186AR), (EEH20258.1; Paracoccidioides brasiliensis Pb03), (EEH44652.1; Paracoccidioides brasiliensis Pb 18), (XP_002582752.1; Uncinocarpus reesii 1704), (EER26377.1; Coccidioides posadasii C735 delta SOWgp), (EEQ28085.1; Microsporum canis CBS 113480), (XP_001819785.1; Aspergillus oryzae RIB40), (XP_001399780.1; Aspergillus niger), (XP_001263382.1; Neosartorya fischeri NRRL 181), (XP_001271080.1; Aspergillus clavatus NRRL 1), (XP_001213784.1; Aspergillus terreus NIH2624), (CBF76492.1; Aspergillus nidulans FGSCA4), (XP_002561913.1; Penicillium chrysogenum Wisconsin 54-1255), (XP_002480391.1; Talaromyces stipitatus ATCC 10500), (XP_002144014.1; Penicillium stipitatus ATCC 10500), (XP_002144014.1; Penicillium mameffei ATCC 18224), (XP_754543.1; Aspergillus fumigatus Af293), (XP_001556635.1; Botryotinia fuckeliana B05.1 0), (XP_001592549.1; Sclerotinia sclerotiorum 1980), (XP_386729.1; Gibberella zeae PH-1), (EEU47171.1; Nectria haematococca mp VI 77-13-4), (EEY16637.1; Verticillium alboatrum VaMs.1 02), (XP_956649.1; Neurospora crassa OR74A), (XP_364271.2; Magnaporthe grisea 70-15), (XP_001904585.1; Podospora anserine), (XP_001836159.1; Coprinopsis cinerea okayama7#130), (NP_595963.1; Schizosaccharomyces pombe), (XP_002173441.1; Schizosaccharomyces japonicus yFS275), (XP_570860.1; Cryptococcus neoformans var. neoformans JEC21), (XP_759561.1; Ustilago maydis 521), (ZP_05027078.1; Microcoleus chthonoplastes PCC 7420), (YP_003101114.1; Actinosynnema mirum DSM 43827), (ZP_03568244.1; Atopobium rimae ATCC 49626), (YP_003180237.1; Atopobium parvulum DSM 20469), (ZP_03946928.1; Atopobium vaginae DSM 15829), (ZP_03296299.1; Collinsella stercoris DSM 13279), (AAR98787.1; Bifidobacterium longum), (ZP_03618909.1; Bifidobacterium breve DSM 20213), (ZP_03646196.1; Bifidobacterium bifidum NCIMB 41171), (ZP_04448101.1; Bifidobacterium angulatum DSM 20098), (ZP_03324204.1; Bifidobacterium catenulatum DSM 16992), (AAR98790.1; Bifidobacterium sp. CFAR 172), (AAR98789.1; Bifidobacterium pullorum), (ZP_03937610.1; Gardnerella vaginalis ATCC 14019), (ZP_05965201.1; Bifidobacterium gallicum DSM 20093), (ZP_02962870.1; Bifidobacterium animalis subsp. lactis HNO19), (AAR98788.1; Bifidobacterium pseudolongum subsp. Globosum), (ZP_03946518.1; Atopobium vaginae DSM 15829), (YP_001511171.1; Frankia sp. EANlpec), (YP_713678.1; Frankia alni ACN14a), (YP_002778395.1; Rhodococcus opacus B4), (YP_701466.1; Rhodococcus jostii RHA1), (ZP_04383880.1; Rhodococcus erythropolis SK121), (YP 947598.1; Arthrobacter aurescens TC 1), (CAD48946.1; Propionibacterium freudenreichii subsp. Shermanii), (NP_791495.1; Pseudomonas syringae pv. Tomato str. DC3000), (YP_003125992.1; Chitinophaga pinensis DSM 2588), (ABX56639.1; Verrucomicrobiae bacterium V4), (YP_002371883.1; Cyanothece sp. PCC 8801), (YP_001806596.1; Cyanothece sp. ATCC 51142), (ZP_01730652.1; Cyanothece sp. CCY0110), (CAQ48286.1; Planktothrix rubescens NIVA-CYA 98), (ZP_03276298.1; Arthrospira maxima CS-328), (ZP_03157277.1; Cyanothece sp. PCC 7822), (YP_002379031.1; Cyanothece sp. PCC 7424), (YP_001658501.1; Microcystis aeruginosa NIES-843), (ZP_01621774.1; Lyngbya sp. PCC 8106), (NP_485524.1; Nostoc sp. PCC 7120), (ZP_05036350.1; Synechococcus sp. PCC 7335), (YP_001514813.1; Acaryochloris marina MBIC 11 017), (ZP_05039537.1; Synechococcus sp. PCC 7335), (ZP_02886235.1; Burkholderia graminis C4 DIM), (ZP_03264503.1; Burkholderia sp. H160), (ZP_01085819.1; Synechococcus sp. WH 5701), (ZP_05045603.1; Cyanobium sp. PCC 7001), (ZP_01123645.1; Synechococcus sp. WH 7805), (YP_001223932.1; Synechococcus sp. WH 7803), (ZP_01079038.1; Synechococcus sp. RS9917), (YP_001889002.1; Burkholderia phytofirmans PsJN), (YP_553967.1; Burkholderia xenovorans LB400), (ZP_02881709.1; Burkholderia graminis C4DIM), (ZP_03270532.1; Burkholderia sp. H160), (YP_001861620.1; Burkholderia phymatum STM815), (YP_002755285.1; Acidobacterium capsulatum ATCC 51196), (EDZ38884.1; Leptospirillum sp. Group II '5-way CO'), (EES53204.1; Leptospirillum ferrodiazotrophum), (YP_172723.1; Synechococcus elongatus PCC 6301), (NP_681976.1; Thermosynechococcus elongatus BP-1), (YP_114037.1; Methylococcus capsulatus str. Bath), (YP_002482577.1; Cyanothece sp. PCC 7425), (NP_442996.1; Synechocystis sp. PCC 6803), (YP_002482735.1; Cyanothece sp. PCC 7425), (ZP_04774866.1; Allochromatium vinosum DSM 180), (ZP_01453148.1; Mariprofundus ferrooxydans PV-1), (ZP_04830548.1; Gallionella ferruginea ES-2), (XP_001273863.1; Aspergillus clavatus NRRL 1), (XP_001258643.1; Neosartorya fischeri NRRL 181), (XP_001727680.1; Aspergillus oryzae RIB40), (XP_001396306.1; Aspergillus niger), (XP_001216075.1; Aspergillus terreus NIH2624), (XP_002567130.1; Penicillium chrysogenum Wisconsin 54-1255), (XP_002143851.1; Penicillium marneffei ATCC 18224), (XP_002480216.1; Talaromyces stipitatus ATCC 10500), (XP_001559949.1; Botryotinia fuckeliana B05.10), (XP_001593100.1; Sclerotinia sclerotiorum 1980), (XP_001932192.1; Pyrenophora triticirepentis Pt-IC-BFP), (XP_001793729.1; Phaeosphaeria nodorum SN 15), (XP_567776.1; Cryptococcus neoformans var. neoforrans JEC21), (XP_386504.1; Oibberella zeae PH-1), (EEU46265.1; Nectria haematococca mp VI 77-13-4), (AC024516.1; Metarhizium anisopliae), (XP_959985.1; Neurospora crassa OR74A), (XP_001904686.1; *Podospora anserine*), (YP_002220141.1; *Acidithiobacillus ferrooxidans* ATCC 53993), (YP_001220128.1; *Acidiphilium cryptum* JF-5), (YP_001471202.1; *Thermotoga lettingae* TMO), (YP_002352287.1; *Dictyoglomus turgidum* DSM 6724), (YP_571790.1; *Nitrobacter hamburgensis* X14), (ZP_01092401.1; *Blastopirellula marina* DSM 3645), (YP_001340809.1; *Marinomonas* sp. MWYL1), (NP_866384.1; *Rhodopirellula baltica* SH 1), (ZP_05108502.1; *Legionella drancourtii* LLAP 12), (ZP_04995817.1; *Streptomyces* sp. Mg1), (ZP_04023055.1; *Lactobacillus reuteri* SD2112), (ZP_03960060.1; *Lactobacillus vaginalis* ATCC 49540), (ZP_03073172.1; *Lactobacillus reuteri* 100-23), (ZP_05553031.1; *Lactobacillus coleohominis* 101-4-CHN), (ZP_05863347.1; *Lactobacillus fermentum* 28-3-CHN), (ZP_04021289.1; *Lactobacillus acidophilus* ATCC 4796), (ZP_03995194.1; *Lactobacillus crispatus* IV-VO1), (ZP_04010922.1; *Lactobacillus ultunensis* DSM 16047), (ZP_05549961.1; *Lactobacillus crispatus* 125-2-CRN), (ZP_03951361.1; *Lactobacillus gasseri* IV-V03), (ZP_05744515.1; *Lactobacillus iners* DSM 13335), (YP_618635.1; *Lactobacillus delbrueckii* subsp. *bulgaricus* ATCC 11842), (ZP_03955917.1; *Lactobacillus jensenii* IV-V16), (ZP_03942415.1; *Lactobacillus buchneri* ATCC 11577), (ZP_01544800.1; *Oenococcus oeni* ATCC BAA-1163), (NP_786060.1; *Lactobacillus plantarum* WCFSI), (Q937F6; XPKA_LACPE), (YP_394903.1; *Lactobacillus sakei* subsp. *sakei* 23K), (YP_803891.1; *Pediococcus pentosaceus* ATCC 25745), (BAI40727.1; *Lactobacillus rhamnosus* GG), (ZP_03940142.1; *Lactobacillus brevis* subsp. *Gravesensis* ATCC 27305), (ZP_04009273.1; *Lactobacillus salivarius* ATCC 11741), (ZP_03958643.1; *Lactobacillus ruminis* ATCC 25644), (ZP_04431433.1; *Bacillus coagulans* 36D1), (ZP_04601906.1; *Kingella oxalis* ATCC 51147), (ZP_05736927.1; *Granulicatella adiacens* ATCC 49175), (YP_001449631.1; *Streptococcus gordonii* str. Challis substr. CHI), (NP_736274.1; *Streptococcus agalactiae* NEM316), (ZP_04442854.1; *Listeria grayi* DSM 20601), (ZP_05646360.1; *Enterococcus casseliflavus* EC30), (ZP_05650322.1; *Enterococcus gallinarum* EG2), (ZP_05675307.1; *Enterococcus faecium* Com12), (BAH69929.1; *Mycoplasma fermentans* PG 18), (YP_002000006.1; *Mycoplasma arthritidis* 15 8L3-1), (YP_001256266.1; *Mycoplasma agalactiae* PG2), (YP_001988835.1; *Lactobacillus casei* BL23), (NP_786753.1; *Lactobacillus plantarum* WCFS 1), (ZP_04009976.1; *Lactobacillus salivarius* ATCC 11741), (YP_818922.1; *Leuconostoc mesenteroides* subsp. *Mesenteroides* ATCC 8293), (YP_794669.1; *Lactobacillus brevis* ATCC 367), (ZP_04782553.1; *Weissella paramesenteroides* ATCC 33313), (YP_001727454.1; *Leuconostoc citreum* KM20), (YP_819405.1; *Leuconostoc mesenteroides* subsp. *mesenteroides* ATCC 8293), (ABX75772.1; *Lactococcus lactis* subsp. *Lactis*), (YP_811314.1; *Oenococcus oeni* PSU-1), (ZP_02951191.1; *Clostridium butyricum* 5521), (ZP_05390294.1; *Clostridium carboxidivorans* P7), (NP_347971.1; *Clostridium acetobutylicum* ATCC 824), (ZP_03800296.1; *Coprococcus comes* ATCC 27758), (ZP_04857624.1; *Ruminococcus* sp. 5_1_39B FAA), (ZP_04743029.2; *Roseburia intestinalis* L 1-82), (ZP_02038271.1; *Bacteroides capillosus* ATCC 29799), (XP_002180542.1; *Phaeodactylum tricomutum* CCAP 1055/1), (YP_568630.1; *Rhodopseudomonas palustris* B is B5), (YP_487462.1; *Rhodopseudomonas palustris* HaA2), (NP_947019.1; *Rhodopseudomonas palustris* CGA009), (YP_533660.1; *Rhodopseudomonas palustris* BisB18), (YP_973512.1; *Polaromonas naphthalenivorans* CJ2), (ZP_01464191.1; *Stigmatella aurantiaca* DW4/3-1), (YP_001267778.1; *Pseudomonas putida* F1), (YP_829644.1; *Arthrobacter* sp. FB24), (YP_002486392.1; *Arthrobacter chlorophenolicus* A6), (ZP_05816651.1; *Sanguibacter keddieii* DSM 10542), (YP_002883053.1; *Beutenbergia cavemae* DSM 12333), (YP_003161540.1; *Jonesia denitrificans* DSM 20603), (ZP_03911482.1; *Xylanimonas cellulosilytica* DSM 15894), (CAJ57850.1; *Cellulomonas flavigena*), (YP_001134605.1; *Mycobacterium gilvum* PYR-GCK), (YP_953877.1; *Mycobacterium vanbaalenii* PYR-1), (YP_003155611.1; *Brachybacterium faecium* DSM 4810), (YP_003148127.1; *Kytococcus sedentarius* DSM 20547), (YP_001221168.1; *Clavibacter michiganensis* subsp. *michiganensis* NCPPB 382), (YP_001158426.1; *Salinispora tropica* CNB-440), (YP_001536420.1; *Salinispora arenicola* CNS-205), (ZP_04608302.1; *Micromonospora* sp. ATCC 39149), (YP_887914.1; *Mycobacterium smegmatis* str. MC2 155), (YP_639956.1; *Mycobacterium* sp. MCS), (ZP_04749157.1; *Mycobacterium kansasii* ATCC 12478), (YP_001851039.1; *Mycobacterium marinum* M), (NP_960507.1; *Mycobacterium avium* subsp. *paratuberculosis* K-10), (ZP_05224330.1; *Mycobacterium intracellulare* ATCC 13950), (YP_001703240.1; *Mycobacterium abscessus*), (YP_00995133.1; *Janibacter* sp. HTCC2649), (YP_291026.1; *Thermobifida fusca* YX), (ZP_04031845.1; *Thermomonospora curvata* DSM 43183), (ZP_04475514.1; *Streptosporangium roseum* DSM 43021), (ZP_04335641.1; *Nocardiopsis dassonvillei* subsp. *dassonvillei* DSM 43111), (ZP_04482201.1; *Stackebrandtia nassauensis* DSM 44728), (YP_003099712.1; *Actinosynnema mirum* DSM 43827), (NP_733508.1; *Streptomyces coelicolor* A3(2)), (CAJ88379.1; *Streptomyces ambofaciens* ATCC 23877), (ZP_05536883.1; *Streptomyces griseoflavus* Tu4000), (ZP_05020421.1; *Streptomyces sviceus* ATCC 29083), (CBG67625.1; *Streptomyces scabiei* 87.22), (NP_822448.1; *Streptomyces avermitilis* MA-4680), (ZP_04689547.1; *Streptomyces ghanaensis* ATCC 14672), (ZP_05530021.1; *Streptomyces viridochromogenes* DSM 40736), (ZP_05512501.1; *Streptomyces hygroscopicus* ATCC 53653), (ZP_05800927.1; *Streptomyces flavogriseus* ATCC 33331), (YP_001828275.1; *Streptomyces griseus* subsp. *griseus* NBRC 13350), (ZP_04705493.1; *Streptomyces albus* J1074), (ZP_04996963.1; *Streptomyces* sp. Mg1), (ZP_05485309.1; *Streptomyces* sp. SPB78), (ZP_03860882.1; *Kribbella flavida* DSM 17836), (YP_117539.1; *Nocardia farcinica* IFM 10152), (YP_001505556.1; *Frankia* sp. EAN1pec), (YP_482627.1; *Frankia* sp. CcI3), (YP_003116893.1; *Catenulispora acidiphila* DSM 44928), (YP_872280.1; *Acidothermus lolyticus* IIB), (YP_924807.1; *Nocardioides* sp. JS614), (YP_001104157.1; *Saccharopolyspora erythraea* NRRL 2338), (YP_002282673.1; *Rhizobium leguminosarum* by. *trifolii* WSM2304), (YP_002977256.1; *Rhizobium leguminosarum* by. *trifolii* WSM1325), (YP_001979796.1; *Rhizobium etli* CIAT 652), (YP_470926.1; *Rhizobium etli* CFN 42), (YP_002540633.1; *Agrobacterium radiobacter* K84), (ZP_05182366.1; *Brucella* sp. 83/13), (ZP_04683384.1; *Ochrobactrum intermedium* LMG 3301), (YP_001373254.1; *Ochrobactrum anthropi* ATCC 49188), (YP_001204109.1; *Bradyrhizobium* sp. ORS278), (YP_001238418.1; *Bradyrhizobium* sp. BTAi1), (NP_769158.1; *Bradyrhizobium japonicum* USDA 110), (YP_577164.1; *Nitrobacter hamburgensis* X14), (YP_002961612.1; *Methylobacterium extorquens* AM 1), (YP_674792.1; *Mesorhizobium* sp. BNC1), (ZP_05813617.1; *Mesorhizobium opportunistum* WSM2075), (YP_318559.1; *Nitrobacter winogradskyi* Nb-255), (YP_001755280.1; *Methylobacterium radiotoler-* ans JCM 2831), (YP_001753119.1; *Methylobacterium radiotolerans* JCM 2831), (YP_003066011.1; *Methylobacterium extorquens* DM4), (YP_002964777.1; *Methylobacterium extorquens* AM 1), (YP_002501292.1; *Methylobacterium nodulans* ORS 2060), (YP_002495265.1; *Methylobacterium nodulans* ORS 2060), (YP_001770387.1; *Methylobacterium* sp. 4-46), (YP_002944712.1; *Variovorax paradoxus* S110), (ZP_01156757.1; *Oceanicola granulosus* HTCC2516), (ZP_01628787.1; *Nodularia spumlgena* CCY9414), (YP_001865546.1; *Nostoc punctiforme* PCC 73102), (YP_321015.1; *Anabaena variabilis* ATCC 29413), (ZP_03769140.1; *Nostoc azollae* '0708), (NP_923943.1; *Gloeobacter violaceus* PCC 7421), (YP_477385.1; *Synechococcus*sp. JA-2-3B'a(2-13)), (YP_001328659.1; *Sinorhizobium medicae* WSM419), (YP_765670.1; *Rhizobium leguminosarum* bv. *viciae* 3841), (NP_384212.2; *Sinorhizobium meliloti* 1021), (ZP_02928455.1; *Verrucomicrobium spinosum* DSM 4136), (YP_001637539.1; *Methylobacterium extorquens* Pal), (ZP_01045825.1; *Nitrobacter* sp. Nb-311A), (ZP_02736602.1; *Gemmata obscuriglobus* UQM 2246), (YP_003157871.1; *Desulfomicrobium baculatum* DSM 4028), (ZP_03631304.1; *bacterium* Ellin514), (ZP_04577558.1; *Oxalobacter formigenes* HOxBLS), (ZP_04579712.1; *Oxalobacter formigenes* OXCC13), (YP_826169.1; *Solibacter usitatus* Ellin6076), (YP_002018753.1; *Pelodictyon phaeoclathratiforme* BU-1), (YP_002016285.1; *Prosthecochloris aestuarii* DSM 271), (YP_001943369.1; *Chlorobium limicola* DSM 245), (NP_662409.1; *Chlorobium tepidum* TLS), (ZP_01386179.1; *Chlorobium ferrooxidans* DSM 13031), (YP_375422.1; *Chlorobium luteolum* DSM 273), (YP_285277.1; *Dechloromonas aromatics* RCB), (YP_314589.1; *Thiobacillus denitrificans* ATCC 25259), (YP_545002.1; *Methylobacillus flagellatus* KT), (NP_842139.1; *Nitrosomonas europaea* ATCC 19718), (YP_748274.1; *Nitrosomonas eutropha* C91), (YP_411688.1; *Nitrosospira multiformis* ATCC 25196), (YP_344700.1; *Nitrosococcus oceani* ATCC 19707), (YP_007004.1; *Candidatus Protochlamydia amoebophila* UWE25), (NP_435833.1; *Sinorhizobium meliloti* 1021), (ZP_04421874.1; *Sulfurospirillum deleyianum* DSM 6946), (NP_107054.1; *Mesorhizobium loti* MAFF303099), (YP_002289797.1; *Oligotropha carboxidovorans* OM5), (YP_001833312.1; *Beijerinckia indica* subsp. *indica* ATCC 9039).

Phosphoketolases also useful in the compositions and methods provided herein include those molecules which are said to be "derivatives" of any of the phosphoketolases described herein. Such a "derivative" has the following characteristics: (1) it shares substantial homology with any of the phosphoketolases described herein; and (2) is capable of catalyzing the conversion of X5P into glyceraldehyde 3-phosphate (G3P) and acetyl phosphate; or F6P into erythrose 4-phosphate (E4P) and acetyl phosphate. A derivative of a phosphoketolase is said to share "substantial homology" with the phosphoketolase if the amino acid sequences of the derivative is at least 80%, and more preferably at least 90%, and most preferably at least 95%, the same as that of the phosphoketolase.

5.3.2 Phosphotransacetylase (PTA)

In some embodiments, the genetically modified host cell provided herein comprises a heterologous nucleotide sequence encoding a phosphotransacetylase. Phosphotransacetylase (EC 2.3.1.8) converts acetyl phosphate into acetyl-CoA.

Numerous examples of polynucleotides, genes and polypeptides encoding phosphotransacetylase activity are known in the art and can be used in the genetically modified host cell provided herein. In some embodiments, such a polynucleotide, gene and/or polypeptide is the phosphotransacetylase from *Clostridium kluyveri*. Representative phosphotransacetylase nucleotide sequences of *Clostridium kluyveri* includes accession number NC_009706.1: 1428554.1429555, and SEQ ID NO: 3 as provided herein. Representative phosphotransacetylase protein sequences of *Clostridium kluyveri* include accession number YP_001394780 and SEQ ID NO: 4 as provided herein. Other useful phosphotransacetylases include, but are not limited to, those from *Lactobacillus reuteri* (NC_010609.1: 460303.461277; YP_001841389.10); *Bacillus subtilis* (NC_014479.1:3671865.3672836; YP_003868063.1); *Methanosarcina thermophile* (L23147.1:207.1208; AAA72041.1); *Lactobacillus sanfranciscensis* (BAB19267.1); *Lactobacillus plantarum* WCFS1 (NP_784550.1); *Lactobacillus fermentum* ATCC 14931 (ZP03944466.1); *Bacillus subtilis* subsp. *subtilis* str. 168 (NP_391646.1); *Methanosarcina thermophile* (AAA72041.1); *Clostridium thermocellum* DSM 4150 (ZP_03152606.1); *Clostridium acetobutylicum* ATCC 824 (NP_348368.1); *Clostridium kluyveri* DSM 555 (YP 001394780.1); *Veillonella parvula* DSM 2008 (ZP 03855267.1); and *Salmonella enterica* subsp. *enterica* serovar *Paratyphi* A str. ATCC 9150 (YP_149725.1).

Other useful phosphotransacetylases include those described in International Publication No. WO 2011/15985, the contents of which are hereby incorporated by reference in their entirety. These phosphotransacetylases include: (ZP_05427766.1; *Eubacterium saphenum* ATCC 49989), (ZP_03627696.1; *bacterium* Ellin514), (ZP_03131770.1; *Chthonio bacter flavus* Ellin428), (YP_001878031.1; *Akkermansia muciniphila* TCCBAA-835), (ZP_04562924.1; *Citrobacter* sp. 30_2), (YP_001451936.1; *Citrobacter koseri* ATCC BAA-895), (YP_149725.1; *Salmonella enterica* subsp. *enterica* serovar *Paratyphi* A str. ATCC 9150), (YP_001569496.1; *Salmonella enterica* subsp. *anzonae* serovar 62:z4,z23:--), (NP_416953.1; *Escherichia coli* str. K-12 substr. MG1655), (YP_002920654.1; *Klebsiella pneumomae* NTUH-K2044), (ZP_04637797.1; *Yersinia intermedia* ATCC 29909), (ZP_01222604.1; *Photobacterium profundum* 3TCK), (ZP_02156855.1; *Shewanella benthica* KT99), (YP_958508.1; *Marinobacter aquaeolei* VT8), (YP_066771.1; *Desulfotalea psychrophila* LSv54), (YP_002780531.1; *Rhodococcus opacus* B4), (YP_703506.1; *Rhodococcus jostii* RHA1), (ZP_05479963.1; *Streptomyces* sp. AA4), (YP_002761398.1; *Gemmatimonas aurantiaca* T-27), (ZP_04670189.1; *Clostridiales bacterium* 1_7_47FAA), (ZP_05493958.1; *Clostridium papyrosolvens* DSM 2782), (YP_003143506.1; *Slackia heliotrinireducens* DSM 20476), (ZP_05090822.1; *Ruegeria* sp. R11), (ZP_01748021.1; *Sagittula stellata* E-37), (NP_604069.1; *Fusobacterium nucleatum* subsp. *nucleatum* ATCC 25586), (ZP_05814734.1; *Fusobacterium* sp. 3_1_33), (ZP_06026613.1; *Fusobacterium periodonticum* ATCC 33693), (ZP_05617632.1; *Fusobacterium* sp. 3_1_5R), (ZP_05628030.1; *Fusobacterium* sp. D12), (ZP_04860946.1; *Fusobacteriumvanum* ATCC 27725), (ZP_04567444.1; *Fusobacterium mortiferum* ATCC 9817), (YP_001489437.1; *Arcobacter butzleri* RM4018), (YP_003163236.1; *Leptotrichia buccalis* C-1013-b), (ZP_05902420.1; *Leptotrichia hofstadii* F0254), (ZP_06011308.1; *Leptotrichia goodfellowii* F0264), (ZP_04479548.1; *Streptobacillus moniliformis* DSM 12112), (ZP_03855267.1; *Veillonella parvula* DSM 2008), (ZP_03928523.1; *Acidaminococcus* sp. D21), (NP_970659.1; *Treponema denticola* ATCC 35405), (ZP_05621510.1; *Treponema vincentii* ATCC 35580), (NP_218534.1; *Treponema pallidum* subsp. *pallidum* str. Nichols), (ZP_04047318.1; *Brachyspira murdochii* DSM 12563), (YP_002720478.1; *Brachyspira hyodysenteriae* WAl), (YP_001740706.1; *Candidatus Cloacamonas acidaminovorans*), (EER05013.1; *Perkinsus mannus* ATCC 50983), (YP_945582.1; *Borrelia turicatae* 91E135), (YP_001884013.1; *Borrelia hermsii* DAH), (YP_002222233.1; *Borrelia duttonii* Ly), (ZP_03675306.1; *Borrelia spielmanii* A14S), (ZP_03435394.1; *Borrelia afzelii* ACA-l), (ZP_03540018.1; *Borrelia garinii* Far04), (ZP_03672928.1; *Borrelia valaisiana* VS116), (NP_212723.1; *Borrelia burgdorferi* B31), (YP_001956287.1; uncultured Termite group 1 bacterium phylotype Rs-D17), (NP_975268.1; *Mycoplasma mycoides* subsp. *mycoides* SC str. PGl), (YP_424216.1; *Mycoplasma capricolumn* subsp. *capricolumn* ATCC 27343), (YP_053283.1; *Mesoplasma florum* Ll), (CAK99540.1; *Spiroplasma citri*), (NP_072966.1; *Mycoplasma genitalium* G37), (NP_110116.1; *Mycoplasma pneumomae* M129), (NP_853403.1; *Mycoplasma gallisepticum* R), (NP_757889.1; *Mycoplasma penetrans* HF-2), (YP_116016.1; *Mycoplasma hyopneumoniea* 232), (YP_002960607.1; *Mycoplasma conjunctivae*), (YP_001256282.1; *Mycoplasma agalactiae* PG2), (BAH69503.1; *Mycoplasma fermentans* PG18), (YP_278771.1; *Mycoplasma synoviae* 53), (NP_326068.1; *Mycoplasma pulmonis* UAB CTIP), (YP_015865.1; *Mycoplasma mobile* 163K), (YP_001256630.1; *Mycoplasma agalactiae* PG2), (YP_802685.1; *Buchnera aphidicola* str. Cc (*Cinara cedri*)), (YP_001885432.1; *Clostridium botulinum* B str. Eklund 17B), (YP_001308302.1; *Clostridium beijerinckii* NUMB 8052), (ZP_05131280.1; *Clostridium* sp. 7_2_43FAA), (ZP_02948604.1; *Clostridium butyricum* 5521), (NP_562641.1; *Clostridium perfringens* str. 13), (ZP_05391232.1; *Clostridium carboxidivorans* P7), (YP_001394780.1; *Clostridium kluyveri* DSM 555), (ZP_02995419.1; *Clostridium sporogenes* ATCC 15579), (NP_781870.1; *Clostridium tetani* E88), (ZP_04862192.1; *Clostridium botulinum* D str. 1873), (YP_878298.1; *Clostridium novyi* N7), (ZP_04804960.1; *Clostridium cellulovorans* 743B), (NP_348368.1; *Clostridium acetobutylicum* ATCC 824), (ACA51668.1; *Thermoanaero bacterium saccharolyticum*), (ZP_05336886.1; *Thermoanaero bacterium thermosaccharolyticum* SM 571), (NP_623097.1; *Thermoanaero bacter tengcongensis* MB4), (YP_001663354.1; *Thermoanaero bacter* sp. X514), (YP_002508771.1; *Halothermoth rix orenii* H 168), (YP_003190679.1; *Desulfotomaculum acetoxidans* DSM 771), (YP_001917776.1; *Natranaerobius thermophiles* JWINM-WN-LF), (YP_360288.1; *Carboxydothermus hydrogenoformans* Z-2901), (EY83551.1; *Bacteroides* sp. 2_1_33B), (ZP_02033408.1; *Parabacteroides merdae* ATCC 43184), (NP_905297.1; *Porphyromonas gingivalis* W83), (ZP_04056000.1; *Porphyromonas uenonis* 60-3), (ZP_04389884.1; *Porphyromonas endodontalis* ATCC 35406), (ZP_02068815.1; *Bacteroides uniformis* ATCC 8492), (ZP_03460749.1; *Bacteroides eggerthii* DSM 20697), (ZP_03676944.1; *Bacteroides cellulosilyticus* DSM 14838), (YP_097761.1; *Bacteroides fragilis* YCH46), (ZP_04545825.1; *Bacteroides* sp. D1), (ZP_03643544.1; *Bacteroides coprophilus* DSM 18228), (ZP_03207078.1; *Bacteroides plebeius* DSM 17135), (YP_001297855.1; *Bacteroides vulgatus* ATCC 8482), (ZP_05736702.1; *Prevotella tannerae* ATCC 51259), (ZP_06007587.1; *Prevotella bergensis* DSM 17361), (ZP_05858935.1; *Prevotella verora-*

*lis* F0319), (ZP_05916997.1; *Prevotella* sp. oral taxon 472 str. F0295), (YP_002308782.1; *Candidatus Azo bacteroides pseudotrichon ymphae genomovar*. CFP2), (YP_753459.1; *Syntrophomonas wolfei* subsp. *wolfei* str. *Goettingen*), (ZP_01771389.1; *Collinsella aerofaciens* ATCC 25986), (ZP_03296849.1; *Collinsella stercoris* DSM 13279), (ZP_04445308.1; *Collinsella ntestinalis* DSM 13280), (ZP_03567515.1; *Atopobium rimae* ATCC 49626), (YP_003179667.1; *Atopobium parvulum* DSM 20469), (ZP_03946133.1; *Atopobium vaginae* DSM 15829), (ZP_03990654.1; *Oribacterium sinus* F0268), (ZP_04450849.1; *Abiotrophia defective* ATCC 49176), (ZP_05797601.1; *Oribacterium* sp. oral taxon 078 str. F0262), (ZP_03730247.1; *Clostridium* sp. M62/1), (ZP_04856252.1; *Ruminococcus* sp. 5_1_39BFAA), (ZP_01966332.1; *Ruminococcus obeum* ATCC 29174), (ZP_05345616.1; *Bryantella formatexigens* DSM 14469), (ZP_03780829.1; *Blautia hydrogenotro phica* DSM 10507), (ZP_03289360.1; *Clostridium nexile* DSM 1787), (ZP_02042092.1; *Ruminococcus gnavus* ATCC 29149), (ZP_03168112.1; *Ruminococcus lactaris* ATCC 29176), (ZP_01968837.1; *Ruminococcus torques* ATCC 27756), (ZP_02430426.1; *Clostridium scindens* ATCC 35704), (ZP_03779744.1; *Clostridium hylemonae DSM* 15053), (ZP_02234595.1; *Dorea formicigenerans ATCC* 27755), (ZP_01994673.1; *Dorea longicatena* DSM 13814), (YP_001558442.1; *Clostridium phytofermentans* ISDg), (ZP_04667085.1; *Clostridiales bacterium* 1_7_47FAA), (ZP_02085391.1; *Clostridium bolteae* ATCC BAA-613), (ZP_05790853.1; *Butyrivibrio crossotus* DSM 2876), (ZP_02026034.1; *Eubacterium ventriosum* ATCC 27560), (YP_002930513.1; *Eubacterium eligens* ATCC 27750), (ZP_04808213.1; *Helicobacter pullorum* MIT 98-5489), (ZP_03656120.1; *Helicobacter Canadensis* MIT 98-5491), (ZP_04583217.1; *Helicobacter winghamensis* ATCCBAA-430), (NP_860840.1; *Helicobacter hepaticus* ATCC 51449), (ZP_03657896.1; *Helicobacter cinaedi* CCUG 18818), (ZP_02417779.1; *Anaerostipes caccae* DSM 14662), (ZP_02437622.1; *Clostridium* sp. SS211), (ZP_02205430.1; *Coprococcus eutactus* ATCC 27759), (ZP_02692616.1; *Epulopiscium* sp. 'N.t. morphotype B'), (YP_003182082.1; *Eggerthella lenta* DSM 2243), (YP_003151027.1; *Cryptobacterium curtum* DSM 15641), (YP_003143601.1; *Slackia heliotrinireducens* DSM 20476), (ZP_05498135.1; *Clostridium papyrosolvens* DSM 2782), (ZP_03152606.1; *Clostridium thermocellum* JW20), (YP_001180817.1; *Caldicellulosiruptor saccharolyticus* DSM 8903), (AAA72041.1; *Methanosarcina thermophile*), (NP_618482.1; *Methanosarcina acetivorans* C2A), (YP_305342.1; *Methanosarcina barkeri* str. Fusaro), (ZP_02142278.1; *Roseobacter litoralis* Och 149), (YP_681184.1; *Roseobacter denitrificans* OCh 114), (YP_001533168.1; *Dinoroseo bacter shibae* DFL 12), (ZP_05124935.1; *Rhodobacteraceae bacterium* KLH11), (ZP_05786337.1; *Silicibacter lacuscaerulensis* ITI-1157), (YP_001313586.1; *Sinorhizobium medicae* WSM419), (NP_437512.1; *Sinorhizobium meliloti* 1021), (ZP_04682129.1; *Ochrobactrum intermedium* LMG 3301), (YP_001372036.1; *Ochrobactrum anthropic* ATCC 49188), (YP_001888115.1; *Burkholderia phytofirmans* PsJN), (YP_554613.1; *Burkholderia xenovorans* LB400), (YP_001862297.1; *Burkholderia phymatum* STM815), (YP_297974.1; *Ralstonia eutropha* JMP134), (YP_002008219.1; *Cupriavidus taiwanensis*), (YP_001584488.1; *Burkholderia multivorans multivorans*), (YP_002233797.1; *Burkholderia cenocepacia* J2315), (ZP_01220235.1; *Photobacterium profundum* 3TCK), (ZP_03698361.1; *Lutiella nitroferrum* 2002), (ZP_01811515.1; *Vibrionales bacterium* SWAT-3), (ZP_00988349.1; *Vibrio splendidus* 12B01), (ZP_01866234.1; *Vibrio shilonii* AK1), (ZP_05885163.1; *Vibrio coralliilyticus* ATCCBAA-450), (AAS78789.1; *Paracoccus denitrificans*), (YP_345196.1; *Rhodobacter sphaeroides* 2.4.1), (AAN08490.1; *Castellaniella defragrans*), (ZP_00961345.1; *Roseovarius nubinhibens* ISM), (YP_168755.1; *Ruegeria pomeroyi* DSS-3), (ZP_01901193.1; *Roseobacter* sp. AzwK-3b), (ZP_01752570.1; *Roseobacter* sp. SK209-2-6), (ZP_02140073.1; *Roseobacter litoralis* Och 149), (YP_510789.1; *Jannaschia* sp. CCS1), (ZP_05073153.1; *Rhodobacteral es bacterium* HTCC2083), (YP_822367.1; *Candidatus Solibacter usitatus* Ellin6076), (ZP_01313101.1; *Desulfuromon as acetoxidans* DSM 684), (YP_357950.1; *Pelobacter carbinolicus* DSM 2380), (YP_002537084.1; *Geobacter* sp. FRC-32), (YP_001232124.1; *Geobacter uraniireducens* Rf4), (NP_953751.1; *Geobacter sulfurreducens* PCA), (YP_384000.1; *Geobacter metallireducens* GS-15), (YP_900968.1; *Pelobacter propionicus* DSM 2379), (YP_001951452.1; *Geobacter lovleyi* SZ), (ZP_05311922.1; *Geobacter* sp. M18), (YP_003021758.1; *Geobacter* sp. M21), (YP_358255.1; *Pelobacter carbinolicus* DSM 2380), (ZP_03906856.1; *Denitrovibrio acetiphilus* DSM 12809), (YP_001997093.1; *Chloroherpeton thalassium* ATCC 35110), (ZP_01924858.1; *Victivallis vadensis* ATCCBAA-548), (ZP_03439825.1; *Helicobacter pylori* 98-10), (YP_003057614.1; *Helicobacter pylori* B38), (YP_001910417.1; *Helicobacter pylori* Shi470), (NP_223559.1; *Helicobacter pylori* J99), (YP_665033.1; *Helicobacter acinonychis* str. Sheeba), (ZP_01810337.1; *Campylobacter jejuni* subsp. *jejuni* CG8486), (ZP_00366840.1; *Campylobacter coli* RM2228), (ZP_00370527.1; *Campylobacter upsaliensis* RM3195), (YP_002575219.1; *Campylobacter lari* RM2100), (YP_001406718.1; *Campylobacter hominis* ATCCBAA-381), (ZP_05624820.1; *Campylobacter gracilis* RM3268), (YP_891988.1; *Campylobacter fetus* subsp. *fetus* 82-40), (YP_001466901.1; *Campylobacter concisus* 13826), (YP_001408221.1; *Campylobacter curvus* 525.92), (ZP_05363348.1; *Campylobacter showae* RM3277), (ZP_03742933.1; *Bifidobacterium pseudocatenulatum* DSM 20438), (ZP_02918887.1; *Bifidobacterium dentium* ATCC 27678), (ZP_02028883.1; *Bifidobacterium adolescentis* L2-32), (ZP_04448100.1; *Bifidobacterium angulatum* DSM 20098), (ZP_03618886.1; *Bifidobacterium breve* DSM 20213), (ZP_03976084.1; *Bifidobacterium longum* subsp. *infantis* ATCC 55813), (YP_002323183.1; *Bifidobacterium longum* subsp. *infantis* ATCC 15697), (ZP_03646187.1; *Bifidobacterium bifidum* NUMB 41171), (ZP_03937611.1; *Gardnerella vaginalis* ATCC 14019), (ZP_02962869.1; *Bifidobacterium animalis* subsp. *lactis* HN019), (ZP_05965185.1; *Bifidobacterium gallicum* DSM 20093), (ZP_02043408.1; *Actinomyces odontolyticus* ATCC 17982), (ZP_03925176.1; *Actinomyces coleocanis* DSM 15436), (NP_601948.1; *Corynebacterium glutamicum* ATCC 13032), (NP_739201.1; *Corynebacteriurn efficiens* YS-314), (NP_940379.1; *Corynebacterium diphtheria* NCTC 13129), (ZP_04835255.1; *Corynebacteriurn glucuronolyticum* ATCC 51867), (ZP_05708623.1; *Corynebacteriurn genitalium* ATCC 33030), (ZP_03977910.1; *Corynebacterium lipophiloflavum* DSM 44291), (ZP_03932064.1; *Corynebacterium accolens* ATCC 49725), (ZP_05366890.1; *Corynebacterium tuberculostearicum* SK141), (YP_002835817.1; *Corynebacterium aunmucosum* ATCC 700975), (YP_250020.1; *Corynebacterium jeikeium* K411), (YP_001801132.1; *Corynebacterium urealyticum* DSM 7109), (YP_002906954.1; *Corynebacterium kroppenstedtii* DSM 44385), (ZP_03393297.1; *Corynebacterium amycolatum* SK46), (ZP_03718987.1; *Neisseria flavescens* NRL30031/H 210), (ZP_05318956.1; *Neisseria sicca* ATCC 29256), (YP_001598731.1; *Neisseria meningitides* 053442), (ZP_04602977.1; *Kingella oxalis* ATCC 51147), (YP_426466.1; *Rhodospirillum rubrum* ATCC 11170), (NP_871183.1; *Wigglesworthia glossinidia* endosymbiont of *Glossina brevipalpis*), (NP_777793.1; *Buchnera aphidicola* str. Bp (*Baizongia pistaciae*)), (YP_003249406.1; *Fibrobacter succmogenes* subsp. *succmogenes* S85), (ZP_03535302.1; *Mycobacterium tuberculosis* T17), (ZP_04056438.1; *Capnocytophaga gingivalis* ATCC 33624), (YP_003108500.1; *Candidatus Sulcia* muelleri SMDSEM), (P77844; *Corynebacterium glutamicum*), (ZP_03994160.1; *Mobiluncus mulieris* ATCC 35243), (ZP_03922640.1; *Mobiluncus curtisii* ATCC 43063), (ZP_03716209.1; *Eubacterium hallii* DSM 3353), (ZP_03718143.1; *Eubacterium hallii* DSM 3353), (ZP_05614434.1; *Faecalibacterium prausnitzii* A2-165), (ZP_02034852.1; *Bacteroides capillosus* ATCC 29799), (ZP_03753543.1; *Roseburia inulinivorans* DSM 16841), (ZP_04745275.2; *Roseburia intestinalis* L1-82), (YP_002937332.1; *Eubacterium rectale* ATCC 33656), (ZP_02074244.1; *Clostridium* sp. L2-50), (ZP_04455374.1; *Shuttleworthia satelles* DSM 14600), (ZP_03488480.1; *Eubacterium biforme* DSM 3989), (ZP_02078327.1; *Eubacterium dolichum* DSM 3991), (ZP_02077559.1; *Eubacterium dolichum* DSM 3991), (ZP_03305532.1; *Anaerococcus hydrogenalis* DSM 7454), (ZP_05473291.1; *Anaerococcus vaginalis* ATCC 51170), (ZP_03931050.1; *Anaerococcus tetradius* ATCC 35098), (YP_003153463.1; *Anaerococcus prevotii* DSM 20548), (ZP_03916048.1; *Anaerococcus lactolyticus* ATCC 51172), (NP_607213.1; *Streptococcus pyogenes* MGAS8232), (AAK34003.1; *Streptococcus pyogenes* M1GAS), (YP_002562185.1; *Streptococcus uberis* 01401), (YP_002744451.1; *Streptococcus equi* subsp. *Zooepidemicus*), (BAH88016.1; *Streptococcus mutans* NN2025), (ZP_02920305.1; *Streptococcus infantarius* subsp. *infantarius* ATCCBAA-102), (YP_329798.1; *Streptococcus agalactiae* A909), (ZP_04061789.1; *Streptococcus salivarius* SK126), (YP_139881.1; *Streptococcus thermophiles* LMG 18311), (ZP_04525024.1; *Streptococcus pneumoae* CCR11974), (ZP_06060573.1; *Streptococcus* sp. 2_1_36FAA), (YP_001198423.1; *Streptococcus suis* 05ZYH33), (NP_964739.1; *Lactobacillus johnsonii* NCC 533), (YP_193610.1; *Lactobacillus acidophilus* NCFM), (ZP_04011019.1; *Lactobacillus ultunensis* DSM 16047), (ZP_03995297.1; *Lactobacillus crispatus* JV-VOl), (ZP_05752753.1; *Lactobacillus helveticus* DSM 20075), (ZP_03956024.1; *Lactobacillus jensenii* JV-V16), (ZP_04645187.1; *Lactobacillus jensenii* 269-3), (YP_618719.1; *Lactobacillus delbrueckii* subsp. *bulgaricus* ATCC 11842), (ZP_05744366.1; *Lactobacillus iners* DSM 13335), (NP_391646.1; *Bacillus subtilis* subsp. *subtilis* str. 168), (YP_001423045.1; *Bacillus amyloliquefaciens* FZB42), (YP_081073.1; *Bacillus licheniformis* ATCC 14580), (ZP_03055101.1; *Bacillus pumilus* ATCC 7061), (YP_002317098.1; *Anoxybacillus flavithermus* WKI), (YP_002951270.1; *Geobacillus* sp. WCH70), (YP_001127443.1; *Geobacillus thermodenitrificans* NG80-2), (YP_149268.1; *Geobacillus kaustophilus* HTA426), (ZP_01861251.1; *Bacillus* sp. SG-1), (ZP_03228176.1; *Bacillus coahuilensis* m4-4), (ZP_01173945.1; *Bacillus* sp. NRRLB-14911), (NP_693944.1; *Oceanobacillus iheyensis* HTE831), (ZP_04314753.1; *Bacillus cereus* BGSC 6E1), (YP_014727.1; *Listeria monocytogen* es str. 4b F2365), (ZP_04443757.1; *Listeria grayi* DSM 20601), (NP_244690.1; *Bacillus halodurans* C-125), (YP_177402.1; *Bacillus clausii* KSM-K16), (YP_002885816.1; *Exiguo bacteriumsp.* AT1b), (YP_001812721.1; *Exiguo bacterium sibiricum* 255-15), (ZP_02169346.1; *Bacillus selenitireducens* MLS10), (ZP_04818386.1; *Staphylococcus epidermidis* M23864: W1), (ZP_03612973.1; *Staphylococcus capitis* SK14), (ZP_04677798.1; *Staphylococcus wameri* L37603), (NP_763914.1; *Staphylococcus epidermidis* ATCC 12228), (ZP_05685678.1; *Staphylococcus aureus* A9635), (YP_254319.1; *Staphylococcus haemolyticus* JCSC1435), (ZP_04059818.1; *Staphylococcus hominis* SKl19), (ABR57177.1; *Staphylococcus xylosus*), (YP_302214.1; *Staphylococcus saprophyticus* subsp. *saprophyticus* ATCC 15305), (YP_002633340.1; *Staphylococcus camosus* subsp. *camosus* TM300), (YP_002561236.1; *Macrococcus caseolyticus* JCSC5402), (ZP_03944466.1; *Lactobacillus fermentum* ATCC 14931), (ZP_05553502.1; *Lactobacillus coleohominis* 101-4-CHN), (ZP_03959629.1; *Lactobacillus vaginalis* ATCC 49540), (YP_001271004.1; *Lactobacillus reuteri* DSM 20016), (ZP_05745668.1; *Lactobacillus antri* DSM 16041), (YP_818931.1; *Leuconostoc mesenteroides* subsp. *mesenteroides* ATCC 8293), (YP_001727831.1; *Leuconostoc citreum* KM20), (ZP_04782044.1; *Weissella paramesentero ides* ATCC 33313), (ZP_01544468.1; *Oenococcus oeni*ATCC BAA-1163), (ZP_05737294.1; *Granulicatella adiacens* ATCC 49175), (ZP_05851915.1; *Granulicatella elegans* ATCC 700633), (ZP_02183965.1; *Camobacterium* sp. AT7), (ZP_05649755.1; *Enterococcus gallinarum* EG2), (ZP_03947918.1; *Enterococcus faecalis* TX0104), (ZP_03982224.1; *Enterococcus faecium* TX1330), (YP_395954.1; *Lactobacillus sakei* subsp. *sakei* 23K), (ZP_04449762.1; *Catonella morbi* ATCC 51271), (YP_001032100.1; *Lactococcus lactis* subsp. *cremons* MG1363), (YP_806234.1; *Lactobacillus casei* ATCC 334), (NP_784550.1; *Lactobacillus plantarum* WCFS1), (YP_794848.1; *Lactobacillus brevis* ATCC 367), (ZP_03954831.1; *Lactobacillus hilgardii* ATCC 8290), (BABI9267.1; *Lactobacillus sanfranciscensis*), (ZP_03958288.1; *Lactobacillus ruminis* ATCC 25644), (YP_536042.1; *Lactobacillus salivarius* UCC118), (ZP_05747635.1; *Erysipelothrix rhusiopathiae* ATCC 19414), (YP_803875.1; *Pediococcus pentosaceus* ATCC 25745), (ZP_02093784.1; *Parvimonas micra*ATCC 33270), (YP_001692923.1; *Finegoldia magna*ATCC 29328), (ZP_04431499.1; *Bacillus coagulans* 36Dl), (ZP_04775813.1; *Gemella haemolysans* ATCC 10379), (YP_001360609.1; *Kineococcus radiotolerans* SRS30216), (ZP_01115869.1; *Reinekea blandensis* MED297), (YP_003074238.1; *Teredinibac turnterrae* T7901), (YP_958411.1; *Marinobacter quaeolei* VT8), (YP_435580.1; *Hahella chejuensis* KCTC 2396), (YP_001189125.1; *Pseudomonas mendocina* ymp), (YP_792443.1; *Pseudomonas aerugmosa* UCBPP-PA14), (NP_791001.1; *Pseudomonas synngae* pv. *tomato* str. DC3000), (YP_258069.1; *Pseudomonas fluorescens* Pf-5), (YP_606637.1; *Pseudomonas entomophila* L48), (YP_002800579.1; *Azotobacter vinelandii* DJ), (YP_001171663.1; *Pseudomonas stutzeri* A1501), (NP_840385.1; *Nitrosomonas europaea* ATCC 19718), (YP_002801221.1; *Azotobacter vinelandii* DJ), (YP_002787111.1; *Deinococcus deserti* VCDl15), (YP_603523.1; *Deinococcus geothermalis* DSM 11300), (NP_293799.1; *Deinococcus radiodurans* R1), (YP_521550.1; *Rhodoferax ferrireducens* T118), (YP_530962.1; *Rhodopseudo monas palustris* BisB18), (YP_531882.1; *Rhodopseudo monas palustris* BisA53), (ZP_02367347.1; *Burkholderia oklahomensis* C6786), (YP_428079.1; *Rhodospirillum rubrum* ATCC 11170), (YP_530535.1; *Rhodopseudo monas palustris* B is B18), (NP_901200.1; *Chromobacterium violaceum* ATCC 12472), (ZP_03698345.1; *Lutiella nitroferrum* 2002), (YP_001279250.1; *Psychrobacter* sp. PRwf-1), (YP_579484.1; *Psychrobacter cryohalolentis* K5), (ZP_05618978.1; *Enhydrobacter aerosaccus* SK60), (ZP_05362319.1; *Acinetobacter radioresistens* SK82), (YP_045288.1; *Acinetobacter* sp. ADP1), (ZP_05823314.1; *Acinetobacter* sp. RUH2624), (ZP_03824416.1; *Acinetobacter* sp. ATCC 27244), (YP_001380280.1; *Anaeromyxobacter* sp. Fw109-5), (YP_466103.1; *Anaeromyxobacter dehalogenans* 2CP-C), (YP_088190.1; *Mannheimia succiniciproducens* MBEL55E), (YP_001344949.1; *Actinobacillus succmogenes* 130Z), (YP_003007411.1; *Aggregatibacter aphrophilus* NJ8700), (ZP_01788798.1; *Haemophilus influenzae* 3655), (YP_719012.1; *Haemophilus somnus* 129PT), (NP_245642.1; *Pasteurella multocida* subsp. *multocida* str. Pm70), (ZP_05920444.1; *Pasteurella dagmatis* ATCC 43325), (ZP_00133992.2; *Actinobacillus pleuropneumoniae* serovar 1 str. 4074), (ZP_04753547.1; *Actinobacillus minor* NM305), (NP_873873.1; *Haemophilus ducreyi* 35000HP), (ZP_04978908.1; *Mannheimia haemolytica* PHL213), (YP_002475022.1; *Haemophilus parasuis* SH0165), (ZP_05730581.1; *Pantoea* sp. At −9b), (YP_001907133.1; *Erwinia tasmaniensis* Et1/99), (YP_455287.1; *Sodalis glossinidius* str. 'morsitans'), (ZP_05723922.1; *Dickeya dadantii* Ech586), (YP_003258889.1; *Pectobacterium wasabiae* WPP 163), (YP_002988159.1; *Dickeya dadantii* Ech703), (NP_668938.1; *Yersinia pestis* KIM 10), (YP_001479543.1; *Serratia proteamaculans* 568), (YP_002934098.1; *Edwardsiella ictaluri* 93-146), (YP_002151502.1; *Proteus mirabilis* HI4320), (NP_930328.1; *Photorhabdus luminescens* subsp. *laumondii* TTO1), (YP_002920553.1; *Klebsiella pneumomae* NTUH-K2044), (YP_001177557.1; *Enterobacter* sp. 638), (YP_003211286.1; *Cronobacter turicensis*), (BAA04663.1; *Escherichia coli*), (YP_002924403.1; *Candidatus Hamiltonella* defensa SAT (*Acyrthosiphon pisum*)), (ZP_03827735.1; *Pectobacterium carotovorum* subsp. *brasiliensis* PBR1692), (ZP_01159282.1; *Photobacterium* sp. SKA34), (YP_130973.1; *Photobacterium profundum* SS9), (ZP_06052481.1; *Grimontia hollisae* CIP 101886), (ZP_05877035.1; *Vibrio fumissii* CIP 102972), (ZP_05881960.1; *Vibrio metschnikoyii* CIP 69.14), (ZP_05881960.1; *Vibrio metschnikoyii* CIP 69.14), (ZP_02196748.1; *Vibrio* sp. AND4), (NP_934927.1; *Vibrio vulnificus* YJ016), (ZP_01866446.1; *Vibrio shilonii* AKI), (YP_002416612.1; *Vibrio splendidus* LGP32), (YP_002263486.1; *Aliiyibrio salmonicida* LFI1238), (ZP_04415114.1; *Vibrio cholerae* by. *albensis* VL426), (YP_001143125.1; *Aeromonas salmonicida* subsp. *salmonicida* A449), (YP_002892091.1; *Tolumonas auensis* DSM 9187), (ZP_01215350.1; *Psychromonas* sp. CNPT3), (YP_944598.1; *Psychromonas ingrahamii* 37), (YP_001473443.1; *Shewanella sediminis* HAW-EB3), (YP_001761257.1; *Shewanella woodyi* ATCC 51908), (YP_001094519.1; *Shewanella loihica* PV-4), (YP_001674811.1; *Shewanella halifaxensis* HAW-EB4), (YP_869191.1; *Shewanella* sp. ANA-3), (YP_927371.1; *Shewanella amazonensis* SB2B), (YP_751160.1; *Shewanella frigidimarina* NUMB 400), (YP_563413.1; *Shewanella denitrificans* OS217), (YP_001475272.1; *Shewanella sediminis* HAW-EB3), (YP_001674949.1; *Shewanella halifaxensis* HAW-EB4), (ZP_04716660.1;

Alteromonas macleodii ATCC 27126), (YP_662160.1; Pseudoalteromonas atlantica T6c), (ZP_01612225.1; Alteromonadales bacterium TW-7), (ZP_01134640.1; Pseudoalteromonas tunicate D2), (YP_269873.1; Colwellia psychrerythrae a 34H), (YP_001341167.1; Marinomonas sp. MWYL1), (ZP_01077352.1; Marinomonas sp. MED121), (YP_001209362.1; Dichelobacter nodosus VCS1703A), (ZP_05705193.1; Cardiobacterium hominis ATCC 15826), (EEY62817.1; Phytophthora infestans T30-4), (EEY62816.1; Phytophthora infestans T30-4), (XP_001694504.1; Chlamydomonas reinhardtii), (XP_001753120.1; Physcomitrella patens subsp. Patens), (YP_001804510.1; Cyanothece sp. ATCC 51142), (ZP_01729220.1; Cyanothece sp. CCY0110), (YP_003138337.1; Cyanothece sp. PCC 8802), (YP_002380034.1; Cyanothece sp. PCC 7424), (YP_001661110.1; Microcystis aerugmosa NIES-843), (YP_002485151.1; Cyanothece sp. PCC 7425), (NP_441027.1; Synechocystis sp. PCC 6803), (ZP_01061171.1; Leeuwenhoeki ella blandensis MED217), (YP_001195862.1; Flavobacterium johnsoniae UW101), (YP_003194927.1; Robiginitalea biformata HTCC2501), (ZP_01107792.1; Flavobacteriales bacterium HTCC2170), (ZP_01051731.1; Polaribacter sp. MED152), (ZP_01119204.1; Polaribacter irgensii 23-P), (ZP_03390929.1; Capnocytophaga sputigena ATCC 33612), (YP_003141977.1; Capnocytophaga ochracea DSM 7271), (YP_012240.1; Desulfovibrio vulgaris str. Hildenborough), (YP_002436276.1; Desulfovibrio vulgaris str. 'Miyazaki F'), (YP_389730.1; Desulfovibrio desulfuricans subsp. desulfuricans str. G20), (YP_002992165.1; Desulfovibrio salexigens DSM 2638), (YP_003197901.1; Desulfohalobium retbaense DSM 5692), (YP_003157577.1; Desulfomicrobium baculatum DSM 4028), (ZP_03737911.1; Desulfonatronospira thiodismutans AS03-1), (YP_002990332.1; Desulfovibrio salexigens DSM 2638), (ZP_03312237.1; Desulfovibrio piger ATCC 29098), (YP_002478890.1; Desulfovibrio desulfuricans subsp. desulfuricans str. ATCC 27774), (YP_064294.1; Desulfotalea psychrophila LSv54), (YP_594656.1; Lawsonia intracellularis PHE/MN1-00), (ZP_01621820.1; Lyngbya sp. PCC 8106), (ZP_03272899.1; Arthrospira maxima CS-328), (YP_845596.1; Syntrophobacter fumaroxidans MPOB), (ZP_04773932.1; Allochromatium vinosum DSM 180), (NP_869002.1; Rhodopirellula baltica SH 1), (YP_392571.1; Sulfurimonas denitrificans DSM 1251), (ZP_05071717.1; Campylobacterales bacterium GD 1), (ZP_04421899.1; Sulfurospirillum deleyianum DSM 6946), (YP_001359295.1; Sulfurovum sp. NBC37-1), (YP_951544.1; Mycobacterium vanbaalenii PYR-1), (YP_001131488.1; Mycobacterium gilvum PYR-GCK), (YP_637714.1; Mycobacterium sp. MCS), (YP_885188.1; Mycobacterium smegmatis str. MC2 155), (YP_001704953.1; Mycobacterium abscessus), (ZP_04747529.1; Mycobacterium kansasii ATCC 12478), (YP_001849024.1; Mycobacterium marinum M), (NP_214922.1; Mycobacterium tuberculosis H37Rv), (NP_962819.1; Mycobacterium avium subsp. paratuberculosis K-10), (ZP_05223872.1; Mycobacterium intracellulare ATCC 13950), (YP_002764919.1; Rhodococcus erythropolis PR4), (YP_702162.1; Rhodococcus jostii RHAI), (YP_121562.1; Nocardia farcinica IFM 10152), (ZP_04025361.1; Tsukamurella paurometabola DSM 20162), (YP_003275431.1; Gordonia bronchialis DSM 43247), (YP_003160610.1; Jonesia denitrificans DSM 20603), (ZP_05816650.1; Sanguibacter keddieii DSM 10542), (ZP_04368027.1; Cellulomonas flavigena DSM 20109), (YP_002883054.1; Beutenbergia cavemae DSM 12333), (ZP_03911481.1; Xylanimonas cellulosilytica DSM 15894), (YP_924143.1; Nocardioides sp. 1S614), (ZP_03864789.1; Kribbella flavida DSM 17836), (ZP_01131057.1; marine actinobacterium PHSC20C1), (YP_001708941.1; Clavibacter michiganensis subsp. Sepedonicus), (YP_061462.1; Leifsonia xyli subsp. xyli str. CTCB07), (YP_748183.1; Nitrosomonas eutropha C91), (YP_003116892.1; Catenulispora acidiphila DSM 44928), (YP_003199983.1; Nakamurella muitipartita DSM 44233), (YP_003154321.1; Brachybacterium faecium DSM 4810), (ZP_03927492.1; Actinomyces urogenitalis DSM 15434), (YP_003148931.1; Kytococcus sedentarius DSM 20547), (ZP_05803950.1; Streptomyces flavogriseus ATCC 33331), (YP_001823623.1; Streptomyces griseus subsp. griseus NBRC 13350), (ZP_05002693.1; Streptomyces clavuligerus ATCC 27064), (ZP_05015493.1; Streptomyces sviceus ATCC 29083), (ZP_05538660.1; Streptomyces griseoflavus Tu4000), (ZP_04685789.1; Streptomyces ghanaensis ATCC 14672), (ZP_05534308.1; Streptomyces viridochromogenes DSM 40736), (ZP_05523554.1; Streptomyces lividans TK24), (NP_823999.1; Streptomyces avermitilis MA-4680), (CBG69921.1; Streptomyces scabiei 87.22), (ZP_04704905.1; Streptomyces albus 11074), (ZP_04997745.1; Streptomyces sp. Mgl), (ZP_05509147.1; Streptomyces sp. C), (ZP_05514718.1; Streptomyces hygroscopicus ATCC 53653), (ZP_04994290.1; Streptomyces sp. SPB74), (ZP_04474082.1; Streptosporangium roseum DSM 43021), (YP_001160501.1; Salinispora tropica CNB-440), (YP_001538853.1; Salinispora arenicola CNS-205), (ZP_04605575.1; Micromonospora sp. ATCC 39149), (YP_832716.1; Arthrobacter sp. FB24), (ABR13603.1; Arthrobacter oxydans), (YP_002956296.1; Micrococcus luteus NCTC 2665), (ZP_05367249.1; Rothia mucilaginosa ATCC 25296), (YP_001854004.1; Kocuria rhizophila DC2201), (ZP_04984463.1; Francisella tularensis subsp. holarctica FSC022), (YP_001677422.1; Francisella philomiragia subsp. philomiragia ATCC 25017), (YP_588827.1; Baumannia cicadellinicola str. Hc (Homalodisca oagulata)), (NP_240007.1; Buchnera aphidicola str. APS (Acyrthosiphonpisum)), (ZP_05057494.1; Verrucomicrobiae bacterium DG1235), (ZP_02930252.1; Verrucomicrobium spinosum DSM 4136), (ZP_01452386.1; Mariprofundus ferrooxydans PV-l), and (ZP_01307392.1; Bermanella marisrubri).

Phosphotransacetylases also useful in the compositions and methods provided herein include those molecules which are said to be "derivatives" of any of the phosphotransacetylases described herein. Such a "derivative" has the following characteristics: (1) it shares substantial homology with any of the phosphotransacetylases described herein; and (2) is capable of catalyzing the conversion of acetyl phosphate into acetyl-CoA. A derivative of a phosphotransacetylase is said to share "substantial homology" with the phosphotransacetylase if the amino acid sequences of the derivative is at least 80%, and more preferably at least 90%, and most preferably at least 95%, the same as that of the phosphotransacetylase.

5.4 Functional Disruption of Acetyl Phosphatase Activity

In some embodiments, the genetically modified host cell provided herein comprises a functional disruption in an enzyme that converts acetyl phosphate to acetate. In some embodiments, the enzyme is native to the host cell.

In some embodiments, the enzyme that converts acetyl phosphate to acetate is a glycerol-1-phosphatase (EC 3.1.3.21). In some embodiments, the enzyme having glycerol-1-phosphatase activity is RHR2 (GPP1/RHR2; systematic name: YIL053W), or a homolog or variant thereof. GPP1/RHR2 is a constitutively expressed glycerol-1-phosphatase involved in glycerol biosynthesis, and is induced in response to both anaerobic and osmotic stress. See, e.g., Norbeck et al., *J Biol Chem* 271(23): 13875-13881 (1996); Norbeck et al., *J Biol Chem* 272(9): 13875-13881 (1996); Pahlman et al., *J Biol Chem* 276(5): 3555-3563 (2001); Nevoigt and Stahl, FEMS Microbiol Rev 21(3):231-41 (1997); Byrne and Wolf, *Genome Res* 15(10):1456-61; and Hirayama et al., *Mol Gen Genet.* 249(2):127-38, the contents of each of which are hereby incorporated by reference in their entireties. The sequence of the GPP1/RHR2 gene of *S. cerevisiae* has been previously described. See, e.g., Norbeck et al., *J Biol Chem* 271(23): 13875-13881 (1996); and Pahlman et al., *J Biol Chem* 276(5): 3555-3563 (2001). Gpp1/Rhr2 has been previously described as catalyzing the following reaction:

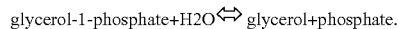

glycerol-1-phosphate+H2O ⇔ glycerol+phosphate.

Representative GPP1/RHR2 nucleotide sequences of *Saccharomyces cerevisiae* include accession number NM_001179403.1, and SEQ ID NO:5 as provided herein. Representative Gpp1/Rhr2 protein sequences of *Saccharomyces cerevisiae* include accession number NP_012211, and SEQ ID NO:6 as provided herein.

A closely related homolog of GPP1/RHR2 which also catalyzes the hydrolysis of acetyl phosphate to acetate is HOR2 (GPP2/HOR2; systematic name: YER062C). Gpp2/Hor2 has also been previously described as a glycerol-1-phosphatase capable of catalyzing the following reaction: glycerol-1-phosphate+H2O⇔ glycerol+phosphate. Accordingly, functional disruption of GPP2/HOR2 also finds use in the compositions and methods provided herein. The sequence of the GPP2/HOR2 gene of *S. cerevisiae* has been previously described. See, e.g., Norbeck et al., *J. of Biological Chemistry* 271(23): 13875-13881 (1996); and Pahlman et al., *J. of Biological Chemistry* 276(5): 3555-3563 (2001). Representative GPP2/HOR2 nucleotide sequences of *Saccharomyces cerevisiae* include accession number NM_001178953.3, and SEQ ID NO:7 as provided herein. Representative Gpp1/Rhr2 protein sequences of *Saccharomyces cerevisiae* include accession number NP_010984, and SEQ ID NO:8 as provided herein.

As would be understood in the art, naturally occurring homologs of GPP1/RHR2 and/or GPP2/HOR2 in yeast other than *S. cerevisiae* can similarly be inactivated using the methods described herein. Moreover, a polynucleotide, gene and/or polypeptide encoding acetyl-phosphatase activity (e.g., RHR2 and/or HOR2) can be used to identify other polynucleotide, gene and/or polypeptide sequences or to identify homologs having acetyl-phosphatase activity in other host cells. Such sequences can be identified, for example, in the literature and/or in bioinformatics databases well known to the skilled person. For example, the identification of sequences encoding acetyl-phosphatase activity in other cell types using bioinformatics can be accomplished through BLAST (as described above) searching of publicly available databases with known DNA and polypeptide sequences encoding acetyl-phosphatase and/or glycerol-1-phosphatase activity, such as those provided herein. Identities can be based on the Clustal W method of alignment using the default parameters of GAP PENALTY=10, GAP LENGTH PENALTY=0.1, and Gonnet 250 series of protein weight matrix.

In some embodiments, the activity or expression of an endogenous enzyme that converts acetyl phosphate to acetate (e.g., RHR2 or HOR2) is reduced by at least about 50%. In another embodiment, the activity or expression of an endogenous enzyme that converts acetyl phosphate to acetate is reduced by at least about 60%, by at least about 65%, by at least about 70%, by at least about 75%, by at least about 80%, by at least about 85%, by at least about 90%, by at least about 95%, or by at least about 99% as compared to a recombinant microorganism not comprising a reduction or deletion of the activity or expression of an endogenous enzyme that converts acetyl phosphate to acetate. In some embodiments, the endogenous enzyme that converts acetyl phosphate to acetate is RHR2, or homologues thereof. In some embodiments, the endogenous enzyme that converts acetyl phosphate to acetate is HOR2, or homologues thereof.

As is understood by those skilled in the art, there are several mechanisms available for reducing or disrupting the activity of a protein that converts acetyl phosphate to acetate, such as a glycerol-1-phosphatase (e.g., RHR2 and/or HOR2), including, but not limited to, the use of a regulated promoter, use of a weak constitutive promoter, disruption of one of the two copies of the gene encoding the protein in a diploid yeast, disruption of both copies of the gene in a diploid yeast, expression of an anti-sense nucleic acid, expression of an siRNA, over expression of a negative regulator of the endogenous promoter, alteration of the activity of an endogenous or heterologous gene, use of a heterologous gene with lower specific activity, the like or combinations thereof.

In some embodiments, the genetically modified host cell comprises a mutation in at least one gene encoding acetyl-phosphatase activity (e.g., RHR2, HOR2 or a homolog or variant thereof), resulting in a reduction of activity of a polypeptide encoded by said gene. In another embodiment, the genetically modified host cell comprises a partial deletion of a gene encoding acetyl-phosphatase activity (e.g., RHR2, HOR2 or a homolog or variant thereof), resulting in a reduction of activity of a polypeptide encoded by the gene. In another embodiment, the genetically modified host cell comprises a complete deletion of a gene encoding acetyl-phosphatase activity (e.g., RHR2, HOR2 or a homolog or variant thereof), resulting in a reduction of activity of a polypeptide encoded by the gene. In yet another embodiment, the genetically modified host cell comprises a modification of the regulatory region associated with the gene encoding acetyl-phosphatase activity (e.g., RHR2, HOR2 or a homolog or variant thereof), resulting in a reduction of expression of a polypeptide encoded by said gene. In yet another embodiment, the genetically modified host cell comprises a modification of the transcriptional regulator resulting in a reduction of transcription of a gene encoding acetyl-phosphatase activity (e.g., RHR2, HOR2 or a homolog or variant thereof).

In some embodiments, disruption of one or more genes encoding a protein capable of catalyzing the conversion of acetyl phosphate to acetate is achieved by using a "disruption construct" that is capable of specifically disrupting such a gene (e.g., RHR2 or HOR2) upon introduction of the construct into the microbial cell, thereby rendering the disrupted gene non-functional. In some embodiments, disruption of the target gene prevents the expression of a functional protein. In some embodiments, disruption of the target gene results in expression of a non-functional protein from the disrupted gene. In some embodiments, disruption of a gene encoding a protein capable of converting acetyl phosphate to acetate is achieved by integration of a "disrupting sequence" within the target gene locus by homologous recombination. In such embodiments, the disruption construct comprises a disrupting sequence flanked by a pair of nucleotide sequences that are homologous to a pair of nucleotide sequences of the target gene locus (homologous sequences). Upon replacement of the targeted portion of the target gene by the disruption construct, the disrupting sequence prevents the expression of a functional protein, or causes expression of a non-functional protein, from the target gene.

Disruption constructs capable of disrupting a gene may be constructed using standard molecular biology techniques well known in the art. See, e.g., Sambrook et al., 2001, *Molecular Cloning—A Laboratory Manual*, 3$^{rd}$ edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, NY. Parameters of disruption constructs that may be varied in the practice of the present methods include, but are not limited to, the lengths of the homologous sequences; the nucleotide sequence of the homologous sequences; the length of the disrupting sequence; the nucleotide sequence of the disrupting sequence; and the nucleotide sequence of the target gene. In some embodiments, an effective range for the length of each homologous sequence is 50 to 5,000 base pairs. In particular embodiments, the length of each homologous sequence is about 500 base pairs. For a discussion of the length of homology required for gene targeting, see Hasty et al., *Mol Cell Biol* 11:5586-91 (1991). In some embodiments, the homologous sequences comprise coding sequences of the target gene. In other embodiments, the homologous sequences comprise upstream or downstream sequences of the target gene. Is some embodiments, one homologous sequence comprises a nucleotide sequence that is homologous to a nucleotide sequence located 5' of the coding sequence of the target gene, and the other homologous sequence comprises a nucleotide sequence that is homologous to a nucleotide sequence located 3' of the coding sequence of the target gene. In some embodiments, the disrupting sequence comprises a nucleotide sequence encoding a selectable marker that enables selection of microbial cells comprising the disrupting sequence. Thus, in such embodiments, the disruption construct has a dual function, i.e., to functionally disrupt the target gene and to provide a selectable marker for the identification of cells in which the target gene is functionally disrupted. In some embodiments, a termination codon is positioned in-frame with and downstream of the nucleotide sequence encoding the selectable marker to prevent translational read-through that might yield a fusion protein having some degree of activity of the wild type protein encoded by the target gene. In some embodiments, the length of the disrupting sequence is one base pair. Insertion of a single base pair can suffice to disrupt a target gene because insertion of the single base pair in a coding sequence could constitute a frame shift mutation that could prevent expression of a functional protein. In some embodiments, the sequence of the disruption sequence differs from the nucleotide sequence of the target gene located between the homologous sequences by a single base pair. Upon replacement of the nucleotide sequence within the target gene with the disrupting sequence, the single base pair substitution that is introduced could result in a single amino acid substitution at a critical site in the protein and the expression of a non-functional protein. It should be recognized, however, that disruptions effected using very short disrupting sequences are susceptible to reversion to the wild type sequence through spontaneous mutation, thus leading to restoration of acetyl-phosphatase function to the host strain. Accordingly, in particular embodiments, the disrupting sequences are longer than one to a few base pairs. At the other extreme, a disrupting sequence of excessive length is unlikely to confer any advantage over a disrupting sequence of moderate length, and might diminish efficiency of transfection or targeting. Excessive length in this context is many times longer than the distance between the chosen homologous sequences in the target gene. Thus, in certain embodiments, the length for the disrupting sequence can be from 2 to 2,000 base pairs. In other embodiments, the length for the disrupting sequence is a length approximately equivalent to the distance between the regions of the target gene locus that match the homologous sequences in the disruption construct.

In some embodiments, the disruption construct is a linear DNA molecule. In other embodiments, the disruption construct is a circular DNA molecule. In some embodiments, the circular disruption construct comprises a pair of homologous sequences separated by a disrupting sequence, as described above. In some embodiments, the circular disruption construct comprises a single homologous sequence. Such circular disruption constructs, upon integration at the target gene locus, would become linearized, with a portion of the homologous sequence positioned at each end and the remaining segments of the disruption construct inserting into and disrupting the target gene without replacing any of the target gene nucleotide sequence. In particular embodiments, the single homologous sequence of a circular disruption construct is homologous to a sequence located within the coding sequence of the target gene.

Disruption constructs can be introduced into a microbial cell by any method known to one of skill in the art without limitation. Such methods include, but are not limited to, direct uptake of the molecule by a cell from solution, or facilitated uptake through lipofection using, e.g., liposomes or immunoliposomes; particle-mediated transfection; etc. See, e.g., U.S. Pat. No. 5,272,065; Goeddel et al., eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY. Particular methods for transforming yeast cells are well known in the art. See Hinnen et al., Proc. Natl. Acad. Sci. USA 75:1292-3 (1978); Cregg et al., Mol. Cell. Biol. 5:3376-3385 (1985). Exemplary techniques include, but are not limited to, spheroplasting, electroporation, PEG 1000 mediated transformation, and lithium acetate or lithium chloride mediated transformation.

5.5 Additional Modifications to Improve Acetyl-CoA Production 5.5.1 ADA

In some embodiments, the genetically modified host cells provided herein further comprise one or more heterologous nucleotide sequences encoding acylating acetaldehyde dehydrogenase (alternately referred to as "acetylaldehyde dehydrogenase, acetylating," "acetylaldehyde dehydrogenase, acylating," or ADA (EC 1.2.1.10)).

Proteins capable of catalyzing this reaction that are useful for the compositions and methods provided herein include the following four types of proteins:

(1) Bifunctional proteins that catalyze the reversible conversion of acetyl-CoA to acetaldehyde, and the subsequent reversible conversion of acetaldehyde to ethanol. An example of this type of protein is the AdhE protein in *E. coli* (Gen Bank No: NP_415757). AdhE appears to be the evolutionary product of a gene fusion. The $NH_2$-terminal region of the AdhE protein is highly homologous to aldehyde:$NAD^+$ oxidoreductases, whereas the COOH-terminal region is homologous to a family of $Fe^{2+}$-dependent ethanol:$NAD^+$ oxidoreductases (Membrillo-Hernandez et al., (2000) *J. Biol. Chem.* 275: 33869-33875). The *E. coli* AdhE is subject to metal-catalyzed oxidation and therefore oxygen-sensitive (Tamarit et al. (1998) *J. Biol. Chem.* 273:3027-32).

(2) Proteins that catalyze the reversible conversion of acetyl-CoA to acetaldehyde in strictly or facultative anaerobic microbes but do not possess alcohol dehydrogenase activity. An example of this type of protein has been reported in *Clostridium kluyveri* (Smith et al. (1980) *Arch. Biochem. Biophys.* 203: 663-675). An ADA has been annotated in the genome of *Clostridium kluyveri* DSM 555 (accession no: EDK33116). A homologous protein AcdH is identified in the genome of *Lactobacillus plantarum* (accession no: NP_784141). Another example of this type of protein is the ald gene product in *Clostridium beijerinckii* NRRL B593 (Toth et al. (1999) *Appl. Environ. Microbiol.* 65: 4973-4980, accession no: AAD31841).

(3) Proteins that are involved in ethanolamine catabolism. Ethanolamine can be utilized both as carbon and nitrogen source by many enterobacteria (Stojiljkovic et al. (1995) *J. Bacteriol.* 177: 1357-1366). Ethanolamine is first converted by ethanolamine ammonia lyase to ammonia and acetaldehyde, subsequently, acetaldehyde is converted by ADA to acetyl-CoA. An example of this type of ADA is the EutE protein in *Salmonella typhimurium* (Stojiljkovic et al. (1995) *J. Bacteriol.* 177: 1357-1366, accession no: AAL21357; see also U18560.1). *E. coli* is also able to utilize ethanolamine (Scarlett et al. (1976) *J. Gen. Microbiol.* 95:173-176) and has an EutE protein (accession no: AAG57564; see also EU897722.1) which is homologous to the EutE protein in *S. typhimurium*.

(4) Proteins that are part of a bifunctional aldolase-dehydrogenase complex involved in 4-hydroxy-2-ketovalerate catabolism. Such bifunctional enzymes catalyze the final two steps of the meta-cleavage pathway for catechol, an intermediate in many bacterial species in the degradation of phenols, toluates, naphthalene, biphenyls and other aromatic compounds (Powlowski and Shingler (1994) *Biodegradation* 5, 219-236). 4-Hydroxy-2-ketovalerate is first converted by 4-hydroxy-2-ketovalerate aldolase to pyruvate and acetaldehyde, subsequently acetaldehyde is converted by ADA to acetyl-CoA. An example of this type of ADA is the DmpF protein in *Pseudomonas* sp. CF600 (accession no: CAA43226) (Shingler et al. (1992) *J. Bacteriol.* 174:71 1-24). *E. coli* has a homologous MphF protein (Ferrandez et al. (1997) *J. Bacteriol.* 179: 2573-2581, accession no: NP_414885) to the DmpF protein in *Pseudomonas* sp. $CF_{600}$.

In some embodiments, an ADA (or nucleic acid sequence encoding such activity) useful for the compositions and methods described herein is selected from the group consisting of *Escherichia coli* adhE, *Entamoeba histolytica* adh2, *Staphylococcus aureus* adhE, *Piromyces* sp. E2 adhE, *Clostridium kluyveri* (EDK33116), *Lactobacillus plantarum* acdH, and *Pseudomonas putida* (YP 001268189), as described in International Publication No. WO 2009/013159, the contents of which are incorporated by reference in their entirety. In some embodiments, the ADA is selected from the group consisting of *Clostridium botulinum* eutE (FR745875.1), *Desulfotalea psychrophila* eutE (CR522870.1), *Acinetobacter* sp. HBS-2 eutE (ABQ44511.2), *Caldithrix abyssi* eutE (ZP_09549576), and *Halorubrum lacusprofundi* ATCC 49239 (YP_002565337.1).

In particular embodiments, the ADA useful for the compositions and methods provided herein is eutE from *Dickeya zeae*. A representative eutE nucleotide sequence of *Dickeya zeae* includes accession number NC_012912.1: 1110476.1111855, and SEQ ID NO: 9 as provided herein. A representative eutE protein sequence of *Dickeya zeae* includes accession number YP_003003316, and SEQ ID NO: 10 as provided herein.

ADAs also useful in the compositions and methods provided herein include those molecules which are said to be "derivatives" of any of the ADAs described herein. Such a "derivative" has the following characteristics: (1) it shares substantial homology with any of the ADAs described herein; and (2) is capable of catalyzing the conversion of acetaldehyde to acetyl-CoA. A derivative of an ADA is said to share "substantial homology" with ADA if the amino acid sequences of the derivative is at least 80%, at least 85% and more preferably at least 90%, and most preferably at least 95%, the same as that of any of the ADAs described herein.

5.5.2 Functional Disruption of the PDH-bypass

Acetyl-CoA can be formed in the mitochondria by oxidative decarboxylation of pyruvate catalyzed by the PDH complex. However, due to the inability of *S. cerevisiae* to transport acetyl-CoA out of the mitochondria, the PDH bypass has an essential role in providing acetyl-CoA in the cytosolic compartment, and provides an alternative route to the PDH reaction for the conversion of pyruvate to acetyl-CoA. The PDH bypass involves the enzymes pyruvate decarboxylase (PDC; EC 4.1.1.1), acetaldehyde dehydrogenase (ACDH; EC 1.2.1.5 and EC 1.2.1.4), and acetyl-CoA synthetase (ACS; EC 6.2.1.1). Pyruvate decarboxylase catalyzes the decarboxylation of pyruvate to acetaldehyde and carbon dioxide. Acetaldehyde dehydrogenase oxidizes acetaldehyde to acetic acid. In *S. cerevisiae*, the family of aldehyde dehydrogenases contains five members. ALD2 (YMR170c), ALD3 (YMR169c), and ALD6 (YPL061w) correspond to the cytosolic isoforms, while ALD4 (YOR374w) and ALD5 (YER073w) encode the mitochondrial enzyme. The main cytosolic acetaldehyde dehydrogenase isoform is encoded by ALD6. The formation of acetyl-CoA from acetate is catalyzed by ACS and involves hydrolysis of ATP. Two structural genes, ACS1 and ACS2, encode ACS.

In some embodiments, the genetically modified host cell provided herein further comprises a functional disruption in one or more genes of the PDH-bypass pathway. In some embodiments, disruption of the one or more genes of the PDH-bypass of the host cell results in a genetically modified microbial cell that is impaired in its ability to catalyze one or more of the following reactions: (1) the decarboxylation of pyruvate into acetaldehyde by pyruvate decarboxylase; (2) the conversion of acetaldehyde into acetate by acetaldehyde dehydrogenase; and (3) the synthesis of acetyl-CoA from acetate and CoA by acetyl-CoA synthetase.

In some embodiments, compared to a parent cell, a host cell comprises a functional disruption in one or more genes of the PDH-bypass pathway, wherein the activity of the reduced-function or non-functional PDH-bypass pathway alone or in combination with a weak ADA is not sufficient to support host cell growth, viability, and/or health.

In some embodiments, the activity or expression of one or more endogenous proteins of the PDH-bypass is reduced by at least about 50%. In another embodiment, the activity or expression of one or more endogenous proteins of the PDH-bypass is reduced by at least about 60%, by at least about 65%, by at least about 70%, by at least about 75%, by at least about 80%, by at least about 85%, by at least about 90%, by at least about 95%, or by at least about 99% as compared to a recombinant microorganism not comprising a reduction or deletion of the activity or expression of one or more endogenous proteins of the PDH-bypass.

5.5.2.1 ALD4 and ALD6

In some embodiments, one or more genes encoding aldehyde dehydrogenase (ACDH) activity are functionally disrupted in the host cell. In some embodiments, the aldehyde dehydrogenase is encoded by a gene selected from the group consisting of ALD2, ALD3, ALD4, ALD5, ALD6, and homologs and variants thereof.

In some embodiments, the genetically modified host cell comprises a functional disruption of ALD4. Representative ALD4 nucleotide sequences of *Saccharomyces cerevisiae* include accession number NM_001183794, and SEQ ID NO:11 as provided herein. Representative Ald4 protein sequences of *Saccharomyces cerevisiae* include accession number NP_015019.1, and SEQ ID NO:12 as provided herein.

In some embodiments, the genetically modified host cell comprises a functional disruption of cytosolic aldehyde dehydrogenase (ALD6). Ald6p functions in the native PDH-bypass to convert acetaldehyde to acetate. Representative ALD6 nucleotide sequences of *Saccharomyces cerevisiae* include accession number SCU56604, and SEQ ID NO:13 as provided herein. Representative Ald6 protein sequences of *Saccharomyces cerevisiae* include accession number AAB01219, and SEQ ID NO:14 as provided herein.

As would be understood in the art, naturally occurring homologs of aldehyde dehydrogenase in yeast other than *S. cerevisiae* can similarly be inactivated using the methods described herein.

As would be understood by one skilled in the art, the activity or expression of more than one aldehyde dehydrogenase can be reduced or eliminated. In one specific embodiment, the activity or expression of ALD4 and ALD6 or homologs or variants thereof is reduced or eliminated. In another specific embodiment, the activity or expression of ALD5 and ALD6 or homologs or variants thereof is reduced or eliminated. In yet another specific embodiment, the activity or expression of ALD4, ALD5, and ALD6 or homologs or variants thereof is reduced or eliminated. In yet another specific embodiment, the activity or expression of the cytosolically localized aldehyde dehydrogenases ALD2, ALD3, and ALD6 or homologs or variants thereof is reduced or eliminated. In yet another specific embodiment, the activity or expression of the mitochondrially localized aldehyde dehydrogenases, ALD4 and ALD5 or homologs or variants thereof, is reduced or eliminated.

5.5.2.2 ACS1 and ACS2

In some embodiments, one or more genes encoding acetyl-CoA synthetase (ACS) activity are functionally disrupted in the host cell. In some embodiments, the acetyl-CoA synthetase is encoded by a gene selected from the group consisting of ACS1, ACS2, and homologs and variants thereof.

In some embodiments, one or more genes encoding acetyl-CoA synthetase (ACS) activity is functionally disrupted in the host cell. ACS1 and ACS2 are both acetyl-CoA synthetases that can convert acetate to acetyl-CoA. ACS1 is expressed only under respiratory conditions, whereas ACS2 is expressed constitutively. When ACS2 is knocked out, strains are able to grow on respiratory conditions (e.g. ethanol, glycerol, or acetate media), but die on fermentable carbon sources (e.g. sucrose, glucose).

In some embodiments, the genetically modified host cell comprises a functional disruption of ACS1. The sequence of the ACS1 gene of *S. cerevisiae* has been previously described. See, e.g., Nagasu et al., *Gene* 37 (1-3):247-253 (1985). Representative ACS1 nucleotide sequences of *Saccharomyces cerevisiae* include accession number X66425, and SEQ ID NO:15 as provided herein. Representative Acs1 protein sequences of *Saccharomyces cerevisiae* include accession number AAC04979, and SEQ ID NO:16 as provided herein.

In some embodiments, the genetically modified host cell comprises a functional disruption of ACS2. The sequence of the ACS2 gene of *S. cerevisiae* has been previously described. See, e.g., Van den Berg et al., *Eur. J. Biochem.* 231(3):704-713 (1995). Representative ACS2 nucleotide sequences of *Saccharomyces cerevisiae* include accession number S79456, and SEQ ID NO:17 as provided herein. Representative Acs2 protein sequences of *Saccharomyces cerevisiae* include accession number CAA97725, and SEQ ID NO:18 as provided herein.

As would be understood in the art, naturally occurring homologs of acetyl-CoA synthetase in yeast other than *S. cerevisiae* can similarly be inactivated using the methods described herein.

In some embodiments, the host cell comprises a cytosolic acetyl-coA synthetase activity that can convert acetate to acetyl-CoA under respiratory conditions (i.e., when the host cell is grown in the presence of e.g. ethanol, glycerol, or acetate). In some such embodiments, the host cell is a yeast cell that comprises ACS1 activity. In other embodiments, the host cell compared to a parent cell comprises no or reduced endogenous acetyl-CoA synthetase activity under respiratory conditions. In some such embodiments, the host cell is a yeast cell that compared to a parent cell comprises no or reduced ACS1 activity.

In some embodiments, the host cell comprises a cytosolic acetyl-coA synthetase activity that can convert acetate to acetyl-CoA under non-respiratory conditions (i.e., when the host cell is grown in the presence of fermentable carbon sources (e.g. sucrose, glucose)). In some such embodiments, the host cell is a yeast cell that comprises ACS2 activity. In other embodiments, the host cell compared to a parent cell comprises no or reduced endogenous acetyl-CoA synthetase activity under non-respiratory conditions. In some such embodiments, the host cell is a yeast cell that compared to a parent cell comprises no or reduced ACS2 activity.

In some embodiments, the host cell comprises a heterologous PK and a cytosolic acetyl-coA synthetase activity (e.g, ACS1 and/or ACS2). In such embodiments, PK produces acetyl phosphate in the host cell. The intact cytosolic ACS activity can convert acetate that accumulates as a result of RHR2 and/or HOR2-catalyzed acetyl phosphate hydrolysis into acetyl-CoA.

5.6 MEV Pathway for Isoprenoid Production

In some embodiments, the genetically modified host cell provided herein comprises one or more heterologous enzymes of the MEV pathway. In some embodiments, the one or more enzymes of the MEV pathway comprise an enzyme that condenses acetyl-CoA with malonyl-CoA to form acetoacetyl-CoA. In some embodiments, the one or more enzymes of the MEV pathway comprise an enzyme that condenses two molecules of acetyl-CoA to form acetoacetyl-CoA. In some embodiments, the one or more enzymes of the MEV pathway comprise an enzyme that condenses acetoacetyl-CoA with acetyl-CoA to form HMG-CoA. In some embodiments, the one or more enzymes of the MEV pathway comprise an enzyme that converts HMG-CoA to mevalonate. In some embodiments, the one or more enzymes of the MEV pathway comprise an enzyme that phosphorylates mevalonate to mevalonate 5-phosphate. In some embodiments, the one or more enzymes of the MEV pathway comprise an enzyme that converts mevalonate 5-phosphate to mevalonate 5-pyrophosphate. In some embodiments, the one or more enzymes of the MEV pathway comprise an enzyme that converts mevalonate 5-pyrophosphate to isopentenyl pyrophosphate.

In some embodiments, the one or more enzymes of the MEV pathway are selected from the group consisting of acetyl-coA thiolase, acetoacetyl-CoA synthetase, HMG-CoA synthase, HMG-CoA reductase, mevalonate kinase, phosphomevalonate kinase and mevalonate pyrophosphate decarboxylase. In some embodiments, with regard to the enzyme of the MEV pathway capable of catalyzing the formation of acetoacetyl-CoA, the genetically modified host cell comprises either an enzyme that condenses two molecules of acetyl-CoA to form acetoacetyl-CoA, e.g., acetyl-CoA thiolase; or an enzyme that condenses acetyl-CoA with malonyl-CoA to form acetoacetyl-CoA, e.g., acetoacetyl-CoA synthase. In some embodiments, the genetically modified host cell comprises both an enzyme that condenses two molecules of acetyl-CoA to form acetoacetyl-CoA, e.g., acetyl-CoA thiolase; and an enzyme that condenses acetyl-CoA with malonyl-CoA to form acetoacetyl-CoA, e.g., acetoacetyl-CoA synthase.

In some embodiments, the host cell comprises one or more heterologous nucleotide sequences encoding more than one enzyme of the MEV pathway. In some embodiments, the host cell comprises one or more heterologous nucleotide sequences encoding two enzymes of the MEV pathway. In some embodiments, the host cell comprises one or more heterologous nucleotide sequences encoding an enzyme that can convert HMG-CoA into mevalonate and an enzyme that can convert mevalonate into mevalonate 5-phosphate. In some embodiments, the host cell comprises one or more heterologous nucleotide sequences encoding three enzymes of the MEV pathway. In some embodiments, the host cell comprises one or more heterologous nucleotide sequences encoding four enzymes of the MEV pathway. In some embodiments, the host cell comprises one or more heterologous nucleotide sequences encoding five enzymes of the MEV pathway. In some embodiments, the host cell comprises one or more heterologous nucleotide sequences encoding six enzymes of the MEV pathway. In some embodiments, the host cell comprises one or more heterologous nucleotide sequences encoding seven enzymes of the MEV pathway. In some embodiments, the host cell comprises a plurality of heterologous nucleic acids encoding all of the enzymes of the MEV pathway.

In some embodiments, the genetically modified host cell further comprises a heterologous nucleic acid encoding an enzyme that can convert isopentenyl pyrophosphate (IPP) into dimethylallyl pyrophosphate (DMAPP). In some embodiments, the genetically modified host cell further comprises a heterologous nucleic acid encoding an enzyme that can condense IPP and/or DMAPP molecules to form a polyprenyl compound. In some embodiments, the genetically modified host cell further comprise a heterologous nucleic acid encoding an enzyme that can modify IPP or a polyprenyl to form an isoprenoid compound.

5.6.1 Conversion of Acetyl-CoA to Acetoacetyl-CoA

In some embodiments, the genetically modified host cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*).

Acetyl-CoA thiolase catalyzes the reversible condensation of two molecules of acetyl-CoA to yield acetoacetyl-CoA, but this reaction is thermodynamically unfavorable; acetoacetyl-CoA thiolysis is favored over acetoacetyl-CoA synthesis. Acetoacetyl-CoA synthase (AACS) (alternately referred to as acetyl-CoA:malonyl-CoA acyltransferase; EC 2.3.1.194) condenses acetyl-CoA with malonyl-CoA to form acetoacetyl-CoA. In contrast to acetyl-CoA thiolase, AACS-catalyzed acetoacetyl-CoA synthesis is essentially an energy-favored reaction, due to the associated decarboxylation of malonyl-CoA. In addition, AACS exhibits no thiolysis activity against acetoacetyl-CoA, and thus the reaction is irreversible.

In host cells comprising acetyl-CoA thiolase and a heterologous ADA and/or phosphotransacetylase (PTA), the reversible reaction catalyzed by acetyl-CoA thiolase, which favors acetoacetyl-CoA thiolysis, may result in a large acetyl-CoA pool. In view of the reversible activity of ADA, this acetyl-CoA pool may in turn drive ADA towards the reverse reaction of converting acetyl-CoA to acetaldehyde, thereby diminishing the benefits provided by ADA towards acetyl-CoA production. Similarly, the activity of PTA is reversible, and thus, a large acetyl-CoA pool may drive PTA towards the reverse reaction of converting acetyl-CoA to acetyl phosphate. Therefore, in some embodiments, in order to provide a strong pull on acetyl-CoA to drive the forward reaction of ADA and PTA, the MEV pathway of the genetically modified host cell provided herein utilizes an acetoacetyl-CoA synthase to form acetoacetyl-CoA from acetyl-CoA and malonyl-CoA.

In some embodiments, the AACS is from *Streptomyces* sp. strain CL190 (Okamura et al., *Proc Natl Acad Sci* USA 107 (25):11265-70 (2010). Representative AACS nucleotide sequences of *Streptomyces* sp. strain CL190 include accession number AB540131.1, and SEQ ID NO:19 as provided herein. Representative AACS protein sequences of *Streptomyces* sp. strain CL190 include accession numbers D7URV0, BAJ10048, and SEQ ID NO:20 as provided herein. Other acetoacetyl-CoA synthases useful for the compositions and methods provided herein include, but are not limited to, *Streptomyces* sp. (AB183750; KO-3988 BAD86806); *S. anulatus* strain 9663 (FN178498; CAX48662); *Streptomyces* sp. KO-3988 (AB212624; BAE78983); *Actinoplanes* sp. A40644 (AB113568; BAD07381); *Streptomyces* sp. C(NZ_ACEW010000640; ZP_05511702); *Nocardiopsis dassonvillei* DSM 43111 (NZ_ABUI01000023; ZP_04335288); *Mycobacterium ulcerans* Agy99 (NC_008611; YP_907152); *Mycobacterium marinum* M (NC_010612; YP_001851502); *Streptomyces* sp. Mg1 (NZ_DS570501; ZP_05002626); *Streptomyces* sp. AA4 (NZ_ACEV01000037; ZP_05478992); *S. roseosporus* NRRL 15998 (NZ_ABYB01000295; ZP_04696763); *Streptomyces* sp. ACTE (NZ_ADFD01000030; ZP_06275834); *S. viridochromogenes* DSM 40736 (NZ_ACEZ01000031; ZP_05529691); *Frankia* sp. CcI3 (NC_007777; YP_480101); *Nocardia brasiliensis* (NC_018681; YP_006812440.1); and *Austwickia chelonae* (NZ_BAGZ01000005; ZP_10950493.1). Additional suitable acetoacetyl-CoA synthases include those described in U.S. Patent Application Publication Nos. 2010/0285549 and 2011/0281315, the contents of which are incorporated by reference in their entireties.

Acetoacetyl-CoA synthases also useful in the compositions and methods provided herein include those molecules which are said to be "derivatives" of any of the acetoacetyl-CoA synthases described herein. Such a "derivative" has the following characteristics: (1) it shares substantial homology with any of the acetoacetyl-CoA synthases described herein; and (2) is capable of catalyzing the irreversible condensation of acetyl-CoA with malonyl-CoA to form acetoacetyl-CoA. A derivative of an acetoacetyl-CoA synthase is said to share "substantial homology" with acetoacetyl-CoA synthase if the amino acid sequences of the derivative is at least 80%, and more preferably at least 90%, and most preferably at least 95%, the same as that of acetoacetyl-CoA synthase.

5.6.2 Conversion of Acetoacetyl-CoA to HMG-CoA

In some embodiments, the host cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

5.6.3 Conversion of HMG-CoA to Mevalonate

In some embodiments, the host cell comprises a heterologous nucleotide sequence encoding an enzyme that can convert HMG-CoA into mevalonate, e.g., a HMG-CoA reductase. In some embodiments, HMG-CoA reductase is an NADH-using hydroxymethylglutaryl-CoA reductase-CoA reductase. HMG-CoA reductases (EC 1.1.1.34; EC 1.1.1.88) catalyze the reductive deacylation of (S)-HMG-CoA to (R)-mevalonate, and can be categorized into two classes, class I and class II HMGrs. Class I includes the enzymes from eukaryotes and most archaea, and class II includes the HMG-CoA reductases of certain prokaryotes and archaea. In addition to the divergence in the sequences, the enzymes of the two classes also differ with regard to their cofactor specificity. Unlike the class I enzymes, which utilize NADPH exclusively, the class II HMG-CoA reductases vary in the ability to discriminate between NADPH and NADH. See, e.g., Hedl et al., *Journal of Bacteriology* 186 (7): 1927-1932 (2004). Co-factor specificities for select class II HMG-CoA reductases are provided below.

TABLE 1

Co-factor specificities for select class II HMG-CoA reductases

| Source | Coenzyme specificity | $K_m^{NADPH}$ (μM) | $K_m^{NADH}$ (μM) |
|---|---|---|---|
| P. mevalonii | NADH | | 80 |
| A. fulgidus | NAD(P)H | 500 | 160 |
| S. aureus | NAD(P)H | 70 | 100 |
| E. faecalis | NADPH | 30 | |

Useful HMG-CoA reductases for the compositions and methods provided herein include HMG-CoA reductases that are capable of utilizing NADH as a cofactor, e.g., HMG-CoA reductase from *P. mevalonii, A. fulgidus* or *S. aureus*. In particular embodiments, the HMG-CoA reductase is capable of only utilizing NADH as a cofactor, e.g., HMG-CoA reductase from *P. mevalonii, S. pomeroyi* or *D. acidovorans*.

In some embodiments, the NADH-using HMG-CoA reductase is from *Pseudomonas mevalonii*. The sequence of the wild-type mvaA gene of *Pseudomonas mevalonii*, which encodes HMG-CoA reductase (EC 1.1.1.88), has been previously described. See Beach and Rodwell, *J. Bacteriol.* 171: 2994-3001 (1989). Representative mvaA nucleotide sequences of *Pseudomonas mevalonii* include accession number M24015, and SEQ ID NO: 21 as provided herein. Representative HMG-CoA reductase protein sequences of *Pseudomonas mevalonii* include accession numbers AAA25837, P13702, MVAA_PSEMV, and SEQ ID NO: 22 as provided herein.

In some embodiments, the NADH-using HMG-CoA reductase is from *Silicibacter pomeroyi*. Representative HMG-CoA reductase nucleotide sequences of *Silicibacter pomeroyi* include accession number NC_006569.1, and SEQ ID NO: 23 as provided herein. Representative HMG-CoA reductase protein sequences of *Silicibacter pomeroyi* include accession number YP_164994, and SEQ ID NO: 24 as provided herein.

In some embodiments, the NADH-using HMG-CoA reductase is from *Delftia acidovorans*. A representative HMG-CoA reductase nucleotide sequences of *Delftia acidovorans* includes NC_010002 REGION: complement (319980.321269), and SEQ ID NO: 25 as provided herein. Representative HMG-CoA reductase protein sequences of *Delftia acidovorans* include accession number YP_001561318, and SEQ ID NO: 26 as provided herein.

In some embodiments, the NADH-using HMG-CoA reductases is from *Solanum tuberosum* (Crane et al., *J. Plant Physiol.* 159:1301-1307 (2002)).

NADH-using HMG-CoA reductases also useful in the compositions and methods provided herein include those molecules which are said to be "derivatives" of any of the NADH-using HMG-CoA reductases described herein, e.g., from *P. mevalonii, S. pomeroyi* and *D. acidovorans*. Such a "derivative" has the following characteristics: (1) it shares substantial homology with any of the NADH-using HMG-CoA reductases described herein; and (2) is capable of catalyzing the reductive deacylation of (S)-HMG-CoA to (R)-mevalonate while preferentially using NADH as a cofactor. A derivative of an NADH-using HMG-CoA reductase is said to share "substantial homology" with NADH-using HMG-CoA reductase if the amino acid sequences of the derivative is at least 80%, and more preferably at least 90%, and most preferably at least 95%, the same as that of NADH-using HMG-CoA reductase.

As used herein, the phrase "NADH-using" means that the NADH-using HMG-CoA reductase is selective for NADH over NADPH as a cofactor, for example, by demonstrating a higher specific activity for NADH than for NADPH. In some embodiments, selectivity for NADH as a cofactor is expressed as a $k_{cat}^{(NADH)}/k_{cat}^{(NADPH)}$ ratio. In some embodiments, the NADH-using HMG-CoA reductase has a $k_{cat}^{(NADH)}/k_{cat}^{(NADPH)}$ ratio of at least 5, 10, 15, 20, 25 or greater than 25. In some embodiments, the NADH-using HMG-CoA reductase uses NADH exclusively. For example, an NADH-using HMG-CoA reductase that uses NADH exclusively displays some activity with NADH supplied as the sole cofactor in vitro, and displays no detectable activity when NADPH is supplied as the sole cofactor. Any method for determining cofactor specificity known in the art can be utilized to identify HMG-CoA reductases having a preference for NADH as cofactor, including those described by Kim et al., *Protein Science* 9:1226-1234 (2000); and Wilding et al., *J. Bacteriol.* 182(18):5147-52 (2000), the contents of which are hereby incorporated in their entireties.

In some embodiments, the NADH-using HMG-CoA reductase is engineered to be selective for NADH over NAPDH, for example, through site-directed mutagenesis of the cofactor-binding pocket. Methods for engineering NADH-selectivity are described in Watanabe et al., *Microbiology* 153:3044-3054 (2007), and methods for determining the cofactor specificity of HMG-CoA reductases are described in Kim et al., *Protein Sci.* 9:1226-1234 (2000), the contents of which are hereby incorporated by reference in their entireties.

In some embodiments, the NADH-using HMG-CoA reductase is derived from a host species that natively comprises a mevalonate degradative pathway, for example, a host species that catabolizes mevalonate as its sole carbon source. Within these embodiments, the NADH-using HMG-CoA reductase, which normally catalyzes the oxidative acylation of internalized (R)-mevalonate to (S)-HMG-CoA within its native host cell, is utilized to catalyze the reverse reaction, that is, the reductive deacylation of (S)-HMG-CoA to (R)-mevalonate, in a genetically modified host cell comprising a mevalonate biosynthetic pathway. Prokaryotes capable of growth on mevalonate as their sole carbon source have been described by: Anderson et al., *J. Bacteriol,* 171(12):6468-6472 (1989); Beach et al., *J. Bacteriol.* 171:2994-3001 (1989); Bensch et al., *J. Biol. Chem.* 245:3755-3762; Fimon-gnari et al., *Biochemistry* 4:2086-2090 (1965); Siddiqi et al., *Biochem. Biophys. Res. Commun.* 8:110-113 (1962); Siddiqi et al., *J. Bacteriol.* 93:207-214 (1967); and Takatsuji et al., *Biochem. Biophys. Res. Commun.* 110:187-193 (1983), the contents of which are hereby incorporated by reference in their entireties.

In some embodiments of the compositions and methods provided herein, the host cell comprises both a NADH-using HMGr and an NADPH-using HMG-CoA reductase. Illustrative examples of nucleotide sequences encoding an NADPH-using HMG-CoA reductase include, but are not limited to: (NM_206548; *Drosophila melanogaster*), (NC_002758, Locus tag SAV2545, GeneID 1122570; *Staphylococcus aureus*), (AB015627; *Streptomyces* sp. KO 3988), (AX128213, providing the sequence encoding a truncated HMG-CoA reductase; *Saccharomyces cerevisiae*), and (NC_001145: complement (115734.118898; *Saccharomyces cerevisiae*).

5.6.4 Conversion of Mevalonate to Mevalonate-5-Phosphate

In some embodiments, the host cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

5.6.5 Conversion of Mevalonate-5-Phosphate to Mevalonate-5-Pyrophosphate

In some embodiments, the host cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM_006556; *Homo sapiens*), and (NC_001145. complement 712315.713670; *Saccharomyces cerevisiae*).

5.6.6 Conversion of Mevalonate-5-Pyrophosphate to IPP

In some embodiments, the host cell comprises a heterologous nucleotide sequence encoding an enzyme that can convert mevalonate 5-pyrophosphate into isopentenyl diphosphate (IPP), e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

5.6.7 Conversion of IPP to DMAPP

In some embodiments, the host cell further comprises a heterologous nucleotide sequence encoding an enzyme that can convert IPP generated via the MEV pathway into dimethylallyl pyrophosphate (DMAPP), e.g., an IPP isomerase. Illustrative examples of nucleotide sequences encoding such an enzyme include, but are not limited to: (NC_000913, 3031087.3031635; *Escherichia coli*), and (AF082326; *Haematococcus pluvialis*).

5.6.8 Polyprenyl Synthases

In some embodiments, the host cell further comprises a heterologous nucleotide sequence encoding a polyprenyl synthase that can condense IPP and/or DMAPP molecules to form polyprenyl compounds containing more than five carbons.

In some embodiments, the host cell comprises a heterologous nucleotide sequence encoding an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha x piperita*), (AF182827; *Mentha x piperita*), (MPI249453; *Mentha x piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

In some embodiments, the host cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar *Copenhageni* str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus* pneumoniae R6), and (NC_004556, Locus NP 779706; *Xylella fastidiosa* Temecula1).

In some embodiments, the host cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar israelensis, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides f. lusitanicus*), (AB016044; *Mus musculus*), (AABX01000298, Locus NCU01427; *Neurospora crassa*), (NCU20940; *Neurospora crassa*), (NZ AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; Sinapis alba), (SSOGDS; *Sulfolobus acidocaldarius*), (NC_007759, Locus YP_461832; *Syntrophus aciditrophicus* SB), (NC_006840, Locus YP_204095; *Vibrio fischeri* ES 114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

5.6.9 Terpene Synthases

In some embodiments, the host cell further comprises a heterologous nucleotide sequence encoding an enzyme that can modify a polyprenyl to form a hemiterpene, a monoterpene, a sesquiterpene, a diterpene, a triterpene, a tetraterpene, a polyterpene, a steroid compound, a carotenoid, or a modified isoprenoid compound.

In some embodiments, the heterologous nucleotide encodes a carene synthase. Illustrative examples of suitable nucleotide sequences include, but are not limited to: (AF461460, REGION 43.1926; *Picea abies*) and (AF527416, REGION: 78.1871; *Salvia stenophylla*).

In some embodiments, the heterologous nucleotide encodes a geraniol synthase. Illustrative examples of suitable nucleotide sequences include, but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*).

In some embodiments, the heterologous nucleotide encodes a linalool synthase. Illustrative examples of a suitable nucleotide sequence include, but are not limited to: (AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM_463918; *Oryza sativa*), (AP004078, Locus BAD07605; *Oryza sativa*), (XM_463918, Locus XP_463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. *crispa* cultivar No. 79).

In some embodiments, the heterologous nucleotide encodes a limonene synthase. Illustrative examples of suitable nucleotide sequences include, but are not limited to: (+)-limonene synthases (AF514287, REGION: 47.1867; *Citrus limon*) and (AY055214, REGION: 48.1889; *Agastache rugosa*) and (−)-limonene synthases (DQ195275, REGION: 1.1905; *Picea sitchensis*), (AF006193, REGION: 73.1986; *Abies grandis*), and (MHC4SLSP, REGION: 29.1828; *Mentha spicata*).

In some embodiments, the heterologous nucleotide encodes a myrcene synthase. Illustrative examples of suitable nucleotide sequences include, but are not limited to: (U87908; *Abies grandis*), (AY195609; *Antirrhinum majus*), (AY195608; *Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

In some embodiments, the heterologous nucleotide encodes a ocimene synthase. Illustrative examples of suitable nucleotide sequences include, but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

In some embodiments, the heterologous nucleotide encodes an α-pinene synthase. Illustrative examples of suitable nucleotide sequences include, but are not limited to: (+) α-pinene synthase (AF543530, REGION: 1.1887; *Pinus taeda*), (−)-α-pinene synthase (AF543527, REGION: 32.1921; *Pinus taeda*), and (+)/(−)α-pinene synthase (AGU87909, REGION: 6111892; *Abies grandis*).

In some embodiments, the heterologous nucleotide encodes a β-pinene synthase. Illustrative examples of suitable nucleotide sequences include, but are not limited to: (−)β-pinene synthases (AF276072, REGION: 1.1749; *Artemisia annua*) and (AF514288, REGION: 26.1834; *Citrus limon*).

In some embodiments, the heterologous nucleotide encodes a sabinene synthase. An illustrative example of a suitable nucleotide sequence includes but is not limited to AF051901, REGION: 26.1798 from *Salvia officinalis*.

In some embodiments, the heterologous nucleotide encodes a γ-terpinene synthase. Illustrative examples of suitable nucleotide sequences include: (AF514286, REGION: 30.1832 from *Citrus limon*) and (AB110640, REGION 1.1803 from *Citrus unshiu*).

In some embodiments, the heterologous nucleotide encodes a terpinolene synthase. Illustrative examples of a suitable nucleotide sequence include, but are not limited to: (AY693650 from *Oscimum basilicum*) and (AY906866, REGION: 10.1887 from *Pseudotsuga menziesii*).

In some embodiments, the heterologous nucleotide encodes an amorphadiene synthase. An illustrative example of a suitable nucleotide sequence is SEQ ID NO. 37 of U.S. Patent Publication No. 2004/0005678.

In some embodiments, the heterologous nucleotide encodes a α-farnesene synthase. Illustrative examples of suitable nucleotide sequences include, but are not limited to: DQ309034 from *Pyrus communis* cultivar d'Anjou (pear;

gene name AFS1) and AY182241 from *Malus domestica* (apple; gene AFS1). Pechouus et al., *Planta* 219(1):84-94 (2004).

In some embodiments, the heterologous nucleotide encodes a β-farnesene synthase. Illustrative examples of suitable nucleotide sequences include but is not limited to accession number AF024615 from *Mentha x piperita* (peppermint; gene Tspall), and AY835398 from *Artemisia annua*. Picaud et al., *Phytochemistry* 66(9): 961-967 (2005).

In some embodiments, the heterologous nucleotide encodes a farnesol synthase. Illustrative examples of suitable nucleotide sequences include, but are not limited to accession number AF529266 from *Zea mays* and YDR481c from *Saccharomyces cerevisiae* (gene Pho8). Song, L., *Applied Biochemistry and Biotechnology* 128:149-158 (2006).

In some embodiments, the heterologous nucleotide encodes a nerolidol synthase. An illustrative example of a suitable nucleotide sequence includes, but is not limited to AF529266 from *Zea mays* (maize; gene tps1).

In some embodiments, the heterologous nucleotide encodes a patchouliol synthase. Illustrative examples of suitable nucleotide sequences include, but are not limited to AY508730 REGION: 1.1659 from *Pogostemon cablin*.

In some embodiments, the heterologous nucleotide encodes a nootkatone synthase. Illustrative examples of suitable nucleotide sequences include, but are not limited to AF441124 REGION: 1.1647 from *Citrus sinensis* and AY917195 REGION: 1.1653 from *Perilla frutescens*.

In some embodiments, the heterologous nucleotide encodes an abietadiene synthase. Illustrative examples of suitable nucleotide sequences include, but are not limited to: (U50768; *Abies grandis*) and (AY473621; *Picea abies*).

In some embodiments, the host cell produces a $C_5$ isoprenoid. These compounds are derived from one isoprene unit and are also called hemiterpenes. An illustrative example of a hemiterpene is isoprene. In other embodiments, the isoprenoid is a $C_{10}$ isoprenoid. These compounds are derived from two isoprene units and are also called monoterpenes. Illustrative examples of monoterpenes are limonene, citranellol, geraniol, menthol, perillyl alcohol, linalool, thujone, and myrcene. In other embodiments, the isoprenoid is a $C_{15}$ isoprenoid. These compounds are derived from three isoprene units and are also called sesquiterpenes. Illustrative examples of sesquiterpenes are periplanone B, gingkolide B, amorphadiene, artemisinin, artemisinic acid, valencene, nootkatone, epi-cedrol, epi-aristolochene, farnesol, gossypol, sanonin, periplanone, forskolin, and patchoulol (which is also known as patchouli alcohol). In other embodiments, the isoprenoid is a $C_{20}$ isoprenoid. These compounds are derived from four isoprene units and also called diterpenes. Illustrative examples of diterpenes are casbene, eleutherobin, paclitaxel, prostratin, pseudopterosin, and taxadiene. In yet other examples, the isoprenoid is a $C_{20+}$ isoprenoid. These compounds are derived from more than four isoprene units and include: triterpenes ($C_{30}$ isoprenoid compounds derived from 6 isoprene units) such as arbrusideE, bruceantin, testosterone, progesterone, cortisone, digitoxin, and squalene; tetraterpenes ($C_{40}$ isoprenoid compounds derived from 8 isoprenoids) such as β-carotene; and polyterpenes ($C_{40+}$ isoprenoid compounds derived from more than 8 isoprene units) such as polyisoprene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene. Isoprenoid compounds also include, but are not limited to, carotenoids (such as lycopene, α- and β-carotene, α- and β-cryptoxanthin, bixin, zeaxanthin, astaxanthin, and lutein), steroid compounds, and compounds that are composed of isoprenoids modified by other chemical groups, such as mixed terpene-alkaloids, and coenzyme Q-10.

5.6.10 Methods of Producing Isoprenoids

In another aspect, provided herein is a method for the production of an isoprenoid, the method comprising the steps of: (a) culturing a population of any of the genetically modified host cells described herein that are capable of producing an isoprenoid in a medium with a carbon source under conditions suitable for making an isoprenoid compound; and (b) recovering said isoprenoid compound from the medium.

In some embodiments, the genetically modified host cell comprises one or more modifications selected from the group consisting of: heterologous expression of a phosphoketolase, heterologous expression of a phosphotransacetylase, heterologous expression of one or more enzymes of the mevalonate pathway; and optionally, heterologous expression of an ADA, heterologous expression of an NADH-using HMG-CoA reductase, and heterologous expression of an AACS; and the genetically modified host cell produces an increased amount of the isoprenoid compound compared to a parent cell not comprising the one or more modifications, or a parent cell comprising only a subset of the one or more modifications of the genetically modified host cell, but is otherwise genetically identical. In some embodiments, the increased amount is at least 1%, 5%, 10%, 15%, 20%, 25%, 30%, 35%, 40%, 45%, 50%, 55%, 60%, 65%, 70%, 75%, 80%, 85%, 90%, 95%, 100% or greater than 100%, as measured, for example, in yield, production, productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the host cell produces an elevated level of isoprenoid that is greater than about 10 grams per liter of fermentation medium. In some such embodiments, the isoprenoid is produced in an amount from about 10 to about 50 grams, more than about 15 grams, more than about 20 grams, more than about 25 grams, or more than about 30 grams per liter of cell culture.

In some embodiments, the host cell produces an elevated level of isoprenoid that is greater than about 50 milligrams per gram of dry cell weight. In some such embodiments, the isoprenoid is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the host cell produces an elevated level of isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by a parent cell, on a per unit volume of cell culture basis.

In some embodiments, the host cell produces an elevated level of isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by the parent cell, on a per unit dry cell weight basis.

In some embodiments, the host cell produces an elevated level of an isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by the parent cell, on a per unit volume of cell culture per unit time basis.

In some embodiments, the host cell produces an elevated isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by the parent cell, on a per unit dry cell weight per unit time basis.

In most embodiments, the production of the elevated level of isoprenoid by the host cell is inducible by an inducing compound. Such a host cell can be manipulated with ease in the absence of the inducing compound. The inducing compound is then added to induce the production of the elevated level of isoprenoid by the host cell. In other embodiments, production of the elevated level of isoprenoid by the host cell is inducible by changing culture conditions, such as, for example, the growth temperature, media constituents, and the like.

5.6.11 Culture Media and Conditions

Materials and methods for the maintenance and growth of microbial cultures are well known to those skilled in the art of microbiology or fermentation science (see, for example, Bailey et al., *Biochemical Engineering Fundamentals, second edition*, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing isoprenoids provided herein may be performed in a suitable culture medium (e.g., with or without pantothenate supplementation) in a suitable container, including but not limited to a cell culture plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany.

In some embodiments, the culture medium is any culture medium in which a genetically modified microorganism capable of producing an isoprenoid can subsist, i.e., maintain growth and viability. In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients, are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, xylose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium should promote cell growth, but not be so high as to repress growth of the microorganism used. Typically, cultures are run with a carbon source, such as glucose, being added at levels to achieve the desired level of growth and biomass, but at undetectable levels (with detection limits being about <0.1 g/l). In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, including pantothenate during the production stage of the fermentation. In some embodiments, the culture may be supplemented with relatively high concentrations of such components at the outset, for example, of the production stage, so that growth and/or isoprenoid production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of isoprenoids. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

In some embodiments, the carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. As stated previously, the carbon source concentration should be kept below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

5.6.12 Recovery of Isoprenoids

Once the isoprenoid is produced by the host cell, it may be recovered or isolated for subsequent use using any suitable separation and purification methods known in the art. In some embodiments, an organic phase comprising the isoprenoid is separated from the fermentation by centrifugation. In other embodiments, an organic phase comprising the isoprenoid separates from the fermentation spontaneously. In other embodiments, an organic phase comprising the isoprenoid is separated from the fermentation by adding a demulsifier and/or a nucleating agent into the fermentation reaction. Illustrative examples of demulsifiers include flocculants and coagulants. Illustrative examples of nucleating agents include droplets of the isoprenoid itself and organic solvents such as dodecane, isopropyl myristrate, and methyl oleate.

The isoprenoid produced in these cells may be present in the culture supernatant and/or associated with the host cells. In embodiments where the isoprenoid is associated with the host cell, the recovery of the isoprenoid may comprise a method of permeabilizing or lysing the cells. Alternatively or simultaneously, the isoprenoid in the culture medium can be recovered using a recovery process including, but not limited to, chromatography, extraction, solvent extraction, membrane separation, electrodialysis, reverse osmosis, distillation, chemical derivatization and crystallization.

In some embodiments, the isoprenoid is separated from other products that may be present in the organic phase. In some embodiments, separation is achieved using adsorption, distillation, gas-liquid extraction (stripping), liquid-liquid extraction (solvent extraction), ultrafiltration, and standard chromatographic techniques.

5.7 Polyketides

In some embodiments, the genetically modified host cell provided herein is capable of producing a polyketide from acetyl-CoA. Polyketides are synthesized by sequential reactions catalyzed by a collection of enzyme activities called polyketide synthases (PKSs), which are large multi-enzyme protein complexes that contain a coordinated group of active sites. Polyketide biosynthesis proceeds stepwise starting from simple 2-, 3-, 4-carbon building blocks such as acetyl-CoA, propionyl CoA, butyryl-CoA and their activated derivatives, malonyl-, methylmalonyl- and ethylmalonyl-CoA, primarily through decarboxylative condensation of malonyl-CoA-derived units via Claisen condensation reactions. The PKS genes are usually organized in one operon in bacteria and in gene clusters in eukaryotes. Three types of polyketide synthases have been characterized: Type I polyketide synthases are large, highly modular proteins subdivided into two classes: 1) iterative PKSs, which reuse domains in a cyclic fashion and 2) modular PKSs, which contain a sequence of separate modules and do not repeat domains. Type II polyketide synthases are aggregates of monofunctional proteins, and Type III polyketide synthases do not use acyl carrier protein domains.

Unlike fatty acid biosynthesis, in which each successive chain elongation step is followed by a fixed sequence of ketoreduction, dehydration and enoyl, reduction as described below, the individual chain elongation intermediates of polyketide biosynthesis undergo all, some, or no functional group modifications, resulting in a large number of chemically diverse products. Additional degrees of complexity arise from the use of different starter units and chain elongation units as well as the generation of new stereo-isomers.

The order of complete polyketide-synthesis as directed by a polyketide synthase follows (in the order N-terminus to C-terminus): starting or loading the initial carbon building blocks onto an acyl carrier protein, elongation modules which catalyze the extension of the growing macrolide chain and termination modules that catalyze the release of the synthesized macrolide. Component domains or separate enzyme functionalities active in this biosynthesis include acyl-transferases for the loading of starter, extender and intermediate acyl units; acyl carrier proteins which hold the growing macrolide as a thiol ester; β-keto-acyl synthases which catalyze chain extension; β-keto reductases responsible for the first reduction to an alcohol functionality; dehydratases which eliminate water to give an unsaturated thiolester; enoyl reductases which catalyze the final reduction to full saturation; and thiolesterases which catalyze macrolide release and cyclization.

In some embodiments, the genetically modified microorganism disclosed herein comprises a heterologous nucleotide sequence encoding an enzyme that can condense at least one of acetyl-CoA and malonyl-CoA with an acyl carrier protein, e.g. an acyl-transferase.

In some embodiments, the genetically modified microorganism disclosed herein comprises a heterologous nucleotide sequence encoding an enzyme that can condense a first reactant selected from the group consisting of acetyl-CoA and malonyl-CoA with a second reactant selected from the group consisting of malonyl-CoA or methylmalonyl-CoA to form a polyketide product, e.g. a β-keto-acyl synthase.

In some embodiments, the genetically modified microorganism disclosed herein comprises a heterologous nucleotide sequence encoding an enzyme that can reduce a β-keto chemical group on a polyketide compound to a β-hydroxy group, e.g. a β-keto reductase.

In some embodiments, the genetically modified microorganism disclosed herein comprises a heterologous nucleotide sequence encoding an enzyme that can dehydrate an alkane chemical group in a polyketide compound to produce an α-β-unsaturated alkene, e.g. a dehydratase.

In some embodiments, the genetically modified microorganism disclosed herein comprises a heterologous nucleotide sequence encoding an enzyme that can reduce an α-β-double-bond in a polyketide compound to a saturated alkane, e.g. an enoyl-reductase.

In some embodiments, the genetically modified microorganism disclosed herein comprises a heterologous nucleotide sequence encoding an enzyme that can hydrolyze a polyketide compound from an acyl carrier protein, e.g. a thioesterase.

In some embodiments, the polyketide producing cell comprises one or more heterologous nucleotide sequences encoding an enzyme comprising a KS catalytic region. In some embodiments, the polyketide producing cell comprises one or more heterologous nucleotide sequences encoding an enzyme comprising an AT catalytic region. In some embodiments, the polyketide producing cell comprises more than one heterologous nucleotide sequence encoding an enzyme comprising an AT catalytic region. In some embodiments, the polyketide producing cell comprises one or more heterologous nucleotide sequences encoding an enzyme comprising a CLF catalytic region. In some embodiments, the polyketide producing cell comprises one or more heterologous nucleotide sequences encoding an enzyme comprising an ACP activity. In some embodiments, the polyketide producing cell comprises more than one heterologous nucleotide sequence encoding an enzyme comprising an ACP activity.

In a particular embodiment, the polyketide producing cell comprises a minimal aromatic PKS system, e.g., heterologous nucleotide sequences encoding an enzyme comprising a KS catalytic region, an enzyme comprising an AT catalytic region, an enzyme comprising a CLF catalytic region, and an enzyme comprising an ACP activity, respectively. In a particular embodiment, the polyketide producing cell comprises a minimal modular PKS system, e.g., heterologous nucleotide sequences encoding an enzyme comprising a KS catalytic region, an enzyme comprising an AT catalytic region, and an enzyme comprising an ACP activity, respectively. In yet another particular embodiment, the polyketide producing cell comprises a modular aromatic PKS system for de novo polyketide synthesis, e.g., heterologous nucleotide sequences encoding an enzyme comprising a KS catalytic region, one or more enzymes comprising an AT catalytic region, and one or more enzymes comprising an ACP activity, respectively.

In some embodiments, the polyketide producing cell comprising a minimal PKS system, e.g., a minimal aromatic PKS system or minimal modular PKS system, further comprises additional catalytic activities which can contribute to production of the end-product polyketide. In some embodiments, the polyketide producing cell comprises one or more heterologous nucleotide sequences encoding an enzyme comprising a cyclase (CYC) catalytic region, which facilitates the cyclization of the nascent polyketide backbone. In some embodiments, the polyketide producing cell comprises one or more heterologous nucleotide sequences encoding an enzyme comprising a ketoreductase (KR) catalytic region. In some embodiments, the polyketide producing cell comprises one or more heterologous nucleotide sequences encoding an enzyme comprising an aromatase (ARO) catalytic region. In some embodiments, the polyketide producing cell comprises one or more heterologous nucleotide sequences encoding an enzyme comprising an enoylreductase (ER) catalytic region. In some embodiments, the polyketide producing cell comprises one or more heterologous nucleotide sequences encoding an enzyme comprising a thioesterase (TE) catalytic region. In some embodiments, the polyketide producing cell further comprises one or more heterologous nucleotide sequences encoding an enzyme comprising a holo ACP synthase activity, which effects pantetheinylation of the ACP.

In some embodiments, the polyketide producing cell further comprises one or more heterologous nucleotide sequences conferring a postsynthesis polyketide modifying activity. In some embodiments, the polyketide producing cell further comprises one or more heterologous nucleotide sequences encoding an enzyme comprising a glycosylase activity, which effects postsynthesis modifications of polyketides, for example, where polyketides having antibiotic activity are desired. In some embodiments, the polyketide producing cell further comprises one or more heterologous nucleotide sequences encoding an enzyme comprising a hydroxylase activity. In some embodiments, the polyketide producing cell further comprises one or more heterologous nucleotide sequences encoding an enzyme comprising an epoxidase activity. In some embodiments, the polyketide producing cell further comprises one or more heterologous nucleotide sequences encoding an enzyme comprising a methylase activity.

In some embodiments, the polyketide producing cell further comprises one or more heterologous nucleotide sequences encoding a biosynthetic enzyme including, but not limited to, at least one polyketide synthesis pathway enzyme, and enzymes that can modify an acetyl-CoA compound to form a polyketide product such as a macrolide, an antibiotic, an antifungal, a cytostatic compound, an anticholesterolemic compound, an antiparasitic compound, a coccidiostatic compound, an animal growth promoter or an insecticide. In some embodiments, the HACD compound is a polyene. In some embodiments, the HACD compound is a cyclic lactone. In some embodiments, the HACD compound comprises a 14, 15, or 16-membered lactone ring. In some embodiments, the HACD compound is a polyketide selected from the group consisting of a polyketide macrolide, antibiotic, antifungal, cytostatic, anticholesterolemic, antiparasitic, a coccidiostatic, animal growth promoter and insecticide.

In some embodiments, the polyketide producing cell comprises heterologous nucleotide sequences, for example sequences encoding PKS enzymes and polyketide modification enzymes, capable of producing a polyketide selected from, but not limited to, the following polyketides: Avermectin (see, e.g., U.S. Pat. No. 5,252,474; U.S. Pat. No. 4,703,009; EP Pub. No. 118,367; MacNeil et al., 1993, "Industrial Microorganisms: Basic and Applied Molecular Genetics"; Baltz, Hegeman, & Skatrud, eds. (ASM), pp. 245-256, "A Comparison of the Genes Encoding the Polyketide Synthases for Avermectin, Erythromycin, and Nemadectin"; MacNeil et al., 1992, *Gene* 115: 119-125; and Ikeda and Omura, 1997, *Chem. Res.* 97: 2599-2609); Candicidin (FR008) (see, e.g., Hu et al., 1994, *Mol. Microbiol.* 14: 163-172); Carbomycin, Curamycin (see, e.g., Bergh et al., *Biotechnol Appl Biochem.* 1992 February; 15(1):80-9); Daunorubicin (see, e.g., *J Bacteriol.* 1994 October; 176(20):6270-80); Epothilone (see, e.g., PCT Pub. No. 99/66028; and PCT Pub. No. 00/031247); Erythromycin (see, e.g., PCT Pub. No. 93/13663; U.S. Pat. No. 6,004,787; U.S. Pat. No. 5,824,513; Donadio et al., 1991, *Science* 252:675-9; and Cortes et al., Nov. 8, 1990, *Nature* 348:176-8); FK-506 (see, e.g., Motamedi et al., 1998; *Eur. J. Biochem.* 256: 528-534; and Motamedi et al., 1997, *Eur. J. Biochem.* 244: 74-80); FK-520 (see, e.g., PCT Pub. No. 00/020601; and Nielsen et al., 1991, *Biochem.* 30:5789-96); Griseusin (see, e.g., Yu et al., *J Bacteriol.* 1994 May; 176(9): 2627-34); Lovastatin (see, e.g., U.S. Pat. No. 5,744,350); Frenolycin (see, e.g., Khosla et al., *Bacteriol.* 1993 April; 175(8):2197-204; and Bibb et al., *Gene* 1994 May 3; 142(1): 31-9); Granaticin (see, e.g., Sherman et al., EMBO J. 1989 September; 8(9):2717-25; and Bechtold et al., *Mol Gen Genet.* 1995 Sep. 20; 248(5):610-20); Medermycin (see, e.g., Ichinose et al., *Microbiology* 2003 July; 149(Pt 7):1633-45); Monensin (see, e.g., Arrowsmith et al., *Mol Gen Genet.* 1992 August; 234(2):254-64); Nonactin (see, e.g., *FEMS Microbiol Lett.* 2000 Feb. 1; 183(1):171-5); Nanaomycin (see, e.g., Kitao et al., *J Antibiot* (Tokyo). 1980 July; 33(7):711-6); Nemadectin (see, e.g., MacNeil et al., 1993, supra); Niddamycin (see, e.g., PCT Pub. No. 98/51695; and Kakavas et al., 1997, *J. Bacteriol.* 179: 7515-7522); Oleandomycin (see e.g., Swan et al., 1994, *Mol. Gen. Genet.* 242: 358-362; PCT Pub. No. 00/026349; Olano et al., 1998, *Mol. Gen. Genet.* 259(3): 299-308; and PCT Pat. App. Pub. No. WO 99/05283); Oxytetracycline (see, e.g., Kim et al., *Gene.* 1994 Apr. 8; 141(1): 141-2); Picromycin (see, e.g., PCT Pub. No. 99/61599; PCT Pub. No. 00/00620; Xue et al., 1998, *Chemistry & Biology* 5(11): 661-667; Xue et al., October 1998, *Proc. Natl. Acad. Sci.* USA 95: 12111 12116); Platenolide (see, e.g., EP Pub. No. 791,656; and U.S. Pat. No. 5,945,320); Rapamycin (see, e.g., Schwecke et al., August 1995, *Proc. Natl. Acad. Sci.* USA 92:7839-7843; and Aparicio et al., 1996, Gene 169: 9-16); Rifamycin (see, e.g., PCT Pub. No. WO 98/07868; and August et al., Feb. 13, 1998, *Chemistry & Biology,* 5(2): 69-79); Sorangium (see, e.g., U.S. Pat. No. 6,090,601); Soraphen (see, e.g., U.S. Pat. No. 5,716,849; Schupp et al., 1995, *J. Bacteriology* 177: 3673-3679); Spinocyn (see, e.g., PCT Pub. No. 99/46387); Spiramycin (see, e.g., U.S. Pat. No. 5,098,837); Tetracenomycin (see, e.g., Summers et al., *J Bacteriol.* 1992 March; 174(6): 1810-20; and Shen et al., *J Bacteriol.* 1992 June; 174(11):3818-21); Tetracycline (see, e.g., *J Am Chem Soc.* 2009 Dec. 9; 131(48):17677-89); Tylosin (see, e.g., U.S. Pat. No. 5,876,991; U.S. Pat. No. 5,672,497; U.S. Pat. No. 5,149,638; EP Pub. No. 791,655; EP Pub. No. 238, 323; Kuhstoss et al., 1996, Gene 183:231-6; and Merson-Davies and Cundliffe, 1994, *Mol. Microbiol.* 13: 349-355); and 6-methylsalicyclic acid (see, e.g., Richardson et al., *Metab Eng.* 1999 April; 1(2):180-7; and Shao et al., *Biochem Biophys Res Commun.* 2006 Jun. 23; 345(1):133-9).

5.8 Fatty Acids

In some embodiments, the genetically modified host cell provided herein is capable of producing a fatty acid from acetyl-CoA. Fatty acids are synthesized by a series of decarboxylative Claisen condensation reactions from acetyl-CoA and malonyl-CoA catalyzed by fatty acid synthases. Similar to polyketide synthases, fatty acid synthases are not a single enzyme but an enzymatic system composed of 272 kDa multifunctional polypeptide in which substrates are handed from one functional domain to the next. Two principal classes of fatty acid synthases have been characterized: Type I fatty acid synthases are single, multifunctional polypeptides common to mammals and fungi (although the structural arrangement of fungal and mammalian synthases differ) and the CMN group of bacteria (corynebacteria, mycobacteria, and *nocardia*). Type II synthases, found in archaebacteria and eubacteria, are a series of discrete, monofunctional enzymes that participate in the synthesis of fatty acids. The mechanisms fatty acid elongation and reduction is the same in the two classes of synthases, as the enzyme domains responsible for these catalytic events are largely homologous amongst the two classes.

Following each round of elongation of the fatty acid chain in the decarboxylative Claisen condensation reactions, the β-keto group is reduced to a fully saturated carbon chain by the sequential action of a ketoreductase, a dehydratase, and an enol reductase. The growing fatty acid chain moves between these active sites attached to an acyl carrier protein and is ultimately released by the action of a thioesterase upon reaching a carbon chain length of 16 (palmitidic acid).

In some embodiments, the genetically modified microorganism disclosed herein comprises a heterologous nucleotide sequence encoding a biosynthetic enzyme including, but not limited to, at least one fatty acid synthesis pathway enzyme, and enzymes that can modify an acetyl-CoA compound to form a fatty acid product such as a palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid. In some embodiments, the HACD compound is a fatty acid selected from the group consisting of palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid.

In some embodiments, the genetically modified microorganism disclosed herein comprises a heterologous nucleotide sequence encoding an enzyme that can covalently link at least one of acetyl-CoA and malonyl-CoA with an acyl carrier protein, e.g. an acyl-transferase.

In some embodiments, the genetically modified microorganism disclosed herein comprises a heterologous nucleotide sequence encoding an enzyme that can condense acetyl chemical moiety and a malonyl chemical moiety, each bound to an acyl carrier protein (ACP), to form acetoacetyl-ACP, e.g. a β-Ketoacyl-ACP synthase.

In some embodiments, the genetically modified microorganism disclosed herein comprises a heterologous nucleotide sequence encoding an enzyme that can reduce the double bond in acetoacetyl-ACP with NADPH to form a hydroxyl group in D-3-hydroxybutyryl hydroxylase-ACP, e.g. a β-Ketoacyl-ACP reductase.

In some embodiments, the genetically modified microorganism disclosed herein comprises a heterologous nucleotide sequence encoding an enzyme that can dehydrate D-3-Hydroxybutyryl hydroxylase-ACP to create a double bond between the beta- and gamma-carbons forming crotonyl-ACP, e.g. a β-hydroxyacyl-ACP dehydrase.

In some embodiments, the genetically modified microorganism disclosed herein comprises a heterologous nucleotide sequence encoding an enzyme that can reduce crotonyl ACP with NADPH to form butyryl-ACP, e.g. an enoyl ACP reductase.

In some embodiments, the genetically modified microorganism disclosed herein comprises a heterologous nucleotide sequence encoding an enzyme that can hydrolyze a C16 acyl compound from an acyl carrier protein to form palmitate, e.g. a thioesterase.

In some embodiments, the fatty acid producing cell comprises one or more heterologous nucleotide sequences encoding acetyl-CoA synthase and/or malonyl-CoA synthase, to effect increased production of one or more fatty acids as compared to a genetically unmodified parent cell.

For example, to increase acetyl-CoA production, one or more of the following genes can be expressed in the cell: pdh, panK, aceEF (encoding the EIp dehydrogenase component and the E2p dihydrolipoamide acyltransferase component of the pyruvate and 2-oxoglutarate dehydrogenase complexes), fabH, fabD, fabG, acpP, and fabF. Illustrative examples of nucleotide sequences encoding such enzymes include, but are not limited to: pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), fabF (AAC74179).

In some embodiments, increased fatty acid levels can be effected in the cell by attenuating or knocking out genes encoding proteins involved in fatty acid degradation. For example, the expression levels of fadE, gpsA, idhA, pflb, adhE, pta, poxB, ackA, and/or ackB can be attenuated or knocked-out in an engineered host cell using techniques known in the art. Illustrative examples of nucleotide sequences encoding such proteins include, but are not limited to: fadE (AAC73325), gspA (AAC76632), IdhA (AAC74462), pflb (AAC73989), adhE (AAC74323), pta (AAC75357), poxB (AAC73958), ackA (AAC75356), and ackB (BAB81430). The resulting host cells will have increased acetyl-CoA production levels when grown in an appropriate environment.

In some embodiments, the fatty acid producing cell comprises a heterologous nucleotide sequence encoding an enzyme that can convert acetyl-CoA into malonyl-CoA, e.g., the multisubunit AccABCD protein. An illustrative example of a suitable nucleotide sequence encoding AccABCD includes but is not limited to accession number AAC73296, EC 6.4.1.2.

In some embodiments, the fatty acid producing cell comprises a heterologous nucleotide sequence encoding a lipase. Illustrative examples of suitable nucleotide sequences encoding a lipase include, but are not limited to accession numbers CAA89087 and CAA98876.

In some embodiments, increased fatty acid levels can be effected in the cell by inhibiting PlsB, which can lead to an increase in the levels of long chain acyl-ACP, which will inhibit early steps in the fatty acid biosynthesis pathway (e.g., accABCD, fabH, and fabl). The expression level of PlsB can be attenuated or knocked-out in an engineered host cell using techniques known in the art. An illustrative example of a suitable nucleotide sequence encoding PlsB includes but is not limited to accession number AAC77011. In particular embodiments, the plsB D31 IE mutation can be used to increase the amount of available acyl-CoA in the cell.

In some embodiments, increased production of monounsaturated fatty acids can be effected in the cell by overexpressing an sfa gene, which would result in suppression of fabA. An illustrative example of a suitable nucleotide sequence encoding sfa includes but is not limited to accession number AAN79592.

In some embodiments, increased fatty acid levels can be effected in the cell by modulating the expression of an enzyme which controls the chain length of a fatty acid substrate, e.g., a thioesterase. In some embodiments, the fatty acid producing cell has been modified to overexpress a tes or fat gene. Illustrative examples of suitable tes nucleotide sequences include but are not limited to accession numbers: (tesA: AAC73596, from *E. coli*, capable of producing $C_{18:1}$ fatty acids) and (tesB: AAC73555 from *E. coli*). Illustrative examples of suitable fat nucleotide sequences include but are not limited to: (fatB: □41635 and AAA34215, from *Umbellularia california*, capable of producing $C_{12:0}$ fatty acids), (fatB2: Q39513 and AAC49269, from *Cuphea hookeriana*, capable of producing $C_{8:0}$-$C_{10:0}$ fatty acids), (fatB3: AAC49269 and AAC72881, from *Cuphea hookeriana*, capable of producing $C_{14:0}$-$C_{16:0}$ fatty acids), (fatB: Q39473 and AAC49151, from *Cinnamonum camphorum*, capable of producing $C_{14:0}$ fatty acids), (fatB [M141T]: CAA85388, from *Arabidopsis thaliana*, capable of producing $C_{16:1}$ fatty acids), (fatA: NP 189147 and NP 193041, from *Arabidopsis thaliana*, capable of producing $C_{18:1}$ fatty acids), (fatA: CAC39106, from *Bradvrhiizobium japonicum*, capable of preferentially producing $C_{18:1}$ fatty acids), (fatA: AAC72883, from *Cuphea hookeriana*, capable of producing $C_{18:1}$ fatty acids), and (fatA1, AAL79361 from *Helianthus annus*).

In some embodiments, increased levels of $C_{10}$ fatty acids can be effected in the cell by attenuating the expression or activity of thioesterase $C_{18}$ using techniques known in the art. Illustrative examples of suitable nucleotide sequences encoding thioesterase $C_{18}$ include, but are not limited to accession numbers AAC73596 and P0ADA1. In other embodiments, increased levels of $C_{10}$ fatty acids can be effected in the cell by increasing the expression or activity of thioesterase $C_{10}$ using techniques known in the art. An illustrative example of a suitable nucleotide sequence encoding thioesterase $C_{10}$ includes, but is not limited to accession number Q39513.

In some embodiments, increased levels of $C_{14}$ fatty acids can be effected in the cell by attenuating the expression or activity of endogenous thioesterases that produce non-$C_{14}$ fatty acids, using techniques known in the art. In other embodiments, increased levels of $C_{14}$ fatty acids can be effected in the cell by increasing the expression or activity of thioesterases that use the substrate $C_{14}$-ACP, using techniques known in the art. An illustrative example of a suitable nucleotide sequence encoding such a thioesterase includes, but is not limited to accession number Q39473.

In some embodiments, increased levels of $C_{12}$ fatty acids can be effected in the cell by attenuating the expression or activity of endogenous thioesterases that produce non-$C_{12}$ fatty acids, using techniques known in the art. In other embodiments, increased levels of $C_{12}$ fatty acids can be effected in the cell by increasing the expression or activity of thioesterases that use the substrate $C_{12}$-ACP, using techniques known in the art. An illustrative example of a suitable nucleotide sequence encoding such a thioesterase includes, but is not limited to accession number Q41635.

5.9 PK/PTA for the Production of Other Compounds

In some embodiments, the genetically modified host cell provided herein (e.g., a host cell comprising PK/PTA and a functional disruption of a polypeptide encoding acetyl phosphatase activity, e.g., RHR2, HOR2, or homologues thereof) is engineered for the expression of biosynthetic pathways that initiate with cellular pyruvate to produce, for example, 2,3-butanediol, 2-butanol, 2-butanone, valine, leucine, lactic acid, malate, isoamyl alcohol, and isobutanol, as described in U.S. Patent Application Publication No. 20120156735. The disruption of the enzyme pyruvate decarboxylase (PDC) in recombinant host cells engineered to express a pyruvate-utilizing biosynthetic pathway has been used to increase the availability of pyruvate for product formation via the biosynthetic pathway. While PDC-KO recombinant host cells can be used to produce the products of pyruvate-utilizing biosynthetic pathways, PDC-KO recombinant host cells require exogenous carbon substrate supplementation (e.g., ethanol or acetate) for their growth. In particular, two exogenous carbon substrates are needed: one of which is converted to a desired product, the other fully or partly converted into acetyl-CoA by recombinant host cells requiring such supplementation for growth. However, expression of a heterologous phosphoketolase pathway reduces or eliminates the need for providing these exogenous carbon substrates for their growth compared to PDC-KO cells not heterologously PK/PTA. Thus, the additional functional disruption of RHR2, HOR2, or homologues thereof capable of catalyzing the hydrolysis of acetyl phosphate to acetate, is expected to further improve the ability of PK/PTA to increase the supply of acetyl-CoA available as a substrate for cellular growth in these cells.

5.10 Methods of Making Genetically Modified Cells

Also provided herein are methods for producing a host cell that is genetically engineered to comprise one or more of the modifications described above, e.g., one or more nucleic heterologous nucleic acids encoding PK, PTA, and/or biosynthetic pathway enzymes, e.g., for an acetyl-CoA derived compound. Expression of a heterologous enzyme in a host cell can be accomplished by introducing into the host cells a nucleic acid comprising a nucleotide sequence encoding the enzyme under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell.

Nucleic acids encoding these proteins can be introduced into the host cell by any method known to one of skill in the art without limitation (see, for example, Hinnen et al. (1978) *Proc. Natl. Acad. Sci. USA* 75:1292-3; Cregg et al. (1985) *Mol. Cell. Biol.* 5:3376-3385; Goeddel et al. eds, 1990, Methods in Enzymology, vol. 185, Academic Press, Inc., CA; Krieger, 1990, *Gene Transfer and Expression—A Laboratory Manual*, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include, but are not limited to, spheroplasting, electroporation, PEG 1000 mediated transformation, and lithium acetate or lithium chloride mediated transformation.

The copy number of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the copy number of an enzyme in a host cell may be altered by modifying the level of translation of an mRNA that encodes the enzyme. This can be achieved for example by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

In some embodiments, a nucleic acid used to genetically modify a host cell comprises one or more selectable markers useful for the selection of transformed host cells and for placing selective pressure on the host cell to maintain the foreign DNA.

In some embodiments, the selectable marker is an antibiotic resistance marker. Illustrative examples of antibiotic resistance markers include, but are not limited to, the BLA, NAT1, PAT, AUR1-C, PDR4, SMR1, CAT, mouse dhfr, HPH, DSDA, $KAN^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the $KAN^R$ gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include, but are not limited to, the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

Described herein are specific genes and proteins useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias."

Optimized coding sequences containing codons preferred by a particular prokaryotic or eukaryotic host (Murray et al., 1989, *Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24: 216-8).

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for the compositions and methods provided herein are encompassed by the disclosure. In some embodiments, two proteins (or a region of the proteins) are substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol Biol* 25: 365-89).

The following six groups each contain amino acids that are conservative substitutions for one another: 1) Serine (S), Threonine (T); 2) Aspartic Acid (D), Glutamic Acid (E); 3)

Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorphs*, *Candida* spp., *Trichosporon* spp., *Yamadazyma* spp., including *Y.* spp. *stipitis*, *Torulaspora pretoriensis*, *Issatchenkia orientalis*, *Schizosaccharomyces* spp., including *S. pombe*, *Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia. coli*, *Zymomonas mobilis*, *Staphylococcus aureus*, *Bacillus* spp., *Clostridium* spp., *Corynebacterium* spp., *Pseudomonas* spp., *Lactococcus* spp., *Enterobacter* spp., and *Salmonella* spp.

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous PK, PTA, RHR2 or HOR2 genes, proteins, or enzymes, techniques may include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., *Branched-Chain Amino Acids Methods Enzymology,* 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein.

6. EXAMPLES

6.1 Example 1

Acetate Production in Host Cells Expressing PK and PTA

This example describes the production of acetate in yeast strains heterologously expressing phosphoketolase and phosphotransacetylase.

6.1.1 Materials and Methods 6.1.1.1 Strain Engineering 6.1.1.1.1 Y967 and Y968

Y967 and Y968 are wildtype prototrophic *Saccharomyces cerevisiae* CEN.PK2, Y967 is MatA, and Y968 is Matalpha. The starting strain for Y12869, Y12746, and all of their derivatives, was *Saccharomyces cerevisiae* strain Y003 (CEN.PK2, Mat alpha, ura3-52, trp1-289, leu2-3,122, his3^1). All DNA-mediated transformation into *S. cerevisiae* was conducted using the standard lithium acetate procedure as described by Gietz R W and Woods R A, *Guide to Yeast Genetics and Molecular and Cell Biology*. Part B. San Diego, Calif.: Academic Press Inc. pp. 87-96 (2002), and in all cases integration of the constructs were confirmed by PCR amplification of genomic DNA.

6.1.1.1.2 Y12869

Y12869 was generated through three successive integrations into Y003. First, the gene ACS2 was deleted by introducing an integration construct (i2235; SEQ ID NO:27) consisting of the native *S. cerevisiae* LEU2 gene, flanked by sequences consisting of upstream and downstream nucleotide sequences of the ACS2 locus. Upon introduction of a *S. cerevisiae* host cell, this construct can integrate by homologous recombination into the ACS2 locus of the genome, functionally disrupting ACS2 by replacing the ACS2 coding sequence with its integrating sequence. Transformants were plated onto CSM-leu plates containing 2% EtOH as the sole carbon source, and were confirmed by PCR amplification. The resulting strain was Y4940.

Next, ALD6 was deleted and *Dickeya zeae* eutE was introduced in Y4940 with the integration construct (i74804; SEQ ID NO:28) pictured below.

| ALD6US | pTDH3 | Dz.eutE | tTEF2 | TRP1 | tTEF2 | Dz.eutE | pTDH3 | ALD6DS |
|---|---|---|---|---|---|---|---|---|

This integration construct comprises a selectable marker (TRP1), as well as two copies a yeast-codon-optimized sequence encoding the gene eutE from *Dickeya zeae* (NCBI Reference Sequence: YP_003003316.1) under control of the TDH3 promoter (840 basepairs upstream of the native *S. cerevisiae* TDH3 coding region), and the TEF2 terminator (508 basepairs downstream of the native *S. cerevisiae* TEF2 coding region). These components are flanked by upstream and downstream nucleotide sequences of the ALD6 locus.

sequence); flanked by homologous sequences consisting of the upstream and downstream nucleotide sequences of the *S. cerevisiae* BUD9 locus. Upon introduction into a host cell, this construct integrates by homologous recombination into the host cell genome, functionally disrupting BUD9 by replacing the BUD9 coding sequence with its integrating sequence. The construct was assembled using the methods described in U.S. Pat. No. 8,221,982. Transformants were selected on CSM-URA plates with 2% glucose. The resulting strain was transformed with the construct (i74810; SEQ ID NO:31) shown below.

| ALD6US | pTDH3 | Lm.PK | tTDH3 | TRP1 | tHDL1 | Xd⁻ʷ˥ | εHαιd | ALD6DS |
|---|---|---|---|---|---|---|---|---|

Upon introduction into a host cell, this construct integrates by homologous recombination into the host cell genome, functionally disrupting ALD6 by replacing the ALD6 coding sequence with its integrating sequence. The construct was assembled using the methods described in U.S. Pat. No. 8,221,982. The construct was transformed into Y4940, and transformants were selected on CSM-TRP plates with 2% glucose and confirmed by PCR amplification. The resulting strain was y12602.

Next, ACS1 was deleted in Y12602 by introducing an integration construct (i76220; SEQ ID NO:29) consisting of the upstream and downstream nucleotide sequences of ACS1, flanking the native *S. cerevisiae* HIS3 gene under its own promoter and terminator. Transformants were plated onto CSM-his plates containing 2% glucose as the sole carbon source, and were confirmed by PCR amplification. The resulting strain was Y12747.

Next, Y12747 was transformed with a PCR product amplified from the native URA3 sequence. This sequence restores the ura3-52 mutation. See Rose and Winston, *Mol Gen Genet* 193:557-560 (1984). Transformants were plated onto CSM-ura plates containing 2% glucose as the sole carbon source, and were confirmed by PCR amplification. The resulting strain was Y12869.

This construct comprising a selectable marker (TRP1); two copies of phosphoketolase from *Leuconostoc mesenteroides* under the TDH3 promoter (870 bp upstream of the TDH3 coding sequence) and TDH3 terminator (259 bp downstream of the TDH3 coding sequence); flanked by homologous sequences consisting of the upstream and downstream nucleotide sequences of the ALD6 locus. Upon introduction into a host cell, this construct integrates by homologous recombination into the host cell genome, functionally disrupting ALD6 by replacing the ALD6 coding sequence with its integrating sequence. The construct was assembled using the methods described in U.S. Pat. No. 8,221,982. Transformants were selected on CSM-URA plates with 2% glucose and confirmed by PCR amplification.

Next, ACS1 was deleted in by introducing an integration construct (i76220; SEQ ID NO:29) consisting of the upstream and downstream nucleotide sequences of ACS1, flanking the native *S. cerevisiae* HIS3 gene under its own promoter and terminator. Transformants were plated onto CSM-his plates containing 2% glucose as the sole carbon source, and were confirmed by PCR amplification.

6.1.1.1.4 Y12746

Y12746 was generated through three successive integrations into Y4940. First, Y4940 was transformed with the integration construct (i73830; SEQ ID NO:30) pictured below.

| BUD9US | pTDH3 | Lm.PK | tTDH3 | URA3 | IXDdɪ | ∀Ld˙ʞƆ | εHαιd | BUD9DS |
|---|---|---|---|---|---|---|---|---|

6.1.1.1.3 Y12745

Y12745 was generated through three successive integrations into Y4940. First, Y4940 was transformed with the integration construct (i73830; SEQ ID NO:30) pictured below.

This integration construct comprises a selectable marker (URA3); a yeast codon-optimized version of phosphoketolase from *Leuconostoc mesenteroides* (NCBI Reference Sequence YP_819405.1) under the TDH3 promoter (870 bp upstream of the TDH3 coding sequence) and TDH3 terminator (259 bp downstream of the TDH3 coding sequence); a yeast codon-optimized version of *Clostridium kluyveri* phosphotransacetylase (NCBI Reference Sequence: YP_001394780.1) under control of the TDH3 promoter (870 bp upstream of the TDH3 coding sequence) and the PGK1 terminator (259 bp downstream of the PGK1 coding

| BUD9US | pTDH3 | Lm.PK | tTDH3 | URA3 | IXDdɪ | ∀Ld˙ʞƆ | εHαιd | BUD9DS |
|---|---|---|---|---|---|---|---|---|

This integration construct comprises a selectable marker (URA3); a yeast codon-optimized version of phosphoketolase from *Leuconostoc mesenteroides* (NCBI Reference Sequence YP_819405.1) under the TDH3 promoter (870 bp upstream of the TDH3 coding sequence) and TDH3 terminator (259 bp downstream of the TDH3 coding sequence); a yeast codon-optimized version of *Clostridium kluyveri* phosphotransacetylase (NCBI Reference Sequence: YP_001394780.1) under control of the TDH3 promoter (870 bp upstream of the TDH3 coding sequence) and the PGK1 terminator (259 bp downstream of the PGK1 coding sequence); flanked by homologous sequences consisting of the upstream and downstream nucleotide sequences of the *S. cerevisiae* BUD9 locus. Upon introduction into a host cell, this construct integrates by homologous recombination into the host cell genome, functionally disrupting BUD9 by replacing the BUD9 coding sequence with its integrating sequence. The construct was assembled using the methods described in U.S. Pat. No. 8,221,982. Transformants were selected on CSM-URA plates with 2% glucose.

The resulting strain was transformed with the construct (i74810; SEQ ID NO:31) shown below.

| ALD6US | pTDH3 | Lm.PK | tTDH3 | TRP1 | tTDH3 | Lm.PK | pTDH3 | ALD6DS |
|---|---|---|---|---|---|---|---|---|

This construct comprising a selectable marker (TRP1); two copies of phosphoketolase from *Leuconostoc mesenteroides* under the TDH3 promoter (870 bp upstream of the TDH3 coding sequence) and TDH3 terminator (259 bp downstream of the TDH3 coding sequence); flanked by homologous sequences consisting of the upstream and downstream nucleotide sequences of the ALD6 locus. Upon introduction into a host cell, this construct integrates by homologous recombination into the host cell genome, functionally disrupting ALD6 by replacing the ALD6 coding sequence with its integrating sequence. The construct was assembled using the methods described in U.S. Pat. No. 8,221,982. Transformants were selected on CSM-URA plates with 2% glucose and confirmed by PCR amplification.

Finally, the resulting strain was transformed with the construct (i76221; SEQ ID NO:32) shown below.

| ACS1US | pTDH3 | Dz.eutE | tTEF2 | HIS3 | tTEF2 | Dz.eutE | pTDH3 | ACS1DS |
|---|---|---|---|---|---|---|---|---|

This construct comprises a selectable marker (HIS3); as well as two copies a yeast-codon-optimized sequence encoding the gene eutE from *Dickeya Zeae* (NCBI Reference Sequence: YP_003003316.1) under control of the TDH3 promoter (840 basepairs upstream of the native *S. cerevisiae* TDH3 coding region) and the TEF2 terminator (508 basepairs downstream of the native *S. cerevisiae* TEF2 coding region). These components are flanked by upstream and downstream nucleotide sequences of the ACS1 locus. Upon introduction into a host cell, this construct integrates by homologous recombination into the host cell genome, functionally disrupting ACS1 by replacing the ACS1 coding sequence with its integrating sequence. The construct was assembled using the methods described in U.S. Pat. No. 8,221,982. Transformants were selected on CSM-HIS plates with 2% glucose and confirmed by PCR amplification. The resulting strain was Y12746.

6.1.1.1.5 Y19390

Y19390 is a direct descendant of Y12869. A ura-auxotrophic derivative of Y12869 was transformed with the integration construct MS49253 (SEQ ID NO:36) shown below:

moter (870 bp upstream of the TDH3 coding sequence) and TDH3 terminator (259 bp downstream of the TDH3 coding sequence); flanked by homologous sequences consisting of the upstream and downstream nucleotide sequences of the *S. cerevisiae* BUD9 locus. Upon introduction into a host cell, this construct integrates by homologous recombination into the host cell genome, functionally disrupting BUD9 by replacing the BUD9 coding sequence with its integrating sequence. The construct was assembled using the methods described in U.S. Pat. No. 8,221,982. Transformants were selected on CSM-URA plates with 2% glucose.

6.1.1.1.6 Y19391

Y19391 is a direct descendant of Y12869. A ura-auxotrophic derivative of Y12869 was transformed with the integration construct MS49298 (SEQ ID NO:37) shown below:

| BUD9US | pTDH3 | Ck.PTA | tPGK1 | URA3 | tPGK1 | Ck.PTA | pTDH3 | BUD9DS |
|---|---|---|---|---|---|---|---|---|

This integration construct comprises a selectable marker (URA3); two copies of a yeast codon-optimized version of phosphotransacetylase from *Clostridium kluyveri* (NCBI Reference Sequence: YP_001394780.1) under control of the TDH3 promoter (870 bp upstream of the TDH3 coding sequence) and the PGK1 terminator (259 bp downstream of the PGK1 coding sequence); flanked by homologous sequences consisting of the upstream and downstream nucleotide sequences of the *S. cerevisiae* BUD9 locus. Upon introduction into a host cell, this construct integrates by homologous recombination into the host cell genome, functionally disrupting BUD9 by replacing the BUD9 coding sequence with its integrating sequence. The construct was assembled using the methods described in U.S. Pat. No. 8,221,982. Transformants were selected on CSM-URA plates with 2% glucose.

6.1.1.2 Culture Conditions

Inoculum cultures of Y967, Y12869, Y12745, Y12746, Y19390 and Y19391 were grown from single colonies overnight in 5 ml of seed media at 30 C and 200 rpm (15 g/L ammonium sulfate, 8 g/L potassium phosphate, 6.1 g/L magnesium sulfate, 150 mg/L EDTA, 57.5 mg/L zinc sulfate, 4.8 mg/L cobalt chloride, 3.24 mg/L manganese chloride, 5 mg/L copper sulfate, 29.4 mg/L calcium chloride, 27.8 mg/L iron sulfate, 4.8 mg/L sodium molybdate, 0.6 mg/L biotin, 12 mg/L calcium pantothenate, 12 mg/L nicotinic acid, 30 mg/L inositol, 12 mg/L thiamin hydrochloride, 12 mg/L pyridoxine hydrochloride, 0.24 mg/L para-aminobenzoic acid) with 50

| BUD9US | pTDH3 | Lm.PK | tTDH3 | URA3 | tTDH3 | Lm.PK | pTDH3 | BUD9DS |
|---|---|---|---|---|---|---|---|---|

This integration construct comprises a selectable marker (URA3); two copies of a yeast codon-optimized version of phosphoketolase from *Leuconostoc mesenteroides* (NCBI Reference Sequence YP_819405.1) under the TDH3 promoter mM succinate pH 5.0, and 20 g/L sucrose. The precultures were then inoculated into a 125 ml flask carrying 25 ml of seed media with 50 mM succinate pH 5.0, and 40 g/L sucrose to an initial OD600 of 0.1, and grown at 30 C and 200 rpm.

6.1.1.3 Quantitation of Acetate, Fructose, Glucose, and Sucrose

Acetate and sugars (fructose, glucose, sucrose) were quantitated by transferring 1 ml of whole cell broth to a 1.5 ml eppendorf tubes, and spinning at 13,000 RPM for 1 minute using a tabletop centrifuge to clarify the supernatant. The supernatant was then diluted (1:1 v/v) in 8 mM sulfuric acid, vortexed, and recentrifuged before transferring to a 1.8 ml vial. Samples were analyzed with an Agilent 1200 HPLC, with variable wavelength and refractive index detection, using a BioRad Aminex HPX-87H 300 mm×7.8 mm column. The mobile phase was 4 mM sulfuric acid, column temperature was 40 C, and the flow rate was 0.5 ml/min.

6.1.1.4 Results

FIG. 3B shows that wildtype Cen.PK2, Y967, produces acetate during growth in batch defined sucrose shakeflask cultures. Y12869, comprising a deletion of the PDH-bypass (acs1Δ acs2Δ ald6Δ) and heterologously expressing acetaldehyde dehydrogenase acylating (Dz.eutE), produces far less acetate than the wildtype control which uses the PDH-bypass, likely due to the deletion of ALD6, the cytosolic acetaldehyde dehydrogenase that converts acetaldehyde to acetate. In the strain Y12746, comprising a deletion of the PDH-bypass (acs1Δ acs2Δ ald6Δ) and heterologously expressing acetaldehyde dehydrogenase acylating (Dz.eutE) as well as phosphoketolase (Lm.PK) and phosphotransacetylase (Ck.PTA), a large increase in acetate is observed, surpassing the amount produced by wildtype Y967. The results with Y12869 indicate that the baseline level of acetate is extremely low in a strain that is acs1Δ acs2 Δ ald6Δ and uses ADA to carry flux to cytosolic acetyl-CoA. In all cases, the rate of sugar consumption is comparable (sugars here are defined as the sum of sucrose, glucose, and fructose in the media), illustrating that the differences in acetate levels are not due to differential consumption of feedstock (FIG. 3A). These results suggest that the increase in acetate in Y12746 is attributable to the presence of phosphoketolase and/or phosphotransacetylase. The catalytic activity of both phosphoketolase and phosphotransacetylase produces acetyl phosphate. Therefore, acetate accumulation may arise from spontaneous or catalyzed hydrolysis of acetyl phosphate in Y12746.

To determine the source of acetate in the strain expressing ADA, PK and PTA (Y12746), we transformed a strain which uses only ADA to provide cytosolic AcCoA (Y12869, comprising a deletion of the PDH-bypass (acs1Δ acs2Δ ald6Δ) and heterologously expressing acetaldehyde dehydrogenase acylating (Dz.eutE)) with either (1) an integration construct encoding two overexpressed copies of PK driven by the strong promoter $P_{TDH3}$, resulting in Y19390, or (2) an integration construct encoding two overexpressed copies of PTA driven by the strong promoter $P_{TDH3}$, resulting in Y19391. As shown in FIG. 3D, we observed an increase in acetate accumulation in strains that expressed either PK or PTA relative to the parent strain. Sugar consumption is shown in FIG. 3C to illustrate that acetate levels are not due to differential sugar consumption. PK converts X5P to Acetyl phosphate and G3P, whereas PTA can interconvert Acetyl CoA+Pi to Acetyl Phosphate+CoA. These observations suggest that acetyl phosphate, whether derived from X5P by PK, or derived from AcCoA by PTA, can be hydrolyzed to acetate as shown in FIG. 1.

6.2 Example 2

Identification of a Major Acetyl Phosphatase in *Saccharomyces cerevisiae*

This example describes the identification of an enzyme capable of hydrolyzing acetyl phosphate in yeast.

6.2.1 Materials and Methods

6.2.1.1 Cell Culture

A single colony of a given yeast strain was cultured in 5 mL Yeast Extract Peptone media with 2% dextrose (YPD) as an overnight starter culture. The following day, 50 ml YPD was inoculated with this starter culture to an OD600 of 0.2. The flasks were incubated at 30° C. by shaking at 200 RPM for 24 hours unless otherwise specified.

6.2.1.2 Cell-Free Extract Preparation

Cell culture was divided into three 15 mL falcon tubes and harvested by centrifugation at 4000×g for 5 minutes. The supernatant was then discarded and cells were washed by resuspending in 10 mL ice cold buffer W (100 mM Tris-HCl pH 8.0, 150 mM NaCl, 10% glycerol) followed by centrifugation at 4000×g for 5 minutes. Supernatant was discarded and cells were resuspended in 1 mL lysis buffer (100 mM Tris-HCl pH 8.0, 150 mM NaCl, 10% glycerol, 1 mM DTT, 1 EDTA free protease inhibitor tablet (Roche) per 10 mL). The cells were then transferred to a 2 mL plastic screw cap microfuge tube with O ring cap (Fisher Brand 520-GRD) and cells were lysed using disruption beads (Disruption beads, 0.5Mm, Fisher) and a bead beater for 1 minute at 6 M/S. The tubes were immediately placed in an ice water bath for at least 5 minutes. The tubes were then placed back in the bead beater again for 1 minute at 6 M/S and returned to the ice bath for 5 minutes. Tubes were spun at a minimum of 16000×g for 20 minutes to pellet cell debris. The supernatant was then transferred to a new cold tube. Protein concentration was measured using the classic Bradford assay for proteins (Bradford MM A rapid and sensitive method for quantitation of microgram quantities of protein utilizing the principle of protein-dye binding. *Anal. Biochem* 72, 248-254 (1976)).

6.2.1.3 Acetyl Phosphatase Reaction and Quantitation of Acetyl Phosphate

Acetyl phosphatase activity assays were carried out at 30° C. in reaction buffer consisting of 100 mM Tris-HCl pH 7.5, 150 mM NaCl, and 1 mM $MgCl^{2+}$. Acetyl phosphate was added to a starting concentration of either 5 mM or 10 mM as indicated. The reaction was initiated by the addition of cell free extract in the amounts indicated. To test for phosphatase inhibition, sodium fluoride was added to select wells at 30 mM concentration. The reactions were carried out in a sealed 96 well plate and total reaction volume of 250 µl. Acetylphosphate concentration was measured by the method developed by Lipmann and Tuttle (Lipmann F, Tuttle LC, J. Biol. Chem. 159, 21-28 (1945)). 50 µl reaction mixture was added to 50 µl 2M hydroxylamine pH 6.8, mixed well and incubated at room temperature for at least 10 minutes. 34 µl 15% trichloroacetic acid was then added and mixed followed by 34 µl 4N HCl and 34 µl 5% $FeCl_3$ mixing well after each addition. Plates were then centrifuged in a Beckman centrifuge J-E with swinging bucket rotor JS-5.3 for 5 minutes at 3000 rpm to pellet precipitated protein. 150 µl supernatant was then transferred to a fresh 96-well clear flat bottom plate (Greiner Bio-One Cat.-No: 655161). Plate was read by a Molecular Devices SpectraMax M5 plate reader at a wavelength of 505 nm.

6.2.1.4 Purification of Active Phosphatase Fraction

A single colony of a given yeast strain was cultured in 5 mL Yeast Extract Peptone media with 2% dextrose (YPD) as an overnight starter culture. The following day, two 2.8 L Fermbach flasks with 500 ml YPD were inoculated with this starter culture to an OD600 of 0.2. The flasks were incubated at 30° C. by shaking at 160 RPM for 24 hours. The culture was harvested by centrifugation at 4000×g for 5 minutes. The cell pellet was washed with 500 mL sterile water and centrifuged at 4000×g for 5 minutes. The cell pellet was then resuspended in 50 mL ice cold lysis buffer (100 mM Tris-HCl pH 8.0, 150 mM NaCl, 10% glycerol, 1 mM DTT, 1 EDTA free protease inhibitor tablet (Roche) per 10 mL). Cell suspension was split into six 15 mL falcon tubes filled with 5 mL disruption beads (Disruption beads, 0.5Mm, Fisher). Tubes were then placed in a bead beater for 45 seconds at 6 M/S. The tubes were immediately placed in an ice water bath for at least 5 minutes. Bead beating was repeated 3 additional times with at least 5 minutes in an ice water bath in between each disruption segment. Tubes were spun for 30 minutes at 16,000 rpm (30,966×g) in a Beckman centrifuge J-E in a JA-20 rotor chilled to 4° C. to pellet cell debris. Cell lysate was additionally clarified by the selective flocculation method described by Salt et al. (Selective flocculation of cellular contaminants from soluble proteins using polyethyleneimine: A study of several organisms and polymer molecular weights. *Enzyme and Microbial Technology* 17, 107-113 (1995)) as follows: cell free lysate was adjusted to pH 7.4 by addition of 5 mM NaOH stock solution. Then equal volume of PEI/Borax solution (0.5M NaCl 0.25% PEI, 100 mM Borax) was added to the cell lysate and mixed well. Mixture was then centrifuged for 30 minutes at 2,500×g at 4° C. Protein was then precipitated by slowly adding ammonium sulfate with constant stirring until 80% of saturation concentration was reached. Stirring continued for 10 more minutes, and then precipitated protein was harvested by centrifugation at 15,000 rpm at 4° C. in a Beckman JA-20 rotor for 10 minutes. Supernatant was removed and protein was gently resuspended in Buffer A (20 mM Tris-Cl, pH 7, 10% glycerol). Protein was then added to a 0.5-3 mL 3,500 Da molecular weight cut off dialysis cassette (Pierce #66300) and dialyzed overnight at 4° C. in 1.5 L buffer A. Dialyzed sample was centrifuged 16000×g for 10 minutes to pellet precipitated protein. Protein concentration was measured using the classic Bradford assay for proteins (Bradford MM, A rapid and sensitive method for quantitation of microgram quantities of protein utilizing the principle of protein-dye binding. *Anal. Biochem* 72, 248-254 (1976)). 20 mg protein was loaded onto a Source 15Q 4.6/100 PE anion exchange column on a GE ÄKTAexplorer FPLC. Protein was eluted with a 0-100% gradient of buffer B (20 mM Tris-Cl pH 7, 1M NaCl, 10% glycerol) over 30 column volumes at a flow rate of 0.5 mL/minute and 1 mL samples were collected. To assay activity of each fraction, 75 µL each fraction was added to 8 mM ACP in a 250 µL reaction containing 100 mM Tris-Cl pH 7, 150 mM NaCl, 1 mM MgCl2 and assayed as described above. The active fraction from this separation was again dialyzed against buffer A overnight. The entire sample was then loaded onto the same a Source 15Q 4.6/100 PE anion exchange column and eluted with a gradient of 0-45% buffer B over 30 column volumes at a flow rate of 0.5 mL/minute and 1 mL samples were collected. Samples were assayed for activity as above.

6.2.1.5 Protein Gel Electrophoresis

Protein fractions were analyzed using a Criterion gel electrophoresis system. 10 µL of fraction was added to 10 µL of 2× Laemmli sample buffer (BioRad Cat #161-0737) with 5% v/v 2-mercaptoethanol and boiled for 10 minutes. Samples were then briefly centrifuged and 15 µl was loaded on a 26 well 4-15% Criterion™ TGX™ Precast Gel and run in 1×Tris-Glycine-SDS buffer (prepared from BioRad 10×Tris/Glycine/SDS #161-0732) for 50 minutes at 130 volts. The gel was rinsed in 200 mL deionized water three times for 5 minutes each. SimplyBlue™ SafeStain (Life Technologies Cat # LC6060) was then added to the gel to completely cover the gel and then incubated at room temperature for 1 hour with gentle rocking. The SafeStain was then discarded and the gel was washed with 200 mL deionized water for 1 hour with rocking 6.2.1.6 Identification of Proteins in Active Phosphatase Fraction Proteolytic Digestion and Separation of Peptides 100 µg of total protein was subjected to proteolysis by trypsin for subsequent identification by LC-MS/MS. 100 µg total protein was reduced with Tris-carboxyethylphosphine (4 mM) for 30 minutes at 37° C., then alkylated with Iodoacetamide (15 mM) for 30 minutes at RT in the dark. 5 µg Trypsin was added to the digest mixture and the entire digestion was allowed to go for 12 hours at 37° C. The reaction was quenched with 0.1% formic acid and injected onto an Ascentis Peptide express column (5 cm×2.1 mm ID, 2.1 um particle size), and separated over a 90 minute gradient from low acetonitrile to high acetonitrile, with 0.1% formic acid as a modifier. The LC pumps were two Shimadzu LC20AD's operated by a Shimadzu CBM20A LC Controller.

Mass Spectrometry Parameters:

A QTRAP 4000 hybrid triple-quadrupole linear ion tram mass spectrometer was used to identify peptides being eluted from the column. IDA parameters were as follows: Select ions from 350 to 1300 da; ER Scan used for charge state determination; 1+ ions rejected, unknowns allowed; Rolling collision energy: yes (AB SCIEX standard for qtrap 4000); Max fill time for each MS/MS: 950 ms.

Peptide Identification by Mascot

Mascot, by Matrix Science was used to identify peptides from a CENPK2 sequence database with the following parameters. Fixed modifications: Carbamidomethyl. Variable modifications: deamidation (NQ), oxidation (MW). Precursor mass tolerance: 0.5 da. Product mass tolerance: 1.0 da. Missed cleavages allowed: 1.

6.2.1.7 Strain Engineering

A version of Y968 lacking a functional URA3 gene was transformed with either ms59858 to knock out RHR2 or ms59971 to knock out HOR2. The construct was assembled using the methods described in U.S. Pat. No. 8,221,982. Transformants were selected on CSM-URA plates with 2% glucose and confirmed by PCR amplification. The URA3 marker in this construct is flanked by direct repeats, facilitating its recycling. To recycle the URA3 marker, cells were grown in YPD overnight, then plated on 5'FOA. The loopout of URA3 was confirmed by PCR amplification and inability to grow on CSM-URA plates. The ura-version of Y968.ms59858 was then transformed with ms59971 to generate a double RHR2 and HOR2 knockout strain Y968.ms59858.ms59971

6.2.2 Results 6.2.2.1 Hydrolysis of Acetyl Phosphate is Enzyme-Catalyzed and Inhibited by Heat and a Broad Spectrum Phosphatase Inhibitor As shown in FIG. 4, addition of cell free extract from wild type *S. cerevisiae* strain Y967 catalyzes the hydrolysis of acetyl phosphate, and the rate of hydrolysis is dependent on the amount of cell free extract added. Increasing the amount of cell free extract increases the rate of hydrolysis. When the cell free extract is boiled, the addition of increasing amounts of cell free extract no longer has an effect on the hydrolysis rate of acetyl phosphate, indicating that the responsible component has been inactivated by heat. Similarly, the addition of 30 mM sodium fluoride, a broad spectrum phosphatase inhibitor, renders the cell free extract ineffective at hydrolyzing acetyl phosphate. These results suggest that a phosphatase is likely responsible for the catalysis of acetyl phosphate hydrolysis.

6.2.2.2 Protein Fractionation Isolates a Single Enriched Active Fraction

Anion exchange chromatography was used to separate soluble protein in the cell free extracts. FIG. 5A shows that nearly all of the phosphatase activity was concentrated in one fraction, and the remaining activity in adjacent fractions. This indicates that the enzyme responsible for this activity in the cell free extract is either a single protein or proteins with similar ionic interactions which co-elute when separated by anion exchange chromatography.

The active fraction #10 from FPLC anion exchange purification was purified a second time using a more shallow gradient 0-45% buffer B. The most active fraction from this purification, #14, shown in FIG. 6A, was analyzed by mass spectrometry to determine the identity of the proteins in the fraction. Of the proteins identified in the active fraction (FIG. 6B), Rhr2 and its homolog Hor2, which cannot be distinguished by mass spectrometry due to significant sequence similarity, were the only proteins on the list identified as phosphatases by the SGD database. Rhr2 is a glycerol-1-phosphatase that is expressed constitutively at high levels. Hor2 catalyzes the identical reaction but is expressed only at low levels under normal conditions and is induced by osmotic stress (Norbeck et. al., Purification and Characterization of Two Isoenzymes of DL-Glycerol-3-phosphatase from *Saccharomyces cerevisiae*, *J. Biol. Chem.*, 271, 13875-13881 (1996)). Acetyl phosphate is not a metabolite that is native to yeast, therefore it is expected that the hydrolysis is caused by a promiscuous reaction of an enzyme that targets a similar substrate. Rhr2/Hor2 were top candidates for this reaction since their native substrate, glycerol-1-phosphate, is also a low molecular weight phosphorylated compound similar to acetyl phosphate, as shown below.

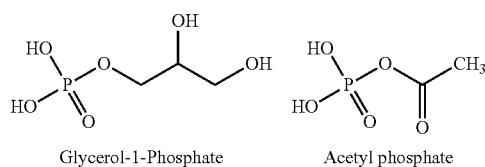

Glycerol-1-Phosphate          Acetyl phosphate

6.2.2.3 Deletion of RHR2 and/or HOR2 Reduces Phosphatase Activity

In order to determine whether Rhr2 and/or Hor2 were responsible for the phosphatase activity observed in *S. cerevisiae*, new strains were created lacking either RHR2 or HOR2 and one strain lacking both RHR2 and HOR2. These strains were cultured as described previously, and cell free extract was prepared and tested for acetyl phosphatase activity. As shown in FIG. 7, deletion of RHR2 dramatically reduces phosphatase activity, while deletion of HOR2 has no effect on the rate of hydrolysis of acetyl phosphate. Deletion of HOR2 does however reduce hydrolysis of acetyl phosphate in a strain that already has RHR2 deleted. This is consistent with published work that indicates that expression of Hor2 is upregulated following deletion of RHR2 (DeLuna et. al., Need-Based Up-Regulation of Protein Levels in Response to Deletion of Their Duplicate Genes, *PLOS Biol.*, 8, e10000347 (2010)). Elimination of both of these phosphatases results in near background levels of acetyl phosphate hydrolysis as shown in FIG. 7. These results confirm that glycerol-1-phosphatases Rhr2 and Hor2 are responsible for the majority of the acetyl phosphatase activity in *S. cerevisiae*.

6.3 Example 3

Deletion of the Acetyl Phosphate Phosphatase Reduces Acetate Secretion and Improves Production of a Compound Derived from Acetyl-CoA

6.3.1 Materials and Methods
6.3.1.1 Strain construction

Versions of Y968, Y12869, and Y12746, lacking a functional URA3 gene, were transformed with either ms63907 or ms63909, and with ms64472, to convert them to farnesene producers.

The ms63907 integration construct (i84022; SEQ ID NO:33) is shown below.

| HO US | GAL4 | pGAL1 | Sp.HMGr | pGAL10 | ERG10 | URA3 | ERG13 | pGAL10 | PGAL1 | Sp.HMGr | HO DS |
|---|---|---|---|---|---|---|---|---|---|---|---|

This construct comprises nucleotide sequences that encode a selectable marker (URA3); a copy of the native yeast GAL4 transcription factor under its own promoter; two native yeast enzymes of the mevalonate pathway (ERG10 which encodes Acetoacetyl-CoA thiolase, and ERG13, which encodes HMG-CoA synthase), as well as two copies of a yeast codon-optimized version of *Silicibacter pomeroyi* HMG-CoA reductase, all under galactose-inducible promoters (promoters of the *S. cerevisiae* genes GAL1 and GAL10, flanked by homologous sequences consisting of upstream and downstream nucleotide sequences of the *S. cerevisiae* HO endonuclease locus. Upon introduction into a host cell, the ms63907 construct integrates by homologous integration into the host cell genome, functionally disrupting HO by replacing the HO coding sequence with its integrating sequence. The construct was assembled using the methods described in U.S. Pat. No. 8,221,982. Transformants were selected on CSM-URA plates with 2% glucose and confirmed by PCR amplification. The URA3 marker in this construct is flanked by direct repeats, facilitating its recycling. To recycle the URA3 marker, cells were grown in YPD overnight, then plated on 5'FOA. The loopout of URA3 was confirmed by PCR amplification and inability to grow on CSM-URA plates. The ms63909 integration construct (i84026; SEQ ID NO:34) is identical to ms63907, with one exception: the sequences encoding *S. pomeroyi* HMG-CoA reductase are replaced by tHMGr, the truncated HMG1 coding sequence which encodes the native *S. cerevisiae* HMG-CoA reductase.

The ms64472 integration construct (i85207; SEQ ID NO:35) is shown below.

| GAL80 uS | pGAL7 | IDI1 | AF4s | pGAL1 | pGAL10 | ERG20 | URA3 | ERG8 | pGAL7 | ERG19 | pGAL10 | pGAL1 | ERG12 | GAL80 DS |
|---|---|---|---|---|---|---|---|---|---|---|---|---|---|---|

This construct comprises nucleotide sequences that encode a selectable marker (URA3); five native yeast enzymes of the ergosterol pathway (ERG12 which encodes mevalonate kinase, ERG8 which encodes phosphomevalonate kinase, ERG19 which encodes mevalonate pyrophosphate decarboxylase, IDI1 which encodes dimethylallyl diphosphate isomerase, and ERG20 which encodes farnesyl pyrophosphate synthetase), as well as an evolved, yeast codon-optimized version of *Artemisia annua* farnesene synthase, all under galactose-inducible promoters (Promoters of the *S. cerevisiae* genes GAL1, GAL10, and GAL7). These sequences are flanked by homologous sequences consisting of the upstream and downstream nucleotide sequences of GAL80. Upon introduction into a host cell, the ms64472 construct integrates by homologous integration into the host cell genome, functionally disrupting GAL80 by replacing the GAL80 coding sequence with its integrating sequence. The construct was assembled using the methods described in U.S. Pat. No. 8,221,982. Transformants were selected on CSM-URA plates with 2% glucose and confirmed by PCR amplification. The URA3 marker in this construct is flanked by direct repeats, facilitating its recycling. To recycle the URA3 marker, cells were grown in YPD overnight, then plated on 5'FOA. The loopout of URA3 was confirmed by PCR amplification and inability to grow on CSM-URA plates.

Next, ura-versions of Y968.ms63907.ms64472, Y12869.ms63907.ms64472, and Y12747.ms63907.ms64472, were transformed with ms59858 to knock out the RHR2 ORF. This integration construct consists of the upstream and downstream nucleotide sequences of RHR2, flanking the native *S. cerevisiae* URA3 gene under its own promoter and terminator. Transformants were plated onto CSM-his plates containing 2% glucose as the sole carbon source, and were confirmed by PCR amplification.

6.3.1.2 Culture Conditions

Single colonies were inoculated in wells of a 96-well plate in 360 µl of seed media (described in Example 1), and grown at 34° C. for three days by shaking at 1000 rpm. Then, 14.4 µl of culture was subcultured into 360 µl of seed media with 50 mM succinate pH 5.0 and 40 g/L galactose, and grown at 34° C. for two days by shaking at 1000 rpm.

6.3.1.3 Quantitation of Acetate and Glycerol

Acetate and glycerol were quantitated by transferring 1 ml of whole cell broth to a 1.5 ml eppendorf tubes, and spinning at 13,000 RPM for 1 minute using a tabletop centrifuge to clarify the supernatant. The supernatant was then diluted (1:1 v/v) in 8 mM sulfuric acid, vortexed, and recentrifuged before transferring to a 1.8 ml vial. Samples were analyzed with an Agilent 1200 HPLC, with variable wavelength and refractive index detection, using a BioRad Aminex HPX-87H 300 mm×7.8 mm column. The mobile phase was 4 mM sulfuric acid, column temperature was 40 C, and the flow rate was 0.5 ml/min.

6.3.1.4 Quantitation of Farnesene

At the end of two days incubation at 34° C., 98 µl of whole cell broth was mixed with 2 µl of Nile Red solution (100 µg/ml in DMSO) in a flat-bottom 96-well assay plate (Costar 3916), and mixed for 30 seconds on a 96-well plate shaker. The plates were then read on a Beckman M5 plate reader with excitation at 500 nm and emission at 550 nm.

6.3.1.5 Quantitation of Optical Density

In a 96-well assay plate, 8 µl of culture was mixed with 92 µl of diluent (20% PEG 200, 20% Ethanol, 2% Triton X-114) and incubated for 30 minutes at room temperature. The assay plate was vortexed before measuring $OD_{600}$ on a Beckman M5 plate reader.

6.3.2 Results

FIG. 8A shows that strain Y12746.ms63909.ms64472, comprising a deletion of the PDH-bypass (acs1Δ acs2Δ ald6Δ), heterologously expressing acetaldehyde dehydrogenase aceylating (Dz.eutE) as well as phosphoketolase (Lm.PK) and phosphotransacetylase (Ck.PTA) and overexpressing genes in the farnesene production pathway, secretes more acetate than a version of Y12746.ms63909.ms64472 in which the RHR2 gene has been deleted. As shown in FIG. 8B, deletion of RHR2 does not impact glycerol production, as glycerol levels of Y12746.ms63909.ms64472 rhr2^ are largely unchanged compared to Y12746.ms63909.ms64472. As shown in FIG. 8C, the substantially reduced levels of acetate in Y12746.ms63909.ms64472 rhr2^ are not due to reduced cell growth, as cell densities are similar for both RHR2+ and rhr2^ populations. These results demonstrate that Rhr2, which was responsible for the acetyl phosphate phosphatase activity in cell free extract, is also the primary cause behind the hydrolysis of acetyl phosphate to acetate in vivo.

To determine whether the reduction of acetate observed upon deletion of RHR2 occurs independent of farnesene production, acetate production was measured in versions of strain 12746 with an intact or deleted RHR2 gene, but not expressing genes in the farnesene production pathway. FIG. 8D shows that strain Y12746, comprising a deletion of the PDH-bypass (acs1Δ acs2Δ ald6Δ), heterologously expressing acetaldehyde dehydrogenase aceylating (Dz.eutE) as well as phosphoketolase (Lm.PK) and phosphotransacetylase (Ck.PTA), secretes more acetate than a version of Y12746 in which the RHR2 gene has been deleted. As shown in FIG. 8E, the substantially reduced levels of acetate in Y12746.ms63909.ms64472 rhr2^ are not due to reduced cell growth, as cell densities are similar for both RHR2+ and rhr2^ populations. These data illustrate that the reduction in acetate occurs regardless of the presence of an overexpressed farnesene production pathway.

FIG. 9 shows that the deletion of rhr2 improves farnesene production in Y12746.ms63907.ms64472 by 2.1-fold, and in Y12745.ms63907.ms64472 by 1.4-fold (In each strain background, the RHR2+ parent is normalized to 1). Moreover, deletion of rhr2 improves the final optical density of Y12746.ms63907.ms64472 at carbon exhaustion. Both Y12745.ms63907.64472 and Y12746.ms63907.ms64472 use phosphoketolase and phosphotransacetylase, and thus acetyl phosphate as a pathway intermediate, to produce cytosolic acetyl-CoA, which is used for synthesis of farnesene. Strains Y968.ms63907.ms64472 and Y12869.ms63907.ms64472 do not express phosphoketolase or phosphotransacetylase, and do not use acetyl phosphate as a pathway intermediate. Deletion of rhr2 in these strain backgrounds has no effect on farnesene production or optical density in either strain background. This indicates that the benefit of knocking out rhr2 specifically applies to strains which use acetyl phosphate as an intermediate metabolite, e.g., strains comprising heterologous PK and/or PTA.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A genetically modified yeast host cell capable of producing an isoprenoid, acetyl-CoA or an acetyl-CoA derived compound, the genetically modified yeast host cell comprising:
   (a) a heterologous nucleic acid encoding a phosphoketolase (PK; EC 4.1.2.9);
   (b) a heterologous nucleic acid encoding a phosphotransacetylase (PTA; EC 2.3.1.8); and
   (c) a functional disruption of an endogenous glycerol-1-phosphatase enzyme (EC 3.1.3.21) that converts acetyl phosphate to acetate,
   wherein the genetically modified yeast host cell produces an increased amount of an isoprenoid, acetyl-CoA or an acetyl-CoA derived compound compared to yeast cells which are not geneically modified in the same way.

2. The genetically modified yeast host cell of claim 1, wherein the glycerol-1-phosphatase is selected from GPP1/RHR2, GPP2/HOR2, and homologues and variants thereof.

3. The genetically modified yeast host cell of claim 2, wherein GPP1/RHR2, or a homologue or variant thereof, is functionally disrupted.

4. The genetically modified yeast host cell of claim 2, wherein GPP2/HOR2, or a homologue or variant thereof, is functionally disrupted.

5. The genetically modified yeast host cell of claim 2, wherein both GPP1/RHR2 and GPP2/HOR2, or both a homologue or variant of GPP1/RHR2 and a homologue or variant of GPP2/HOR2, are functionally disrupted.

6. The genetically modified yeast host cell of claim 1, wherein the genetically modified host cell comprises one or more heterologous nucleic acids encoding one or more enzymes of a mevalonate (MEV) pathway for making isopentenyl pyrophosphate.

7. The genetically modified yeast host cell of claim 6, wherein the one or more enzymes of the MEV pathway comprise an NADH-using HMG-CoA reductase.

8. The genetically modified yeast host cell of claim 6, wherein the one or more enzymes of the MEV pathway comprise an enzyme that condenses two molecules of acetyl-CoA to form acetoacetyl-CoA.

9. The genetically modified yeast host cell of claim 6, wherein the one or more enzymes of the MEV pathway comprise an enzyme that condenses acetoacetyl-CoA with acetyl-CoA to form HMG-CoA.

10. The genetically modified yeast host cell of claim 6, wherein the one or more enzymes of the MEV pathway comprise an enzyme that converts HMG-CoA to mevalonate.

11. The genetically modified yeast host cell of claim 6, wherein the one or more enzymes of the MEV pathway comprise an enzyme that phosphorylates mevalonate to mevalonate 5-phosphate.

12. The genetically modified yeast host cell of claim 6, wherein the one or more enzymes of the MEV pathway comprise an enzyme that converts mevalonate 5-phosphate to mevalonate 5-pyrophosphate.

13. The genetically modified yeast host cell of claim 6, wherein the one or more enzymes of the MEV pathway comprise an enzyme that converts mevalonate 5-pyrophosphate to isopentenyl pyrophosphate.

14. The genetically modified yeast host cell of claim 6, wherein the one or more enzymes of the MEV pathway are selected from HMG-CoA synthase, mevalonate kinase, phosphomevalonate kinase and mevalonate pyrophosphate decarboxylase.

15. The genetically modified yeast host cell of claim 6, wherein the host cell comprises a plurality of heterologous nucleic acids encoding all of the enzymes of the MEV pathway.

16. The genetically modified yeast host cell of claim 6, wherein the one or more heterologous nucleic acids encoding one or more enzymes of the MEV pathway are under control of a single transcriptional regulator.

17. The genetically modified yeast host cell of claim 6, wherein the one or more heterologous nucleic acids encoding one or more enzymes of the MEV pathway are under control of multiple heterologous transcriptional regulators.

18. The genetically modified yeast host cell of claim 6, further comprising a heterologous nucleic acid encoding an enzyme that can convert isopentenyl pyrophosphate (IPP) into dimethylallyl pyrophosphate (DMAPP).

19. The genetically modified yeast host cell of claim 6, further comprising a heterologous nucleic acid encoding an enzyme that can condense IPP and/or DMAPP molecules to form a polyprenyl compound.

20. The genetically modified yeast host cell of claim 6, further comprising a heterologous nucleic acid encoding an enzyme that can modify IPP or a polyprenyl to form an isoprenoid compound.

21. The genetically modified yeast host cell of claim 20, wherein the enzyme that can modify IPP or a polyprenyl to form an isoprenoid compound is selected from the group consisting of carene synthase, geraniol synthase, linalool synthase, limonene synthase, myrcene synthase, ocimene synthase, α-pinene synthase, β-pinene synthase, γ-terpinene synthase, terpinolene synthase, amorphadiene synthase, α-farnesene synthase, β-farnesene synthase, farnesol synthase, nerolidol synthase, patchouliol synthase, nootkatone synthase, and abietadiene synthase.

22. The genetically modified yeast host cell of claim 1, wherein the isoprenoid is selected from the group consisting of a hemiterpene, monoterpene, diterpene, triterpene, tetraterpene, sesquiterpene, and polyterpene.

23. The genetically modified yeast host cell of claim 1, wherein the isoprenoid is a $C_5$-$C_{20}$ isoprenoid.

24. The genetically modified yeast host cell of claim 1, wherein the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, and valencene.

25. The genetically modified yeast host cell of claim 1, wherein the genetically modified yeast host cell is *Saccharomyces cerevisiae*.

26. A method for producing an isoprenoid comprising:
  (a) culturing a population of the genetically modified yeast host cell of claim 1 in a medium with a carbon source under conditions suitable for making said isoprenoid compound; and
  (b) recovering said isoprenoid compound from the medium.

27. A method for increasing the production of acetyl-CoA or an acetyl-CoA derived compound in a yeast host cell, the method comprising:
  (a) expressing in the yeast host cell a heterologous nucleic acid encoding a phosphoketolase (PK; EC 4.1.2.9);
  (b) expressing in the yeast host cell a heterologous nucleic acid encoding a phosphotransacetylase (PTA; EC 2.3.1.8); and
  (c) functionally disrupting an endogenous glycerol-1-phosphatase enzyme (EC 3.1.3.21) that converts acetyl phosphate to acetate,
  wherein the genetically modified yeast host cell produces an increased amount of acetyl-CoA or an acetyl-CoA derived compound compared to yeast cells which are not genetically modified in the same way.

28. The method of claim 27, wherein the glycerol-1-phosphatase is selected from GPP1/RHR2, GPP2/HOR2, and homologues and variants thereof.

29. The method of claim 28, wherein GPP1/RHR2, or a homologue or variant thereof, is functionally disrupted.

30. The method of claim 28, wherein GPP2/HOR2, or a homologue or variant thereof, is functionally disrupted.

31. The method of claim 28, wherein both GPP1/RHR2 and GPP2/HOR2, or both a homologue or variant of GPP1/RHR2 and a homologue or variant of GPP2/HOR2, are functionally disrupted.

32. The method of claim 27, wherein the yeast host cell is *Saccharomyces cerevisiae*.

* * * * *